US009782474B2

(12) United States Patent
Long et al.

(10) Patent No.: US 9,782,474 B2

(45) Date of Patent: Oct. 10, 2017

(54) VACCINES AGAINST HERPES SIMPLEX VIRUS TYPE 2: COMPOSITIONS AND METHODS FOR ELICITING AN IMMUNE RESPONSE

(75) Inventors: Deborah Long, Monroe, NY (US); Jessica Flechtner, Sudbury, MA (US); Mojca Skoberne, Cambridge, MA (US)

(73) Assignee: Genocea Biosciences, Inc., Cambridge, MA (US)

(*) Notice: Subject to any disclaimer, the term of this patent is extended or adjusted under 35 U.S.C. 154(b) by 0 days.

(21) Appl. No.: 13/989,119

(22) PCT Filed: Nov. 23, 2011

(86) PCT No.: PCT/US2011/062120

§ 371 (c)(1),
(2), (4) Date: Sep. 9, 2013

(87) PCT Pub. No.: WO2012/074881

PCT Pub. Date: Jun. 7, 2012

(65) Prior Publication Data

US 2013/0337000 A1 Dec. 19, 2013

Related U.S. Application Data

(60) Provisional application No. 61/417,089, filed on Nov. 24, 2010.

(51) Int. Cl.

| | |
|---|---|
| ***A61K 39/245*** | (2006.01) |
| ***A61K 39/12*** | (2006.01) |
| ***A61K 39/205*** | (2006.01) |
| ***A61K 39/00*** | (2006.01) |

(52) U.S. Cl.

CPC ............ *A61K 39/245* (2013.01); *A61K 39/12* (2013.01); *A61K 39/205* (2013.01); *A61K 2039/5252* (2013.01); *A61K 2039/53* (2013.01); *A61K 2039/545* (2013.01); *A61K 2039/55505* (2013.01); *A61K 2039/55538* (2013.01); *A61K 2039/55577* (2013.01); *A61K 2039/55583* (2013.01); *C12N 2710/16034* (2013.01); *C12N 2710/16634* (2013.01)

(58) Field of Classification Search

CPC .... A61K 2300/00; A61K 38/00; A61K 39/12; A61K 2039/53; A61K 39/245; A61K 2039/522; A61K 2039/5252; A61K 39/42; C07K 14/005; C07K 16/087; C12N 7/00; C12N 15/86; C12N 2710/16622

See application file for complete search history.

(56) References Cited

U.S. PATENT DOCUMENTS

| | | | | |
|---|---|---|---|---|
| 4,818,694 | A | | 4/1989 | Watson et al. |
| 5,149,529 | A | | 9/1992 | Ho et al. |
| 5,612,041 | A | | 3/1997 | Burke et al. |
| 5,648,079 | A | | 7/1997 | Burke et al. |
| 5,654,174 | A | | 8/1997 | Cohen et al. |
| 5,656,457 | A | | 8/1997 | Parkes et al. |
| 5,679,348 | A | * | 10/1997 | Nesburn et al. ........... 424/186.1 |
| 5,750,114 | A | | 5/1998 | Burke et al. |
| 5,763,406 | A | | 6/1998 | Pedersen et al. |
| 5,795,579 | A | | 8/1998 | Burke et al. |
| 5,807,557 | A | * | 9/1998 | Dubin ........................ 424/231.1 |
| 5,851,533 | A | | 12/1998 | Berman et al. |
| 5,876,923 | A | | 3/1999 | Leopardi et al. |
| 5,955,088 | A | * | 9/1999 | Ghiasi et al. ............. 424/231.1 |
| 5,958,895 | A | | 9/1999 | Pachuk et al. |
| 5,962,428 | A | | 10/1999 | Carrano et al. |
| 6,027,730 | A | | 2/2000 | Francotte et al. |
| 6,156,319 | A | | 12/2000 | Cohen et al. |
| 6,197,497 | B1 | | 3/2001 | Goade et al. |
| 6,207,168 | B1 | | 3/2001 | Aurelian |
| 6,352,697 | B1 | * | 3/2002 | Cox et al. .................. 424/278.1 |
| 6,413,518 | B1 | | 7/2002 | Koelle et al. |
| 6,468,982 | B1 | | 10/2002 | Weiner et al. |
| 6,537,555 | B2 | | 3/2003 | Hosken et al. |
| 6,635,258 | B2 | | 10/2003 | Burke et al. |
| 6,682,892 | B2 | | 1/2004 | Homa et al. |
| 6,692,752 | B1 | | 2/2004 | Slaoui et al. |
| 6,814,969 | B2 | | 11/2004 | Koelle et al. |
| 6,867,000 | B2 | | 3/2005 | Mishkin et al. |
| 6,932,972 | B2 | | 8/2005 | Stephenne et al. |
| 6,936,255 | B1 | | 8/2005 | Wettendorff |
| 6,962,709 | B2 | | 11/2005 | Koelle et al. |

(Continued)

FOREIGN PATENT DOCUMENTS

| | | | |
|---|---|---|---|
| EP | 0139417 | A1 | 5/1985 |
| WO | WO-94/29456 | A2 | 12/1994 |

(Continued)

OTHER PUBLICATIONS

World Health Organization (WHO). "Status of Vaccine Research and Development of Vaccines for Herpes Simplex Virus Prepared for WHO PD-VAC." http://www.who.int/immunization/research/meetings_workshops/HSV_vaccineRD_Sept2014.pdf. Pub. Sep. 24, 2014.*

Dolan A. Virion glycoprotein L [human herpesvirus 2] NCBI Reference Sequence: NP_044470.1. Dep. Apr. 3, 2000.*

Dolan A. Envelope glycoprotein D [Human herpesvirus 2]. NCBI Reference Sequence: NP_044536.1. Dep. Apr. 3, 2000.*

Dolan A. transcriptional regulator ICP4 [Human herpesvirus 2]. NCBI Reference Sequence: NP_044530.1. Dep. Apr. 3, 2000.*

Dolan A. Human herpesvirus 2, complete genome. NCBI Reference Sequence: NC_001798. Dep. Apr. 3, 2000.*

Bowie JU, Reidhaar-Olson JF, Lim WA, Sauer RT. Deciphering the message in protein sequences: tolerance to amino acid substitutions. Science. Mar. 16, 1990;247(4948):1306-10.*

Dasgupta, et al., New Concepts in Herpes Simplex Virus Vaccine Development: Notes from the Battlefield, Expert Rev. Vaccines, 8(8):1023-1035 (2009).

GenBank Direct Submission UniProtKB/Swiss-Prot: P28278.1, Envelope glycoprotein L; Short=gL; Flags: Precursor, <http://www.ncbi.nlm.nih.gov/protein/136776?sat=13&satkey=1212127> (2010).

(Continued)

*Primary Examiner* — Rachel B Gill

(74) *Attorney, Agent, or Firm* — Choate, Hall & Stewart, LLP; Brenda Herschbach Jarrell; Rolando Medina

(57) ABSTRACT

Herpes Simplex Virus-2 (HSV-2) infection is a major health concern. Highly effective vaccines and immunogenic compositions against HSV-2, which can be used therapeutically or prophylactically, are described.

36 Claims, 21 Drawing Sheets

(56) References Cited

U.S. PATENT DOCUMENTS

| | | | | |
|---|---|---|---|---|
| 7,037,509 | B2 | 5/2006 | Koelle et al. | |
| 7,078,041 | B2 | 7/2006 | Koelle et al. | |
| 7,094,767 | B2 | 8/2006 | Armstrong et al. | |
| 7,157,437 | B2 | 1/2007 | Van Nest | |
| 7,196,066 | B1 | 3/2007 | Swain et al. | |
| 7,264,817 | B1 | 9/2007 | Berman et al. | |
| 7,267,940 | B2 | 9/2007 | Chen et al. | |
| 7,569,218 | B2 | 8/2009 | Weiner et al. | |
| 7,628,993 | B2 | 12/2009 | Vilalta et al. | |
| 7,666,434 | B2 | 2/2010 | Koelle et al. | |
| 7,744,903 | B2 | 6/2010 | Koelle et al. | |
| 8,197,824 | B2 | 6/2012 | Koelle et al. | |
| 8,313,894 | B2 | 11/2012 | Flechtner et al. | |
| 8,617,564 | B2 | 12/2013 | Long et al. | |
| 2002/0058021 | A1 | 5/2002 | Audonnet et al. | |
| 2003/0017174 | A1 | 1/2003 | Burke et al. | |
| 2003/0165537 | A1* | 9/2003 | Fehler et al. | 424/199.1 |
| 2003/0165819 | A1 | 9/2003 | McGowan et al. | |
| 2004/0220076 | A1 | 11/2004 | Aurelian et al. | |
| 2007/0196389 | A1 | 8/2007 | Caligiuri et al. | |
| 2008/0145375 | A1 | 6/2008 | Bembridge et al. | |
| 2008/0299140 | A1 | 12/2008 | Georges et al. | |
| 2009/0148467 | A1 | 6/2009 | Friedman et al. | |
| 2010/0203073 | A1 | 8/2010 | Koelle | |
| 2010/0330112 | A1 | 12/2010 | Long et al. | |
| 2011/0293664 | A1 | 12/2011 | Cohane et al. | |
| 2012/0135025 | A1 | 5/2012 | Flechtner et al. | |
| 2013/0171234 | A1* | 7/2013 | Fairman et al. | 424/450 |
| 2013/0337000 | A1* | 12/2013 | Long et al. | 424/186.1 |
| 2014/0227307 | A1 | 8/2014 | Long et al. | |
| 2014/0328870 | A1 | 11/2014 | Long et al. | |

FOREIGN PATENT DOCUMENTS

| | | | | |
|---|---|---|---|---|
| WO | WO-95/06055 | A1 | 3/1995 | |
| WO | WO-95/16779 | A1 | 6/1995 | |
| WO | WO-98/20016 | | 5/1998 | |
| WO | WO-98/20016 | A1 | 5/1998 | |
| WO | WO-00/77043 | A2 | 12/2000 | |
| WO | WO-01/44477 | A1 | 6/2001 | |
| WO | WO-02/02131 | A2 | 1/2002 | |
| WO | WO-03/020108 | A2 | 3/2003 | |
| WO | WO-03/086308 | A2 | 10/2003 | |
| WO | WO-03/099860 | A2 | 12/2003 | |
| WO | WO-2004/009021 | A2 | 1/2004 | |
| WO | WO-2005/028496 | A2 | 3/2005 | |
| WO | WO-2007/106404 | A2 | 9/2007 | |
| WO | WO-2008/011609 | A2 | 1/2008 | |
| WO | WO-2008/027394 | A2 | 3/2008 | |
| WO | WO-2008/030560 | A2 | 3/2008 | |
| WO | WO-2008/085486 | A1 | 7/2008 | |
| WO | WO-2008/140478 | A2 | 11/2008 | |
| WO | WO-2009/006618 | A2 | 1/2009 | |
| WO | WO-2009/006680 | A1 | 1/2009 | |
| WO | WO 2010023260 | A1 * | 3/2010 | A61K 39/015 |
| WO | WO-2010/103017 | A2 | 9/2010 | |
| WO | WO-2010/135747 | A1 | 11/2010 | |
| WO | WO-2011/112717 | A1 | 9/2011 | |

OTHER PUBLICATIONS

International Search Report for PCT/US11/62120, dated Jul. 10, 2012, published as WO 2012/074881 (6 pages).

Rajaguru, Inhibition of Herpes Simplex Virus Replication Using Small Interfering RNA That Target ICP4 Gene of Herpes Simplex Type 2, Master of Science Thesis, University of Florida (2004).

Sedlackova and Rice, Herpes Simplex Virus Type 1 Immediate-Early Protein ICP27 is Required for Efficient Incorporation of ICPO and ICP4 into Virions, Journal of Virology, 82(1):268-277 (2008).

Written Opinion for PCT/US11/62120, dated Jul. 10, 2012, published as WO 2012/074881 (9 pages).

Genbank BAA01264.1 (May 29, 2002).

Genbank CAB06713.1 (Nov. 14, 2006).

Jones, C.A. et al., Vaccination strategies to prevent genital herpes and neonatal herpes simplex virus (HSV) disease, The Journal of the IHMF (England), 11(1):12-7 (2004). Abstract only.

Mertz, G.J. Asymptomatic Shedding of Herpes Simplex Virus 1 and 2: Implications for Prevention of Transmission, The Journal of Infectious Diseases, 198:1-2 (2008).

Watari, E. et al., A synthetic peptide induces long-term protection from lethal infection with herpes simplex virus 2, The Journal of Experimental Medicine, 165:459-470 (1987).

Ashley, R. et al., Humoral Immune Response to Herpes Simplex Virus Type 2 Glycoproteins in Patients Receiving a Glycoprotein Subunit Vaccine, Journal of Virology, 56(2):475-481 (1985).

Braun, R.P. et al., Characterization of the IFN-γ T-cell responses to immediate early antigens in humans with genital herpes, Virology Journal, 3(54):1-15 (2006).

Cattamanchi, A. et al., Phase I Study of a Herpes Simplex Virus Type 2 (HSV-2) DNA Vaccine Administered to Healthy, HSV-2-Seronegative Adults by a Needle-Free Injection System, Clinical and Vaccine Immunology, 15(11):1638-1643 (2008).

International Search Report for PCT/US2010/035998, 7 pages (Oct. 26, 2010).

International Search Report for PCT/US2010/036000, 7 pages (Sep. 7, 2010).

Koelle, D.M. et al., Antigenic Specificities of Human CD4+ T-Cell Clones Recovered from Recurrent Genital Herpes Simplex Virus Type 2 Lesions, Journal of Virology, 68(5):2803-2810 (1994).

Koelle, D.M. et al., Immunodominance among herpes simplex virus-specific CD8 T cells expressing a tissue-specific homing receptor, PNAS, 100(22):12899-12904 (2003).

Langenberg, A.G.M. et al., A Recombinant Glycoprotein Vaccine for Herpes Simplex Type 2: Safety and Efficacy, Annals of Internal Medicine, 122(12):889-898 (1995).

Liljeqvist, J.A. et al., Monoclonal antibodies and human sera directed to the secreted glycoprotein G of herpes simplex virus type 2 recognize type-specific antigenic determinants, Journal of General Virology, 83:157-165 (2002).

Meseda, C.A. et al., A Prime-Boost Immunization with DNA and Modified Vaccinia Virus Ankara Vectors Expressing Herpes Simplex Virus-2 Glycoprotein D Elicits Greater Specific Antibody and Cytokine Responses than DNA Vaccine Alone, The Journal of Infectious Diseases, 186:1065-1073 (2002).

Shlapobersky, M. et al., Vaxfectin-adjuvanted plasmid DNA vaccine improves protection and immunogenecity in a murine model of genital herpes infection, Journal of General Virology, 93:1305-1315 (2012).

Strasser, J.E. et al., Herpes Simplex Virus DNA Vaccine Efficacy: Effect of Glycoprotein D Plasmid Constructs, The Journal of Infectious Diseases, 182:1304-1310 (2000).

Tigges, M.A. et al., Human CD8+ Herpes Simplex Virus-Specific Cytotoxic T-Lymphocyte Clones Recognize Diverse Virion Protein Antigens, Journal of Virology, 66(3):1622-1634 (1992).

Zhou, J. et al., Research Progress of Envelope Glycoprotein gG-2 of HSV, Foreign Medical Sciences, 11(4):123-126 (2004). (English Abstract).

Yang, Huilan et al., High effective expression of gD2 gene of herpes virus in *Escherichia coli,* Chinese Journal of Dermatology, 3:157-159, Abstract Only (1997).

Baccari, A. et al., Both HSV-2 and HSV-1 neutralizing antibody titers are boosted in subjects with genital herpes after vaccination with GEN-0003, a novel HSV-2 immunotherapy, Paper Poster Session 1, Abstract, P0279 (2015).

Fife, K.H. et al., An International, Randomized, Double-Blind, Placebo-Controlled, Study of Valacyclovir for the Suppression of Herpes Simplex Virus Type 2 Genital Herpes in Newly Diagnosed Patients, Sexually Transmitted Diseases 35(7): 668-673 (2008).

Freeman, E.F. et al., Herpes simplex virus 2 infection increases HIV acquisition in men and women: systematic review and meta-analysis of longitudinal studies, AIDS, 73-83 (2006).

Garland, S.M. et al., Genital herpes, Best Practice & Research Clinical Obstetrics and Gynaecology, 28: 1095-110 (2014).

Genocea Biosciences, Genocea Announces Positive Durability Data from 6-Month Analysis of Phase 2 Clinical Trial of Genital Herpes Immunotherapy GEN-003, Business Wire, Cambridge, MA, 3 pages (Oct. 7, 2015).

Knipe, D.M. et al., Summary and recommendations from a National Institute of Allergy and Infectious Diseases (NIAID) workshop on "Next Generation Herpes Simplex Virus Vaccines", Vaccine, 32: 1561-1562 (2014).

Roth, K. et al., HSV-2 vaccine: Current state and insights into development of a vaccine that targets genital mucosal protection, Microbiol Pathogenesis, 1-10 (2012).

Schiffer, J.T. et al., Herpes simplex virus-2 transmission probability estimates based on quantity of viral shedding, Journal of the Royal Society Interface, 1-12 (2014).

Bernstein, D.J. et al., Effects of herpes simplex virus type 2 glycoprotein vaccines and CLDC adjuvant on genital herpes infection in the guinea pig, Vaccine, 29: 2071-2078 (2011).

Boursnell, M. et al., A Genetically Inactivated Herpes Simplex Virus Type 2 (HSV-2) Vaccine Provides Effective Protection against Primary and Recurrent HSV-2 Disease, The Journal of Infectious Diseases, 175(1): 16-25 (1997).

Braun, R.P. et al., Multi-antigenic DNA immunization using herpes simplex virus type 2 genomic fragments, Human Vaccines, 4(1): 36-43 (2008).

Database EMBL P28278 (GL_HHV2H), Jan. 12, 1992 [retrieved on Sep. 1, 2013]. Retrieved from the internet: <URL:http//www.uniprot.org/uniprot/P28278>).

Database EMBL Q69467 (GD_HHV2H), Jan. 11, 1996 [retrieved on Sep. 1, 2013]. Retrieved from the internet: <URL:http//www.uniprot.org/uniprot/Q69467>).

Dolan, A., Herpes simplex virus type 2 (strain HG52), complete genome, GenBank Acc No. Z86099.2, Dep. Mar. 5, 1997, Rev. Nov. 14, 2006.

Dolan, et al., The Genome Sequence of Herpes Simplex Virus Type 2, J. Virol., 72(3):2010-2021 (1998).

Fló, J., Co-immunization with plasmids coding the full length and a soluble form of glycoprotein D of HSV-2 induces protective cellular and humoral immune response in mice, Vaccine, 21(11-12): 1239-1245 (2003).

Fló, J., et al., Superiority of intramuscular route and full length glycoprotein D for DNA vaccination against herpes simplex 2. Enhancement of protection by the co-delivery of the GM-CSF gene. Vaccine, 18(28): 3242-3253 (2000).

GenBank ABU45435.1, glycoprotein D [Human herpesvirus 2] (Nov. 29, 2007).

Grabowska, A.M. et al., Immunisation with Phage Displaying Peptides Representing Single Epitopes of the Glycoprotein G can give rise to Partial Protective Immunity to HSV-2, Virology, 269: 47-53 (2000).

International Search Report for PCT/US2012/066241, dated Feb. 28, 2013, published as WO 2013/078299 (2 pages).

Lasky, L.A. et al., DNA Sequence Analysis of the Type-Common Glycoprotein-D Genes of Herpes Simplex Virus Types 1 and 2, DNA, 3(1): 23-29 (1984).

McClements, W.L. et al., Immunization with DNA vaccines encoding glycoprotein D or glycoprotein B, alone or in combination, induces protective immunity in animal models of herpes simplex virus-2 disease, Proceedings of the National Academy of Sciences, National Academy of Sciences, 93(21): 11414-11420 (1996).

McGeoch et al., Comparative sequence analysis of the long repeat regions and adjoining parts of the long unique regions in the genomes of herpes simplex viruses types 1 and 2. J. Gen. Virol., 71:3057-3075 (1991).

Mikloaska, Z. et al., Monophosphoryl Lipid A and QS21 Increa CD8 T Lymphocyte Cytotoxicity to Herpes implex Virus-2 Infected Cell Proteins 4 and 27 Through IFN-g and IL-12 Production, J. Immuno., 164: 5167-5176 (2000).

Posavad, C.M. et al., Detailed Characterization of T Cell responses to herpes simplex virus-2 in immune seronegative persons, J. Immunol., 184(4): 3250-3259 (2010).

Sin, J-I. et al., DNA vaccines encoding interleukin-8 and RANTES enhance antigen-specific Thl-type CD4(+) T-cell-mediated protective immunity against herpes simplex virus type 2 in vivo, Journal of Virology, 74(23): 11173-11180 (2000).

Sin, J-I. et al., IL-12 gene as a DNA vaccine adjuvant in a herpes mouse model: 7-15 IL-12 enhances Th1-type CD4+ T cell-mediated protective immunity against herpes simplex virus-2 challenge, The Journal of Immunology, 162(5): 2912-2921 (1999).

Skoberne, M. et al., An Adjuvanted Herpes Simplex Virus 2 Subunit Vaccine Elicits a T Cell Response in Mice and is an Effective Therapeutic Vaccine in Guinea Pig, J. Virol., 87(7): 3930-3942 (2013).

Sojikul, P. et al., A plant signal peptide-hepatitis B surface antigen fusion protein with enhanced stability and immunogenicity expressed in plant cells, PNAS, 100(5): 2209-2214 (2003).

Written Opinion for PCT/US2012/066241, dated Feb. 28, 2013, published as WO 2013/078299 (3 pages).

* cited by examiner

306t: Us6 protein without transmembrane (TMR) or cytoplasmic region dTMR: Us6 protein without transmembrane (TMR) region

Us6: full-length Us6 protein

All proteins were expressed in E. coli

Results are interferon-gamma spot forming units per 200,000 T cells (CD4+ or CD8+) seeded per well of Elispot plate

Fig. 5

IgG responses

Coating Protein: gL2s

| | IgG Total | IgG1 | IgG2c |
|---|---|---|---|
| gL2s | 20,385<br>42,470<br>2,641 | 21,736 | 12,300 |
| UL40 | 2,609<br>1,643<br>473 | 1,909 | - |
| gL2s + UL40 | 25,564<br>16,549<br>15,348 | 11,128 | 21,484 |

Coating Protein: UL40

| | IgG Total | IgG1 | IgG2c |
|---|---|---|---|
| gL2s | 1,006<br>304<br>394 | - | - |
| UL40 | 64,184<br>283,505<br>7,526 | 106,201 | 1,906 |
| gL2s + UL40 | 304,057<br>2,009<br>38,994 | 55,010 | 11,181 |

Antibody responses

SEQUENCE LISTING

<160> NUMBER OF SEQ ID NOS: 144

<210> SEQ ID NO 1
<211> LENGTH: 1317
<212> TYPE: PRT
<213> ORGANISM: Human herpesvirus 2

<400> SEQUENCE: 1

```
Ser Ala Glu Gln Arg Lys Lys Lys Lys Thr Thr Thr Thr Thr Gln Gly
1               5                   10                  15

Arg Gly Ala Glu Val Ala Met Ala Asp Glu Asp Gly Gly Arg Leu Arg
            20                  25                  30
```

```
Ala Ala Ala Glu Thr Thr Gly Gly Pro Gly Ser Pro Asp Pro Ala Asp
        35                  40                  45

Gly Pro Pro Pro Thr Pro Asn Pro Asp Arg Arg Pro Ala Ala Arg Pro
    50                  55                  60

Gly Phe Gly Trp His Gly Gly Pro Glu Glu Asn Glu Asp Glu Ala Asp
65                  70                  75                  80

Asp Ala Ala Ala Asp Ala Asp Ala Asp Glu Ala Ala Pro Ala Ser Gly
                85                  90                  95

Glu Ala Val Asp Glu Pro Ala Ala Asp Gly Val Val Ser Pro Arg Gln
            100                 105                 110

Leu Ala Leu Leu Ala Ser Met Val Asp Glu Ala Val Arg Thr Ile Pro
        115                 120                 125

Ser Pro Pro Pro Glu Arg Asp Gly Ala Gln Glu Glu Ala Ala Arg Ser
    130                 135                 140

Pro Ser Pro Pro Arg Thr Pro Ser Met Arg Ala Asp Tyr Gly Glu Glu
145                 150                 155                 160

Asn Asp Asp Asp Asp Asp Asp Asp Asp Asp Asp Asp Arg Asp Ala Gly
                165                 170                 175

Arg Trp Val Arg Gly Pro Glu Thr Thr Ser Ala Val Arg Gly Ala Tyr
            180                 185                 190

Pro Asp Pro Met Ala Ser Leu Ser Pro Arg Pro Pro Ala Pro Arg Arg
        195                 200                 205

His His His His His His His Arg Arg Arg Arg Ala Pro Arg Arg Arg
    210                 215                 220

Ser Ala Ala Ser Asp Ser Ser Lys Ser Gly Ser Ser Ser Ser Ala Ser
225                 230                 235                 240

Ser Ala Ser Ser Ser Ala Ser Ser Ser Ser Ser Ala Ser Ala Ser Ser
                245                 250                 255

Ser Asp Asp Asp Asp Asp Asp Asp Ala Ala Arg Ala Pro Ala Ser Ala
            260                 265                 270

Ala Asp His Ala Ala Gly Gly Thr Leu Gly Ala Asp Asp Glu Glu Ala
        275                 280                 285

Gly Val Pro Ala Arg Ala Pro Gly Ala Ala Pro Arg Pro Ser Pro Pro
    290                 295                 300

Arg Ala Glu Pro Ala Pro Ala Arg Thr Pro Ala Ala Thr Ala Gly Arg
305                 310                 315                 320

Leu Glu Arg Arg Arg Ala Arg Ala Ala Val Ala Gly Arg Asp Ala Thr
                325                 330                 335

Gly Arg Phe Thr Ala Gly Arg Pro Arg Arg Val Glu Leu Asp Ala Asp
            340                 345                 350

Ala Ala Ser Gly Ala Phe Tyr Ala Arg Tyr Arg Asp Gly Tyr Val Ser
        355                 360                 365

Gly Glu Pro Trp Pro Gly Ala Gly Pro Pro Pro Pro Gly Arg Val Leu
    370                 375                 380

Tyr Gly Gly Leu Gly Asp Ser Arg Pro Gly Leu Trp Gly Ala Pro Glu
385                 390                 395                 400

Ala Glu Glu Ala Arg Ala Arg Phe Glu Ala Ser Gly Ala Pro Ala Pro
                405                 410                 415

Val Trp Ala Pro Glu Leu Gly Asp Ala Ala Gln Gln Tyr Ala Leu Ile
            420                 425                 430

Thr Arg Leu Leu Tyr Thr Pro Asp Ala Glu Ala Met Gly Trp Leu Gln
        435                 440                 445

Asn Pro Arg Val Ala Pro Gly Asp Val Ala Leu Asp Gln Ala Cys Phe
```

-continued

```
    450                 455                 460

Arg Ile Ser Gly Ala Ala Arg Asn Ser Ser Ser Phe Ile Ser Gly Ser
465                 470                 475                 480

Val Ala Arg Ala Val Pro His Leu Gly Tyr Ala Met Ala Ala Gly Arg
                485                 490                 495

Phe Gly Trp Gly Leu Ala His Val Ala Ala Ala Val Ala Met Ser Arg
            500                 505                 510

Arg Tyr Asp Arg Ala Gln Lys Gly Phe Leu Leu Thr Ser Leu Arg Arg
        515                 520                 525

Ala Tyr Ala Pro Leu Leu Ala Arg Glu Asn Ala Ala Leu Thr Gly Ala
    530                 535                 540

Arg Thr Pro Asp Asp Gly Gly Asp Ala Asn Arg His Asp Gly Asp Asp
545                 550                 555                 560

Ala Arg Gly Lys Pro Ala Ala Ala Ala Ala Pro Leu Pro Ser Ala Ala
                565                 570                 575

Ala Ser Pro Ala Asp Glu Arg Ala Val Pro Ala Gly Tyr Gly Ala Ala
            580                 585                 590

Gly Val Leu Ala Ala Leu Gly Arg Leu Ser Ala Ala Pro Ala Ser Ala
        595                 600                 605

Pro Ala Gly Ala Asp Asp Asp Asp Asp Asp Asp Gly Ala Gly Gly Gly
    610                 615                 620

Gly Gly Gly Arg Arg Ala Glu Ala Gly Arg Val Ala Val Glu Cys Leu
625                 630                 635                 640

Ala Ala Cys Arg Gly Ile Leu Glu Ala Leu Ala Glu Gly Phe Asp Gly
                645                 650                 655

Asp Leu Ala Ala Val Pro Gly Leu Ala Gly Ala Arg Pro Ala Ala Pro
            660                 665                 670

Pro Arg Pro Gly Pro Ala Gly Ala Ala Ala Pro Pro His Ala Asp Ala
        675                 680                 685

Pro Arg Leu Arg Ala Trp Leu Arg Glu Leu Arg Phe Val Arg Asp Ala
    690                 695                 700

Leu Val Leu Met Arg Leu Arg Gly Asp Leu Arg Val Ala Gly Gly Ser
705                 710                 715                 720

Glu Ala Ala Val Ala Ala Val Arg Ala Val Ser Leu Val Ala Gly Ala
                725                 730                 735

Leu Gly Pro Ala Leu Pro Arg Ser Pro Arg Leu Leu Ser Ser Ala Ala
            740                 745                 750

Ala Ala Ala Ala Asp Leu Leu Phe Gln Asn Gln Ser Leu Arg Pro Leu
        755                 760                 765

Leu Ala Asp Thr Val Ala Ala Ala Asp Ser Leu Ala Ala Pro Ala Ser
    770                 775                 780

Ala Pro Arg Glu Ala Arg Lys Arg Lys Ser Pro Ala Pro Ala Arg Ala
785                 790                 795                 800

Pro Pro Gly Gly Ala Pro Arg Pro Pro Lys Lys Ser Arg Ala Asp Ala
                805                 810                 815

Pro Arg Pro Ala Ala Ala Pro Pro Ala Gly Ala Ala Pro Pro Ala Pro
            820                 825                 830

Pro Thr Pro Pro Pro Arg Pro Pro Arg Pro Ala Ala Leu Thr Arg Arg
        835                 840                 845

Pro Ala Glu Gly Pro Asp Pro Gln Gly Gly Trp Arg Arg Gln Pro Pro
    850                 855                 860

Gly Pro Ser His Thr Pro Ala Pro Ser Ala Ala Ala Leu Glu Ala Tyr
865                 870                 875                 880
```

-continued

```
Cys Ala Pro Arg Ala Val Ala Glu Leu Thr Asp His Pro Leu Phe Pro
                885                 890                 895

Ala Pro Trp Arg Pro Ala Leu Met Phe Asp Pro Arg Ala Leu Ala Ser
            900                 905                 910

Leu Ala Ala Arg Cys Ala Ala Pro Pro Pro Gly Gly Ala Pro Ala Ala
        915                 920                 925

Phe Gly Pro Leu Arg Ala Ser Gly Pro Leu Arg Arg Ala Ala Ala Trp
    930                 935                 940

Met Arg Gln Val Pro Asp Pro Glu Asp Val Arg Val Val Ile Leu Tyr
945                 950                 955                 960

Ser Pro Leu Pro Gly Glu Asp Leu Ala Ala Gly Arg Ala Gly Gly Gly
                965                 970                 975

Pro Pro Pro Glu Trp Ser Ala Glu Arg Gly Gly Leu Ser Cys Leu Leu
            980                 985                 990

Ala Ala Leu Gly Asn Arg Leu Cys  Gly Pro Ala Thr Ala  Ala Trp Ala
        995                 1000                 1005

Gly Asn  Trp Thr Gly Ala Pro  Asp Val Ser Ala Leu  Gly Ala Gln
    1010                 1015                 1020

Gly Val  Leu Leu Leu Ser Thr  Arg Asp Leu Ala Phe  Ala Gly Ala
    1025                 1030                 1035

Val Glu  Phe Leu Gly Leu Leu  Ala Gly Ala Cys Asp  Arg Arg Leu
    1040                 1045                 1050

Ile Val  Val Asn Ala Val Arg  Ala Ala Asp Trp Pro  Ala Asp Gly
    1055                 1060                 1065

Pro Val  Val Ser Arg Gln His  Ala Tyr Leu Ala Cys  Glu Val Leu
    1070                 1075                 1080

Pro Ala  Val Gln Cys Ala Val  Arg Trp Pro Ala Ala  Arg Asp Leu
    1085                 1090                 1095

Arg Arg  Thr Val Leu Ala Ser  Gly Arg Val Phe Gly  Pro Gly Val
    1100                 1105                 1110

Phe Ala  Arg Val Glu Ala Ala  His Ala Arg Leu Tyr  Pro Asp Ala
    1115                 1120                 1125

Pro Pro  Leu Arg Leu Cys Arg  Gly Ala Asn Val Arg  Tyr Arg Val
    1130                 1135                 1140

Arg Thr  Arg Phe Gly Pro Asp  Thr Leu Val Pro Met  Ser Pro Arg
    1145                 1150                 1155

Glu Tyr  Arg Arg Ala Val Leu  Pro Ala Leu Asp Gly  Arg Ala Ala
    1160                 1165                 1170

Ala Ser  Gly Ala Gly Asp Ala  Met Ala Pro Gly Ala  Pro Asp Phe
    1175                 1180                 1185

Cys Glu  Asp Glu Ala His Ser  His Arg Ala Cys Ala  Arg Trp Gly
    1190                 1195                 1200

Leu Gly  Ala Pro Leu Arg Pro  Val Tyr Val Ala Leu  Gly Arg Asp
    1205                 1210                 1215

Ala Val  Arg Gly Gly Pro Ala  Glu Leu Arg Gly Pro  Arg Arg Glu
    1220                 1225                 1230

Phe Cys  Ala Arg Ala Leu Leu  Glu Pro Asp Gly Asp  Ala Pro Pro
    1235                 1240                 1245

Leu Val  Leu Arg Asp Asp Ala  Asp Ala Gly Pro Pro  Pro Gln Ile
    1250                 1255                 1260

Arg Trp  Ala Ser Ala Ala Gly  Arg Ala Gly Thr Val  Leu Ala Ala
    1265                 1270                 1275
```

```
Ala Gly  Gly Gly Val Glu Val  Val Gly Thr Ala Ala  Gly Leu Ala
    1280                1285                1290

Thr Pro  Pro Arg Arg Glu Pro  Val Asp Met Asp Ala  Glu Leu Glu
    1295                1300                1305

Asp Asp  Asp Asp Gly Leu Phe  Gly Glu
    1310                1315


<210> SEQ ID NO 2
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Val Leu Tyr Gly Gly Leu Gly Asp Ser Arg Pro Gly Leu Trp Gly
1               5                   10                  15

Ala Pro Glu Ala Glu Glu Ala Arg Ala Arg Phe Glu Ala Ser Gly Ala
            20                  25                  30

Pro Ala Pro Val Trp Ala Pro Glu Leu Gly Asp Ala Ala Gln Gln Tyr
        35                  40                  45

Ala Leu Ile Thr Arg Leu Leu Tyr Thr Pro Asp Ala Glu Ala Met Gly
    50                  55                  60

Trp Leu Gln Asn Pro Arg Val Ala Pro Gly Asp Val Ala Leu Asp Gln
65                  70                  75                  80

Ala Cys Phe Arg Ile Ser Gly Ala Ala Arg Asn Ser Ser Ser Phe Ile
                85                  90                  95

Ser Gly Ser Val Ala Arg Ala Val Pro His Leu Gly Tyr Ala Met Ala
            100                 105                 110

Ala Gly Arg Phe Gly Trp Gly Leu Ala His Val Ala Ala Ala Val Ala
        115                 120                 125

Met Ser Arg Arg Tyr Asp Arg Ala Gln Lys Gly Phe Leu Leu Thr Ser
    130                 135                 140

Leu Arg Arg Ala Tyr Ala Pro Leu Leu Ala Arg Glu Asn Ala Ala Leu
145                 150                 155                 160

Thr Gly Ala Arg Thr Pro Asp Asp Gly Gly Asp Ala Asn Arg Arg Asp
                165                 170                 175

Gly Asp Asp Ala Arg Gly Lys Pro Ala Ala Ala Ala Ala Pro Leu Pro
            180                 185                 190

Ser Ala Ala Ala Ser Pro Ala Asp Glu Arg Ala Val Pro Ala Gly Tyr
        195                 200                 205

Gly Ala Ala Gly Val Leu Ala Ala Leu Gly Arg Leu Ser Ala Ala Pro
    210                 215                 220

Ala Ser Ala Pro Ala Gly Ala Asp Asp Asp Asp Asp Asp Asp Asp Gly
225                 230                 235                 240

Ala Gly Gly Gly Gly Gly Gly Gly Gly Gly Gly Gly Gly Arg Arg Ala
                245                 250                 255

Glu Ala Gly Arg Val Ala Val Glu Cys Leu Ala Ala Cys Arg Gly Ile
            260                 265                 270

Leu Glu Ala Leu Ala Glu Gly Phe Asp Gly Asp Leu Ala Ala Val Pro
        275                 280                 285

Gly Leu Ala Gly Ala Arg Pro Ala Ala Pro Pro Arg Pro Gly Pro Ala
    290                 295                 300

Gly Ala Ala Ala Pro Pro His Ala Asp Ala Pro Arg Leu Arg Ala Trp
305                 310                 315                 320
```

-continued

Leu Arg Glu Leu Arg Phe Val Arg Asp Ala Leu Val Leu Met Arg Leu
325 330 335

Arg Gly Asp Leu Arg Val Ala Gly Gly Ser Glu Ala Ala Val Ala Ala
340 345 350

Val Arg Ala Val Ser Leu Val Ala Gly Ala Leu Gly Pro Ala Leu Pro
355 360 365

Arg Ser Pro Arg Leu Leu Ser Ser Ala Ala Ala Ala Ala Ala Asp Leu
370 375 380

Leu Phe Gln Asn Gln Ser Leu
385 390

<210> SEQ ID NO 3
<211> LENGTH: 224
<212> TYPE: PRT
<213> ORGANISM: Human herpesvirus 2

<400> SEQUENCE: 3

Met Gly Phe Val Cys Leu Phe Gly Leu Val Val Met Gly Ala Trp Gly
1 5 10 15

Ala Trp Gly Gly Ser Gln Ala Thr Glu Tyr Val Leu Arg Ser Val Ile
20 25 30

Ala Lys Glu Val Gly Asp Ile Leu Arg Val Pro Cys Met Arg Thr Pro
35 40 45

Ala Asp Asp Val Ser Trp Arg Tyr Glu Ala Pro Ser Val Ile Asp Tyr
50 55 60

Ala Arg Ile Asp Gly Ile Phe Leu Arg Tyr His Cys Pro Gly Leu Asp
65 70 75 80

Thr Phe Leu Trp Asp Arg His Ala Gln Arg Ala Tyr Leu Val Asn Pro
85 90 95

Phe Leu Phe Ala Ala Gly Phe Leu Glu Asp Leu Ser His Ser Val Phe
100 105 110

Pro Ala Asp Thr Gln Glu Thr Thr Thr Arg Arg Ala Leu Tyr Lys Glu
115 120 125

Ile Arg Asp Ala Leu Gly Ser Arg Lys Gln Ala Val Ser His Ala Pro
130 135 140

Val Arg Ala Gly Cys Val Asn Phe Asp Tyr Ser Arg Thr Arg Arg Cys
145 150 155 160

Val Gly Arg Arg Asp Leu Arg Pro Ala Asn Thr Thr Ser Thr Trp Glu
165 170 175

Pro Pro Val Ser Ser Asp Asp Glu Ala Ser Ser Gln Ser Lys Pro Leu
180 185 190

Ala Thr Gln Pro Pro Val Leu Ala Leu Ser Asn Ala Pro Pro Arg Arg
195 200 205

Val Ser Pro Thr Arg Gly Arg Arg Arg His Thr Arg Leu Arg Arg Asn
210 215 220

<210> SEQ ID NO 4
<211> LENGTH: 347
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 4

Asn Arg Trp Lys Tyr Ala Leu Ala Asp Pro Ser Leu Lys Met Ala Asp
1 5 10 15

```
Pro Asn Arg Phe Arg Gly Lys Asn Leu Pro Val Leu Asp Gln Leu Thr
            20                  25                  30

Asp Pro Pro Gly Val Lys Arg Val Tyr His Ile Gln Pro Ser Leu Glu
        35                  40                  45

Asp Pro Phe Gln Pro Pro Ser Ile Pro Ile Thr Val Tyr Tyr Ala Val
    50                  55                  60

Leu Glu Arg Ala Cys Arg Ser Val Leu Leu His Ala Pro Ser Glu Ala
65                  70                  75                  80

Pro Gln Ile Val Arg Gly Ala Ser Asp Glu Ala Arg Lys His Thr Tyr
                85                  90                  95

Asn Leu Thr Ile Ala Trp Tyr Arg Met Gly Asp Asn Cys Ala Ile Pro
            100                 105                 110

Ile Thr Val Met Glu Tyr Thr Glu Cys Pro Tyr Asn Lys Ser Leu Gly
        115                 120                 125

Val Cys Pro Ile Arg Thr Gln Pro Arg Trp Ser Tyr Tyr Asp Ser Phe
    130                 135                 140

Ser Ala Val Ser Glu Asp Asn Leu Gly Phe Leu Met His Ala Pro Ala
145                 150                 155                 160

Phe Glu Thr Ala Gly Thr Tyr Leu Arg Leu Val Lys Ile Asn Asp Trp
                165                 170                 175

Thr Glu Ile Thr Gln Phe Ile Leu Glu His Arg Ala Arg Ala Ser Cys
            180                 185                 190

Lys Tyr Ala Leu Pro Leu Arg Ile Pro Pro Ala Ala Cys Leu Thr Ser
        195                 200                 205

Lys Ala Tyr Gln Gln Gly Val Thr Val Asp Ser Ile Gly Met Leu Pro
    210                 215                 220

Arg Phe Ile Pro Glu Asn Gln Arg Thr Val Ala Leu Tyr Ser Leu Lys
225                 230                 235                 240

Ile Ala Gly Trp His Gly Pro Lys Pro Pro Tyr Thr Ser Thr Leu Leu
                245                 250                 255

Pro Pro Glu Leu Ser Asp Thr Thr Asn Ala Thr Gln Pro Glu Leu Val
            260                 265                 270

Pro Glu Asp Pro Glu Asp Ser Ala Leu Leu Glu Asp Pro Ala Gly Thr
        275                 280                 285

Val Ser Ser Gln Ile Pro Pro Asn Trp His Ile Pro Ser Ile Gln Asp
    290                 295                 300

Val Ala Pro His His Ala Pro Ala Ala Pro Ser Asn Pro Arg Arg Arg
305                 310                 315                 320

Ala Gln Met Ala Pro Lys Arg Leu Arg Leu Pro His Ile Arg Asp Asp
                325                 330                 335

Asp Ala Pro Pro Ser His Gln Pro Leu Phe Tyr
            340                 345
```

<210> SEQ ID NO 5
<211> LENGTH: 393
<212> TYPE: PRT
<213> ORGANISM: human herpesvirus 2

<400> SEQUENCE: 5

```
Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
```

-continued

```
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
        355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390


<210> SEQ ID NO 6
<211> LENGTH: 261
<212> TYPE: PRT
<213> ORGANISM: Human herpesvirus 2

<400> SEQUENCE: 6

Met Ser Arg Arg Arg Gly Pro Arg Arg Arg Gly Pro Arg Arg Arg Pro
1               5                   10                  15
```

Arg Pro Gly Ala Pro Ala Val Pro Arg Pro Gly Ala Pro Ala Val Pro
20 25 30

Arg Pro Gly Ala Leu Pro Thr Ala Asp Ser Gln Met Val Pro Ala Tyr
35 40 45

Asp Ser Gly Thr Ala Val Glu Ser Ala Pro Ala Ala Ser Ser Leu Leu
50 55 60

Arg Arg Trp Leu Leu Val Pro Gln Ala Asp Asp Ser Asp Asp Ala Asp
65 70 75 80

Tyr Ala Gly Asn Asp Asp Ala Glu Trp Ala Asn Ser Pro Pro Ser Glu
85 90 95

Gly Gly Gly Lys Ala Pro Glu Ala Pro His Ala Ala Pro Ala Ala Ala
100 105 110

Cys Pro Pro Pro Pro Pro Arg Lys Glu Arg Gly Pro Gln Arg Pro Leu
115 120 125

Pro Pro His Leu Ala Leu Arg Leu Arg Thr Thr Thr Glu Tyr Leu Ala
130 135 140

Arg Leu Ser Leu Arg Arg Arg Arg Pro Pro Ala Ser Pro Pro Ala Asp
145 150 155 160

Ala Pro Arg Gly Lys Val Cys Phe Ser Pro Arg Val Gln Val Arg His
165 170 175

Leu Val Ala Trp Glu Thr Ala Ala Arg Leu Ala Arg Arg Gly Ser Trp
180 185 190

Ala Arg Glu Arg Ala Asp Arg Asp Arg Phe Arg Arg Arg Val Ala Ala
195 200 205

Ala Glu Ala Val Ile Gly Pro Cys Leu Glu Pro Glu Ala Arg Ala Arg
210 215 220

Ala Arg Ala Arg Ala Arg Ala His Glu Asp Gly Gly Pro Ala Glu Glu
225 230 235 240

Glu Glu Ala Ala Ala Ala Ala Arg Gly Ser Ser Ala Ala Ala Gly Pro
245 250 255

Gly Arg Arg Ala Val
260

<210> SEQ ID NO 7
<211> LENGTH: 825
<212> TYPE: PRT
<213> ORGANISM: Human herpesvirus 2

<400> SEQUENCE: 7

Met Glu Pro Arg Pro Gly Thr Ser Ser Arg Ala Asp Pro Gly Pro Glu
1 5 10 15

Arg Pro Pro Arg Gln Thr Pro Gly Thr Gln Pro Ala Ala Pro His Ala
20 25 30

Trp Gly Met Leu Asn Asp Met Gln Trp Leu Ala Ser Ser Asp Ser Glu
35 40 45

Glu Glu Thr Glu Val Gly Ile Ser Asp Asp Asp Leu His Arg Asp Ser
50 55 60

Thr Ser Glu Ala Gly Ser Thr Asp Thr Glu Met Phe Glu Ala Gly Leu
65 70 75 80

Met Asp Ala Ala Thr Pro Pro Ala Arg Pro Pro Ala Glu Arg Gln Gly
85 90 95

Ser Pro Thr Pro Ala Asp Ala Gln Gly Ser Cys Gly Gly Gly Pro Val
100 105 110

Gly Glu Glu Glu Ala Glu Ala Gly Gly Gly Gly Asp Val Cys Ala Val
115 120 125

```
Cys Thr Asp Glu Ile Ala Pro Pro Leu Arg Cys Gln Ser Phe Pro Cys
    130                 135                 140

Leu His Pro Phe Cys Ile Pro Cys Met Lys Thr Trp Ile Pro Leu Arg
145                 150                 155                 160

Asn Thr Cys Pro Leu Cys Asn Thr Pro Val Ala Tyr Leu Ile Val Gly
                165                 170                 175

Val Thr Ala Ser Gly Ser Phe Ser Thr Ile Pro Ile Val Asn Asp Pro
            180                 185                 190

Arg Thr Arg Val Glu Ala Glu Ala Ala Val Arg Ala Gly Thr Ala Val
        195                 200                 205

Asp Phe Ile Trp Thr Gly Asn Pro Arg Thr Ala Pro Arg Ser Leu Ser
    210                 215                 220

Leu Gly Gly His Thr Val Arg Ala Leu Ser Pro Thr Pro Pro Trp Pro
225                 230                 235                 240

Gly Thr Asp Asp Glu Asp Asp Asp Leu Ala Asp Val Asp Tyr Val Pro
                245                 250                 255

Pro Ala Pro Arg Arg Ala Pro Arg Arg Gly Gly Gly Gly Ala Gly Ala
            260                 265                 270

Thr Arg Gly Thr Ser Gln Pro Ala Ala Thr Arg Pro Ala Pro Pro Gly
        275                 280                 285

Ala Pro Arg Ser Ser Ser Ser Gly Gly Ala Pro Leu Arg Ala Gly Val
    290                 295                 300

Gly Ser Gly Ser Gly Gly Gly Pro Ala Val Ala Ala Val Val Pro Arg
305                 310                 315                 320

Val Ala Ser Leu Pro Pro Ala Ala Gly Gly Gly Arg Ala Gln Ala Arg
                325                 330                 335

Arg Val Gly Glu Asp Ala Ala Ala Ala Glu Gly Arg Thr Pro Pro Ala
            340                 345                 350

Arg Gln Pro Arg Ala Ala Gln Glu Pro Pro Ile Val Ile Ser Asp Ser
        355                 360                 365

Pro Pro Pro Ser Pro Arg Arg Pro Ala Gly Pro Gly Pro Leu Ser Phe
    370                 375                 380

Val Ser Ser Ser Ser Ala Gln Val Ser Ser Gly Pro Gly Gly Gly Gly
385                 390                 395                 400

Leu Pro Gln Ser Ser Gly Arg Ala Ala Arg Pro Arg Ala Ala Val Ala
                405                 410                 415

Pro Arg Val Arg Ser Pro Pro Arg Ala Ala Ala Ala Pro Val Val Ser
            420                 425                 430

Ala Ser Ala Asp Ala Ala Gly Pro Ala Pro Pro Ala Val Pro Val Asp
        435                 440                 445

Ala His Arg Ala Pro Arg Ser Arg Met Thr Gln Ala Gln Thr Asp Thr
    450                 455                 460

Gln Ala Gln Ser Leu Gly Arg Ala Gly Ala Thr Asp Ala Arg Gly Ser
465                 470                 475                 480

Gly Gly Pro Gly Ala Glu Gly Gly Pro Gly Val Pro Arg Gly Thr Asn
                485                 490                 495

Thr Pro Gly Ala Ala Pro His Ala Ala Glu Gly Ala Ala Ala Arg Pro
            500                 505                 510

Arg Lys Arg Arg Gly Ser Asp Ser Gly Pro Ala Ala Ser Ser Ser Ala
        515                 520                 525

Ser Ser Ser Ala Ala Pro Arg Ser Pro Leu Ala Pro Gln Gly Val Gly
    530                 535                 540
```

-continued

```
Ala Lys Arg Ala Ala Pro Arg Arg Ala Pro Asp Ser Asp Ser Gly Asp
545                 550                 555                 560

Arg Gly His Gly Pro Leu Ala Pro Ala Ser Ala Gly Ala Ala Pro Pro
                565                 570                 575

Ser Ala Ser Pro Ser Ser Gln Ala Ala Val Ala Ala Ala Ser Ser Ser
            580                 585                 590

Ser Ala Ser Ser Ser Ser Ala Ser Ser Ser Ser Ala Ser Ser Ser Ser
        595                 600                 605

Ala Ser Ser Ser Ser Ala Ser Ser Ser Ser Ala Ser Ser Ser Ser Ala
    610                 615                 620

Ser Ser Ser Ala Gly Gly Ala Gly Gly Ser Val Ala Ser Ala Ser Gly
625                 630                 635                 640

Ala Gly Glu Arg Arg Glu Thr Ser Leu Gly Pro Arg Ala Ala Ala Pro
                645                 650                 655

Arg Gly Pro Arg Lys Cys Ala Arg Lys Thr Arg His Ala Glu Gly Gly
            660                 665                 670

Pro Glu Pro Gly Ala Arg Asp Pro Ala Pro Gly Leu Thr Arg Tyr Leu
        675                 680                 685

Pro Ile Ala Gly Val Ser Ser Val Val Ala Leu Ala Pro Tyr Val Asn
    690                 695                 700

Lys Thr Val Thr Gly Asp Cys Leu Pro Val Leu Asp Met Glu Thr Gly
705                 710                 715                 720

His Ile Gly Ala Tyr Val Val Leu Val Asp Gln Thr Gly Asn Val Ala
                725                 730                 735

Asp Leu Leu Arg Ala Ala Ala Pro Ala Trp Ser Arg Arg Thr Leu Leu
            740                 745                 750

Pro Glu His Ala Arg Asn Cys Val Arg Pro Pro Asp Tyr Pro Thr Pro
        755                 760                 765

Pro Ala Ser Glu Trp Asn Ser Leu Trp Met Thr Pro Val Gly Asn Met
    770                 775                 780

Leu Phe Asp Gln Gly Thr Leu Val Gly Ala Leu Asp Phe His Gly Leu
785                 790                 795                 800

Arg Ser Arg His Pro Trp Ser Arg Glu Gln Gly Ala Pro Ala Pro Ala
                805                 810                 815

Gly Asp Ala Pro Ala Gly His Gly Glu
            820                 825


<210> SEQ ID NO 8
<211> LENGTH: 400
<212> TYPE: PRT
<213> ORGANISM: human herpesvirus 2

<400> SEQUENCE: 8

Met Ser Ala Glu Gln Arg Lys Lys Lys Lys Thr Thr Thr Thr Thr Gln
1               5                   10                  15

Gly Arg Gly Ala Glu Val Ala Met Ala Asp Glu Asp Gly Gly Arg Leu
            20                  25                  30

Arg Ala Ala Ala Glu Thr Thr Gly Gly Pro Gly Ser Pro Asp Pro Ala
        35                  40                  45

Asp Gly Pro Pro Pro Thr Pro Asn Pro Asp Arg Arg Pro Ala Ala Arg
    50                  55                  60

Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Ala Pro Ala Ser
                85                  90                  95
```

```
Gly Glu Ala Val Asp Glu Pro Ala Ala Asp Gly Val Val Ser Pro Arg
            100                 105                 110

Gln Leu Ala Leu Leu Ala Ser Met Val Asp Glu Ala Val Arg Thr Ile
        115                 120                 125

Pro Ser Pro Pro Pro Glu Arg Asp Gly Ala Gln Glu Glu Ala Ala Arg
    130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Asp Asp Arg Asp Ala
                165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Pro Ala Pro Arg
        195                 200                 205

Arg His His His His His His His Arg Arg Arg Arg Ala Pro Arg Arg
    210                 215                 220

Arg Ser Ala Ala Ser Asp Ser Ser Lys Ser Gly Ser Ser Ser Ser Ala
225                 230                 235                 240

Ser Ser Ala Ser Ser Ser Ala Ser Ser Ser Ser Ser Ala Ser Ala Ser
                245                 250                 255

Ser Ser Asp Asp Asp Asp Asp Asp Asp Ala Ala Arg Ala Pro Ala Ser
            260                 265                 270

Ala Ala Asp His Ala Ala Gly Gly Thr Leu Gly Ala Asp Asp Glu Glu
        275                 280                 285

Ala Gly Val Pro Ala Arg Ala Pro Gly Ala Ala Pro Arg Pro Ser Pro
    290                 295                 300

Pro Arg Ala Glu Pro Ala Pro Ala Arg Thr Pro Ala Ala Thr Ala Gly
305                 310                 315                 320

Arg Leu Glu Arg Arg Arg Ala Arg Ala Ala Val Ala Gly Arg Asp Ala
                325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
        355                 360                 365

Ser Gly Glu Pro Trp Pro Gly Ala Gly Pro Pro Pro Pro Gly Arg Val
    370                 375                 380

Leu Tyr Gly Gly Leu Gly Asp Ser Arg Pro Gly Leu Trp Gly Ala Pro
385                 390                 395                 400


<210> SEQ ID NO 9
<211> LENGTH: 275
<212> TYPE: PRT
<213> ORGANISM: human herpesvirus 2

<400> SEQUENCE: 9

Ser Ser Ala Ala Ala Ala Ala Ala Asp Leu Leu Phe Gln Asn Gln Ser
1               5                   10                  15

Leu Arg Pro Leu Leu Ala Asp Thr Val Ala Ala Ala Asp Ser Leu Ala
            20                  25                  30

Ala Pro Ala Ser Ala Pro Arg Glu Ala Arg Lys Arg Lys Ser Pro Ala
        35                  40                  45

Pro Ala Arg Ala Pro Pro Gly Gly Ala Pro Arg Pro Pro Lys Lys Ser
    50                  55                  60

Arg Ala Asp Ala Pro Arg Pro Ala Ala Ala Pro Pro Ala Gly Ala Ala
```

```
65                  70                  75                  80

Pro Pro Ala Pro Pro Thr Pro Pro Pro Arg Pro Pro Arg Pro Ala Ala
                85                  90                  95

Leu Thr Arg Arg Pro Ala Glu Gly Pro Asp Pro Gln Gly Gly Trp Arg
            100                 105                 110

Arg Gln Pro Pro Gly Pro Ser His Thr Pro Ala Pro Ser Ala Ala Ala
        115                 120                 125

Leu Glu Ala Tyr Cys Ala Pro Arg Ala Val Ala Glu Leu Thr Asp His
    130                 135                 140

Pro Leu Phe Pro Ala Pro Trp Arg Pro Ala Leu Met Phe Asp Pro Arg
145                 150                 155                 160

Ala Leu Ala Ser Leu Ala Ala Arg Cys Ala Ala Pro Pro Pro Gly Gly
                165                 170                 175

Ala Pro Ala Ala Phe Gly Pro Leu Arg Ala Ser Gly Pro Leu Arg Arg
            180                 185                 190

Ala Ala Ala Trp Met Arg Gln Val Pro Asp Pro Glu Asp Val Arg Val
        195                 200                 205

Val Ile Leu Tyr Ser Pro Leu Pro Gly Glu Asp Leu Ala Ala Gly Arg
    210                 215                 220

Ala Gly Gly Gly Pro Pro Pro Glu Trp Ser Ala Glu Arg Gly Gly Leu
225                 230                 235                 240

Ser Cys Leu Leu Ala Ala Leu Gly Asn Arg Leu Cys Gly Pro Ala Thr
                245                 250                 255

Ala Ala Trp Ala Gly Asn Trp Thr Gly Ala Pro Asp Val Ser Ala Leu
            260                 265                 270

Gly Ala Gln
        275


<210> SEQ ID NO 10
<211> LENGTH: 311
<212> TYPE: PRT
<213> ORGANISM: human herpesvirus 2

<400> SEQUENCE: 10

Trp Ala Gly Asn Trp Thr Gly Ala Pro Asp Val Ser Ala Leu Gly Ala
1               5                   10                  15

Gln Gly Val Leu Leu Leu Ser Thr Arg Asp Leu Ala Phe Ala Gly Ala
            20                  25                  30

Val Glu Phe Leu Gly Leu Leu Ala Gly Ala Cys Asp Arg Arg Leu Ile
        35                  40                  45

Val Val Asn Ala Val Arg Ala Ala Asp Trp Pro Ala Asp Gly Pro Val
    50                  55                  60

Val Ser Arg Gln His Ala Tyr Leu Ala Cys Glu Val Leu Pro Ala Val
65                  70                  75                  80

Gln Cys Ala Val Arg Trp Pro Ala Ala Arg Asp Leu Arg Arg Thr Val
                85                  90                  95

Leu Ala Ser Gly Arg Val Phe Gly Pro Gly Val Phe Ala Arg Val Glu
            100                 105                 110

Ala Ala His Ala Arg Leu Tyr Pro Asp Ala Pro Pro Leu Arg Leu Cys
        115                 120                 125

Arg Gly Ala Asn Val Arg Tyr Arg Val Arg Thr Arg Phe Gly Pro Asp
    130                 135                 140

Thr Leu Val Pro Met Ser Pro Arg Glu Tyr Arg Arg Ala Val Leu Pro
145                 150                 155                 160
```

-continued

```
Ala Leu Asp Gly Arg Ala Ala Ala Ser Gly Ala Gly Asp Ala Met Ala
                165                 170                 175

Pro Gly Ala Pro Asp Phe Cys Glu Asp Glu Ala His Ser His Arg Ala
            180                 185                 190

Cys Ala Arg Trp Gly Leu Gly Ala Pro Leu Arg Pro Val Tyr Val Ala
        195                 200                 205

Leu Gly Arg Asp Ala Val Arg Gly Gly Pro Ala Glu Leu Arg Gly Pro
    210                 215                 220

Arg Arg Glu Phe Cys Ala Arg Ala Leu Leu Glu Pro Asp Gly Asp Ala
225                 230                 235                 240

Pro Pro Leu Val Leu Arg Asp Asp Ala Asp Ala Gly Pro Pro Pro Gln
                245                 250                 255

Ile Arg Trp Ala Ser Ala Ala Gly Arg Ala Gly Thr Val Leu Ala Ala
            260                 265                 270

Ala Gly Gly Gly Val Glu Val Val Gly Thr Ala Ala Gly Leu Ala Thr
        275                 280                 285

Pro Pro Arg Arg Glu Pro Val Asp Met Asp Ala Glu Leu Glu Asp Asp
    290                 295                 300

Asp Asp Gly Leu Phe Gly Glu
305                 310


<210> SEQ ID NO 11
<211> LENGTH: 569
<212> TYPE: PRT
<213> ORGANISM: human herpesvirus 2

<400> SEQUENCE: 11

Ser Ser Ala Ala Ala Ala Ala Ala Asp Leu Leu Phe Gln Asn Gln Ser
1               5                   10                  15

Leu Arg Pro Leu Leu Ala Asp Thr Val Ala Ala Ala Asp Ser Leu Ala
            20                  25                  30

Ala Pro Ala Ser Ala Pro Arg Glu Ala Arg Lys Arg Lys Ser Pro Ala
        35                  40                  45

Pro Ala Arg Ala Pro Pro Gly Gly Ala Pro Arg Pro Pro Lys Lys Ser
    50                  55                  60

Arg Ala Asp Ala Pro Arg Pro Ala Ala Ala Pro Pro Ala Gly Ala Ala
65                  70                  75                  80

Pro Pro Ala Pro Pro Thr Pro Pro Pro Arg Pro Pro Arg Pro Ala Ala
                85                  90                  95

Leu Thr Arg Arg Pro Ala Glu Gly Pro Asp Pro Gln Gly Gly Trp Arg
            100                 105                 110

Arg Gln Pro Pro Gly Pro Ser His Thr Pro Ala Pro Ser Ala Ala Ala
        115                 120                 125

Leu Glu Ala Tyr Cys Ala Pro Arg Ala Val Ala Glu Leu Thr Asp His
    130                 135                 140

Pro Leu Phe Pro Ala Pro Trp Arg Pro Ala Leu Met Phe Asp Pro Arg
145                 150                 155                 160

Ala Leu Ala Ser Leu Ala Ala Arg Cys Ala Ala Pro Pro Pro Gly Gly
                165                 170                 175

Ala Pro Ala Ala Phe Gly Pro Leu Arg Ala Ser Gly Pro Leu Arg Arg
            180                 185                 190

Ala Ala Ala Trp Met Arg Gln Val Pro Asp Pro Glu Asp Val Arg Val
        195                 200                 205

Val Ile Leu Tyr Ser Pro Leu Pro Gly Glu Asp Leu Ala Ala Gly Arg
    210                 215                 220
```

Ala Gly Gly Gly Pro Pro Pro Glu Trp Ser Ala Glu Arg Gly Gly Leu
225 230 235 240

Ser Cys Leu Leu Ala Ala Leu Gly Asn Arg Leu Cys Gly Pro Ala Thr
245 250 255

Ala Ala Trp Ala Gly Asn Trp Thr Gly Ala Pro Asp Val Ser Ala Leu
260 265 270

Gly Ala Gln Gly Val Leu Leu Leu Ser Thr Arg Asp Leu Ala Phe Ala
275 280 285

Gly Ala Val Glu Phe Leu Gly Leu Leu Ala Gly Ala Cys Asp Arg Arg
290 295 300

Leu Ile Val Val Asn Ala Val Arg Ala Ala Asp Trp Pro Ala Asp Gly
305 310 315 320

Pro Val Val Ser Arg Gln His Ala Tyr Leu Ala Cys Glu Val Leu Pro
325 330 335

Ala Val Gln Cys Ala Val Arg Trp Pro Ala Ala Arg Asp Leu Arg Arg
340 345 350

Thr Val Leu Ala Ser Gly Arg Val Phe Gly Pro Gly Val Phe Ala Arg
355 360 365

Val Glu Ala Ala His Ala Arg Leu Tyr Pro Asp Ala Pro Pro Leu Arg
370 375 380

Leu Cys Arg Gly Ala Asn Val Arg Tyr Arg Val Arg Thr Arg Phe Gly
385 390 395 400

Pro Asp Thr Leu Val Pro Met Ser Pro Arg Glu Tyr Arg Arg Ala Val
405 410 415

Leu Pro Ala Leu Asp Gly Arg Ala Ala Ala Ser Gly Ala Gly Asp Ala
420 425 430

Met Ala Pro Gly Ala Pro Asp Phe Cys Glu Asp Glu Ala His Ser His
435 440 445

Arg Ala Cys Ala Arg Trp Gly Leu Gly Ala Pro Leu Arg Pro Val Tyr
450 455 460

Val Ala Leu Gly Arg Asp Ala Val Arg Gly Gly Pro Ala Glu Leu Arg
465 470 475 480

Gly Pro Arg Arg Glu Phe Cys Ala Arg Ala Leu Leu Glu Pro Asp Gly
485 490 495

Asp Ala Pro Pro Leu Val Leu Arg Asp Asp Ala Asp Ala Gly Pro Pro
500 505 510

Pro Gln Ile Arg Trp Ala Ser Ala Ala Gly Arg Ala Gly Thr Val Leu
515 520 525

Ala Ala Ala Gly Gly Gly Val Glu Val Val Gly Thr Ala Ala Gly Leu
530 535 540

Ala Thr Pro Pro Arg Arg Glu Pro Val Asp Met Asp Ala Glu Leu Glu
545 550 555 560

Asp Asp Asp Asp Gly Leu Phe Gly Glu
565

<210> SEQ ID NO 12
<211> LENGTH: 543
<212> TYPE: PRT
<213> ORGANISM: human herpesvirus 2

<400> SEQUENCE: 12

Thr Ala Gly Arg Pro Arg Arg Val Glu Leu Asp Ala Asp Ala Ala Ser
1 5 10 15

Gly Ala Phe Tyr Ala Arg Tyr Arg Asp Gly Tyr Val Ser Gly Glu Pro

```
            20                  25                  30

Trp Pro Gly Ala Gly Pro Pro Pro Pro Gly Arg Val Leu Tyr Gly Gly
        35                  40                  45

Leu Gly Asp Ser Arg Pro Gly Leu Trp Gly Ala Pro Glu Ala Glu Glu
    50                  55                  60

Ala Arg Ala Arg Phe Glu Ala Ser Gly Ala Pro Ala Pro Val Trp Ala
65                  70                  75                  80

Pro Glu Leu Gly Asp Ala Ala Gln Gln Tyr Ala Leu Ile Thr Arg Leu
                85                  90                  95

Leu Tyr Thr Pro Asp Ala Glu Ala Met Gly Trp Leu Gln Asn Pro Arg
            100                 105                 110

Val Ala Pro Gly Asp Val Ala Leu Asp Gln Ala Cys Phe Arg Ile Ser
        115                 120                 125

Gly Ala Ala Arg Asn Ser Ser Ser Phe Ile Ser Gly Ser Val Ala Arg
    130                 135                 140

Ala Val Pro His Leu Gly Tyr Ala Met Ala Ala Gly Arg Phe Gly Trp
145                 150                 155                 160

Gly Leu Ala His Val Ala Ala Ala Val Ala Met Ser Arg Arg Tyr Asp
                165                 170                 175

Arg Ala Gln Lys Gly Phe Leu Leu Thr Ser Leu Arg Arg Ala Tyr Ala
            180                 185                 190

Pro Leu Leu Ala Arg Glu Asn Ala Ala Leu Thr Gly Ala Arg Thr Pro
        195                 200                 205

Asp Asp Gly Gly Asp Ala Asn Arg His Asp Gly Asp Asp Ala Arg Gly
    210                 215                 220

Lys Pro Ala Ala Ala Ala Ala Pro Leu Pro Ser Ala Ala Ala Ser Pro
225                 230                 235                 240

Ala Asp Glu Arg Ala Val Pro Ala Gly Tyr Gly Ala Ala Gly Val Leu
                245                 250                 255

Ala Ala Leu Gly Arg Leu Ser Ala Ala Pro Ala Ser Ala Pro Ala Gly
            260                 265                 270

Ala Asp Asp Asp Asp Asp Asp Asp Gly Ala Gly Gly Gly Gly Gly Gly
        275                 280                 285

Arg Arg Ala Glu Ala Gly Arg Val Ala Val Glu Cys Leu Ala Ala Cys
    290                 295                 300

Arg Gly Ile Leu Glu Ala Leu Ala Glu Gly Phe Asp Gly Asp Leu Ala
305                 310                 315                 320

Ala Val Pro Gly Leu Ala Gly Ala Arg Pro Ala Ala Pro Pro Arg Pro
                325                 330                 335

Gly Pro Ala Gly Ala Ala Ala Pro Pro His Ala Asp Ala Pro Arg Leu
            340                 345                 350

Arg Ala Trp Leu Arg Glu Leu Arg Phe Val Arg Asp Ala Leu Val Leu
        355                 360                 365

Met Arg Leu Arg Gly Asp Leu Arg Val Ala Gly Gly Ser Glu Ala Ala
    370                 375                 380

Val Ala Ala Val Arg Ala Val Ser Leu Val Ala Gly Ala Leu Gly Pro
385                 390                 395                 400

Ala Leu Pro Arg Ser Pro Arg Leu Leu Ser Ser Ala Ala Ala Ala Ala
                405                 410                 415

Ala Asp Leu Leu Phe Gln Asn Gln Ser Leu Arg Pro Leu Leu Ala Asp
            420                 425                 430

Thr Val Ala Ala Ala Asp Ser Leu Ala Ala Pro Ala Ser Ala Pro Arg
        435                 440                 445
```

-continued

```
Glu Ala Arg Lys Arg Lys Ser Pro Ala Pro Ala Arg Ala Pro Pro Gly
    450                 455                 460

Gly Ala Pro Arg Pro Pro Lys Lys Ser Arg Ala Asp Ala Pro Arg Pro
465                 470                 475                 480

Ala Ala Ala Pro Pro Ala Gly Ala Ala Pro Pro Ala Pro Pro Thr Pro
                485                 490                 495

Pro Pro Arg Pro Pro Arg Pro Ala Ala Leu Thr Arg Arg Pro Ala Glu
            500                 505                 510

Gly Pro Asp Pro Gln Gly Gly Trp Arg Arg Gln Pro Pro Gly Pro Ser
        515                 520                 525

His Thr Pro Ala Pro Ser Ala Ala Ala Leu Glu Ala Tyr Cys Ala
    530                 535                 540


<210> SEQ ID NO 13
<211> LENGTH: 544
<212> TYPE: PRT
<213> ORGANISM: human herpesvirus 2

<400> SEQUENCE: 13

Ala Ala Ala Asp Ser Leu Ala Ala Pro Ala Ser Ala Pro Arg Glu Ala
1               5                   10                  15

Arg Lys Arg Lys Ser Pro Ala Pro Ala Arg Ala Pro Pro Gly Gly Ala
            20                  25                  30

Pro Arg Pro Pro Lys Lys Ser Arg Ala Asp Ala Pro Arg Pro Ala Ala
        35                  40                  45

Ala Pro Pro Ala Gly Ala Ala Pro Pro Ala Pro Pro Thr Pro Pro Pro
    50                  55                  60

Arg Pro Pro Arg Pro Ala Ala Leu Thr Arg Arg Pro Ala Glu Gly Pro
65                  70                  75                  80

Asp Pro Gln Gly Gly Trp Arg Arg Gln Pro Pro Gly Pro Ser His Thr
                85                  90                  95

Pro Ala Pro Ser Ala Ala Ala Leu Glu Ala Tyr Cys Ala Pro Arg Ala
            100                 105                 110

Val Ala Glu Leu Thr Asp His Pro Leu Phe Pro Ala Pro Trp Arg Pro
        115                 120                 125

Ala Leu Met Phe Asp Pro Arg Ala Leu Ala Ser Leu Ala Ala Arg Cys
    130                 135                 140

Ala Ala Pro Pro Pro Gly Gly Ala Pro Ala Ala Phe Gly Pro Leu Arg
145                 150                 155                 160

Ala Ser Gly Pro Leu Arg Arg Ala Ala Ala Trp Met Arg Gln Val Pro
                165                 170                 175

Asp Pro Glu Asp Val Arg Val Val Ile Leu Tyr Ser Pro Leu Pro Gly
            180                 185                 190

Glu Asp Leu Ala Ala Gly Arg Ala Gly Gly Gly Pro Pro Pro Glu Trp
        195                 200                 205

Ser Ala Glu Arg Gly Gly Leu Ser Cys Leu Leu Ala Ala Leu Gly Asn
    210                 215                 220

Arg Leu Cys Gly Pro Ala Thr Ala Ala Trp Ala Gly Asn Trp Thr Gly
225                 230                 235                 240

Ala Pro Asp Val Ser Ala Leu Gly Ala Gln Gly Val Leu Leu Leu Ser
                245                 250                 255

Thr Arg Asp Leu Ala Phe Ala Gly Ala Val Glu Phe Leu Gly Leu Leu
            260                 265                 270

Ala Gly Ala Cys Asp Arg Arg Leu Ile Val Val Asn Ala Val Arg Ala
```

```
        275                 280                 285

Ala Asp Trp Pro Ala Asp Gly Pro Val Val Ser Arg Gln His Ala Tyr
    290                 295                 300

Leu Ala Cys Glu Val Leu Pro Ala Val Gln Cys Ala Val Arg Trp Pro
305                 310                 315                 320

Ala Ala Arg Asp Leu Arg Arg Thr Val Leu Ala Ser Gly Arg Val Phe
                325                 330                 335

Gly Pro Gly Val Phe Ala Arg Val Glu Ala Ala His Ala Arg Leu Tyr
            340                 345                 350

Pro Asp Ala Pro Pro Leu Arg Leu Cys Arg Gly Ala Asn Val Arg Tyr
        355                 360                 365

Arg Val Arg Thr Arg Phe Gly Pro Asp Thr Leu Val Pro Met Ser Pro
    370                 375                 380

Arg Glu Tyr Arg Arg Ala Val Leu Pro Ala Leu Asp Gly Arg Ala Ala
385                 390                 395                 400

Ala Ser Gly Ala Gly Asp Ala Met Ala Pro Gly Ala Pro Asp Phe Cys
                405                 410                 415

Glu Asp Glu Ala His Ser His Arg Ala Cys Ala Arg Trp Gly Leu Gly
            420                 425                 430

Ala Pro Leu Arg Pro Val Tyr Val Ala Leu Gly Arg Asp Ala Val Arg
        435                 440                 445

Gly Gly Pro Ala Glu Leu Arg Gly Pro Arg Arg Glu Phe Cys Ala Arg
    450                 455                 460

Ala Leu Leu Glu Pro Asp Gly Asp Ala Pro Pro Leu Val Leu Arg Asp
465                 470                 475                 480

Asp Ala Asp Ala Gly Pro Pro Pro Gln Ile Arg Trp Ala Ser Ala Ala
                485                 490                 495

Gly Arg Ala Gly Thr Val Leu Ala Ala Ala Gly Gly Gly Val Glu Val
            500                 505                 510

Val Gly Thr Ala Ala Gly Leu Ala Thr Pro Pro Arg Arg Glu Pro Val
        515                 520                 525

Asp Met Asp Ala Glu Leu Glu Asp Asp Asp Asp Gly Leu Phe Gly Glu
    530                 535                 540


<210> SEQ ID NO 14
<211> LENGTH: 1109
<212> TYPE: PRT
<213> ORGANISM: human herpesvirus 2

<400> SEQUENCE: 14

His His His His His His His Arg Arg Arg Arg Ala Pro Arg Arg Arg
1               5                   10                  15

Ser Ala Ala Ser Asp Ser Ser Lys Ser Gly Ser Ser Ser Ser Ala Ser
            20                  25                  30

Ser Ala Ser Ser Ser Ala Ser Ser Ser Ser Ser Ala Ser Ala Ser Ser
        35                  40                  45

Ser Asp Asp Asp Asp Asp Asp Asp Ala Ala Arg Ala Pro Ala Ser Ala
    50                  55                  60

Ala Asp His Ala Ala Gly Gly Thr Leu Gly Ala Asp Asp Glu Glu Ala
65                  70                  75                  80

Gly Val Pro Ala Arg Ala Pro Gly Ala Ala Pro Arg Pro Ser Pro Pro
                85                  90                  95

Arg Ala Glu Pro Ala Pro Ala Arg Thr Pro Ala Ala Thr Ala Gly Arg
            100                 105                 110
```

```
Leu Glu Arg Arg Arg Ala Arg Ala Ala Val Ala Gly Arg Asp Ala Thr
        115                 120                 125

Gly Arg Phe Thr Ala Gly Arg Pro Arg Arg Val Glu Leu Asp Ala Asp
    130                 135                 140

Ala Ala Ser Gly Ala Phe Tyr Ala Arg Tyr Arg Asp Gly Tyr Val Ser
145                 150                 155                 160

Gly Glu Pro Trp Pro Gly Ala Gly Pro Pro Pro Pro Gly Arg Val Leu
                165                 170                 175

Tyr Gly Gly Leu Gly Asp Ser Arg Pro Gly Leu Trp Gly Ala Pro Glu
            180                 185                 190

Ala Glu Glu Ala Arg Ala Arg Phe Glu Ala Ser Gly Ala Pro Ala Pro
        195                 200                 205

Val Trp Ala Pro Glu Leu Gly Asp Ala Ala Gln Gln Tyr Ala Leu Ile
    210                 215                 220

Thr Arg Leu Leu Tyr Thr Pro Asp Ala Glu Ala Met Gly Trp Leu Gln
225                 230                 235                 240

Asn Pro Arg Val Ala Pro Gly Asp Val Ala Leu Asp Gln Ala Cys Phe
                245                 250                 255

Arg Ile Ser Gly Ala Ala Arg Asn Ser Ser Ser Phe Ile Ser Gly Ser
            260                 265                 270

Val Ala Arg Ala Val Pro His Leu Gly Tyr Ala Met Ala Ala Gly Arg
        275                 280                 285

Phe Gly Trp Gly Leu Ala His Val Ala Ala Ala Val Ala Met Ser Arg
    290                 295                 300

Arg Tyr Asp Arg Ala Gln Lys Gly Phe Leu Leu Thr Ser Leu Arg Arg
305                 310                 315                 320

Ala Tyr Ala Pro Leu Leu Ala Arg Glu Asn Ala Ala Leu Thr Gly Ala
                325                 330                 335

Arg Thr Pro Asp Asp Gly Gly Asp Ala Asn Arg His Asp Gly Asp Asp
            340                 345                 350

Ala Arg Gly Lys Pro Ala Ala Ala Ala Ala Pro Leu Pro Ser Ala Ala
        355                 360                 365

Ala Ser Pro Ala Asp Glu Arg Ala Val Pro Ala Gly Tyr Gly Ala Ala
    370                 375                 380

Gly Val Leu Ala Ala Leu Gly Arg Leu Ser Ala Ala Pro Ala Ser Ala
385                 390                 395                 400

Pro Ala Gly Ala Asp Asp Asp Asp Asp Asp Asp Gly Ala Gly Gly Gly
                405                 410                 415

Gly Gly Gly Arg Arg Ala Glu Ala Gly Arg Val Ala Val Glu Cys Leu
            420                 425                 430

Ala Ala Cys Arg Gly Ile Leu Glu Ala Leu Ala Glu Gly Phe Asp Gly
        435                 440                 445

Asp Leu Ala Ala Val Pro Gly Leu Ala Gly Ala Arg Pro Ala Ala Pro
    450                 455                 460

Pro Arg Pro Gly Pro Ala Gly Ala Ala Ala Pro Pro His Ala Asp Ala
465                 470                 475                 480

Pro Arg Leu Arg Ala Trp Leu Arg Glu Leu Arg Phe Val Arg Asp Ala
                485                 490                 495

Leu Val Leu Met Arg Leu Arg Gly Asp Leu Arg Val Ala Gly Gly Ser
            500                 505                 510

Glu Ala Ala Val Ala Ala Val Arg Ala Val Ser Leu Val Ala Gly Ala
        515                 520                 525

Leu Gly Pro Ala Leu Pro Arg Ser Pro Arg Leu Leu Ser Ser Ala Ala
```

-continued

```
    530                 535                 540

Ala Ala Ala Ala Asp Leu Leu Phe Gln Asn Gln Ser Leu Arg Pro Leu
545                 550                 555                 560

Leu Ala Asp Thr Val Ala Ala Ala Asp Ser Leu Ala Ala Pro Ala Ser
                565                 570                 575

Ala Pro Arg Glu Ala Arg Lys Arg Lys Ser Pro Ala Pro Ala Arg Ala
            580                 585                 590

Pro Pro Gly Gly Ala Pro Arg Pro Pro Lys Lys Ser Arg Ala Asp Ala
        595                 600                 605

Pro Arg Pro Ala Ala Ala Pro Pro Ala Gly Ala Ala Pro Pro Ala Pro
    610                 615                 620

Pro Thr Pro Pro Pro Arg Pro Pro Arg Pro Ala Ala Leu Thr Arg Arg
625                 630                 635                 640

Pro Ala Glu Gly Pro Asp Pro Gln Gly Gly Trp Arg Arg Gln Pro Pro
                645                 650                 655

Gly Pro Ser His Thr Pro Ala Pro Ser Ala Ala Ala Leu Glu Ala Tyr
            660                 665                 670

Cys Ala Pro Arg Ala Val Ala Glu Leu Thr Asp His Pro Leu Phe Pro
        675                 680                 685

Ala Pro Trp Arg Pro Ala Leu Met Phe Asp Pro Arg Ala Leu Ala Ser
    690                 695                 700

Leu Ala Ala Arg Cys Ala Ala Pro Pro Pro Gly Gly Ala Pro Ala Ala
705                 710                 715                 720

Phe Gly Pro Leu Arg Ala Ser Gly Pro Leu Arg Arg Ala Ala Ala Trp
                725                 730                 735

Met Arg Gln Val Pro Asp Pro Glu Asp Val Arg Val Val Ile Leu Tyr
            740                 745                 750

Ser Pro Leu Pro Gly Glu Asp Leu Ala Ala Gly Arg Ala Gly Gly Gly
        755                 760                 765

Pro Pro Pro Glu Trp Ser Ala Glu Arg Gly Gly Leu Ser Cys Leu Leu
    770                 775                 780

Ala Ala Leu Gly Asn Arg Leu Cys Gly Pro Ala Thr Ala Ala Trp Ala
785                 790                 795                 800

Gly Asn Trp Thr Gly Ala Pro Asp Val Ser Ala Leu Gly Ala Gln Gly
                805                 810                 815

Val Leu Leu Leu Ser Thr Arg Asp Leu Ala Phe Ala Gly Ala Val Glu
            820                 825                 830

Phe Leu Gly Leu Leu Ala Gly Ala Cys Asp Arg Arg Leu Ile Val Val
        835                 840                 845

Asn Ala Val Arg Ala Ala Asp Trp Pro Ala Asp Gly Pro Val Val Ser
    850                 855                 860

Arg Gln His Ala Tyr Leu Ala Cys Glu Val Leu Pro Ala Val Gln Cys
865                 870                 875                 880

Ala Val Arg Trp Pro Ala Ala Arg Asp Leu Arg Arg Thr Val Leu Ala
                885                 890                 895

Ser Gly Arg Val Phe Gly Pro Gly Val Phe Ala Arg Val Glu Ala Ala
            900                 905                 910

His Ala Arg Leu Tyr Pro Asp Ala Pro Pro Leu Arg Leu Cys Arg Gly
        915                 920                 925

Ala Asn Val Arg Tyr Arg Val Arg Thr Arg Phe Gly Pro Asp Thr Leu
    930                 935                 940

Val Pro Met Ser Pro Arg Glu Tyr Arg Arg Ala Val Leu Pro Ala Leu
945                 950                 955                 960
```

Asp Gly Arg Ala Ala Ala Ser Gly Ala Gly Asp Ala Met Ala Pro Gly
965 970 975

Ala Pro Asp Phe Cys Glu Asp Glu Ala His Ser His Arg Ala Cys Ala
980 985 990

Arg Trp Gly Leu Gly Ala Pro Leu Arg Pro Val Tyr Val Ala Leu Gly
995 1000 1005

Arg Asp Ala Val Arg Gly Gly Pro Ala Glu Leu Arg Gly Pro Arg
1010 1015 1020

Arg Glu Phe Cys Ala Arg Ala Leu Leu Glu Pro Asp Gly Asp Ala
1025 1030 1035

Pro Pro Leu Val Leu Arg Asp Asp Ala Asp Ala Gly Pro Pro Pro
1040 1045 1050

Gln Ile Arg Trp Ala Ser Ala Ala Gly Arg Ala Gly Thr Val Leu
1055 1060 1065

Ala Ala Ala Gly Gly Gly Val Glu Val Val Gly Thr Ala Ala Gly
1070 1075 1080

Leu Ala Thr Pro Pro Arg Arg Glu Pro Val Asp Met Asp Ala Glu
1085 1090 1095

Leu Glu Asp Asp Asp Asp Gly Leu Phe Gly Glu
1100 1105

<210> SEQ ID NO 15
<211> LENGTH: 1164
<212> TYPE: PRT
<213> ORGANISM: human herpesvirus 2

<400> SEQUENCE: 15

Met Ser Ala Glu Gln Arg Lys Lys Lys Lys Thr Thr Thr Thr Thr Gln
1 5 10 15

Gly Arg Gly Ala Glu Val Ala Met Ala Asp Glu Asp Gly Gly Arg Leu
20 25 30

Arg Ala Ala Ala Glu Thr Thr Gly Gly Pro Gly Ser Pro Asp Pro Ala
35 40 45

Asp Gly Pro Pro Pro Thr Pro Asn Pro Asp Arg Arg Pro Ala Ala Arg
50 55 60

Pro Gly Phe Gly Trp His Gly Gly Pro Glu Glu Asn Glu Asp Glu Ala
65 70 75 80

Asp Asp Ala Ala Ala Asp Ala Asp Ala Asp Glu Ala Ala Pro Ala Ser
85 90 95

Gly Glu Ala Val Asp Glu Pro Ala Ala Asp Gly Val Val Ser Pro Arg
100 105 110

Gln Leu Ala Leu Leu Ala Ser Met Val Asp Glu Ala Val Arg Thr Ile
115 120 125

Pro Ser Pro Pro Pro Glu Arg Asp Gly Ala Gln Glu Glu Ala Ala Arg
130 135 140

Ser Pro Ser Pro Pro Arg Thr Pro Ser Met Arg Ala Asp Tyr Gly Glu
145 150 155 160

Glu Asn Asp Asp Asp Asp Asp Asp Asp Asp Asp Asp Asp Arg Asp Ala
165 170 175

Gly Arg Trp Val Arg Gly Pro Glu Thr Thr Ser Ala Val Arg Gly Ala
180 185 190

Tyr Pro Asp Pro Met Ala Ser Leu Ser Pro Arg Pro Pro Ala Pro Arg
195 200 205

Arg His His His His His His His Arg Arg Arg Arg Ala Pro Arg Arg

```
    210                 215                 220

Arg Ser Ala Ala Ser Asp Ser Ser Lys Ser Gly Ser Ser Ser Ser Ala
225                 230                 235                 240

Ser Ser Ala Ser Ser Ser Ala Ser Ser Ser Ser Ser Ala Ser Ala Ser
                245                 250                 255

Ser Ser Asp Asp Asp Asp Asp Asp Asp Ala Ala Arg Ala Pro Ala Ser
            260                 265                 270

Ala Ala Asp His Ala Ala Gly Gly Thr Leu Gly Ala Asp Asp Glu Glu
        275                 280                 285

Ala Gly Val Pro Ala Arg Ala Pro Gly Ala Ala Pro Arg Pro Ser Pro
    290                 295                 300

Pro Arg Ala Glu Pro Ala Pro Ala Arg Thr Pro Ala Ala Thr Ala Gly
305                 310                 315                 320

Arg Leu Glu Arg Arg Arg Ala Arg Ala Ala Val Ala Gly Arg Asp Ala
                325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
        355                 360                 365

Ser Gly Glu Pro Trp Pro Gly Ala Gly Pro Pro Pro Pro Gly Arg Val
    370                 375                 380

Leu Tyr Gly Gly Leu Gly Ala Arg Thr Pro Asp Asp Gly Gly Asp Ala
385                 390                 395                 400

Asn Arg His Asp Gly Asp Asp Ala Arg Gly Lys Pro Ala Ala Ala Ala
                405                 410                 415

Ala Pro Leu Pro Ser Ala Ala Ala Ser Pro Ala Asp Glu Arg Ala Val
            420                 425                 430

Pro Ala Gly Tyr Gly Ala Ala Gly Val Leu Ala Ala Leu Gly Arg Leu
        435                 440                 445

Ser Ala Ala Pro Ala Ser Ala Pro Ala Gly Ala Asp Asp Asp Asp Asp
    450                 455                 460

Asp Asp Gly Ala Gly Gly Gly Gly Gly Gly Arg Arg Ala Glu Ala Gly
465                 470                 475                 480

Arg Val Ala Val Glu Cys Leu Ala Ala Cys Arg Gly Ile Leu Glu Ala
                485                 490                 495

Leu Ala Glu Gly Phe Asp Gly Asp Leu Ala Ala Val Pro Gly Leu Ala
            500                 505                 510

Gly Ala Arg Pro Ala Ala Pro Pro Arg Pro Gly Pro Ala Gly Ala Ala
        515                 520                 525

Ala Pro Pro His Ala Asp Ala Pro Arg Leu Arg Ala Trp Leu Arg Glu
    530                 535                 540

Leu Arg Phe Val Arg Asp Ala Leu Val Leu Met Arg Leu Arg Gly Asp
545                 550                 555                 560

Leu Arg Val Ala Gly Gly Ser Glu Ala Ala Val Ala Ala Val Arg Ala
                565                 570                 575

Val Ser Leu Val Ala Gly Ala Leu Gly Pro Ala Leu Pro Arg Ser Pro
            580                 585                 590

Arg Leu Leu Ser Ser Ala Ala Ala Ala Ala Ala Asp Leu Leu Phe Gln
        595                 600                 605

Asn Gln Ser Leu Arg Pro Leu Leu Ala Asp Thr Val Ala Ala Ala Asp
    610                 615                 620

Ser Leu Ala Ala Pro Ala Ser Ala Pro Arg Glu Ala Arg Lys Arg Lys
625                 630                 635                 640
```

-continued

```
Ser Pro Ala Pro Ala Arg Ala Pro Pro Gly Gly Ala Pro Arg Pro Pro
                645                 650                 655

Lys Lys Ser Arg Ala Asp Ala Pro Arg Pro Ala Ala Ala Pro Pro Ala
            660                 665                 670

Gly Ala Ala Pro Pro Ala Pro Pro Thr Pro Pro Pro Arg Pro Pro Arg
        675                 680                 685

Pro Ala Ala Leu Thr Arg Arg Pro Ala Glu Gly Pro Asp Pro Gln Gly
    690                 695                 700

Gly Trp Arg Arg Gln Pro Pro Gly Pro Ser His Thr Pro Ala Pro Ser
705                 710                 715                 720

Ala Ala Ala Leu Glu Ala Tyr Cys Ala Pro Arg Ala Val Ala Glu Leu
                725                 730                 735

Thr Asp His Pro Leu Phe Pro Ala Pro Trp Arg Pro Ala Leu Met Phe
            740                 745                 750

Asp Pro Arg Ala Leu Ala Ser Leu Ala Ala Arg Cys Ala Ala Pro Pro
        755                 760                 765

Pro Gly Gly Ala Pro Ala Ala Phe Gly Pro Leu Arg Ala Ser Gly Pro
    770                 775                 780

Leu Arg Arg Ala Ala Ala Trp Met Arg Gln Val Pro Asp Pro Glu Asp
785                 790                 795                 800

Val Arg Val Val Ile Leu Tyr Ser Pro Leu Pro Gly Glu Asp Leu Ala
                805                 810                 815

Ala Gly Arg Ala Gly Gly Gly Pro Pro Pro Glu Trp Ser Ala Glu Arg
            820                 825                 830

Gly Gly Leu Ser Cys Leu Leu Ala Ala Leu Gly Asn Arg Leu Cys Gly
        835                 840                 845

Pro Ala Thr Ala Ala Trp Ala Gly Asn Trp Thr Gly Ala Pro Asp Val
    850                 855                 860

Ser Ala Leu Gly Ala Gln Gly Val Leu Leu Leu Ser Thr Arg Asp Leu
865                 870                 875                 880

Ala Phe Ala Gly Ala Val Glu Phe Leu Gly Leu Leu Ala Gly Ala Cys
                885                 890                 895

Asp Arg Arg Leu Ile Val Val Asn Ala Val Arg Ala Ala Asp Trp Pro
            900                 905                 910

Ala Asp Gly Pro Val Val Ser Arg Gln His Ala Tyr Leu Ala Cys Glu
        915                 920                 925

Val Leu Pro Ala Val Gln Cys Ala Val Arg Trp Pro Ala Ala Arg Asp
    930                 935                 940

Leu Arg Arg Thr Val Leu Ala Ser Gly Arg Val Phe Gly Pro Gly Val
945                 950                 955                 960

Phe Ala Arg Val Glu Ala Ala His Ala Arg Leu Tyr Pro Asp Ala Pro
                965                 970                 975

Pro Leu Arg Leu Cys Arg Gly Ala Asn Val Arg Tyr Arg Val Arg Thr
            980                 985                 990

Arg Phe Gly Pro Asp Thr Leu Val  Pro Met Ser Pro Arg  Glu Tyr Arg
        995                 1000                1005

Arg Ala  Val Leu Pro Ala Leu  Asp Gly Arg Ala Ala  Ala Ser Gly
    1010                1015                1020

Ala Gly  Asp Ala Met Ala Pro  Gly Ala Pro Asp Phe  Cys Glu Asp
    1025                1030                1035

Glu Ala  His Ser His Arg Ala  Cys Ala Arg Trp Gly  Leu Gly Ala
    1040                1045                1050
```

-continued

```
Pro Leu  Arg Pro Val Tyr Val  Ala Leu Gly Arg Asp  Ala Val Arg
    1055                 1060                 1065

Gly Gly  Pro Ala Glu Leu Arg  Gly Pro Arg Arg Glu  Phe Cys Ala
    1070                 1075                 1080

Arg Ala  Leu Leu Glu Pro Asp  Gly Asp Ala Pro Pro  Leu Val Leu
    1085                 1090                 1095

Arg Asp  Asp Ala Asp Ala Gly  Pro Pro Pro Gln Ile  Arg Trp Ala
    1100                 1105                 1110

Ser Ala  Ala Gly Arg Ala Gly  Thr Val Leu Ala Ala  Ala Gly Gly
    1115                 1120                 1125

Gly Val  Glu Val Val Gly Thr  Ala Ala Gly Leu Ala  Thr Pro Pro
    1130                 1135                 1140

Arg Arg  Glu Pro Val Asp Met  Asp Ala Glu Leu Glu  Asp Asp Asp
    1145                 1150                 1155

Asp Gly  Leu Phe Gly Glu
    1160


<210> SEQ ID NO 16
<211> LENGTH: 1234
<212> TYPE: PRT
<213> ORGANISM: human herpesvirus 2

<400> SEQUENCE: 16

Met Ser Ala Glu Gln Arg Lys Lys Lys Lys Thr Thr Thr Thr Thr Gln
1               5                   10                  15

Gly Arg Gly Ala Glu Val Ala Met Ala Asp Glu Asp Gly Gly Arg Leu
            20                  25                  30

Arg Ala Ala Ala Glu Thr Thr Gly Gly Pro Gly Ser Pro Asp Pro Ala
        35                  40                  45

Asp Gly Pro Pro Pro Thr Pro Asn Pro Asp Arg Arg Pro Ala Ala Arg
    50                  55                  60

Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Ala Pro Ala Ser
                85                  90                  95

Gly Glu Ala Val Asp Glu Pro Ala Ala Asp Gly Val Val Ser Pro Arg
            100                 105                 110

Gln Leu Ala Leu Leu Ala Ser Met Val Asp Glu Ala Val Arg Thr Ile
        115                 120                 125

Pro Ser Pro Pro Pro Glu Arg Asp Gly Ala Gln Glu Glu Ala Ala Arg
    130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Asp Asp Arg Asp Ala
                165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Pro Ala Pro Arg
        195                 200                 205

Arg His His His His His His His Arg Arg Arg Arg Ala Pro Arg Arg
    210                 215                 220

Arg Ser Ala Ala Ser Asp Ser Ser Lys Ser Gly Ser Ser Ser Ser Ala
225                 230                 235                 240

Ser Ser Ala Ser Ser Ser Ala Ser Ser Ser Ser Ser Ala Ser Ala Ser
                245                 250                 255
```

```
Ser Ser Asp Asp Asp Asp Asp Asp Asp Ala Ala Arg Ala Pro Ala Ser
            260                 265                 270

Ala Ala Asp His Ala Ala Gly Gly Thr Leu Gly Ala Asp Asp Glu Glu
        275                 280                 285

Ala Gly Val Pro Ala Arg Ala Pro Gly Ala Ala Pro Arg Pro Ser Pro
    290                 295                 300

Pro Arg Ala Glu Pro Ala Pro Ala Arg Thr Pro Ala Ala Thr Ala Gly
305                 310                 315                 320

Arg Leu Glu Arg Arg Arg Ala Arg Ala Ala Val Ala Gly Arg Asp Ala
                325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
        355                 360                 365

Ser Gly Glu Pro Trp Pro Gly Ala Gly Pro Pro Pro Pro Gly Arg Val
    370                 375                 380

Leu Tyr Gly Gly Leu Gly Asp Ser Arg Pro Gly Leu Trp Gly Ala Pro
385                 390                 395                 400

Glu Ala Glu Glu Ala Arg Ala Arg Phe Glu Ala Ser Gly Ala Pro Ala
                405                 410                 415

Pro Val Trp Ala Pro Glu Leu Gly Asp Ala Ala Gln Gln Tyr Ala Leu
            420                 425                 430

Ile Thr Arg Leu Leu Tyr Thr Pro Asp Ala Glu Ala Met Gly Trp Leu
        435                 440                 445

Gln Asn Pro Arg Val Ala Pro Gly Asp Val Ala Leu Asp Gln Ala Cys
    450                 455                 460

Phe Arg Ile Ser Gly Ala Ala Arg Asn Ser Ser Ser Phe Ile Ser Gly
465                 470                 475                 480

Ser Val Ala Arg Ala Val Pro His Leu Gly Tyr Ala Met Ala Ala Gly
                485                 490                 495

Arg Phe Gly Trp Gly Leu Ala His Val Ala Ala Ala Val Ala Met Ser
            500                 505                 510

Arg Arg Tyr Asp Arg Ala Gln Lys Gly Phe Leu Leu Thr Ser Leu Arg
        515                 520                 525

Arg Ala Tyr Ala Pro Leu Leu Ala Arg Glu Asn Ala Ala Leu Thr Gly
    530                 535                 540

Ala Arg Thr Pro Asp Asp Gly Gly Asp Ala Asn Arg His Asp Gly Asp
545                 550                 555                 560

Asp Ala Arg Gly Lys Pro Ala Ala Ala Ala Ala Pro Leu Pro Ser Ala
                565                 570                 575

Ala Ala Ser Pro Ala Asp Glu Arg Ala Val Pro Ala Gly Tyr Gly Ala
            580                 585                 590

Ala Gly Val Leu Ala Ala Leu Gly Arg Leu Ser Ala Ala Pro Ala Ser
        595                 600                 605

Ala Pro Ala Gly Ala Asp Asp Asp Asp Asp Asp Asp Gly Ala Gly Gly
    610                 615                 620

Gly Gly Gly Gly Arg Arg Ala Glu Ala Gly Arg Val Ala Val Glu Cys
625                 630                 635                 640

Leu Ala Ala Cys Arg Gly Ile Leu Glu Ala Leu Ala Glu Gly Phe Asp
                645                 650                 655

Gly Asp Leu Ala Ala Val Pro Gly Leu Ala Gly Ala Arg Pro Ala Ala
            660                 665                 670
```

-continued

```
Pro Pro Arg Pro Gly Pro Ala Gly Ala Ala Ala Pro Pro His Ala Asp
        675                 680                 685

Ala Pro Arg Leu Arg Ala Trp Leu Arg Glu Leu Arg Phe Val Arg Asp
    690                 695                 700

Ala Leu Val Leu Met Arg Leu Arg Gly Asp Leu Arg Val Ala Gly Gly
705                 710                 715                 720

Ser Glu Ala Ala Val Ala Ala Val Arg Ala Val Ser Leu Val Ala Gly
                725                 730                 735

Ala Leu Gly Pro Ala Leu Pro Arg Ser Pro Arg Leu Leu Ser Ser Ala
            740                 745                 750

Ala Ala Ala Ala Ala Asp Leu Leu Phe Gln Asn Gln Ser Leu Arg Pro
        755                 760                 765

Leu Leu Ala Asp Thr Val Ala Ala Ala Asp Ser Leu Ala Ala Pro Ala
    770                 775                 780

Ser Thr Pro Ala Pro Ser Ala Ala Ala Leu Glu Ala Tyr Cys Ala Pro
785                 790                 795                 800

Arg Ala Val Ala Glu Leu Thr Asp His Pro Leu Phe Pro Ala Pro Trp
                805                 810                 815

Arg Pro Ala Leu Met Phe Asp Pro Arg Ala Leu Ala Ser Leu Ala Ala
            820                 825                 830

Arg Cys Ala Ala Pro Pro Pro Gly Gly Ala Pro Ala Ala Phe Gly Pro
        835                 840                 845

Leu Arg Ala Ser Gly Pro Leu Arg Arg Ala Ala Ala Trp Met Arg Gln
    850                 855                 860

Val Pro Asp Pro Glu Asp Val Arg Val Val Ile Leu Tyr Ser Pro Leu
865                 870                 875                 880

Pro Gly Glu Asp Leu Ala Ala Gly Arg Ala Gly Gly Gly Pro Pro Pro
                885                 890                 895

Glu Trp Ser Ala Glu Arg Gly Gly Leu Ser Cys Leu Leu Ala Ala Leu
            900                 905                 910

Gly Asn Arg Leu Cys Gly Pro Ala Thr Ala Ala Trp Ala Gly Asn Trp
        915                 920                 925

Thr Gly Ala Pro Asp Val Ser Ala Leu Gly Ala Gln Gly Val Leu Leu
    930                 935                 940

Leu Ser Thr Arg Asp Leu Ala Phe Ala Gly Ala Val Glu Phe Leu Gly
945                 950                 955                 960

Leu Leu Ala Gly Ala Cys Asp Arg Arg Leu Ile Val Val Asn Ala Val
                965                 970                 975

Arg Ala Ala Asp Trp Pro Ala Asp Gly Pro Val Val Ser Arg Gln His
            980                 985                 990

Ala Tyr Leu Ala Cys Glu Val Leu  Pro Ala Val Gln Cys  Ala Val Arg
        995                 1000                 1005

Trp Pro  Ala Ala Arg Asp Leu  Arg Arg Thr Val Leu  Ala Ser Gly
    1010                 1015                 1020

Arg Val  Phe Gly Pro Gly Val  Phe Ala Arg Val Glu  Ala Ala His
    1025                 1030                 1035

Ala Arg  Leu Tyr Pro Asp Ala  Pro Pro Leu Arg Leu  Cys Arg Gly
    1040                 1045                 1050

Ala Asn  Val Arg Tyr Arg Val  Arg Thr Arg Phe Gly  Pro Asp Thr
    1055                 1060                 1065

Leu Val  Pro Met Ser Pro Arg  Glu Tyr Arg Arg Ala  Val Leu Pro
    1070                 1075                 1080

Ala Leu  Asp Gly Arg Ala Ala  Ala Ser Gly Ala Gly  Asp Ala Met
```

1085 1090 1095

Ala Pro Gly Ala Pro Asp Phe Cys Glu Asp Glu Ala His Ser His
1100 1105 1110

Arg Ala Cys Ala Arg Trp Gly Leu Gly Ala Pro Leu Arg Pro Val
1115 1120 1125

Tyr Val Ala Leu Gly Arg Asp Ala Val Arg Gly Gly Pro Ala Glu
1130 1135 1140

Leu Arg Gly Pro Arg Arg Glu Phe Cys Ala Arg Ala Leu Leu Glu
1145 1150 1155

Pro Asp Gly Asp Ala Pro Pro Leu Val Leu Arg Asp Asp Ala Asp
1160 1165 1170

Ala Gly Pro Pro Pro Gln Ile Arg Trp Ala Ser Ala Ala Gly Arg
1175 1180 1185

Ala Gly Thr Val Leu Ala Ala Ala Gly Gly Gly Val Glu Val Val
1190 1195 1200

Gly Thr Ala Ala Gly Leu Ala Thr Pro Pro Arg Arg Glu Pro Val
1205 1210 1215

Asp Met Asp Ala Glu Leu Glu Asp Asp Asp Asp Gly Leu Phe Gly
1220 1225 1230

Glu

<210> SEQ ID NO 17
<211> LENGTH: 255
<212> TYPE: PRT
<213> ORGANISM: human herpesvirus 2

<400> SEQUENCE: 17

Met Phe Ser Ala Ser Thr Thr Pro Glu Gln Pro Leu Gly Leu Ser Gly
1 5 10 15

Asp Ala Thr Pro Pro Leu Pro Thr Ser Val Pro Leu Asp Trp Ala Ala
20 25 30

Phe Arg Arg Ala Phe Leu Ile Asp Asp Ala Trp Arg Pro Leu Leu Glu
35 40 45

Pro Glu Leu Ala Asn Pro Leu Thr Ala Arg Leu Leu Ala Glu Tyr Asp
50 55 60

Arg Arg Cys Gln Thr Glu Glu Val Leu Pro Pro Arg Glu Asp Val Phe
65 70 75 80

Ser Trp Thr Arg Tyr Cys Thr Pro Asp Asp Val Arg Val Val Ile Ile
85 90 95

Gly Gln Asp Pro Tyr His His Pro Gly Gln Ala His Gly Leu Ala Phe
100 105 110

Ser Val Arg Ala Asp Val Pro Val Pro Pro Ser Leu Arg Asn Val Leu
115 120 125

Ala Ala Val Lys Asn Cys Tyr Pro Asp Ala Arg Met Ser Gly Arg Gly
130 135 140

Cys Leu Glu Lys Trp Ala Arg Asp Gly Val Leu Leu Leu Asn Thr Thr
145 150 155 160

Leu Thr Val Lys Arg Gly Ala Ala Ala Ser His Ser Lys Leu Gly Trp
165 170 175

Asp Arg Phe Val Gly Gly Val Val Gln Arg Leu Ala Ala Arg Arg Pro
180 185 190

Gly Leu Val Phe Met Leu Trp Gly Ala His Ala Gln Asn Ala Ile Arg
195 200 205

Pro Asp Pro Arg Gln His Tyr Val Leu Lys Phe Ser His Pro Ser Pro

-continued

```
    210                 215                 220

Leu Ser Lys Val Pro Phe Gly Thr Cys Gln His Phe Leu Ala Ala Asn
225                 230                 235                 240

Arg Tyr Leu Glu Thr Arg Asp Ile Met Pro Ile Asp Trp Ser Val
                245                 250                 255


<210> SEQ ID NO 18
<211> LENGTH: 96
<212> TYPE: PRT
<213> ORGANISM: human herpesvirus 2

<400> SEQUENCE: 18

Met Gly Leu Ala Phe Ser Gly Ala Arg Pro Cys Cys Cys Arg His Asn
1               5                   10                  15

Val Ile Thr Thr Asp Gly Gly Glu Val Val Ser Leu Thr Ala His Glu
            20                  25                  30

Phe Asp Val Val Asp Ile Glu Ser Glu Glu Glu Gly Asn Phe Tyr Val
        35                  40                  45

Pro Pro Asp Val Arg Val Val Thr Arg Ala Pro Gly Pro Gln Tyr Arg
    50                  55                  60

Arg Ala Ser Asp Pro Pro Ser Arg His Thr Arg Arg Arg Asp Pro Asp
65                  70                  75                  80

Val Ala Arg Pro Pro Ala Thr Leu Thr Pro Pro Leu Ser Asp Ser Glu
                85                  90                  95


<210> SEQ ID NO 19
<211> LENGTH: 226
<212> TYPE: PRT
<213> ORGANISM: Human herpesvirus 2

<400> SEQUENCE: 19

Asn Arg Trp Gly Phe Val Cys Leu Phe Gly Leu Val Val Met Gly Ala
1               5                   10                  15

Trp Gly Ala Trp Gly Gly Ser Gln Ala Thr Glu Tyr Val Leu Arg Ser
            20                  25                  30

Val Ile Ala Lys Glu Val Gly Asp Ile Leu Arg Val Pro Cys Met Arg
        35                  40                  45

Thr Pro Ala Asp Asp Val Ser Trp Arg Tyr Glu Ala Pro Ser Val Ile
    50                  55                  60

Asp Tyr Ala Arg Ile Asp Gly Ile Phe Leu Arg Tyr His Cys Pro Gly
65                  70                  75                  80

Leu Asp Thr Phe Leu Trp Asp Arg His Ala Gln Arg Ala Tyr Leu Val
                85                  90                  95

Asn Pro Phe Leu Phe Ala Ala Gly Phe Leu Glu Asp Leu Ser His Ser
            100                 105                 110

Val Phe Pro Ala Asp Thr Gln Glu Thr Thr Thr Arg Arg Ala Leu Tyr
        115                 120                 125

Lys Glu Ile Arg Asp Ala Leu Gly Ser Arg Lys Gln Ala Val Ser His
    130                 135                 140

Ala Pro Val Arg Ala Gly Cys Val Asn Phe Asp Tyr Ser Arg Thr Arg
145                 150                 155                 160

Arg Cys Val Gly Arg Arg Asp Leu Arg Pro Ala Asn Thr Thr Ser Thr
                165                 170                 175

Trp Glu Pro Pro Val Ser Ser Asp Asp Glu Ala Ser Ser Gln Ser Lys
            180                 185                 190

Pro Leu Ala Thr Gln Pro Pro Val Leu Ala Leu Ser Asn Ala Pro Pro
```

```
        195                 200                 205

Arg Arg Val Ser Pro Thr Arg Gly Arg Arg Arg His Thr Arg Leu Arg
    210                 215                 220

Arg Asn
225


<210> SEQ ID NO 20
<211> LENGTH: 1388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Tyr Asp Ile Pro Thr Thr Glu Asn Leu Tyr Phe Gln Gly Met Ala
1               5                   10                  15

Ala Pro Ala Arg Asp Pro Pro Gly Tyr Arg Tyr Ala Ala Ala Met Val
            20                  25                  30

Pro Thr Gly Ser Ile Leu Ser Thr Ile Glu Val Ala Ser His Arg Arg
        35                  40                  45

Leu Phe Asp Phe Phe Ala Arg Val Arg Ser Asp Glu Asn Ser Leu Tyr
    50                  55                  60

Asp Val Glu Phe Asp Ala Leu Leu Gly Ser Tyr Cys Asn Thr Leu Ser
65                  70                  75                  80

Leu Val Arg Phe Leu Glu Leu Gly Leu Ser Val Ala Cys Val Cys Thr
                85                  90                  95

Lys Phe Pro Glu Leu Ala Tyr Met Asn Glu Gly Arg Val Gln Phe Glu
            100                 105                 110

Val His Gln Pro Leu Ile Ala Arg Asp Gly Pro His Pro Val Glu Gln
        115                 120                 125

Pro Val His Asn Tyr Met Thr Lys Val Ile Asp Arg Arg Ala Leu Asn
    130                 135                 140

Ala Ala Phe Ser Leu Ala Thr Glu Ala Ile Ala Leu Leu Thr Gly Glu
145                 150                 155                 160

Ala Leu Asp Gly Thr Gly Ile Ser Leu His Arg Gln Leu Arg Ala Ile
                165                 170                 175

Gln Gln Leu Ala Arg Asn Val Gln Ala Val Leu Gly Ala Phe Glu Arg
            180                 185                 190

Gly Thr Ala Asp Gln Met Leu His Val Leu Leu Glu Lys Ala Pro Pro
        195                 200                 205

Leu Ala Leu Leu Leu Pro Met Gln Arg Tyr Leu Asp Asn Gly Arg Leu
    210                 215                 220

Ala Thr Arg Val Ala Arg Ala Thr Leu Val Ala Glu Leu Lys Arg Ser
225                 230                 235                 240

Phe Cys Asp Thr Ser Phe Phe Leu Gly Lys Ala Gly His Arg Arg Glu
                245                 250                 255

Ala Ile Glu Ala Trp Leu Val Asp Leu Thr Thr Ala Thr Gln Pro Ser
            260                 265                 270

Val Ala Val Pro Arg Leu Thr His Ala Asp Thr Arg Gly Arg Pro Val
        275                 280                 285

Asp Gly Val Leu Val Thr Thr Ala Ala Ile Lys Gln Arg Leu Leu Gln
    290                 295                 300

Ser Phe Leu Lys Val Glu Asp Thr Glu Ala Asp Val Pro Val Thr Tyr
305                 310                 315                 320
```

-continued

```
Gly Glu Met Val Leu Asn Gly Ala Asn Leu Val Thr Ala Leu Val Met
                325                 330                 335

Gly Lys Ala Val Arg Ser Leu Asp Asp Val Gly Arg His Leu Leu Glu
            340                 345                 350

Met Gln Glu Glu Gln Leu Glu Ala Asn Arg Glu Thr Leu Asp Glu Leu
        355                 360                 365

Glu Ser Ala Pro Gln Thr Thr Arg Val Arg Ala Asp Leu Val Ala Ile
    370                 375                 380

Gly Asp Arg Leu Val Phe Leu Glu Ala Leu Glu Lys Arg Ile Tyr Ala
385                 390                 395                 400

Ala Thr Asn Val Pro Tyr Pro Leu Val Gly Ala Met Asp Leu Thr Phe
                405                 410                 415

Val Leu Pro Leu Gly Leu Phe Asn Pro Ala Met Glu Arg Phe Ala Ala
            420                 425                 430

His Ala Gly Asp Leu Val Pro Ala Pro Gly His Pro Glu Pro Arg Ala
        435                 440                 445

Phe Pro Pro Arg Gln Leu Phe Phe Trp Gly Lys Asp His Gln Val Leu
    450                 455                 460

Arg Leu Ser Met Glu Asn Ala Val Gly Thr Val Cys His Pro Ser Leu
465                 470                 475                 480

Met Asn Ile Asp Ala Ala Val Gly Gly Val Asn His Asp Pro Val Glu
                485                 490                 495

Ala Ala Asn Pro Tyr Gly Ala Tyr Val Ala Ala Pro Ala Gly Pro Gly
            500                 505                 510

Ala Asp Met Gln Gln Arg Phe Leu Asn Ala Trp Arg Gln Arg Leu Ala
        515                 520                 525

His Gly Arg Val Arg Trp Val Ala Glu Cys Gln Met Thr Ala Glu Gln
    530                 535                 540

Phe Met Gln Pro Asp Asn Ala Asn Leu Ala Leu Glu Leu His Pro Ala
545                 550                 555                 560

Phe Asp Phe Phe Ala Gly Val Ala Asp Val Glu Leu Pro Gly Gly Glu
                565                 570                 575

Val Pro Pro Ala Gly Pro Gly Ala Ile Gln Ala Thr Trp Arg Val Val
            580                 585                 590

Asn Gly Asn Leu Pro Leu Ala Leu Cys Pro Val Ala Phe Arg Asp Ala
        595                 600                 605

Arg Gly Leu Glu Leu Gly Val Gly Arg His Ala Met Ala Pro Ala Thr
    610                 615                 620

Ile Ala Ala Val Arg Gly Ala Phe Glu Asp Arg Ser Tyr Pro Ala Val
625                 630                 635                 640

Phe Tyr Leu Leu Gln Ala Ala Ile His Gly Ser Glu His Val Phe Cys
                645                 650                 655

Ala Leu Ala Arg Leu Val Thr Gln Cys Ile Thr Ser Tyr Trp Asn Asn
            660                 665                 670

Thr Arg Cys Ala Ala Phe Val Asn Asp Tyr Ser Leu Val Ser Tyr Ile
        675                 680                 685

Val Thr Tyr Leu Gly Gly Asp Leu Pro Glu Glu Cys Met Ala Val Tyr
    690                 695                 700

Arg Asp Leu Val Ala His Val Glu Ala Leu Ala Gln Leu Val Asp Asp
705                 710                 715                 720

Phe Thr Leu Pro Gly Pro Glu Leu Gly Gly Gln Ala Gln Ala Glu Leu
                725                 730                 735

Asn His Leu Met Arg Asp Pro Ala Leu Leu Pro Pro Leu Val Trp Asp
```

-continued

```
            740                 745                 750

Cys Asp Gly Leu Met Arg His Ala Ala Leu Asp Arg His Arg Asp Cys
        755                 760                 765

Arg Ile Asp Ala Gly Glu His Glu Pro Val Tyr Ala Ala Ala Cys Asn
    770                 775                 780

Val Ala Thr Ala Asp Phe Asn Arg Asn Asp Gly Arg Leu Leu His Asn
785                 790                 795                 800

Thr Gln Ala Arg Ala Ala Asp Ala Ala Asp Asp Arg Pro His Arg Pro
                805                 810                 815

Ala Asp Trp Thr Val His His Lys Ile Tyr Tyr Tyr Val Leu Val Pro
            820                 825                 830

Ala Phe Ser Arg Gly Arg Cys Cys Thr Ala Gly Val Arg Phe Asp Arg
        835                 840                 845

Val Tyr Ala Thr Leu Gln Asn Met Val Val Pro Glu Ile Ala Pro Gly
    850                 855                 860

Glu Glu Cys Pro Ser Asp Pro Val Thr Asp Pro Ala His Pro Leu His
865                 870                 875                 880

Pro Ala Asn Leu Val Ala Asn Thr Val Asn Ala Met Phe His Asn Gly
                885                 890                 895

Arg Val Val Val Asp Gly Pro Ala Met Leu Thr Leu Gln Val Leu Ala
            900                 905                 910

His Asn Met Ala Glu Arg Thr Thr Ala Leu Leu Cys Ser Ala Ala Pro
        915                 920                 925

Asp Ala Gly Ala Asn Thr Ala Ser Thr Ala Asn Met Arg Ile Phe Asp
    930                 935                 940

Gly Ala Leu His Ala Gly Val Leu Leu Met Ala Pro Gln His Leu Asp
945                 950                 955                 960

His Thr Ile Gln Asn Gly Glu Tyr Phe Tyr Val Leu Pro Val His Ala
                965                 970                 975

Leu Phe Ala Gly Ala Asp His Val Ala Asn Ala Pro Asn Phe Pro Pro
            980                 985                 990

Ala Leu Arg Asp Leu Ala Arg His  Val Pro Leu Val Pro  Pro Ala Leu
        995                 1000                1005

Gly Ala  Asn Tyr Phe Ser Ser  Ile Arg Gln Pro Val  Val Gln His
    1010                1015                1020

Ala Arg  Glu Ser Ala Ala Gly  Glu Asn Ala Leu Thr  Tyr Ala Leu
    1025                1030                1035

Met Ala  Gly Tyr Phe Lys Met  Ser Pro Val Ala Leu  Tyr His Gln
    1040                1045                1050

Leu Lys  Thr Gly Leu His Pro  Gly Phe Gly Phe Thr  Val Val Arg
    1055                1060                1065

Gln Asp  Arg Phe Val Thr Glu  Asn Val Leu Phe Ser  Glu Arg Ala
    1070                1075                1080

Ser Glu  Ala Tyr Phe Leu Gly  Gln Leu Gln Val Ala  Arg His Glu
    1085                1090                1095

Thr Gly  Gly Gly Val Ser Phe  Thr Leu Thr Gln Pro  Arg Gly Asn
    1100                1105                1110

Val Asp  Leu Gly Val Gly Tyr  Thr Ala Val Ala Ala  Thr Ala Thr
    1115                1120                1125

Val Arg  Asn Pro Val Thr Asp  Met Gly Asn Leu Pro  Gln Asn Phe
    1130                1135                1140

Tyr Leu  Gly Arg Gly Ala Pro  Pro Leu Leu Asp Asn  Ala Ala Ala
    1145                1150                1155
```

Val Tyr Leu Arg Asn Ala Val Val Ala Gly Asn Arg Leu Gly Pro
1160 1165 1170

Ala Gln Pro Leu Pro Val Phe Gly Cys Ala Gln Val Pro Arg Arg
1175 1180 1185

Ala Gly Met Asp His Gly Gln Asp Ala Val Cys Glu Phe Ile Ala
1190 1195 1200

Thr Pro Val Ala Thr Asp Ile Asn Tyr Phe Arg Arg Pro Cys Asn
1205 1210 1215

Pro Arg Gly Arg Ala Ala Gly Gly Val Tyr Ala Gly Asp Lys Glu
1220 1225 1230

Gly Asp Val Ile Ala Leu Met Tyr Asp His Gly Gln Ser Asp Pro
1235 1240 1245

Ala Arg Pro Phe Ala Ala Thr Ala Asn Pro Trp Ala Ser Gln Arg
1250 1255 1260

Phe Ser Tyr Gly Asp Leu Leu Tyr Asn Gly Ala Tyr His Leu Asn
1265 1270 1275

Gly Ala Ser Pro Val Leu Ser Pro Cys Phe Lys Phe Phe Thr Ala
1280 1285 1290

Ala Asp Ile Thr Ala Lys His Arg Cys Leu Glu Arg Leu Ile Val
1295 1300 1305

Glu Thr Gly Ser Ala Val Ser Thr Ala Thr Ala Ala Ser Asp Val
1310 1315 1320

Gln Phe Lys Arg Pro Pro Gly Cys Arg Glu Leu Val Glu Asp Pro
1325 1330 1335

Cys Gly Leu Phe Gln Glu Ala Tyr Pro Ile Thr Cys Ala Ser Asp
1340 1345 1350

Pro Ala Leu Leu Arg Ser Ala Arg Asp Gly Glu Ala His Ala Arg
1355 1360 1365

Glu Thr His Phe Thr Gln Tyr Leu Ile Tyr Asp Ala Ser Pro Leu
1370 1375 1380

Lys Gly Leu Ser Leu
1385

<210> SEQ ID NO 21
<211> LENGTH: 1374
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Met Ala Ala Pro Ala Arg Asp Pro Pro Gly Tyr Arg Tyr Ala Ala Ala
1 5 10 15

Met Val Pro Thr Gly Ser Ile Leu Ser Thr Ile Glu Val Ala Ser His
20 25 30

Arg Arg Leu Phe Asp Phe Phe Ala Arg Val Arg Ser Asp Glu Asn Ser
35 40 45

Leu Tyr Asp Val Glu Phe Asp Ala Leu Leu Gly Ser Tyr Cys Asn Thr
50 55 60

Leu Ser Leu Val Arg Phe Leu Glu Leu Gly Leu Ser Val Ala Cys Val
65 70 75 80

Cys Thr Lys Phe Pro Glu Leu Ala Tyr Met Asn Glu Gly Arg Val Gln
85 90 95

Phe Glu Val His Gln Pro Leu Ile Ala Arg Asp Gly Pro His Pro Val

-continued

```
            100                 105                 110

Glu Gln Pro Val His Asn Tyr Met Thr Lys Val Ile Asp Arg Arg Ala
        115                 120                 125

Leu Asn Ala Ala Phe Ser Leu Ala Thr Glu Ala Ile Ala Leu Leu Thr
    130                 135                 140

Gly Glu Ala Leu Asp Gly Thr Gly Ile Ser Leu His Arg Gln Leu Arg
145                 150                 155                 160

Ala Ile Gln Gln Leu Ala Arg Asn Val Gln Ala Val Leu Gly Ala Phe
                165                 170                 175

Glu Arg Gly Thr Ala Asp Gln Met Leu His Val Leu Leu Glu Lys Ala
            180                 185                 190

Pro Pro Leu Ala Leu Leu Leu Pro Met Gln Arg Tyr Leu Asp Asn Gly
        195                 200                 205

Arg Leu Ala Thr Arg Val Ala Arg Ala Thr Leu Val Ala Glu Leu Lys
    210                 215                 220

Arg Ser Phe Cys Asp Thr Ser Phe Phe Leu Gly Lys Ala Gly His Arg
225                 230                 235                 240

Arg Glu Ala Ile Glu Ala Trp Leu Val Asp Leu Thr Thr Ala Thr Gln
                245                 250                 255

Pro Ser Val Ala Val Pro Arg Leu Thr His Ala Asp Thr Arg Gly Arg
            260                 265                 270

Pro Val Asp Gly Val Leu Val Thr Thr Ala Ala Ile Lys Gln Arg Leu
        275                 280                 285

Leu Gln Ser Phe Leu Lys Val Glu Asp Thr Glu Ala Asp Val Pro Val
    290                 295                 300

Thr Tyr Gly Glu Met Val Leu Asn Gly Ala Asn Leu Val Thr Ala Leu
305                 310                 315                 320

Val Met Gly Lys Ala Val Arg Ser Leu Asp Asp Val Gly Arg His Leu
                325                 330                 335

Leu Glu Met Gln Glu Glu Gln Leu Glu Ala Asn Arg Glu Thr Leu Asp
            340                 345                 350

Glu Leu Glu Ser Ala Pro Gln Thr Thr Arg Val Arg Ala Asp Leu Val
        355                 360                 365

Ala Ile Gly Asp Arg Leu Val Phe Leu Glu Ala Leu Glu Lys Arg Ile
    370                 375                 380

Tyr Ala Ala Thr Asn Val Pro Tyr Pro Leu Val Gly Ala Met Asp Leu
385                 390                 395                 400

Thr Phe Val Leu Pro Leu Gly Leu Phe Asn Pro Ala Met Glu Arg Phe
                405                 410                 415

Ala Ala His Ala Gly Asp Leu Val Pro Ala Pro Gly His Pro Glu Pro
            420                 425                 430

Arg Ala Phe Pro Pro Arg Gln Leu Phe Phe Trp Gly Lys Asp His Gln
        435                 440                 445

Val Leu Arg Leu Ser Met Glu Asn Ala Val Gly Thr Val Cys His Pro
    450                 455                 460

Ser Leu Met Asn Ile Asp Ala Ala Val Gly Gly Val Asn His Asp Pro
465                 470                 475                 480

Val Glu Ala Ala Asn Pro Tyr Gly Ala Tyr Val Ala Ala Pro Ala Gly
                485                 490                 495

Pro Gly Ala Asp Met Gln Gln Arg Phe Leu Asn Ala Trp Arg Gln Arg
            500                 505                 510

Leu Ala His Gly Arg Val Arg Trp Val Ala Glu Cys Gln Met Thr Ala
        515                 520                 525
```

-continued

```
Glu Gln Phe Met Gln Pro Asp Asn Ala Asn Leu Ala Leu Glu Leu His
    530                 535                 540

Pro Ala Phe Asp Phe Phe Ala Gly Val Ala Asp Val Glu Leu Pro Gly
545                 550                 555                 560

Gly Glu Val Pro Pro Ala Gly Pro Gly Ala Ile Gln Ala Thr Trp Arg
                565                 570                 575

Val Val Asn Gly Asn Leu Pro Leu Ala Leu Cys Pro Val Ala Phe Arg
            580                 585                 590

Asp Ala Arg Gly Leu Glu Leu Gly Val Gly Arg His Ala Met Ala Pro
        595                 600                 605

Ala Thr Ile Ala Ala Val Arg Gly Ala Phe Glu Asp Arg Ser Tyr Pro
    610                 615                 620

Ala Val Phe Tyr Leu Leu Gln Ala Ala Ile His Gly Ser Glu His Val
625                 630                 635                 640

Phe Cys Ala Leu Ala Arg Leu Val Thr Gln Cys Ile Thr Ser Tyr Trp
                645                 650                 655

Asn Asn Thr Arg Cys Ala Ala Phe Val Asn Asp Tyr Ser Leu Val Ser
            660                 665                 670

Tyr Ile Val Thr Tyr Leu Gly Gly Asp Leu Pro Glu Glu Cys Met Ala
        675                 680                 685

Val Tyr Arg Asp Leu Val Ala His Val Glu Ala Leu Ala Gln Leu Val
    690                 695                 700

Asp Asp Phe Thr Leu Pro Gly Pro Glu Leu Gly Gly Gln Ala Gln Ala
705                 710                 715                 720

Glu Leu Asn His Leu Met Arg Asp Pro Ala Leu Leu Pro Pro Leu Val
                725                 730                 735

Trp Asp Cys Asp Gly Leu Met Arg His Ala Ala Leu Asp Arg His Arg
            740                 745                 750

Asp Cys Arg Ile Asp Ala Gly Glu His Glu Pro Val Tyr Ala Ala Ala
        755                 760                 765

Cys Asn Val Ala Thr Ala Asp Phe Asn Arg Asn Asp Gly Arg Leu Leu
    770                 775                 780

His Asn Thr Gln Ala Arg Ala Ala Asp Ala Ala Asp Asp Arg Pro His
785                 790                 795                 800

Arg Pro Ala Asp Trp Thr Val His His Lys Ile Tyr Tyr Tyr Val Leu
                805                 810                 815

Val Pro Ala Phe Ser Arg Gly Arg Cys Cys Thr Ala Gly Val Arg Phe
            820                 825                 830

Asp Arg Val Tyr Ala Thr Leu Gln Asn Met Val Val Pro Glu Ile Ala
        835                 840                 845

Pro Gly Glu Glu Cys Pro Ser Asp Pro Val Thr Asp Pro Ala His Pro
    850                 855                 860

Leu His Pro Ala Asn Leu Val Ala Asn Thr Val Asn Ala Met Phe His
865                 870                 875                 880

Asn Gly Arg Val Val Val Asp Gly Pro Ala Met Leu Thr Leu Gln Val
                885                 890                 895

Leu Ala His Asn Met Ala Glu Arg Thr Thr Ala Leu Leu Cys Ser Ala
            900                 905                 910

Ala Pro Asp Ala Gly Ala Asn Thr Ala Ser Thr Ala Asn Met Arg Ile
        915                 920                 925

Phe Asp Gly Ala Leu His Ala Gly Val Leu Leu Met Ala Pro Gln His
    930                 935                 940
```

-continued

```
Leu Asp His Thr Ile Gln Asn Gly Glu Tyr Phe Tyr Val Leu Pro Val
945                 950                 955                 960

His Ala Leu Phe Ala Gly Ala Asp His Val Ala Asn Ala Pro Asn Phe
                965                 970                 975

Pro Pro Ala Leu Arg Asp Leu Ala Arg His Val Pro Leu Val Pro Pro
            980                 985                 990

Ala Leu Gly Ala Asn Tyr Phe Ser  Ser Ile Arg Gln Pro  Val Val Gln
        995                 1000                 1005

His Ala  Arg Glu Ser Ala Ala  Gly Glu Asn Ala Leu  Thr Tyr Ala
    1010                 1015                 1020

Leu Met  Ala Gly Tyr Phe Lys  Met Ser Pro Val Ala  Leu Tyr His
    1025                 1030                 1035

Gln Leu  Lys Thr Gly Leu His  Pro Gly Phe Gly Phe  Thr Val Val
    1040                 1045                 1050

Arg Gln  Asp Arg Phe Val Thr  Glu Asn Val Leu Phe  Ser Glu Arg
    1055                 1060                 1065

Ala Ser  Glu Ala Tyr Phe Leu  Gly Gln Leu Gln Val  Ala Arg His
    1070                 1075                 1080

Glu Thr  Gly Gly Gly Val Ser  Phe Thr Leu Thr Gln  Pro Arg Gly
    1085                 1090                 1095

Asn Val  Asp Leu Gly Val Gly  Tyr Thr Ala Val Ala  Ala Thr Ala
    1100                 1105                 1110

Thr Val  Arg Asn Pro Val Thr  Asp Met Gly Asn Leu  Pro Gln Asn
    1115                 1120                 1125

Phe Tyr  Leu Gly Arg Gly Ala  Pro Pro Leu Leu Asp  Asn Ala Ala
    1130                 1135                 1140

Ala Val  Tyr Leu Arg Asn Ala  Val Val Ala Gly Asn  Arg Leu Gly
    1145                 1150                 1155

Pro Ala  Gln Pro Leu Pro Val  Phe Gly Cys Ala Gln  Val Pro Arg
    1160                 1165                 1170

Arg Ala  Gly Met Asp His Gly  Gln Asp Ala Val Cys  Glu Phe Ile
    1175                 1180                 1185

Ala Thr  Pro Val Ala Thr Asp  Ile Asn Tyr Phe Arg  Arg Pro Cys
    1190                 1195                 1200

Asn Pro  Arg Gly Arg Ala Ala  Gly Gly Val Tyr Ala  Gly Asp Lys
    1205                 1210                 1215

Glu Gly  Asp Val Ile Ala Leu  Met Tyr Asp His Gly  Gln Ser Asp
    1220                 1225                 1230

Pro Ala  Arg Pro Phe Ala Ala  Thr Ala Asn Pro Trp  Ala Ser Gln
    1235                 1240                 1245

Arg Phe  Ser Tyr Gly Asp Leu  Leu Tyr Asn Gly Ala  Tyr His Leu
    1250                 1255                 1260

Asn Gly  Ala Ser Pro Val Leu  Ser Pro Cys Phe Lys  Phe Phe Thr
    1265                 1270                 1275

Ala Ala  Asp Ile Thr Ala Lys  His Arg Cys Leu Glu  Arg Leu Ile
    1280                 1285                 1290

Val Glu  Thr Gly Ser Ala Val  Ser Thr Ala Thr Ala  Ala Ser Asp
    1295                 1300                 1305

Val Gln  Phe Lys Arg Pro Pro  Gly Cys Arg Glu Leu  Val Glu Asp
    1310                 1315                 1320

Pro Cys  Gly Leu Phe Gln Glu  Ala Tyr Pro Ile Thr  Cys Ala Ser
    1325                 1330                 1335

Asp Pro  Ala Leu Leu Arg Ser  Ala Arg Asp Gly Glu  Ala His Ala
```

```
    1340                1345                1350

Arg Glu  Thr His Phe Thr Gln  Tyr Leu Ile Tyr Asp  Ala Ser Pro
    1355                1360                1365

Leu Lys  Gly Leu Ser Leu
    1370


<210> SEQ ID NO 22
<211> LENGTH: 3122
<212> TYPE: PRT
<213> ORGANISM: human herpesvirus 2

<400> SEQUENCE: 22

Met Ile Pro Ala Ala Leu Pro His Pro Thr Met Lys Arg Gln Gly Asp
1               5                   10                  15

Arg Asp Ile Val Val Thr Gly Val Arg Asn Gln Phe Ala Thr Asp Leu
            20                  25                  30

Glu Pro Gly Gly Ser Val Ser Cys Met Arg Ser Ser Leu Ser Phe Leu
        35                  40                  45

Ser Leu Leu Phe Asp Val Gly Pro Arg Asp Val Leu Ser Ala Glu Ala
    50                  55                  60

Ile Glu Gly Cys Leu Val Glu Gly Gly Glu Trp Thr Arg Ala Ala Ala
65                  70                  75                  80

Gly Ser Gly Pro Pro Arg Met Cys Ser Ile Ile Glu Leu Pro Asn Phe
                85                  90                  95

Leu Glu Tyr Pro Ala Ala Arg Gly Gly Leu Arg Cys Val Phe Ser Arg
            100                 105                 110

Val Tyr Gly Glu Val Gly Phe Phe Gly Glu Pro Thr Ala Gly Leu Leu
        115                 120                 125

Glu Thr Gln Cys Pro Ala His Thr Phe Phe Ala Gly Pro Trp Ala Met
    130                 135                 140

Arg Pro Leu Ser Tyr Thr Leu Leu Thr Ile Gly Pro Leu Gly Met Gly
145                 150                 155                 160

Leu Tyr Arg Asp Gly Asp Thr Ala Tyr Leu Phe Asp Pro His Gly Leu
                165                 170                 175

Pro Ala Gly Thr Pro Ala Phe Ile Ala Lys Val Arg Ala Gly Asp Val
            180                 185                 190

Tyr Pro Tyr Leu Thr Tyr Tyr Ala His Asp Arg Pro Lys Val Arg Trp
        195                 200                 205

Ala Gly Ala Met Val Phe Phe Val Pro Ser Gly Pro Gly Ala Val Ala
    210                 215                 220

Pro Ala Asp Leu Thr Ala Ala Ala Leu His Leu Tyr Gly Ala Ser Glu
225                 230                 235                 240

Thr Tyr Leu Gln Asp Glu Pro Phe Val Glu Arg Arg Val Ala Ile Thr
                245                 250                 255

His Pro Leu Arg Gly Glu Ile Gly Gly Leu Gly Ala Leu Phe Val Gly
            260                 265                 270

Val Val Pro Arg Gly Asp Gly Glu Gly Ser Gly Pro Val Val Pro Ala
        275                 280                 285

Leu Pro Ala Pro Thr His Val Gln Thr Pro Gly Ala Asp Arg Pro Pro
    290                 295                 300

Glu Ala Pro Arg Gly Ala Ser Gly Pro Pro Asp Thr Pro Gln Ala Gly
305                 310                 315                 320

His Pro Asn Arg Pro Pro Asp Asp Val Trp Ala Ala Ala Leu Glu Gly
                325                 330                 335
```

-continued

```
Thr Pro Pro Ala Lys Pro Ser Ala Pro Asp Ala Ala Ala Ser Gly Pro
            340                 345                 350

Pro His Ala Ala Pro Pro Pro Gln Thr Pro Ala Gly Asp Ala Ala Glu
        355                 360                 365

Glu Ala Glu Asp Leu Arg Val Leu Glu Val Gly Ala Val Pro Val Gly
    370                 375                 380

Arg His Arg Ala Arg Tyr Ser Thr Gly Leu Pro Lys Arg Arg Arg Pro
385                 390                 395                 400

Thr Trp Thr Pro Pro Ser Ser Val Glu Asp Leu Thr Ser Gly Glu Arg
                405                 410                 415

Pro Ala Pro Lys Ala Pro Pro Ala Lys Ala Lys Lys Lys Ser Ala Pro
            420                 425                 430

Lys Lys Lys Ala Pro Val Ala Ala Glu Val Pro Ala Ser Ser Pro Thr
        435                 440                 445

Pro Ile Ala Ala Thr Val Pro Pro Ala Pro Asp Thr Pro Pro Gln Ser
    450                 455                 460

Gly Gln Gly Gly Gly Asp Asp Gly Pro Ala Ser Pro Ser Ser Pro Ser
465                 470                 475                 480

Val Leu Glu Thr Leu Gly Ala Arg Arg Pro Pro Glu Pro Pro Gly Ala
                485                 490                 495

Asp Leu Ala Gln Leu Phe Glu Val His Pro Asn Val Ala Ala Thr Ala
            500                 505                 510

Val Arg Leu Ala Ala Arg Asp Ala Ala Leu Ala Arg Glu Val Ala Ala
        515                 520                 525

Cys Ser Gln Leu Thr Ile Asn Ala Leu Arg Ser Pro Tyr Pro Ala His
    530                 535                 540

Pro Gly Leu Leu Glu Leu Cys Val Ile Phe Phe Phe Glu Arg Val Leu
545                 550                 555                 560

Ala Phe Leu Ile Glu Asn Gly Ala Arg Thr His Thr Gln Ala Gly Val
                565                 570                 575

Ala Gly Pro Ala Ala Ala Leu Leu Asp Phe Thr Leu Arg Met Leu Pro
            580                 585                 590

Arg Lys Thr Ala Val Gly Asp Phe Leu Ala Ser Thr Arg Met Ser Leu
        595                 600                 605

Ala Asp Val Ala Ala His Arg Pro Leu Ile Gln His Val Leu Asp Glu
    610                 615                 620

Asn Ser Gln Ile Gly Arg Leu Ala Leu Ala Lys Leu Val Leu Val Ala
625                 630                 635                 640

Arg Asp Val Ile Arg Glu Thr Asp Ala Phe Tyr Gly Asp Leu Ala Asp
                645                 650                 655

Leu Asp Leu Gln Leu Arg Ala Ala Pro Pro Ala Asn Leu Tyr Ala Arg
            660                 665                 670

Leu Gly Glu Trp Leu Leu Glu Arg Ser Arg Ala His Pro Asn Thr Leu
        675                 680                 685

Phe Ala Pro Ala Thr Pro Thr His Pro Glu Pro Leu Leu His Arg Ile
    690                 695                 700

Gln Ala Leu Ala Gln Phe Ala Arg Gly Glu Glu Met Arg Val Glu Ala
705                 710                 715                 720

Glu Ala Arg Glu Met Arg Glu Ala Leu Asp Ala Leu Ala Arg Gly Val
                725                 730                 735

Asp Ser Val Ser Gln Arg Ala Gly Pro Leu Thr Val Met Pro Val Pro
            740                 745                 750

Ala Ala Pro Gly Ala Gly Gly Arg Ala Pro Cys Pro Pro Ala Leu Gly
```

-continued

```
        755                 760                 765

Pro Glu Ala Ile Gln Ala Arg Leu Glu Asp Val Arg Ile Gln Ala Arg
    770                 775                 780

Arg Ala Ile Glu Ser Ala Val Lys Glu Tyr Phe His Arg Gly Ala Val
785                 790                 795                 800

Tyr Ser Ala Lys Ala Leu Gln Ala Ser Asp Ser His Asp Cys Arg Phe
                805                 810                 815

His Val Ala Ser Ala Ala Val Val Pro Met Val Gln Leu Leu Glu Ser
            820                 825                 830

Leu Pro Ala Phe Asp Gln His Thr Arg Asp Val Ala Gln Arg Ala Ala
        835                 840                 845

Leu Pro Pro Pro Pro Pro Leu Ala Thr Ser Pro Gln Ala Ile Leu Leu
    850                 855                 860

Arg Asp Leu Leu Gln Arg Gly Gln Pro Leu Asp Ala Pro Glu Asp Leu
865                 870                 875                 880

Ala Ala Trp Leu Ser Val Leu Thr Asp Ala Ala Thr Gln Gly Leu Ile
                885                 890                 895

Glu Arg Lys Pro Leu Glu Glu Leu Ala Arg Ser Ile His Gly Ile Asn
            900                 905                 910

Asp Gln Gln Ala Arg Arg Ser Ser Gly Leu Ala Glu Leu Gln Arg Phe
        915                 920                 925

Asp Ala Leu Asp Ala Ala Leu Ala Gln Gln Leu Asp Ser Asp Ala Ala
    930                 935                 940

Phe Val Pro Ala Thr Gly Pro Ala Pro Tyr Val Asp Gly Gly Gly Leu
945                 950                 955                 960

Ser Pro Glu Ala Thr Arg Met Ala Glu Asp Ala Leu Arg Gln Ala Arg
                965                 970                 975

Ala Met Glu Ala Ala Lys Met Thr Ala Glu Leu Ala Pro Glu Ala Arg
            980                 985                 990

Ser Arg Leu Arg Glu Arg Ala His  Ala Leu Glu Ala Met  Leu Asn Asp
        995                 1000                1005

Ala Arg  Glu Arg Ala Lys Val  Ala His Asp Ala Arg  Glu Lys Phe
    1010                1015                1020

Leu His  Lys Leu Gln Gly Val  Leu Arg Pro Leu Pro  Asp Phe Val
    1025                1030                1035

Gly Leu  Lys Ala Cys Pro Ala  Val Leu Ala Thr Leu  Arg Ala Ser
    1040                1045                1050

Leu Pro  Ala Gly Trp Thr Asp  Leu Ala Asp Ala Val  Arg Gly Pro
    1055                1060                1065

Pro Pro  Glu Val Thr Ala Ala  Leu Arg Ala Asp Leu  Trp Gly Leu
    1070                1075                1080

Leu Gly  Gln Tyr Arg Glu Ala  Leu Glu His Pro Thr  Pro Asp Thr
    1085                1090                1095

Ala Thr  Ala Leu Ala Gly Leu  His Pro Ala Phe Val  Val Val Leu
    1100                1105                1110

Lys Thr  Leu Phe Ala Asp Ala  Pro Glu Thr Pro Val  Leu Val Gln
    1115                1120                1125

Phe Phe  Ser Asp His Ala Pro  Thr Ile Ala Lys Ala  Val Ser Asn
    1130                1135                1140

Ala Ile  Asn Ala Gly Ser Ala  Ala Val Ala Thr Ala  Ser Pro Ala
    1145                1150                1155

Ala Thr  Val Asp Ala Ala Val  Arg Ala His Gly Ala  Leu Ala Asp
    1160                1165                1170
```

```
Ala Val Ser Ala Leu Gly Ala Ala Ala Arg Asp Pro Ala Ser Pro
    1175                1180                1185

Leu Ser Phe Leu Ala Val Leu Ala Asp Ser Ala Ala Gly Tyr Val
    1190                1195                1200

Lys Ala Thr Arg Leu Ala Leu Glu Ala Arg Gly Ala Ile Asp Glu
    1205                1210                1215

Leu Thr Thr Leu Gly Ser Ala Ala Ala Asp Leu Val Val Gln Ala
    1220                1225                1230

Arg Arg Ala Cys Ala Gln Pro Glu Gly Asp His Ala Ala Leu Ile
    1235                1240                1245

Asp Ala Ala Ala Arg Ala Thr Thr Ala Ala Arg Glu Ser Leu Ala
    1250                1255                1260

Gly His Glu Ala Gly Phe Gly Gly Leu Leu His Ala Glu Gly Thr
    1265                1270                1275

Ala Gly Asp His Ser Pro Ser Gly Arg Ala Leu Gln Glu Leu Gly
    1280                1285                1290

Lys Val Ile Gly Ala Thr Arg Arg Arg Ala Asp Glu Leu Glu Ala
    1295                1300                1305

Ala Val Ala Asp Leu Thr Ala Lys Met Ala Ala Gln Arg Ala Arg
    1310                1315                1320

Gly Ser Ser Glu Arg Trp Ala Ala Gly Val Glu Ala Ala Leu Asp
    1325                1330                1335

Arg Val Glu Asn Arg Ala Glu Phe Asp Val Val Glu Leu Arg Arg
    1340                1345                1350

Leu Gln Ala Leu Ala Gly Thr His Gly Tyr Asn Pro Arg Asp Phe
    1355                1360                1365

Arg Lys Arg Ala Glu Gln Ala Leu Ala Ala Asn Ala Glu Ala Val
    1370                1375                1380

Thr Leu Ala Leu Asp Thr Ala Phe Ala Phe Asn Pro Tyr Thr Pro
    1385                1390                1395

Glu Asn Gln Arg His Pro Met Leu Pro Pro Leu Ala Ala Ile His
    1400                1405                1410

Arg Leu Gly Trp Ser Ala Ala Phe His Ala Ala Ala Glu Thr Tyr
    1415                1420                1425

Ala Asp Met Phe Arg Val Asp Ala Glu Pro Leu Ala Arg Leu Leu
    1430                1435                1440

Arg Ile Ala Glu Gly Leu Leu Glu Met Ala Gln Ala Gly Asp Gly
    1445                1450                1455

Phe Ile Asp Tyr His Glu Ala Val Gly Arg Leu Ala Asp Asp Met
    1460                1465                1470

Thr Ser Val Pro Gly Leu Arg Arg Tyr Val Pro Phe Phe Gln His
    1475                1480                1485

Gly Tyr Ala Asp Tyr Val Glu Leu Arg Asp Arg Leu Asp Ala Ile
    1490                1495                1500

Arg Ala Asp Val His Arg Ala Leu Gly Gly Val Pro Leu Asp Leu
    1505                1510                1515

Ala Ala Ala Ala Glu Gln Ile Ser Ala Ala Arg Asn Asp Pro Glu
    1520                1525                1530

Ala Thr Ala Glu Leu Val Arg Thr Gly Val Thr Leu Pro Cys Pro
    1535                1540                1545

Ser Glu Asp Ala Leu Val Ala Cys Ala Ala Ala Leu Glu Arg Val
    1550                1555                1560
```

-continued

```
Asp Gln  Ser Pro Val Lys Asn  Thr Ala Tyr Ala Glu  Tyr Val Ala
    1565                 1570                 1575

Phe Val  Thr Arg Gln Asp Thr  Ala Glu Thr Lys Asp  Ala Val Val
    1580                 1585                 1590

Arg Ala  Lys Gln Gln Arg Ala  Glu Ala Thr Glu Arg  Val Met Ala
    1595                 1600                 1605

Gly Leu  Arg Glu Ala Leu Ala  Ala Arg Glu Arg Arg  Ala Gln Ile
    1610                 1615                 1620

Glu Ala  Glu Gly Leu Ala Asn  Leu Lys Thr Met Leu  Lys Val Val
    1625                 1630                 1635

Ala Val  Pro Ala Thr Val Ala  Lys Thr Leu Asp Gln  Ala Arg Ser
    1640                 1645                 1650

Val Ala  Glu Ile Ala Asp Gln  Val Glu Val Leu Leu  Asp Gln Thr
    1655                 1660                 1665

Glu Lys  Thr Arg Glu Leu Asp  Val Pro Ala Val Ile  Trp Leu Glu
    1670                 1675                 1680

His Ala  Gln Arg Thr Phe Glu  Thr His Pro Leu Ser  Ala Ala Arg
    1685                 1690                 1695

Gly Asp  Gly Pro Gly Pro Leu  Ala Arg His Ala Gly  Arg Leu Gly
    1700                 1705                 1710

Ala Leu  Phe Asp Thr Arg Arg  Arg Val Asp Ala Leu  Arg Arg Ser
    1715                 1720                 1725

Leu Glu  Glu Ala Glu Ala Glu  Trp Asp Glu Val Trp  Gly Arg Phe
    1730                 1735                 1740

Gly Arg  Val Arg Gly Gly Ala  Trp Lys Ser Pro Glu  Gly Phe Arg
    1745                 1750                 1755

Ala Met  His Glu Gln Leu Arg  Ala Leu Gln Asp Thr  Thr Asn Thr
    1760                 1765                 1770

Val Ser  Gly Leu Arg Ala Gln  Pro Ala Tyr Glu Arg  Leu Ser Ala
    1775                 1780                 1785

Arg Tyr  Gln Gly Val Leu Gly  Ala Lys Gly Ala Glu  Arg Ala Glu
    1790                 1795                 1800

Ala Val  Glu Glu Leu Gly Ala  Arg Val Thr Lys His  Thr Ala Leu
    1805                 1810                 1815

Cys Ala  Arg Leu Arg Asp Glu  Val Val Arg Arg Val  Pro Trp Glu
    1820                 1825                 1830

Met Asn  Phe Asp Ala Leu Gly  Gly Leu Leu Ala Glu  Phe Asp Ala
    1835                 1840                 1845

Ala Ala  Ala Asp Leu Ala Pro  Trp Ala Val Glu Glu  Phe Arg Gly
    1850                 1855                 1860

Ala Arg  Glu Leu Ile Gln Tyr  Arg Met Gly Leu Tyr  Ser Ala Tyr
    1865                 1870                 1875

Ala Arg  Ala Gly Gly Gln Thr  Gly Ala Gly Ala Glu  Ser Ala Pro
    1880                 1885                 1890

Ala Pro  Leu Leu Val Asp Leu  Arg Ala Leu Asp Ala  Arg Ala Arg
    1895                 1900                 1905

Ala Ser  Ser Ser Pro Glu Gly  His Glu Val Asp Pro  Gln Leu Leu
    1910                 1915                 1920

Arg Arg  Arg Gly Glu Ala Tyr  Leu Arg Ala Gly Gly  Asp Pro Gly
    1925                 1930                 1935

Pro Leu  Val Leu Arg Glu Ala  Val Ser Ala Leu Asp  Leu Pro Phe
    1940                 1945                 1950

Ala Thr  Ser Phe Leu Ala Pro  Asp Gly Thr Pro Leu  Gln Tyr Ala
```

1955 1960 1965

Leu Cys Phe Pro Ala Val Thr Asp Lys Leu Gly Ala Leu Leu Met
1970 1975 1980

Arg Pro Glu Ala Ala Cys Val Arg Pro Pro Leu Pro Thr Asp Val
1985 1990 1995

Leu Glu Ser Ala Pro Thr Val Thr Ala Met Tyr Val Leu Thr Val
2000 2005 2010

Val Asn Arg Leu Gln Leu Ala Leu Ser Asp Ala Gln Ala Ala Asn
2015 2020 2025

Phe Gln Leu Phe Gly Arg Phe Val Arg His Arg Gln Ala Thr Trp
2030 2035 2040

Gly Ala Ser Met Asp Ala Ala Ala Glu Leu Tyr Val Ala Leu Val
2045 2050 2055

Ala Thr Thr Leu Thr Arg Glu Phe Gly Cys Arg Trp Ala Gln Leu
2060 2065 2070

Gly Trp Ala Ser Gly Ala Ala Ala Pro Arg Pro Pro Pro Gly Pro
2075 2080 2085

Arg Gly Ser Gln Arg His Cys Val Ala Phe Asn Glu Asn Asp Val
2090 2095 2100

Leu Val Ala Leu Val Ala Gly Val Pro Glu His Ile Tyr Asn Phe
2105 2110 2115

Trp Arg Leu Asp Leu Val Arg Gln His Glu Tyr Met His Leu Thr
2120 2125 2130

Leu Glu Arg Ala Phe Glu Asp Ala Ala Glu Ser Met Leu Phe Val
2135 2140 2145

Gln Arg Leu Thr Pro His Pro Asp Ala Arg Ile Arg Val Leu Pro
2150 2155 2160

Thr Phe Leu Asp Gly Gly Pro Pro Thr Arg Gly Leu Leu Phe Gly
2165 2170 2175

Thr Arg Leu Ala Asp Trp Arg Arg Gly Lys Leu Ser Glu Thr Asp
2180 2185 2190

Pro Leu Ala Pro Trp Arg Ser Ala Leu Glu Leu Gly Thr Gln Arg
2195 2200 2205

Arg Asp Val Pro Ala Leu Gly Lys Leu Ser Pro Ala Gln Ala Leu
2210 2215 2220

Ala Ala Val Ser Val Leu Gly Arg Met Cys Leu Pro Ser Ala Ala
2225 2230 2235

Leu Ala Ala Leu Trp Thr Cys Met Phe Pro Asp Asp Tyr Thr Glu
2240 2245 2250

Tyr Asp Ser Phe Asp Ala Leu Leu Ala Ala Arg Leu Glu Ser Gly
2255 2260 2265

Gln Thr Leu Gly Pro Ala Gly Gly Arg Glu Ala Ser Leu Pro Glu
2270 2275 2280

Ala Pro His Ala Leu Tyr Arg Pro Thr Gly Gln His Val Ala Val
2285 2290 2295

Leu Ala Ala Ala Thr His Arg Thr Pro Ala Ala Arg Val Thr Ala
2300 2305 2310

Met Asp Leu Val Leu Ala Ala Val Leu Leu Gly Ala Pro Val Val
2315 2320 2325

Val Ala Leu Arg Asn Thr Thr Ala Phe Ser Arg Glu Ser Glu Leu
2330 2335 2340

Glu Leu Cys Leu Thr Leu Phe Asp Ser Arg Pro Gly Gly Pro Asp
2345 2350 2355

-continued

```
Ala Ala  Leu Arg Asp Val Val  Ser Ser Asp Ile Glu  Thr Trp Ala
    2360                 2365                 2370

Val Gly  Leu Leu His Thr Asp  Leu Asn Pro Ile Glu  Asn Ala Cys
    2375                 2380                 2385

Leu Ala  Ala Gln Leu Pro Arg  Leu Ser Ala Leu Ile  Ala Glu Arg
    2390                 2395                 2400

Pro Leu  Ala Asp Gly Pro Pro  Cys Leu Val Leu Val  Asp Ile Ser
    2405                 2410                 2415

Met Thr  Pro Val Ala Val Leu  Trp Glu Ala Pro Glu  Pro Pro Gly
    2420                 2425                 2430

Pro Pro  Asp Val Arg Phe Val  Gly Ser Glu Ala Thr  Glu Glu Leu
    2435                 2440                 2445

Pro Phe  Val Ala Thr Ala Gly  Asp Val Leu Ala Ala  Ser Ala Ala
    2450                 2455                 2460

Asp Ala  Asp Pro Phe Phe Ala  Arg Ala Ile Leu Gly  Arg Pro Phe
    2465                 2470                 2475

Asp Ala  Ser Leu Leu Thr Gly  Glu Leu Phe Pro Gly  His Pro Val
    2480                 2485                 2490

Tyr Gln  Arg Pro Leu Ala Asp  Glu Ala Gly Pro Ser  Ala Pro Thr
    2495                 2500                 2505

Ala Ala  Arg Asp Pro Arg Asp  Leu Ala Gly Gly Asp  Gly Gly Ser
    2510                 2515                 2520

Gly Pro  Glu Asp Pro Ala Ala  Pro Pro Ala Arg Gln  Ala Asp Pro
    2525                 2530                 2535

Gly Val  Leu Ala Pro Thr Leu  Leu Thr Asp Ala Thr  Thr Gly Glu
    2540                 2545                 2550

Pro Val  Pro Pro Arg Met Trp  Ala Trp Ile His Gly  Leu Glu Glu
    2555                 2560                 2565

Leu Ala  Ser Asp Asp Ala Gly  Gly Pro Thr Pro Asn  Pro Ala Pro
    2570                 2575                 2580

Ala Leu  Leu Pro Pro Pro Ala  Thr Asp Gln Ser Val  Pro Thr Ser
    2585                 2590                 2595

Gln Tyr  Ala Pro Arg Pro Ile  Gly Pro Ala Ala Thr  Ala Arg Glu
    2600                 2605                 2610

Thr Arg  Pro Ser Val Pro Pro  Gln Gln Asn Thr Gly  Arg Val Pro
    2615                 2620                 2625

Val Ala  Pro Arg Asp Asp Pro  Arg Pro Ser Pro Pro  Thr Pro Ser
    2630                 2635                 2640

Pro Pro  Ala Asp Ala Ala Leu  Pro Pro Pro Ala Phe  Ser Gly Ser
    2645                 2650                 2655

Ala Ala  Ala Phe Ser Ala Ala  Val Pro Arg Val Arg  Arg Ser Arg
    2660                 2665                 2670

Arg Thr  Arg Ala Lys Ser Arg  Ala Pro Arg Ala Ser  Ala Pro Pro
    2675                 2680                 2685

Glu Gly  Trp Arg Pro Pro Ala  Leu Pro Ala Pro Val  Ala Pro Val
    2690                 2695                 2700

Ala Ala  Ser Ala Arg Pro Pro  Asp Gln Pro Pro Thr  Pro Glu Ser
    2705                 2710                 2715

Ala Pro  Pro Ala Trp Val Ser  Ala Leu Pro Leu Pro  Pro Gly Pro
    2720                 2725                 2730

Ala Ser  Ala Arg Gly Ala Phe  Pro Ala Pro Thr Leu  Ala Pro Ile
    2735                 2740                 2745
```

-continued

```
Pro Pro Pro Pro Ala Glu Gly Ala Val Val Pro Gly Gly Asp Arg
    2750                2755                2760

Arg Arg Gly Arg Arg Gln Thr Thr Ala Gly Pro Ser Pro Thr Pro
    2765                2770                2775

Pro Arg Gly Pro Ala Ala Gly Pro Pro Arg Arg Leu Thr Arg Pro
    2780                2785                2790

Ala Val Ala Ser Leu Ser Ala Ser Leu Asn Ser Leu Pro Ser Pro
    2795                2800                2805

Arg Asp Pro Ala Asp His Ala Ala Ala Val Ser Ala Ala Ala Ala
    2810                2815                2820

Ala Val Pro Pro Ser Pro Gly Leu Ala Pro Pro Thr Ser Ala Val
    2825                2830                2835

Gln Thr Ser Pro Pro Pro Leu Ala Pro Gly Pro Val Ala Pro Ser
    2840                2845                2850

Glu Pro Leu Cys Gly Trp Val Val Pro Gly Gly Pro Val Ala Arg
    2855                2860                2865

Arg Pro Pro Pro Gln Ser Pro Ala Thr Lys Pro Ala Ala Arg Thr
    2870                2875                2880

Arg Ile Arg Ala Arg Ser Val Pro Gln Pro Pro Leu Pro Gln Pro
    2885                2890                2895

Pro Leu Pro Gln Pro Pro Leu Pro Gln Pro Pro Leu Pro Gln Pro
    2900                2905                2910

Pro Leu Pro Gln Pro Pro Leu Pro Gln Pro Pro Leu Pro Gln Pro
    2915                2920                2925

Pro Leu Pro Gln Pro Pro Leu Pro Gln Pro Pro Leu Pro Gln Pro
    2930                2935                2940

Pro Leu Pro Pro Val Thr Arg Thr Leu Thr Pro Gln Ser Arg Asp
    2945                2950                2955

Ser Val Pro Thr Pro Glu Ser Pro Thr His Thr Asn Thr His Leu
    2960                2965                2970

Pro Val Ser Ala Val Thr Ser Trp Ala Ser Ser Leu Ala Leu His
    2975                2980                2985

Val Asp Ser Ala Pro Pro Pro Ala Ser Leu Leu Gln Thr Leu His
    2990                2995                3000

Ile Ser Ser Asp Asp Glu His Ser Asp Ala Asp Ser Leu Arg Phe
    3005                3010                3015

Ser Asp Ser Asp Asp Thr Glu Ala Leu Asp Pro Leu Pro Pro Glu
    3020                3025                3030

Pro His Leu Pro Pro Ala Asp Glu Pro Pro Gly Pro Leu Ala Ala
    3035                3040                3045

Asp His Leu Gln Ser Pro His Ser Gln Phe Gly Pro Leu Pro Val
    3050                3055                3060

Gln Ala Asn Ala Val Leu Ser Arg Arg Tyr Val Arg Ser Thr Gly
    3065                3070                3075

Arg Ser Ala Leu Ala Val Leu Ile Arg Ala Cys Arg Arg Ile Gln
    3080                3085                3090

Gln Gln Leu Gln Arg Thr Arg Arg Ala Leu Phe Gln Arg Ser Asn
    3095                3100                3105

Ala Val Leu Thr Ser Leu His His Val Arg Met Leu Leu Gly
    3110                3115                3120
```

<210> SEQ ID NO 23
<211> LENGTH: 964
<212> TYPE: PRT

<213> ORGANISM: human herpesvirus 2

<400> SEQUENCE: 23

Ala Ala Gln Arg Ala Arg Gly Ser Ser Glu Arg Trp Ala Ala Gly Val
1               5                   10                  15

Glu Ala Ala Leu Asp Arg Val Glu Asn Arg Ala Glu Phe Asp Val Val
            20                  25                  30

Glu Leu Arg Arg Leu Gln Ala Leu Ala Gly Thr His Gly Tyr Asn Pro
        35                  40                  45

Arg Asp Phe Arg Lys Arg Ala Glu Gln Ala Leu Ala Ala Asn Ala Glu
    50                  55                  60

Ala Val Thr Leu Ala Leu Asp Thr Ala Phe Ala Phe Asn Pro Tyr Thr
65                  70                  75                  80

Pro Glu Asn Gln Arg His Pro Met Leu Pro Pro Leu Ala Ala Ile His
                85                  90                  95

Arg Leu Gly Trp Ser Ala Ala Phe His Ala Ala Ala Glu Thr Tyr Ala
            100                 105                 110

Asp Met Phe Arg Val Asp Ala Glu Pro Leu Ala Arg Leu Leu Arg Ile
        115                 120                 125

Ala Glu Gly Leu Leu Glu Met Ala Gln Ala Gly Asp Gly Phe Ile Asp
    130                 135                 140

Tyr His Glu Ala Val Gly Arg Leu Ala Asp Asp Met Thr Ser Val Pro
145                 150                 155                 160

Gly Leu Arg Arg Tyr Val Pro Phe Phe Gln His Gly Tyr Ala Asp Tyr
                165                 170                 175

Val Glu Leu Arg Asp Arg Leu Asp Ala Ile Arg Ala Asp Val His Arg
            180                 185                 190

Ala Leu Gly Gly Val Pro Leu Asp Leu Ala Ala Ala Ala Glu Gln Ile
        195                 200                 205

Ser Ala Ala Arg Asn Asp Pro Glu Ala Thr Ala Glu Leu Val Arg Thr
    210                 215                 220

Gly Val Thr Leu Pro Cys Pro Ser Glu Asp Ala Leu Val Ala Cys Ala
225                 230                 235                 240

Ala Ala Leu Glu Arg Val Asp Gln Ser Pro Val Lys Asn Thr Ala Tyr
                245                 250                 255

Ala Glu Tyr Val Ala Phe Val Thr Arg Gln Asp Thr Ala Glu Thr Lys
            260                 265                 270

Asp Ala Val Val Arg Ala Lys Gln Gln Arg Ala Glu Ala Thr Glu Arg
        275                 280                 285

Val Met Ala Gly Leu Arg Glu Ala Leu Ala Ala Arg Glu Arg Arg Ala
    290                 295                 300

Gln Ile Glu Ala Glu Gly Leu Ala Asn Leu Lys Thr Met Leu Lys Val
305                 310                 315                 320

Val Ala Val Pro Ala Thr Val Ala Lys Thr Leu Asp Gln Ala Arg Ser
                325                 330                 335

Val Ala Glu Ile Ala Asp Gln Val Glu Val Leu Leu Asp Gln Thr Glu
            340                 345                 350

Lys Thr Arg Glu Leu Asp Val Pro Ala Val Ile Trp Leu Glu His Ala
        355                 360                 365

Gln Arg Thr Phe Glu Thr His Pro Leu Ser Ala Ala Arg Gly Asp Gly
    370                 375                 380

Pro Gly Pro Leu Ala Arg His Ala Gly Arg Leu Gly Ala Leu Phe Asp
385                 390                 395                 400

-continued

Thr Arg Arg Arg Val Asp Ala Leu Arg Arg Ser Leu Glu Glu Ala Glu
405 410 415

Ala Glu Trp Asp Glu Val Trp Gly Arg Phe Gly Arg Val Arg Gly Gly
420 425 430

Ala Trp Lys Ser Pro Glu Gly Phe Arg Ala Met His Glu Gln Leu Arg
435 440 445

Ala Leu Gln Asp Thr Thr Asn Thr Val Ser Gly Leu Arg Ala Gln Pro
450 455 460

Ala Tyr Glu Arg Leu Ser Ala Arg Tyr Gln Gly Val Leu Gly Ala Lys
465 470 475 480

Gly Ala Glu Arg Ala Glu Ala Val Glu Glu Leu Gly Ala Arg Val Thr
485 490 495

Lys His Thr Ala Leu Cys Ala Arg Leu Arg Asp Glu Val Val Arg Arg
500 505 510

Val Pro Trp Glu Met Asn Phe Asp Ala Leu Gly Gly Leu Leu Ala Glu
515 520 525

Phe Asp Ala Ala Ala Ala Asp Leu Ala Pro Trp Ala Val Glu Glu Phe
530 535 540

Arg Gly Ala Arg Glu Leu Ile Gln Tyr Arg Met Gly Leu Tyr Ser Ala
545 550 555 560

Tyr Ala Arg Ala Gly Gly Gln Thr Gly Ala Gly Ala Glu Ser Ala Pro
565 570 575

Ala Pro Leu Leu Val Asp Leu Arg Ala Leu Asp Ala Arg Ala Arg Ala
580 585 590

Ser Ser Ser Pro Glu Gly His Glu Val Asp Pro Gln Leu Leu Arg Arg
595 600 605

Arg Gly Glu Ala Tyr Leu Arg Ala Gly Gly Asp Pro Gly Pro Leu Val
610 615 620

Leu Arg Glu Ala Val Ser Ala Leu Asp Leu Pro Phe Ala Thr Ser Phe
625 630 635 640

Leu Ala Pro Asp Gly Thr Pro Leu Gln Tyr Ala Leu Cys Phe Pro Ala
645 650 655

Val Thr Asp Lys Leu Gly Ala Leu Leu Met Arg Pro Glu Ala Ala Cys
660 665 670

Val Arg Pro Pro Leu Pro Thr Asp Val Leu Glu Ser Ala Pro Thr Val
675 680 685

Thr Ala Met Tyr Val Leu Thr Val Val Asn Arg Leu Gln Leu Ala Leu
690 695 700

Ser Asp Ala Gln Ala Ala Asn Phe Gln Leu Phe Gly Arg Phe Val Arg
705 710 715 720

His Arg Gln Ala Thr Trp Gly Ala Ser Met Asp Ala Ala Ala Glu Leu
725 730 735

Tyr Val Ala Leu Val Ala Thr Thr Leu Thr Arg Glu Phe Gly Cys Arg
740 745 750

Trp Ala Gln Leu Gly Trp Ala Ser Gly Ala Ala Ala Pro Arg Pro Pro
755 760 765

Pro Gly Pro Arg Gly Ser Gln Arg His Cys Val Ala Phe Asn Glu Asn
770 775 780

Asp Val Leu Val Ala Leu Val Ala Gly Val Pro Glu His Ile Tyr Asn
785 790 795 800

Phe Trp Arg Leu Asp Leu Val Arg Gln His Glu Tyr Met His Leu Thr
805 810 815

Leu Glu Arg Ala Phe Glu Asp Ala Ala Glu Ser Met Leu Phe Val Gln

```
            820                 825                 830

Arg Leu Thr Pro His Pro Asp Ala Arg Ile Arg Val Leu Pro Thr Phe
        835                 840                 845

Leu Asp Gly Gly Pro Pro Thr Arg Gly Leu Leu Phe Gly Thr Arg Leu
    850                 855                 860

Ala Asp Trp Arg Arg Gly Lys Leu Ser Glu Thr Asp Pro Leu Ala Pro
865                 870                 875                 880

Trp Arg Ser Ala Leu Glu Leu Gly Thr Gln Arg Arg Asp Val Pro Ala
                885                 890                 895

Leu Gly Lys Leu Ser Pro Ala Gln Ala Leu Ala Ala Val Ser Val Leu
            900                 905                 910

Gly Arg Met Cys Leu Pro Ser Ala Ala Leu Ala Ala Leu Trp Thr Cys
        915                 920                 925

Met Phe Pro Asp Asp Tyr Thr Glu Tyr Asp Ser Phe Asp Ala Leu Leu
    930                 935                 940

Ala Ala Arg Leu Glu Ser Gly Gln Thr Leu Gly Pro Ala Gly Gly Arg
945                 950                 955                 960

Glu Ala Ser Leu


<210> SEQ ID NO 24
<211> LENGTH: 870
<212> TYPE: PRT
<213> ORGANISM: human herpesvirus 2

<400> SEQUENCE: 24

Glu Tyr Asp Ser Phe Asp Ala Leu Leu Ala Ala Arg Leu Glu Ser Gly
1               5                   10                  15

Gln Thr Leu Gly Pro Ala Gly Gly Arg Glu Ala Ser Leu Pro Glu Ala
            20                  25                  30

Pro His Ala Leu Tyr Arg Pro Thr Gly Gln His Val Ala Val Leu Ala
        35                  40                  45

Ala Ala Thr His Arg Thr Pro Ala Ala Arg Val Thr Ala Met Asp Leu
    50                  55                  60

Val Leu Ala Ala Val Leu Leu Gly Ala Pro Val Val Val Ala Leu Arg
65                  70                  75                  80

Asn Thr Thr Ala Phe Ser Arg Glu Ser Glu Leu Glu Leu Cys Leu Thr
                85                  90                  95

Leu Phe Asp Ser Arg Pro Gly Gly Pro Asp Ala Ala Leu Arg Asp Val
            100                 105                 110

Val Ser Ser Asp Ile Glu Thr Trp Ala Val Gly Leu Leu His Thr Asp
        115                 120                 125

Leu Asn Pro Ile Glu Asn Ala Cys Leu Ala Ala Gln Leu Pro Arg Leu
    130                 135                 140

Ser Ala Leu Ile Ala Glu Arg Pro Leu Ala Asp Gly Pro Pro Cys Leu
145                 150                 155                 160

Val Leu Val Asp Ile Ser Met Thr Pro Val Ala Val Leu Trp Glu Ala
                165                 170                 175

Pro Glu Pro Pro Gly Pro Pro Asp Val Arg Phe Val Gly Ser Glu Ala
            180                 185                 190

Thr Glu Glu Leu Pro Phe Val Ala Thr Ala Gly Asp Val Leu Ala Ala
        195                 200                 205

Ser Ala Ala Asp Ala Asp Pro Phe Phe Ala Arg Ala Ile Leu Gly Arg
    210                 215                 220

Pro Phe Asp Ala Ser Leu Leu Thr Gly Glu Leu Phe Pro Gly His Pro
```

-continued

```
225                 230                 235                 240

Val Tyr Gln Arg Pro Leu Ala Asp Glu Ala Gly Pro Ser Ala Pro Thr
                245                 250                 255

Ala Ala Arg Asp Pro Arg Asp Leu Ala Gly Gly Asp Gly Gly Ser Gly
            260                 265                 270

Pro Glu Asp Pro Ala Ala Pro Pro Ala Arg Gln Ala Asp Pro Gly Val
        275                 280                 285

Leu Ala Pro Thr Leu Leu Thr Asp Ala Thr Thr Gly Glu Pro Val Pro
    290                 295                 300

Pro Arg Met Trp Ala Trp Ile His Gly Leu Glu Glu Leu Ala Ser Asp
305                 310                 315                 320

Asp Ala Gly Gly Pro Thr Pro Asn Pro Ala Pro Ala Leu Leu Pro Pro
                325                 330                 335

Pro Ala Thr Asp Gln Ser Val Pro Thr Ser Gln Tyr Ala Pro Arg Pro
            340                 345                 350

Ile Gly Pro Ala Ala Thr Ala Arg Glu Thr Arg Pro Ser Val Pro Pro
        355                 360                 365

Gln Gln Asn Thr Gly Arg Val Pro Val Ala Pro Arg Asp Asp Pro Arg
    370                 375                 380

Pro Ser Pro Pro Thr Pro Ser Pro Pro Ala Asp Ala Ala Leu Pro Pro
385                 390                 395                 400

Pro Ala Phe Ser Gly Ser Ala Ala Ala Phe Ser Ala Ala Val Pro Arg
                405                 410                 415

Val Arg Arg Ser Arg Arg Thr Arg Ala Lys Ser Arg Ala Pro Arg Ala
            420                 425                 430

Ser Ala Pro Pro Glu Gly Trp Arg Pro Pro Ala Leu Pro Ala Pro Val
        435                 440                 445

Ala Pro Val Ala Ala Ser Ala Arg Pro Pro Asp Gln Pro Pro Thr Pro
    450                 455                 460

Glu Ser Ala Pro Pro Ala Trp Val Ser Ala Leu Pro Leu Pro Pro Gly
465                 470                 475                 480

Pro Ala Ser Ala Arg Gly Ala Phe Pro Ala Pro Thr Leu Ala Pro Ile
                485                 490                 495

Pro Pro Pro Pro Ala Glu Gly Ala Val Val Pro Gly Gly Asp Arg Arg
            500                 505                 510

Arg Gly Arg Arg Gln Thr Thr Ala Gly Pro Ser Pro Thr Pro Pro Arg
        515                 520                 525

Gly Pro Ala Ala Gly Pro Pro Arg Arg Leu Thr Arg Pro Ala Val Ala
    530                 535                 540

Ser Leu Ser Ala Ser Leu Asn Ser Leu Pro Ser Pro Arg Asp Pro Ala
545                 550                 555                 560

Asp His Ala Ala Ala Val Ser Ala Ala Ala Ala Ala Val Pro Pro Ser
                565                 570                 575

Pro Gly Leu Ala Pro Pro Thr Ser Ala Val Gln Thr Ser Pro Pro Pro
            580                 585                 590

Leu Ala Pro Gly Pro Val Ala Pro Ser Glu Pro Leu Cys Gly Trp Val
        595                 600                 605

Val Pro Gly Gly Pro Val Ala Arg Arg Pro Pro Pro Gln Ser Pro Ala
    610                 615                 620

Thr Lys Pro Ala Ala Arg Thr Arg Ile Arg Ala Arg Ser Val Pro Gln
625                 630                 635                 640

Pro Pro Leu Pro Gln Pro Pro Leu Pro Gln Pro Pro Leu Pro Gln Pro
                645                 650                 655
```

Pro Leu Pro Gln Pro Pro Leu Pro Gln Pro Pro Leu Pro Gln Pro Pro
660 665 670

Leu Pro Gln Pro Pro Leu Pro Gln Pro Pro Leu Pro Gln Pro Pro Leu
675 680 685

Pro Gln Pro Pro Leu Pro Pro Val Thr Arg Thr Leu Thr Pro Gln Ser
690 695 700

Arg Asp Ser Val Pro Thr Pro Glu Ser Pro Thr His Thr Asn Thr His
705 710 715 720

Leu Pro Val Ser Ala Val Thr Ser Trp Ala Ser Ser Leu Ala Leu His
725 730 735

Val Asp Ser Ala Pro Pro Pro Ala Ser Leu Leu Gln Thr Leu His Ile
740 745 750

Ser Ser Asp Asp Glu His Ser Asp Ala Asp Ser Leu Arg Phe Ser Asp
755 760 765

Ser Asp Asp Thr Glu Ala Leu Asp Pro Leu Pro Pro Glu Pro His Leu
770 775 780

Pro Pro Ala Asp Glu Pro Pro Gly Pro Leu Ala Ala Asp His Leu Gln
785 790 795 800

Ser Pro His Ser Gln Phe Gly Pro Leu Pro Val Gln Ala Asn Ala Val
805 810 815

Leu Ser Arg Arg Tyr Val Arg Ser Thr Gly Arg Ser Ala Leu Ala Val
820 825 830

Leu Ile Arg Ala Cys Arg Arg Ile Gln Gln Gln Leu Gln Arg Thr Arg
835 840 845

Arg Ala Leu Phe Gln Arg Ser Asn Ala Val Leu Thr Ser Leu His His
850 855 860

Val Arg Met Leu Leu Gly
865 870

<210> SEQ ID NO 25
<211> LENGTH: 337
<212> TYPE: PRT
<213> ORGANISM: human herpesvirus 2

<400> SEQUENCE: 25

Met Asp Pro Ala Val Ser Pro Ala Ser Thr Asp Pro Leu Asp Thr His
1 5 10 15

Ala Ser Gly Ala Gly Ala Ala Pro Ile Pro Val Cys Pro Thr Pro Glu
20 25 30

Arg Tyr Phe Tyr Thr Ser Gln Cys Pro Asp Ile Asn His Leu Arg Ser
35 40 45

Leu Ser Ile Leu Asn Arg Trp Leu Glu Thr Glu Leu Val Phe Val Gly
50 55 60

Asp Glu Glu Asp Val Ser Lys Leu Ser Glu Gly Glu Leu Gly Phe Tyr
65 70 75 80

Arg Phe Leu Phe Ala Phe Leu Ser Ala Ala Asp Asp Leu Val Thr Glu
85 90 95

Asn Leu Gly Gly Leu Ser Gly Leu Phe Glu Gln Lys Asp Ile Leu His
100 105 110

Tyr Tyr Val Glu Gln Glu Cys Ile Glu Val Val His Ser Arg Val Tyr
115 120 125

Asn Ile Ile Gln Leu Val Leu Phe His Asn Asn Asp Gln Ala Arg Arg
130 135 140

Ala Tyr Val Ala Arg Thr Ile Asn His Pro Ala Ile Arg Val Lys Val 145 150 155 160

Asp Trp Leu Glu Ala Arg Val Arg Glu Cys Asp Ser Ile Pro Glu Lys
165 170 175

Phe Ile Leu Met Ile Leu Ile Glu Gly Val Phe Phe Ala Ala Ser Phe
180 185 190

Ala Ala Ile Ala Tyr Leu Arg Thr Asn Asn Leu Leu Arg Val Thr Cys
195 200 205

Gln Ser Asn Asp Leu Ile Ser Arg Asp Glu Ala Val His Thr Thr Ala
210 215 220

Ser Cys Tyr Ile Tyr Asn Asn Tyr Leu Gly Gly His Ala Lys Pro Glu
225 230 235 240

Ala Ala Arg Val Tyr Arg Leu Phe Arg Glu Ala Val Asp Ile Glu Ile
245 250 255

Gly Phe Ile Arg Ser Gln Ala Pro Thr Asp Ser Ser Ile Leu Ser Pro
260 265 270

Gly Ala Leu Ala Ala Ile Glu Asn Tyr Val Arg Phe Ser Ala Asp Arg
275 280 285

Leu Leu Gly Leu Ile His Met Gln Pro Leu Tyr Ser Ala Pro Ala Pro
290 295 300

Asp Ala Ser Phe Pro Leu Ser Leu Met Ser Thr Asp Lys His Thr Asn
305 310 315 320

Phe Phe Glu Cys Arg Ser Thr Ser Tyr Ala Gly Ala Val Val Asn Asp
325 330 335

Leu

<210> SEQ ID NO 26
<211> LENGTH: 86
<212> TYPE: PRT
<213> ORGANISM: human herpesvirus 2

<400> SEQUENCE: 26

Met Ser Trp Ala Leu Lys Thr Thr Asp Met Phe Leu Asp Ser Ser Arg
1 5 10 15

Cys Thr His Arg Thr Tyr Gly Asp Val Cys Ala Glu Ile His Lys Arg
20 25 30

Glu Arg Glu Asp Arg Glu Ala Ala Arg Thr Ala Val Thr Asp Pro Glu
35 40 45

Leu Pro Leu Leu Cys Pro Pro Asp Val Arg Ser Asp Pro Ala Ser Arg
50 55 60

Asn Pro Thr Gln Gln Thr Arg Gly Cys Ala Arg Ser Asn Glu Arg Gln
65 70 75 80

Asp Arg Val Leu Ala Pro
85

<210> SEQ ID NO 27
<211> LENGTH: 467
<212> TYPE: PRT
<213> ORGANISM: Human herpesvirus 2

<400> SEQUENCE: 27

Met Gly Arg Arg Ala Pro Arg Gly Ser Pro Glu Ala Ala Pro Gly Ala
1 5 10 15

Asp Val Ala Pro Gly Ala Arg Ala Ala Trp Trp Val Trp Cys Val Gln
20 25 30

Val Ala Thr Phe Ile Val Ser Ala Ile Cys Val Val Gly Leu Leu Val
35 40 45

```
Leu Ala Ser Val Phe Arg Asp Arg Phe Pro Cys Leu Tyr Ala Pro Ala
    50                  55                  60

Thr Ser Tyr Ala Lys Ala Asn Ala Thr Val Glu Val Arg Gly Gly Val
65                  70                  75                  80

Ala Val Pro Leu Arg Leu Asp Thr Gln Ser Leu Leu Ala Thr Tyr Ala
                85                  90                  95

Ile Thr Ser Thr Leu Leu Leu Ala Ala Ala Val Tyr Ala Ala Val Gly
            100                 105                 110

Ala Val Thr Ser Arg Tyr Glu Arg Ala Leu Asp Ala Ala Arg Arg Leu
        115                 120                 125

Ala Ala Ala Arg Met Ala Met Pro His Ala Thr Leu Ile Ala Gly Asn
    130                 135                 140

Val Cys Ala Trp Leu Leu Gln Ile Thr Val Leu Leu Leu Ala His Arg
145                 150                 155                 160

Ile Ser Gln Leu Ala His Leu Ile Tyr Val Leu His Phe Ala Cys Leu
                165                 170                 175

Val Tyr Leu Ala Ala His Phe Cys Thr Arg Gly Val Leu Ser Gly Thr
            180                 185                 190

Tyr Leu Arg Gln Val His Gly Leu Ile Asp Pro Ala Pro Thr His His
        195                 200                 205

Arg Ile Val Gly Pro Val Arg Ala Val Met Thr Asn Ala Leu Leu Leu
    210                 215                 220

Gly Thr Leu Leu Cys Thr Ala Ala Ala Ala Val Ser Leu Asn Thr Ile
225                 230                 235                 240

Ala Ala Leu Asn Phe Asn Phe Ser Ala Pro Ser Met Leu Ile Cys Leu
                245                 250                 255

Thr Thr Leu Phe Ala Leu Leu Val Val Ser Leu Leu Leu Val Val Glu
            260                 265                 270

Gly Val Leu Cys His Tyr Val Arg Val Leu Val Gly Pro His Leu Gly
        275                 280                 285

Ala Ile Ala Ala Thr Gly Ile Val Gly Leu Ala Cys Glu His Tyr His
    290                 295                 300

Thr Gly Gly Tyr Tyr Val Val Glu Gln Gln Trp Pro Gly Ala Gln Thr
305                 310                 315                 320

Gly Val Arg Val Ala Leu Ala Leu Val Ala Ala Phe Ala Leu Ala Met
                325                 330                 335

Ala Val Leu Arg Cys Thr Arg Ala Tyr Leu Tyr His Arg Arg His His
            340                 345                 350

Thr Lys Phe Phe Val Arg Met Arg Asp Thr Arg His Arg Ala His Ser
        355                 360                 365

Ala Leu Arg Arg Val Arg Ser Ser Met Arg Gly Ser Arg Arg Gly Gly
    370                 375                 380

Pro Pro Gly Asp Pro Gly Tyr Ala Glu Thr Pro Tyr Ala Ser Val Ser
385                 390                 395                 400

His His Ala Glu Ile Asp Arg Tyr Gly Asp Ser Asp Gly Asp Pro Ile
                405                 410                 415

Tyr Asp Glu Val Ala Pro Asp His Glu Ala Glu Leu Tyr Ala Arg Val
            420                 425                 430

Gln Arg Pro Gly Pro Val Pro Asp Ala Glu Pro Ile Tyr Asp Thr Val
        435                 440                 445

Glu Gly Tyr Ala Pro Arg Ser Ala Gly Glu Pro Val Tyr Ser Thr Val
    450                 455                 460
```

```
Arg Arg Trp
465


<210> SEQ ID NO 28
<211> LENGTH: 734
<212> TYPE: PRT
<213> ORGANISM: human herpesvirus 2

<400> SEQUENCE: 28

Met Phe Gly Gln Gln Leu Ala Ser Asp Val Gln Gln Tyr Leu Glu Arg
1               5                   10                  15

Leu Glu Lys Gln Arg Gln Gln Lys Val Gly Val Asp Glu Ala Ser Ala
            20                  25                  30

Gly Leu Thr Leu Gly Gly Asp Ala Leu Arg Val Pro Phe Leu Asp Phe
        35                  40                  45

Ala Thr Ala Thr Pro Lys Arg His Gln Thr Val Val Pro Gly Val Gly
    50                  55                  60

Thr Leu His Asp Cys Cys Glu His Ser Pro Leu Phe Ser Ala Val Ala
65                  70                  75                  80

Arg Arg Leu Leu Phe Asn Ser Leu Val Pro Ala Gln Leu Arg Gly Arg
                85                  90                  95

Asp Phe Gly Gly Asp His Thr Ala Lys Leu Glu Phe Leu Ala Pro Glu
            100                 105                 110

Leu Val Arg Ala Val Ala Arg Leu Arg Phe Arg Glu Cys Ala Pro Glu
        115                 120                 125

Asp Ala Val Pro Gln Arg Asn Ala Tyr Tyr Ser Val Leu Asn Thr Phe
    130                 135                 140

Gln Ala Leu His Arg Ser Glu Ala Phe Arg Gln Leu Val His Phe Val
145                 150                 155                 160

Arg Asp Phe Ala Gln Leu Leu Lys Thr Ser Phe Arg Ala Ser Ser Leu
                165                 170                 175

Ala Glu Thr Thr Gly Pro Pro Lys Lys Arg Ala Lys Val Asp Val Ala
            180                 185                 190

Thr His Gly Gln Thr Tyr Gly Thr Leu Glu Leu Phe Gln Lys Met Ile
        195                 200                 205

Leu Met His Ala Thr Tyr Phe Leu Ala Ala Val Leu Leu Gly Asp His
    210                 215                 220

Ala Glu Gln Val Asn Thr Phe Leu Arg Leu Val Phe Glu Ile Pro Leu
225                 230                 235                 240

Phe Ser Asp Thr Ala Val Arg His Phe Arg Gln Arg Ala Thr Val Phe
                245                 250                 255

Leu Val Pro Arg Arg His Gly Lys Thr Trp Phe Leu Val Pro Leu Ile
            260                 265                 270

Ala Leu Ser Leu Ala Ser Phe Arg Gly Ile Lys Ile Gly Tyr Thr Ala
        275                 280                 285

His Ile Arg Lys Ala Thr Glu Pro Val Phe Asp Glu Ile Asp Ala Cys
    290                 295                 300

Leu Arg Gly Trp Phe Gly Ser Ser Arg Val Asp His Val Lys Gly Glu
305                 310                 315                 320

Thr Ile Ser Phe Ser Phe Pro Asp Gly Ser Arg Ser Thr Ile Val Phe
                325                 330                 335

Ala Ser Ser His Asn Thr Asn Gly Ile Arg Gly Gln Asp Phe Asn Leu
            340                 345                 350

Leu Phe Val Asp Glu Ala Asn Phe Ile Arg Pro Asp Ala Val Gln Thr
        355                 360                 365
```

-continued

Ile Met Gly Phe Leu Asn Gln Ala Asn Cys Lys Ile Ile Phe Val Ser
370 375 380

Ser Thr Asn Thr Gly Lys Ala Ser Thr Ser Phe Leu Tyr Asn Leu Arg
385 390 395 400

Gly Ala Ala Asp Glu Leu Leu Asn Val Val Thr Tyr Ile Cys Asp Asp
405 410 415

His Met Pro Arg Val Val Thr His Thr Asn Ala Thr Ala Cys Ser Cys
420 425 430

Tyr Ile Leu Asn Lys Pro Val Phe Ile Thr Met Asp Gly Ala Val Arg
435 440 445

Arg Thr Ala Asp Leu Phe Leu Pro Asp Ser Phe Met Gln Glu Ile Ile
450 455 460

Gly Gly Gln Ala Arg Glu Thr Gly Asp Asp Arg Pro Val Leu Thr Lys
465 470 475 480

Ser Ala Gly Glu Arg Phe Leu Leu Tyr Arg Pro Ser Thr Thr Thr Asn
485 490 495

Ser Gly Leu Met Ala Pro Glu Leu Tyr Val Tyr Val Asp Pro Ala Phe
500 505 510

Thr Ala Asn Thr Arg Ala Ser Gly Thr Gly Ile Ala Val Val Gly Arg
515 520 525

Tyr Arg Asp Asp Phe Ile Ile Phe Ala Leu Glu His Phe Phe Leu Arg
530 535 540

Ala Leu Thr Gly Ser Ala Pro Ala Asp Ile Ala Arg Cys Val Val His
545 550 555 560

Ser Leu Ala Gln Val Leu Ala Leu His Pro Gly Ala Phe Arg Ser Val
565 570 575

Arg Val Ala Val Glu Gly Asn Ser Ser Gln Asp Ser Ala Val Ala Ile
580 585 590

Ala Thr His Val His Thr Glu Met His Arg Ile Leu Ala Ser Ala Gly
595 600 605

Ala Asn Gly Pro Gly Pro Glu Leu Leu Phe Tyr His Cys Glu Pro Pro
610 615 620

Gly Gly Ala Val Leu Tyr Pro Phe Phe Leu Leu Asn Lys Gln Lys Thr
625 630 635 640

Pro Ala Phe Glu Tyr Phe Ile Lys Lys Phe Asn Ser Gly Gly Val Met
645 650 655

Ala Ser Gln Glu Leu Val Ser Val Thr Val Arg Leu Gln Thr Asp Pro
660 665 670

Val Glu Tyr Leu Ser Glu Gln Leu Asn Asn Leu Ile Glu Thr Val Ser
675 680 685

Pro Asn Thr Asp Val Arg Met Tyr Ser Gly Lys Arg Asn Gly Ala Ala
690 695 700

Asp Asp Leu Met Val Ala Val Ile Met Ala Ile Tyr Leu Ala Ala Pro
705 710 715 720

Thr Gly Ile Pro Pro Ala Phe Phe Pro Ile Thr Arg Thr Ser
725 730

<210> SEQ ID NO 29
<211> LENGTH: 329
<212> TYPE: PRT
<213> ORGANISM: human herpesvirus 2

<400> SEQUENCE: 29

Met Asn Pro Val Ser Ala Ser Gly Ala Pro Ala Pro Pro Pro Pro Gly

-continued

```
1               5                   10                  15

Asp Gly Ser Tyr Leu Trp Ile Pro Ala Ser His Tyr Asn Gln Leu Val
            20                  25                  30

Thr Gly Gln Ser Ala Pro Arg His Pro Pro Leu Thr Ala Cys Gly Leu
        35                  40                  45

Pro Ala Ala Gly Thr Val Ala Tyr Gly His Pro Gly Ala Gly Pro Ser
    50                  55                  60

Pro His Tyr Pro Pro Pro Pro Ala His Pro Tyr Pro Gly Met Leu Phe
65                  70                  75                  80

Ala Gly Pro Ser Pro Leu Glu Ala Gln Ile Ala Ala Leu Val Gly Ala
                85                  90                  95

Ile Ala Ala Asp Arg Gln Ala Gly Gly Leu Pro Ala Ala Ala Gly Asp
            100                 105                 110

His Gly Ile Arg Gly Ser Ala Lys Arg Arg Arg His Glu Val Glu Gln
        115                 120                 125

Pro Glu Tyr Asp Cys Gly Arg Asp Glu Pro Asp Arg Asp Phe Pro Tyr
    130                 135                 140

Tyr Pro Gly Glu Ala Arg Pro Glu Pro Arg Pro Val Asp Ser Arg Arg
145                 150                 155                 160

Ala Ala Arg Gln Ala Ser Gly Pro His Glu Thr Ile Thr Ala Leu Val
                165                 170                 175

Gly Ala Val Thr Ser Leu Gln Gln Glu Leu Ala His Met Arg Ala Arg
            180                 185                 190

Thr His Ala Pro Tyr Gly Pro Tyr Pro Pro Val Gly Pro Tyr His His
        195                 200                 205

Pro His Ala Asp Thr Glu Thr Pro Ala Gln Pro Pro Arg Tyr Pro Ala
    210                 215                 220

Lys Ala Val Tyr Leu Pro Pro Pro His Ile Ala Pro Pro Gly Pro Pro
225                 230                 235                 240

Leu Ser Gly Ala Val Pro Pro Pro Ser Tyr Pro Pro Val Ala Val Thr
                245                 250                 255

Pro Gly Pro Ala Pro Pro Leu His Gln Pro Ser Pro Ala His Ala His
            260                 265                 270

Pro Pro Pro Pro Pro Pro Gly Pro Thr Pro Pro Pro Ala Ala Ser Leu
        275                 280                 285

Pro Gln Pro Glu Ala Pro Gly Ala Glu Ala Gly Ala Leu Val Asn Ala
    290                 295                 300

Ser Ser Ala Ala His Val Asn Val Asp Thr Ala Arg Ala Ala Asp Leu
305                 310                 315                 320

Phe Val Ser Gln Met Met Gly Ser Arg
                325
```

<210> SEQ ID NO 30
<211> LENGTH: 1240
<212> TYPE: PRT
<213> ORGANISM: human herpesvirus 2

<400> SEQUENCE: 30

```
Met Phe Cys Ala Ala Gly Gly Pro Ala Ser Pro Gly Gly Lys Pro Ala
1               5                   10                  15

Ala Arg Ala Ala Ser Gly Phe Phe Ala Pro His Asn Pro Arg Gly Ala
            20                  25                  30

Thr Gln Thr Ala Pro Pro Pro Cys Arg Arg Gln Asn Phe Tyr Asn Pro
        35                  40                  45
```

```
His Leu Ala Gln Thr Gly Thr Gln Pro Lys Ala Leu Gly Pro Ala Gln
    50                  55                  60

Arg His Thr Tyr Tyr Ser Glu Cys Asp Glu Phe Arg Phe Ile Ala Pro
65                  70                  75                  80

Arg Ser Leu Asp Glu Asp Ala Pro Ala Glu Gln Arg Thr Gly Val His
                85                  90                  95

Asp Gly Arg Leu Arg Arg Ala Pro Lys Val Tyr Cys Gly Gly Asp Glu
            100                 105                 110

Arg Asp Val Leu Arg Val Gly Pro Glu Gly Phe Trp Pro Arg Arg Leu
        115                 120                 125

Arg Leu Trp Gly Gly Ala Asp His Ala Pro Glu Gly Phe Asp Pro Thr
    130                 135                 140

Val Thr Val Phe His Val Tyr Asp Ile Leu Glu His Val Glu His Ala
145                 150                 155                 160

Tyr Ser Met Arg Ala Ala Gln Leu His Glu Arg Phe Met Asp Ala Ile
                165                 170                 175

Thr Pro Ala Gly Thr Val Ile Thr Leu Leu Gly Leu Thr Pro Glu Gly
            180                 185                 190

His Arg Val Ala Val His Val Tyr Gly Thr Arg Gln Tyr Phe Tyr Met
        195                 200                 205

Asn Lys Ala Glu Val Asp Arg His Leu Gln Cys Arg Ala Pro Arg Asp
    210                 215                 220

Leu Cys Glu Arg Leu Ala Ala Ala Leu Arg Glu Ser Pro Gly Ala Ser
225                 230                 235                 240

Phe Arg Gly Ile Ser Ala Asp His Phe Glu Ala Glu Val Val Glu Arg
                245                 250                 255

Ala Asp Val Tyr Tyr Tyr Glu Thr Arg Pro Thr Leu Tyr Tyr Arg Val
            260                 265                 270

Phe Val Arg Ser Gly Arg Ala Leu Ala Tyr Leu Cys Asp Asn Phe Cys
        275                 280                 285

Pro Ala Ile Arg Lys Tyr Glu Gly Gly Val Asp Ala Thr Thr Arg Phe
    290                 295                 300

Ile Leu Asp Asn Pro Gly Phe Val Thr Phe Gly Trp Tyr Arg Leu Lys
305                 310                 315                 320

Pro Gly Arg Gly Asn Ala Pro Ala Gln Pro Arg Pro Pro Thr Ala Phe
                325                 330                 335

Gly Thr Ser Ser Asp Val Glu Phe Asn Cys Thr Ala Asp Asn Leu Ala
            340                 345                 350

Val Glu Gly Ala Met Cys Asp Leu Pro Ala Tyr Lys Leu Met Cys Phe
        355                 360                 365

Asp Ile Glu Cys Lys Ala Gly Gly Glu Asp Glu Leu Ala Phe Pro Val
    370                 375                 380

Ala Glu Arg Pro Glu Asp Leu Val Ile Gln Ile Ser Cys Leu Leu Tyr
385                 390                 395                 400

Asp Leu Ser Thr Thr Ala Leu Glu His Ile Leu Leu Phe Ser Leu Gly
                405                 410                 415

Ser Cys Asp Leu Pro Glu Ser His Leu Ser Asp Leu Ala Ser Arg Gly
            420                 425                 430

Leu Pro Ala Pro Val Val Leu Glu Phe Asp Ser Glu Phe Glu Met Leu
        435                 440                 445

Leu Ala Phe Met Thr Phe Val Lys Gln Tyr Gly Pro Glu Phe Val Thr
    450                 455                 460

Gly Tyr Asn Ile Ile Asn Phe Asp Trp Pro Phe Val Leu Thr Lys Leu
```

-continued

```
465                 470                 475                 480

Thr Glu Ile Tyr Lys Val Pro Leu Asp Gly Tyr Gly Arg Met Asn Gly
                485                 490                 495

Arg Gly Val Phe Arg Val Trp Asp Ile Gly Gln Ser His Phe Gln Lys
            500                 505                 510

Arg Ser Lys Ile Lys Val Asn Gly Met Val Asn Ile Asp Met Tyr Gly
        515                 520                 525

Ile Ile Thr Asp Lys Val Lys Leu Ser Ser Tyr Lys Leu Asn Ala Val
    530                 535                 540

Ala Glu Ala Val Leu Lys Asp Lys Lys Lys Asp Leu Ser Tyr Arg Asp
545                 550                 555                 560

Ile Pro Ala Tyr Tyr Ala Ser Gly Pro Ala Gln Arg Gly Val Ile Gly
                565                 570                 575

Glu Tyr Cys Val Gln Asp Ser Leu Leu Val Gly Gln Leu Phe Phe Lys
            580                 585                 590

Phe Leu Pro His Leu Glu Leu Ser Ala Val Ala Arg Leu Ala Gly Ile
        595                 600                 605

Asn Ile Thr Arg Thr Ile Tyr Asp Gly Gln Gln Ile Arg Val Phe Thr
    610                 615                 620

Cys Leu Leu Arg Leu Ala Gly Gln Lys Gly Phe Ile Leu Pro Asp Thr
625                 630                 635                 640

Gln Gly Arg Phe Arg Gly Leu Asp Lys Glu Ala Pro Lys Arg Pro Ala
                645                 650                 655

Val Pro Arg Gly Glu Gly Glu Arg Pro Gly Asp Gly Asn Gly Asp Glu
            660                 665                 670

Asp Lys Asp Asp Asp Glu Asp Gly Asp Glu Asp Gly Asp Glu Arg Glu
        675                 680                 685

Glu Val Ala Arg Glu Thr Gly Gly Arg His Val Gly Tyr Gln Gly Ala
    690                 695                 700

Arg Val Leu Asp Pro Thr Ser Gly Phe His Val Asp Pro Val Val Val
705                 710                 715                 720

Phe Asp Phe Ala Ser Leu Tyr Pro Ser Ile Ile Gln Ala His Asn Leu
                725                 730                 735

Cys Phe Ser Thr Leu Ser Leu Arg Pro Glu Ala Val Ala His Leu Glu
            740                 745                 750

Ala Asp Arg Asp Tyr Leu Glu Ile Glu Val Gly Gly Arg Arg Leu Phe
        755                 760                 765

Phe Val Lys Ala His Val Arg Glu Ser Leu Leu Ser Ile Leu Leu Arg
    770                 775                 780

Asp Trp Leu Ala Met Arg Lys Gln Ile Arg Ser Arg Ile Pro Gln Ser
785                 790                 795                 800

Thr Pro Glu Glu Ala Val Leu Leu Asp Lys Gln Gln Ala Ala Ile Lys
                805                 810                 815

Val Val Cys Asn Ser Val Tyr Gly Phe Thr Gly Val Gln His Gly Leu
            820                 825                 830

Leu Pro Cys Leu His Val Ala Ala Thr Val Thr Thr Ile Gly Arg Glu
        835                 840                 845

Met Leu Leu Ala Thr Arg Ala Tyr Val His Ala Arg Trp Ala Glu Phe
    850                 855                 860

Asp Gln Leu Leu Ala Asp Phe Pro Glu Ala Ala Gly Met Arg Ala Pro
865                 870                 875                 880

Gly Pro Tyr Ser Met Arg Ile Ile Tyr Gly Asp Thr Asp Ser Ile Phe
                885                 890                 895
```

```
Val Leu Cys Arg Gly Leu Thr Ala Ala Gly Leu Val Ala Met Gly Asp
            900                 905                 910

Lys Met Ala Ser His Ile Ser Arg Ala Leu Phe Leu Pro Pro Ile Lys
        915                 920                 925

Leu Glu Cys Glu Lys Thr Phe Thr Lys Leu Leu Leu Ile Ala Lys Lys
    930                 935                 940

Lys Tyr Ile Gly Val Ile Cys Gly Gly Lys Met Leu Ile Lys Gly Val
945                 950                 955                 960

Asp Leu Val Arg Lys Asn Asn Cys Ala Phe Ile Asn Arg Thr Ser Arg
                965                 970                 975

Ala Leu Val Asp Leu Leu Phe Tyr Asp Asp Thr Val Ser Gly Ala Ala
            980                 985                 990

Ala Ala Leu Ala Glu Arg Pro Ala  Glu Glu Trp Leu Ala  Arg Pro Leu
        995                 1000                1005

Pro Glu  Gly Leu Gln Ala Phe  Gly Ala Val Leu Val  Asp Ala His
    1010                 1015                1020

Arg Arg  Ile Thr Asp Pro Glu  Arg Asp Ile Gln Asp  Phe Val Leu
    1025                 1030                1035

Thr Ala  Glu Leu Ser Arg His  Pro Arg Ala Tyr Thr  Asn Lys Arg
    1040                 1045                1050

Leu Ala  His Leu Thr Val Tyr  Tyr Lys Leu Met Ala  Arg Arg Ala
    1055                 1060                1065

Gln Val  Pro Ser Ile Lys Asp  Arg Ile Pro Tyr Val  Ile Val Ala
    1070                 1075                1080

Gln Thr  Arg Glu Val Glu Glu  Thr Val Ala Arg Leu  Ala Ala Leu
    1085                 1090                1095

Arg Glu  Leu Asp Ala Ala Ala  Pro Gly Asp Glu Pro  Ala Pro Pro
    1100                 1105                1110

Ala Ala  Leu Pro Ser Pro Ala  Lys Arg Pro Arg Glu  Thr Pro Ser
    1115                 1120                1125

His Ala  Asp Pro Pro Gly Gly  Ala Ser Lys Pro Arg  Lys Leu Leu
    1130                 1135                1140

Val Ser  Glu Leu Ala Glu Asp  Pro Gly Tyr Ala Ile  Ala Arg Gly
    1145                 1150                1155

Val Pro  Leu Asn Thr Asp Tyr  Tyr Phe Ser His Leu  Leu Gly Ala
    1160                 1165                1170

Ala Cys  Val Thr Phe Lys Ala  Leu Phe Gly Asn Asn  Ala Lys Ile
    1175                 1180                1185

Thr Glu  Ser Leu Leu Lys Arg  Phe Ile Pro Glu Thr  Trp His Pro
    1190                 1195                1200

Pro Asp  Asp Val Ala Ala Arg  Leu Arg Ala Ala Gly  Phe Gly Pro
    1205                 1210                1215

Ala Gly  Ala Gly Ala Thr Ala  Glu Glu Thr Arg Arg  Met Leu His
    1220                 1225                1230

Arg Ala  Phe Asp Thr Leu Ala
    1235                 1240


<210> SEQ ID NO 31
<211> LENGTH: 881
<212> TYPE: PRT
<213> ORGANISM: human herpesvirus 2

<400> SEQUENCE: 31

Met Ala Ala Ser Gly Gly Glu Gly Ser Arg Asp Val Arg Ala Pro Gly
```

-continued

```
1               5                   10                  15

Pro Pro Pro Gln Gln Pro Gly Ala Arg Pro Ala Val Arg Phe Arg Asp
            20                  25                  30

Glu Ala Phe Leu Asn Phe Thr Ser Met His Gly Val Gln Pro Ile Ile
        35                  40                  45

Ala Arg Ile Arg Glu Leu Ser Gln Gln Gln Leu Asp Val Thr Gln Val
    50                  55                  60

Pro Arg Leu Gln Trp Phe Arg Asp Val Ala Ala Leu Glu Val Pro Thr
65                  70                  75                  80

Gly Leu Pro Leu Arg Glu Phe Pro Phe Ala Ala Tyr Leu Ile Thr Gly
                85                  90                  95

Asn Ala Gly Ser Gly Lys Ser Thr Cys Val Gln Thr Leu Asn Glu Val
            100                 105                 110

Leu Asp Cys Val Val Thr Gly Ala Thr Arg Ile Ala Ala Gln Asn Met
        115                 120                 125

Tyr Val Lys Leu Ser Gly Ala Phe Leu Ser Arg Pro Ile Asn Thr Ile
    130                 135                 140

Phe His Glu Phe Gly Phe Arg Gly Asn His Val Gln Ala Gln Leu Gly
145                 150                 155                 160

Gln His Pro Tyr Thr Leu Ala Ser Ser Pro Ala Ser Leu Glu Asp Leu
                165                 170                 175

Gln Arg Arg Asp Leu Thr Tyr Tyr Trp Glu Val Ile Leu Asp Ile Thr
            180                 185                 190

Lys Arg Ala Leu Ala Ala His Gly Gly Glu Asp Ala Arg Asn Glu Phe
        195                 200                 205

His Ala Leu Thr Ala Leu Glu Gln Thr Leu Gly Leu Gly Gln Gly Ala
    210                 215                 220

Leu Thr Arg Leu Ala Ser Val Thr His Gly Ala Leu Pro Ala Phe Thr
225                 230                 235                 240

Arg Ser Asn Ile Ile Val Ile Asp Glu Ala Gly Leu Leu Gly Arg His
                245                 250                 255

Leu Leu Thr Thr Val Val Tyr Cys Trp Trp Met Ile Asn Ala Leu Tyr
            260                 265                 270

His Thr Pro Gln Tyr Ala Gly Arg Leu Arg Pro Val Leu Val Cys Val
        275                 280                 285

Gly Ser Pro Thr Gln Thr Ala Ser Leu Glu Ser Thr Phe Glu His Gln
    290                 295                 300

Lys Leu Arg Cys Ser Val Arg Gln Ser Glu Asn Val Leu Thr Tyr Leu
305                 310                 315                 320

Ile Cys Asn Arg Thr Leu Arg Glu Tyr Thr Arg Leu Ser His Ser Trp
                325                 330                 335

Ala Ile Phe Ile Asn Asn Lys Arg Cys Val Glu His Glu Phe Gly Asn
            340                 345                 350

Leu Met Lys Val Leu Glu Tyr Gly Leu Pro Ile Thr Glu Glu His Met
        355                 360                 365

Gln Phe Val Asp Arg Phe Val Val Pro Glu Ser Tyr Ile Thr Asn Pro
    370                 375                 380

Ala Asn Leu Pro Gly Trp Thr Arg Leu Phe Ser Ser His Lys Glu Val
385                 390                 395                 400

Ser Ala Tyr Met Ala Lys Leu His Ala Tyr Leu Lys Val Thr Arg Glu
                405                 410                 415

Gly Glu Phe Val Val Phe Thr Leu Pro Val Leu Thr Phe Val Ser Val
            420                 425                 430
```

```
Lys Glu Phe Asp Glu Tyr Arg Arg Leu Thr Gln Gln Pro Thr Leu Thr
        435                 440                 445

Met Glu Lys Trp Ile Thr Ala Asn Ala Ser Arg Ile Thr Asn Tyr Ser
    450                 455                 460

Gln Ser Gln Asp Gln Asp Ala Gly His Val Arg Cys Glu Val His Ser
465                 470                 475                 480

Lys Gln Gln Leu Val Val Ala Arg Asn Asp Ile Thr Tyr Val Leu Asn
                485                 490                 495

Ser Gln Val Ala Val Thr Ala Arg Leu Arg Lys Met Val Phe Gly Phe
            500                 505                 510

Asp Gly Thr Phe Arg Thr Phe Glu Ala Val Leu Arg Asp Asp Ser Phe
        515                 520                 525

Val Lys Thr Gln Gly Glu Thr Ser Val Glu Phe Ala Tyr Arg Phe Leu
    530                 535                 540

Ser Arg Leu Met Phe Gly Gly Leu Ile His Phe Tyr Asn Phe Leu Gln
545                 550                 555                 560

Arg Pro Gly Leu Asp Ala Thr Gln Arg Thr Leu Ala Tyr Gly Arg Leu
                565                 570                 575

Gly Glu Leu Thr Ala Glu Leu Leu Ser Leu Arg Arg Asp Ala Ala Gly
            580                 585                 590

Ala Ser Ala Thr Arg Ala Ala Asp Thr Ser Asp Arg Ser Pro Gly Glu
        595                 600                 605

Arg Ala Phe Asn Phe Lys His Leu Gly Pro Arg Asp Gly Gly Pro Asp
    610                 615                 620

Asp Phe Pro Asp Asp Asp Leu Asp Val Ile Phe Ala Gly Leu Asp Glu
625                 630                 635                 640

Gln Gln Leu Asp Val Phe Tyr Cys His Tyr Ala Leu Glu Glu Pro Glu
                645                 650                 655

Thr Thr Ala Ala Val His Ala Gln Phe Gly Leu Leu Lys Arg Ala Phe
            660                 665                 670

Leu Gly Arg Tyr Leu Ile Leu Arg Glu Leu Phe Gly Glu Val Phe Glu
        675                 680                 685

Ser Ala Pro Phe Ser Thr Tyr Val Asp Asn Val Ile Phe Arg Gly Cys
    690                 695                 700

Glu Leu Leu Thr Gly Ser Pro Arg Gly Gly Leu Met Ser Val Ala Leu
705                 710                 715                 720

Gln Thr Asp Asn Tyr Thr Leu Met Gly Tyr Thr Tyr Thr Arg Val Phe
                725                 730                 735

Ala Phe Ala Glu Glu Leu Arg Arg Arg His Ala Thr Ala Gly Val Ala
            740                 745                 750

Glu Phe Leu Glu Glu Ser Pro Leu Pro Tyr Ile Val Leu Arg Asp Gln
        755                 760                 765

His Gly Phe Met Ser Val Val Asn Thr Asn Ile Ser Glu Phe Val Glu
    770                 775                 780

Ser Ile Asp Ser Thr Glu Leu Ala Met Ala Ile Asn Ala Asp Tyr Gly
785                 790                 795                 800

Ile Ser Ser Lys Leu Ala Met Thr Ile Thr Arg Ser Gln Gly Leu Ser
                805                 810                 815

Leu Asp Lys Val Ala Ile Cys Phe Thr Pro Gly Asn Leu Arg Leu Asn
            820                 825                 830

Ser Ala Tyr Val Ala Met Ser Arg Thr Thr Ser Ser Glu Phe Leu His
        835                 840                 845
```

Met Asn Leu Asn Pro Leu Arg Glu Arg His Glu Arg Asp Asp Val Ile
    850                 855                 860

Ser Glu His Ile Leu Ser Ala Leu Arg Asp Pro Asn Val Val Ile Val
865                 870                 875                 880

Tyr

<210> SEQ ID NO 32
<211> LENGTH: 752
<212> TYPE: PRT
<213> ORGANISM: human herpesvirus 2

<400> SEQUENCE: 32

Met Glu Ala Pro Gly Ile Val Trp Val Glu Glu Ser Val Ser Ala Ile
1               5                   10                  15

Thr Leu Tyr Ala Val Trp Leu Pro Pro Arg Thr Arg Asp Cys Leu His
            20                  25                  30

Ala Leu Leu Tyr Leu Val Cys Arg Asp Ala Ala Gly Glu Ala Arg Ala
        35                  40                  45

Arg Phe Ala Glu Val Ser Val Gly Ser Ser Asp Leu Gln Asp Phe Tyr
    50                  55                  60

Gly Ser Pro Asp Val Ser Ala Pro Gly Ala Val Ala Ala Ala Arg Ala
65                  70                  75                  80

Ala Thr Ala Pro Ala Ala Ser Pro Leu Glu Pro Leu Gly Asp Pro Thr
                85                  90                  95

Leu Trp Arg Ala Leu Tyr Ala Cys Val Leu Ala Ala Leu Glu Arg Gln
            100                 105                 110

Thr Gly Arg Trp Ala Leu Phe Val Pro Leu Arg Leu Gly Trp Asp Pro
        115                 120                 125

Gln Thr Gly Leu Val Val Arg Val Glu Arg Ala Ser Trp Gly Pro Pro
    130                 135                 140

Ala Ala Pro Arg Ala Ala Leu Leu Asp Val Glu Ala Lys Val Asp Val
145                 150                 155                 160

Asp Pro Leu Ala Leu Ser Ala Arg Val Ala Glu His Pro Gly Ala Arg
                165                 170                 175

Leu Ala Trp Ala Arg Leu Ala Ala Ile Arg Asp Ser Pro Gln Cys Ala
            180                 185                 190

Ser Ser Ala Ser Leu Ala Val Thr Ile Thr Thr Arg Thr Ala Arg Phe
        195                 200                 205

Ala Arg Glu Tyr Thr Thr Leu Ala Phe Pro Pro Thr Arg Lys Glu Gly
    210                 215                 220

Ala Phe Ala Asp Leu Val Glu Val Cys Glu Val Gly Leu Arg Pro Arg
225                 230                 235                 240

Gly His Pro Gln Arg Val Thr Ala Arg Val Leu Leu Pro Arg Gly Tyr
                245                 250                 255

Asp Tyr Phe Val Ser Ala Gly Asp Gly Phe Ser Ala Pro Ala Leu Val
            260                 265                 270

Ala Leu Phe Arg Gln Trp His Thr Thr Val His Ala Ala Pro Gly Ala
        275                 280                 285

Leu Ala Pro Val Phe Ala Phe Leu Gly Pro Gly Phe Glu Val Arg Gly
    290                 295                 300

Gly Pro Val Gln Tyr Phe Ala Val Leu Gly Phe Pro Gly Trp Pro Thr
305                 310                 315                 320

Phe Thr Val Pro Ala Ala Ala Ala Ala Glu Ser Ala Arg Asp Leu Val
                325                 330                 335

-continued

```
Arg Gly Ala Ala Ala Thr His Ala Ala Cys Leu Gly Ala Trp Pro Ala
            340                 345                 350

Val Gly Ala Arg Val Val Leu Pro Pro Arg Ala Trp Pro Ala Val Ala
        355                 360                 365

Ser Glu Ala Ala Gly Arg Leu Leu Pro Ala Phe Arg Glu Ala Val Ala
    370                 375                 380

Arg Trp His Pro Thr Ala Thr Thr Ile Gln Leu Leu Asp Pro Pro Ala
385                 390                 395                 400

Ala Val Gly Pro Val Trp Thr Ala Arg Phe Cys Phe Ser Gly Leu Gln
                405                 410                 415

Ala Gln Leu Leu Ala Ala Leu Ala Gly Leu Gly Glu Ala Gly Leu Pro
            420                 425                 430

Glu Ala Arg Gly Arg Ala Gly Leu Glu Arg Leu Asp Ala Leu Val Ala
        435                 440                 445

Ala Ala Pro Ser Glu Pro Trp Ala Arg Ala Val Leu Glu Arg Leu Val
    450                 455                 460

Pro Asp Ala Cys Asp Ala Cys Pro Ala Leu Arg Gln Leu Leu Gly Gly
465                 470                 475                 480

Val Met Ala Ala Val Cys Leu Gln Ile Glu Gln Thr Ala Ser Ser Val
                485                 490                 495

Lys Phe Ala Val Cys Gly Gly Thr Gly Ala Ala Phe Trp Gly Leu Phe
            500                 505                 510

Asn Val Asp Pro Gly Asp Ala Asp Ala Ala His Gly Ala Ile Gln Asp
        515                 520                 525

Ala Arg Arg Ala Leu Glu Ala Ser Val Arg Ala Val Leu Ser Ala Asn
    530                 535                 540

Gly Ile Arg Pro Arg Leu Ala Pro Ser Leu Ala Pro Glu Gly Val Tyr
545                 550                 555                 560

Thr His Val Val Thr Trp Ser Gln Thr Gly Ala Trp Phe Trp Asn Ser
                565                 570                 575

Arg Asp Asp Thr Asp Phe Leu Gln Gly Phe Pro Leu Arg Gly Ala Ala
            580                 585                 590

Tyr Ala Ala Ala Ala Glu Val Met Arg Asp Ala Leu Arg Arg Ile Leu
        595                 600                 605

Arg Arg Pro Ala Ala Gly Pro Pro Glu Glu Ala Val Cys Ala Ala Arg
    610                 615                 620

Gly Val Met Glu Asp Ala Cys Asp Arg Phe Val Leu Asp Ala Phe Gly
625                 630                 635                 640

Arg Arg Leu Asp Ala Glu Tyr Trp Ser Val Leu Thr Pro Pro Gly Glu
                645                 650                 655

Ala Asp Asp Pro Leu Pro Gln Thr Ala Phe Arg Gly Gly Ala Leu Leu
            660                 665                 670

Asp Ala Glu Gln Tyr Trp Arg Arg Val Val Arg Val Cys Pro Gly Gly
        675                 680                 685

Gly Glu Ser Val Gly Val Pro Val Asp Leu Tyr Pro Arg Pro Leu Val
    690                 695                 700

Leu Pro Pro Val Asp Cys Ala His His Leu Arg Glu Ile Leu Arg Glu
705                 710                 715                 720

Ile Gln Leu Val Phe Thr Gly Val Leu Glu Gly Val Trp Gly Glu Gly
                725                 730                 735

Gly Ser Phe Val Tyr Pro Phe Asp Glu Lys Ile Arg Phe Leu Phe Pro
            740                 745                 750
```

-continued

<210> SEQ ID NO 33
<211> LENGTH: 292
<212> TYPE: PRT
<213> ORGANISM: human herpesvirus 2

<400> SEQUENCE: 33

Met Asp Gly Ala Val Arg Arg Thr Ala Asp Leu Phe Leu Pro Asp Ser
1 5 10 15

Phe Met Gln Glu Ile Ile Gly Gly Gln Ala Arg Glu Thr Gly Asp Asp
20 25 30

Arg Pro Val Leu Thr Lys Ser Ala Gly Glu Arg Phe Leu Leu Tyr Arg
35 40 45

Pro Ser Thr Thr Thr Asn Ser Gly Leu Met Ala Pro Glu Leu Tyr Val
50 55 60

Tyr Val Asp Pro Ala Phe Thr Ala Asn Thr Arg Ala Ser Gly Thr Gly
65 70 75 80

Ile Ala Val Val Gly Arg Tyr Arg Asp Asp Phe Ile Ile Phe Ala Leu
85 90 95

Glu His Phe Phe Leu Arg Ala Leu Thr Gly Ser Ala Pro Ala Asp Ile
100 105 110

Ala Arg Cys Val Val His Ser Leu Ala Gln Val Leu Ala Leu His Pro
115 120 125

Gly Ala Phe Arg Ser Val Arg Val Ala Val Glu Gly Asn Ser Ser Gln
130 135 140

Asp Ser Ala Val Ala Ile Ala Thr His Val His Thr Glu Met His Arg
145 150 155 160

Ile Leu Ala Ser Ala Gly Ala Asn Gly Pro Gly Pro Glu Leu Leu Phe
165 170 175

Tyr His Cys Glu Pro Pro Gly Gly Ala Val Leu Tyr Pro Phe Phe Leu
180 185 190

Leu Asn Lys Gln Lys Thr Pro Ala Phe Glu Tyr Phe Ile Lys Lys Phe
195 200 205

Asn Ser Gly Gly Val Met Ala Ser Gln Glu Leu Val Ser Val Thr Val
210 215 220

Arg Leu Gln Thr Asp Pro Val Glu Tyr Leu Ser Glu Gln Leu Asn Asn
225 230 235 240

Leu Ile Glu Thr Val Ser Pro Asn Thr Asp Val Arg Met Tyr Ser Gly
245 250 255

Lys Arg Asn Gly Ala Ala Asp Asp Leu Met Val Ala Val Ile Met Ala
260 265 270

Ile Tyr Leu Ala Ala Pro Thr Gly Ile Pro Pro Ala Phe Phe Pro Ile
275 280 285

Thr Arg Thr Ser
290

<210> SEQ ID NO 34
<211> LENGTH: 598
<212> TYPE: PRT
<213> ORGANISM: human herpesvirus 2

<400> SEQUENCE: 34

Met Ala Thr Ser Ala Pro Gly Val Pro Ser Ser Ala Ala Val Arg Glu
1 5 10 15

Glu Ser Pro Gly Ser Ser Trp Lys Glu Gly Ala Phe Glu Arg Pro Tyr
20 25 30

Val Ala Phe Asp Pro Asp Leu Leu Ala Leu Asn Glu Ala Leu Cys Ala

-continued

```
        35                  40                  45

Glu Leu Leu Ala Ala Cys His Val Val Gly Val Pro Pro Ala Ser Ala
    50                  55                  60

Leu Asp Glu Asp Val Glu Ser Asp Val Ala Pro Ala Pro Pro Arg Pro
65                  70                  75                  80

Arg Gly Ala Ala Arg Glu Ala Ser Gly Gly Arg Gly Pro Gly Ser Ala
                85                  90                  95

Arg Gly Pro Pro Ala Asp Pro Thr Ala Glu Gly Leu Leu Asp Thr Gly
            100                 105                 110

Pro Phe Ala Ala Ala Ser Val Asp Thr Phe Ala Leu Asp Arg Pro Cys
        115                 120                 125

Leu Val Cys Arg Thr Ile Glu Leu Tyr Lys Gln Ala Tyr Arg Leu Ser
    130                 135                 140

Pro Gln Trp Val Ala Asp Tyr Ala Phe Leu Cys Ala Lys Cys Leu Gly
145                 150                 155                 160

Ala Pro His Cys Ala Ala Ser Ile Phe Val Ala Ala Phe Glu Phe Val
                165                 170                 175

Tyr Val Met Asp His His Phe Leu Arg Thr Lys Lys Ala Thr Leu Val
            180                 185                 190

Gly Ser Phe Ala Arg Phe Ala Leu Thr Ile Asn Asp Ile His Arg His
        195                 200                 205

Phe Phe Leu His Cys Cys Phe Arg Thr Asp Gly Gly Val Pro Gly Arg
    210                 215                 220

His Ala Gln Lys Gln Pro Arg Pro Thr Pro Ser Pro Gly Ala Ala Lys
225                 230                 235                 240

Val Gln Tyr Ser Asn Tyr Ser Phe Leu Ala Gln Ser Ala Thr Arg Ala
                245                 250                 255

Leu Ile Gly Thr Leu Ala Ser Gly Gly Asp Asp Gly Ala Gly Ala Gly
            260                 265                 270

Ala Gly Gly Gly Ser Gly Thr Gln Pro Ser Leu Thr Thr Ala Leu Met
        275                 280                 285

Asn Trp Lys Asp Cys Ala Arg Leu Leu Asp Cys Thr Glu Gly Lys Arg
    290                 295                 300

Gly Gly Gly Asp Ser Cys Cys Thr Arg Ala Ala Ala Arg Asn Gly Glu
305                 310                 315                 320

Phe Glu Ala Ala Ala Gly Ala Leu Ala Gln Gly Gly Glu Pro Glu Thr
                325                 330                 335

Trp Ala Tyr Ala Asp Leu Ile Leu Leu Leu Leu Ala Gly Thr Pro Ala
            340                 345                 350

Val Trp Glu Ser Gly Pro Arg Leu Arg Ala Ala Ala Asp Ala Arg Arg
        355                 360                 365

Ala Ala Val Ser Glu Ser Trp Glu Ala His Arg Gly Ala Arg Met Arg
    370                 375                 380

Asp Ala Ala Pro Arg Phe Ala Gln Phe Ala Glu Pro Gln Pro Gln Pro
385                 390                 395                 400

Asp Leu Asp Leu Gly Pro Leu Met Ala Thr Val Leu Lys His Gly Arg
                405                 410                 415

Gly Arg Gly Arg Thr Gly Gly Glu Cys Leu Leu Cys Asn Leu Leu Leu
            420                 425                 430

Val Arg Ala Tyr Trp Leu Ala Met Arg Arg Leu Arg Ala Ser Val Val
        435                 440                 445

Arg Tyr Ser Glu Asn Asn Thr Ser Leu Phe Asp Cys Ile Val Pro Val
    450                 455                 460
```

Val Asp Gln Leu Glu Ala Asp Pro Glu Ala Gln Pro Gly Asp Gly Gly
465 470 475 480

Arg Phe Val Ser Leu Leu Arg Ala Ala Gly Pro Glu Ala Ile Phe Lys
485 490 495

His Met Phe Cys Asp Pro Met Cys Ala Ile Thr Glu Met Glu Val Asp
500 505 510

Pro Trp Val Leu Phe Gly His Pro Arg Ala Asp His Arg Asp Glu Leu
515 520 525

Gln Leu His Lys Ala Lys Leu Ala Cys Gly Asn Glu Phe Glu Gly Arg
530 535 540

Val Cys Ile Ala Leu Arg Ala Leu Ile Tyr Thr Phe Lys Thr Tyr Gln
545 550 555 560

Val Phe Val Pro Lys Pro Thr Ala Leu Ala Thr Phe Val Arg Glu Ala
565 570 575

Gly Ala Leu Leu Arg Arg His Ser Ile Ser Leu Leu Ser Leu Glu His
580 585 590

Thr Leu Cys Thr Tyr Val
595

<210> SEQ ID NO 35
<211> LENGTH: 327
<212> TYPE: PRT
<213> ORGANISM: human herpesvirus 2

<400> SEQUENCE: 35

Met Glu Tyr Asp Ser Phe Asp Ala Leu Leu Ala Ala Arg Leu Glu Ser
1 5 10 15

Gly Gln Thr Leu Gly Pro Ala Gly Gly Arg Glu Ala Ser Leu Pro Glu
20 25 30

Ala Pro His Ala Leu Tyr Arg Pro Thr Gly Gln His Val Ala Val Leu
35 40 45

Ala Ala Ala Thr His Arg Thr Pro Ala Ala Arg Val Thr Ala Met Asp
50 55 60

Leu Val Leu Ala Ala Val Leu Leu Gly Ala Pro Val Val Val Ala Leu
65 70 75 80

Arg Asn Thr Thr Ala Phe Ser Arg Glu Ser Glu Leu Glu Leu Cys Leu
85 90 95

Thr Leu Phe Asp Ser Arg Pro Gly Gly Pro Asp Ala Ala Leu Arg Asp
100 105 110

Val Val Ser Ser Asp Ile Glu Thr Trp Ala Val Gly Leu Leu His Thr
115 120 125

Asp Leu Asn Pro Ile Glu Asn Ala Cys Leu Ala Ala Gln Leu Pro Arg
130 135 140

Leu Ser Ala Leu Ile Ala Glu Arg Pro Leu Ala Asp Gly Pro Pro Cys
145 150 155 160

Leu Val Leu Val Asp Ile Ser Met Thr Pro Val Ala Val Leu Trp Glu
165 170 175

Ala Pro Glu Pro Pro Gly Pro Pro Asp Val Arg Phe Val Gly Ser Glu
180 185 190

Ala Thr Glu Glu Leu Pro Phe Val Ala Thr Ala Gly Asp Val Leu Ala
195 200 205

Ala Ser Ala Ala Asp Ala Asp Pro Phe Phe Ala Arg Ala Ile Leu Gly
210 215 220

Arg Pro Phe Asp Ala Ser Leu Leu Thr Gly Glu Leu Phe Pro Gly His

```
225                 230                 235                 240

Pro Val Tyr Gln Arg Pro Leu Ala Asp Glu Ala Gly Pro Ser Ala Pro
                245                 250                 255

Thr Ala Ala Arg Asp Pro Arg Asp Leu Ala Gly Gly Asp Gly Gly Ser
            260                 265                 270

Gly Pro Glu Asp Pro Ala Ala Pro Pro Ala Arg Gln Ala Asp Pro Gly
        275                 280                 285

Val Leu Ala Pro Thr Leu Leu Thr Asp Ala Thr Thr Gly Glu Pro Val
    290                 295                 300

Pro Pro Arg Met Trp Ala Trp Ile His Gly Leu Glu Glu Leu Ala Ser
305                 310                 315                 320

Asp Asp Ala Gly Gly Pro Thr
                325


<210> SEQ ID NO 36
<211> LENGTH: 512
<212> TYPE: PRT
<213> ORGANISM: human herpesvirus 2

<400> SEQUENCE: 36

Met Ala Thr Asp Ile Asp Met Leu Ile Asp Leu Gly Leu Asp Leu Ser
1               5                   10                  15

Asp Ser Glu Leu Glu Glu Asp Ala Leu Glu Arg Asp Glu Glu Gly Arg
            20                  25                  30

Arg Asp Asp Pro Glu Ser Asp Ser Ser Gly Glu Cys Ser Ser Ser Asp
        35                  40                  45

Glu Asp Met Glu Asp Pro Cys Gly Asp Gly Gly Ala Glu Ala Ile Asp
    50                  55                  60

Ala Ala Ile Pro Lys Gly Pro Pro Ala Arg Pro Glu Asp Ala Gly Thr
65                  70                  75                  80

Pro Glu Ala Ser Thr Pro Arg Pro Ala Ala Arg Arg Gly Ala Asp Asp
                85                  90                  95

Pro Pro Pro Ala Thr Thr Gly Val Trp Ser Arg Leu Gly Thr Arg Arg
            100                 105                 110

Ser Ala Ser Pro Arg Glu Pro His Gly Gly Lys Val Ala Arg Ile Gln
        115                 120                 125

Pro Pro Ser Thr Lys Ala Pro His Pro Arg Gly Gly Arg Arg Gly Arg
    130                 135                 140

Arg Arg Gly Arg Gly Arg Tyr Gly Pro Gly Gly Ala Asp Ser Thr Pro
145                 150                 155                 160

Lys Pro Arg Arg Arg Val Ser Arg Asn Ala His Asn Gln Gly Gly Arg
                165                 170                 175

His Pro Ala Ser Ala Arg Thr Asp Gly Pro Gly Ala Thr His Gly Glu
            180                 185                 190

Ala Arg Arg Gly Gly Glu Gln Leu Asp Val Ser Gly Gly Pro Arg Pro
        195                 200                 205

Arg Gly Thr Arg Gln Ala Pro Pro Pro Leu Met Ala Leu Ser Leu Thr
    210                 215                 220

Pro Pro His Ala Asp Gly Arg Ala Pro Val Pro Glu Arg Lys Ala Pro
225                 230                 235                 240

Ser Ala Asp Thr Ile Asp Pro Ala Val Arg Ala Val Leu Arg Ser Ile
                245                 250                 255

Ser Glu Arg Ala Ala Val Glu Arg Ile Ser Glu Ser Phe Gly Arg Ser
            260                 265                 270
```

```
Ala Leu Val Met Gln Asp Pro Phe Gly Gly Met Pro Phe Pro Ala Ala
        275                 280                 285

Asn Ser Pro Trp Ala Pro Val Leu Ala Thr Gln Ala Gly Gly Phe Asp
    290                 295                 300

Ala Glu Thr Arg Arg Val Ser Trp Glu Thr Leu Val Ala His Gly Pro
305                 310                 315                 320

Ser Leu Tyr Arg Thr Phe Ala Ala Asn Pro Arg Ala Ala Ser Thr Ala
                325                 330                 335

Lys Ala Met Arg Asp Cys Val Leu Arg Gln Glu Asn Leu Ile Glu Ala
            340                 345                 350

Leu Ala Ser Ala Asp Glu Thr Leu Ala Trp Cys Lys Met Cys Ile His
        355                 360                 365

His Asn Leu Pro Leu Arg Pro Gln Asp Pro Ile Ile Gly Thr Ala Ala
    370                 375                 380

Ala Val Leu Glu Asn Leu Ala Thr Arg Leu Arg Pro Phe Leu Gln Cys
385                 390                 395                 400

Tyr Leu Lys Ala Arg Gly Leu Cys Gly Leu Asp Asp Leu Cys Ser Arg
                405                 410                 415

Arg Arg Leu Ser Asp Ile Lys Asp Ile Ala Ser Phe Val Leu Val Ile
            420                 425                 430

Leu Ala Arg Leu Ala Asn Arg Val Glu Arg Gly Val Ser Glu Ile Asp
        435                 440                 445

Tyr Thr Thr Val Gly Val Gly Ala Gly Glu Thr Met His Phe Tyr Ile
    450                 455                 460

Pro Gly Ala Cys Met Ala Gly Leu Ile Glu Ile Leu Asp Thr His Arg
465                 470                 475                 480

Gln Glu Cys Ser Ser Arg Val Cys Glu Leu Thr Ala Ser His Thr Ile
                485                 490                 495

Ala Pro Leu Tyr Val His Gly Lys Tyr Phe Tyr Cys Asn Ser Leu Phe
            500                 505                 510
```

<210> SEQ ID NO 37
<211> LENGTH: 87
<212> TYPE: PRT
<213> ORGANISM: Human herpesvirus 2

<400> SEQUENCE: 37

```
Met Thr Gly Lys Pro Ala Arg Leu Gly Arg Trp Val Val Leu Leu Phe
1               5                   10                  15

Val Ala Leu Val Ala Gly Val Pro Gly Glu Pro Pro Asn Ala Ala Gly
            20                  25                  30

Ala Arg Gly Val Ile Gly Asp Ala Gln Cys Arg Gly Asp Ser Ala Gly
        35                  40                  45

Val Val Ser Val Pro Gly Val Leu Val Pro Phe Tyr Leu Gly Met Thr
    50                  55                  60

Ser Met Gly Val Cys Met Ile Ala His Val Tyr Gln Ile Cys Gln Arg
65                  70                  75                  80

Ala Leu Ala Ala Gly Ser Ala
                85
```

<210> SEQ ID NO 38
<211> LENGTH: 302
<212> TYPE: PRT
<213> ORGANISM: Human herpesvirus 2

<400> SEQUENCE: 38

```
Asn Arg Trp Gly Ser Gly Val Pro Gly Pro Ile Asn Pro Pro Asn Ser
1               5                   10                  15

Asp Val Val Phe Pro Gly Gly Ser Pro Val Ala Gln Tyr Cys Tyr Ala
            20                  25                  30

Tyr Pro Arg Leu Asp Asp Pro Gly Pro Leu Gly Ser Ala Asp Ala Gly
        35                  40                  45

Arg Gln Asp Leu Pro Arg Arg Val Val Arg His Glu Pro Leu Gly Arg
    50                  55                  60

Ser Phe Leu Thr Gly Gly Leu Val Leu Leu Ala Pro Pro Val Arg Gly
65                  70                  75                  80

Phe Gly Ala Pro Asn Ala Thr Tyr Ala Ala Arg Val Thr Tyr Tyr Arg
                85                  90                  95

Leu Thr Arg Ala Cys Arg Gln Pro Ile Leu Leu Arg Gln Tyr Gly Gly
            100                 105                 110

Cys Arg Gly Gly Glu Pro Pro Ser Pro Lys Thr Cys Gly Ser Tyr Thr
        115                 120                 125

Tyr Thr Tyr Gln Gly Gly Gly Pro Pro Thr Arg Tyr Ala Leu Val Asn
    130                 135                 140

Ala Ser Leu Leu Val Pro Ile Trp Asp Arg Ala Ala Glu Thr Phe Glu
145                 150                 155                 160

Tyr Gln Ile Glu Leu Gly Gly Glu Leu His Val Gly Leu Leu Trp Val
                165                 170                 175

Glu Val Gly Gly Glu Gly Pro Gly Pro Thr Ala Pro Pro Gln Ala Ala
            180                 185                 190

Arg Ala Glu Gly Gly Pro Cys Val Pro Pro Val Pro Ala Gly Arg Pro
        195                 200                 205

Trp Arg Ser Val Pro Pro Val Trp Tyr Ser Ala Pro Asn Pro Gly Phe
    210                 215                 220

Arg Gly Leu Arg Phe Arg Glu Arg Cys Leu Pro Pro Gln Thr Pro Ala
225                 230                 235                 240

Ala Pro Ser Asp Leu Pro Arg Val Ala Phe Ala Pro Gln Ser Leu Leu
                245                 250                 255

Val Gly Ile Thr Gly Arg Thr Phe Ile Arg Met Ala Arg Pro Thr Glu
            260                 265                 270

Asp Val Gly Val Leu Pro Pro His Trp Ala Pro Gly Ala Leu Asp Asp
        275                 280                 285

Gly Pro Tyr Ala Pro Phe Pro Pro Arg Pro Arg Phe Arg Arg
    290                 295                 300
```

<210> SEQ ID NO 39
<211> LENGTH: 3987
<212> TYPE: DNA
<213> ORGANISM: Human herpesvirus 2

<400> SEQUENCE: 39

```
atgtcgtact accatcacca tcaccatcac agtgccgaac agcgtaaaaa gaaaaaaacc      60

accaccacga cccaaggacg tggagctgaa gttgctatgg cggatgagga tggaggccgc     120

ttgagagctg ctgctgagac tactggagga cctggatcac cggaccctgc cgatggaccc     180

ccccctacac caaaccccga tcgtagaccg gctgctagac ctggattcgg atggcatgga     240

ggacccgagg aaaacgagga cgaggcggac gacgccgctg ccgacgccga cgccgatgag     300

gctgcccctg cttctggaga ggcggtagac gaacctgctg ccgatggagt tgttagccct     360

aggcaattgg ctttgttggc gagcatggta gacgaggctg tgagaacaat cccttcccct     420
```

-continued

```
ccccctgaac gtgatggagc acaagaggag gcggctagga gtccctcacc accccgtaca    480
ccttctatga gagcggatta cggcgaggaa aacgacgacg acgacgatga tgatgacgac    540
gatgatcgtg atgccggacg ctgggttagg ggacctgaaa ccacttctgc tgtccgtgga    600
gcataccccg atcctatggc gagtttgagc cctagaccac ctgccccgag gagacaccac    660
caccaccacc atcataggcg tagacgtgct cctagacgtc gttctgccgc tagtgactct    720
tccaaatctg gctcttcttc atctgcctct tccgcttcat cttcggcctc atcgtcctct    780
tcggcatccg cttcgagtag tgatgatgat gatgacgacg acgctgctag agcccccgct    840
tctgctgccg accacgctgc tggcggaact ttgggagccg acgacgagga ggcgggagtt    900
cctgctcgtg ccccgggagc tgctccgagg ccttctccac cccgtgctga acctgctccg    960
gctagaacac cggccgctac tgctggtaga ctggagcgta gacgtgcccg tgctgctgtg   1020
gctggtagag atgctactgg ccgcttcact gctggccgtc ctagacgtgt tgaactggac   1080
gccgatgctg cttctggtgc tttctacgcc cgttaccgtg atggttacgt gtctggtgaa   1140
ccttggcctg gcgctggtcc acctccgccc ggacgtgtac tctacggtgg attgggcgat   1200
tctcgccctg gtctgtgggg cgctccggag gctgaggagg ctagagcccg tttcgaggct   1260
tctggtgccc ctgctcctgt ttgggctcct gaattgggcg acgctgctca acaatacgcc   1320
ctcatcacac gcttgctgta cactcccgac gccgaggcta tgggatggct ccaaaaccct   1380
agagttgccc ctggtgatgt tgctctggat caggcttgtt tccgtatctc cggcgctgct   1440
cgtaactctt cttcgttcat ctccggttct gtggctagag ctgtgcctca cttgggatac   1500
gccatggccg ctggacgttt cggctgggga ctggctcatg ttgctgccgc tgtagcaatg   1560
tctagacgct acgaccgtgc tcaaaaagga ttcttgctca cgtcactgag gcgtgcttac   1620
gcccctttgt tggcccgtga aaacgctgcc ctcactggcg cccgtacccc cgatgacggt   1680
ggcgacgcca accgccacga tggtgatgat gctagaggca aacccgctgc cgctgctgct   1740
cctttgccct ctgccgccgc ttcccctgcc gatgaacgtg ctgttcctgc cggttacggt   1800
gccgctggtg tgttggctgc tttgggacgc ttgagtgctg ccccggctag tgccccccgct   1860
ggtgccgatg acgatgacga tgacgatggt gctggcggag gcggtggcgg tagacgtgct   1920
gaggctggac gtgttgctgt tgaatgcctg gctgcctgta gaggaatctt ggaggctctg   1980
gccgagggat tcgacggaga cttggcggct gtaccgggac tggcgggagc gaggcctgcc   2040
gctccacctc gccccggtcc tgctggtgct gccgctcctc ctcatgccga cgctcctaga   2100
ctccgtgctt ggctccgtga actccgtttc gttcgtgacg ctttggttct gatgagactg   2160
agaggcgact tgagagtggc tggaggatcc gaggctgctg ttgctgctgt ccgtgctgtt   2220
tctttggttg ctggtgcttt gggccctgct ttgccgagat ctccccgttt gttgtcgagt   2280
gccgccgctg ctgccgccga tttgttgttc caaaaccaat ccctccgccc tctgctcgcc   2340
gacactgttg ccgctgccga ttctctggct gctccggctt ctgccccacg tgaagctcgt   2400
aaacgtaaat cacccgctcc ggctcgtgct ccccctggtg gcgcccctag acccccctaaa   2460
aaatcccgtg ccgatgcccc tagacctgct gctgctcccc ccgctggtgc tgctcccccc   2520
gctcccccta ctcccccccc acgcccacct cgtcccgctg ccctcacacg ccgtcctgct   2580
gagggacccg atccacaagg cggctggcgt agacaacctc ctggcccatc ccatacaccg   2640
gcaccatctg ccgctgcttt ggaggcttac tgtgctcctc gtgctgtggc tgaactcacc   2700
gatcatccgc tgttccctgc tccctggcgt cccgccctca tgttcgatcc tagagctttg   2760
gcttccttgg ccgctcgttg tgctgcccct ccccctggcg gtgctccggc tgctttcggt   2820
```

cctctccgtg cctctggtcc actccgccgt gccgctgcct ggatgagaca agttcccgac 2880
cctgaggatg ttagagttgt gatcttgtac tcgcccttgc ctggcgagga tttggccgct 2940
ggtagagctg gcggtggccc ccctcctgaa tggtctgctg aacgtggtgg tttgtcttgc 3000
ttgttggccg ccctgggaaa ccgtctgtgt ggtcctgcta ctgctgcttg ggctggaaac 3060
tggactggcg ctcccgatgt ttctgctctc ggtgctcaag gagttttgct gctctctact 3120
cgtgacttgg cattcgctgg agctgttgaa ttcctgggac tcttggctgg cgcttgtgat 3180
aggagactca tcgtcgtaaa cgctgtgaga gctgccgatt ggcctgccga tggtcctgtt 3240
gtgtctcgtc aacacgctta cttggcttgt gaagtgttgc ccgctgtcca atgtgctgtt 3300
cgctggcctg ctgctcgtga tctgaggcgt actgttctgg ctagtggtcg tgttttcgga 3360
cctggtgttt tcgctcgtgt cgaagctgct cacgctagac tgtaccccga tgccccaccc 3420
ctccgtttgt gtcgtggagc aaacgttcgc taccgtgtcc gtactcgttt cggacccgat 3480
actctggttc caatgtcccc tcgtgaatac cgtcgtgctg ttctgcctgc cctcgatgga 3540
cgtgctgccg cttctggcgc tggtgacgct atggctcctg gcgctccgga cttctgtgag 3600
gatgaggctc actcacatcg tgcctgtgcc cgctggggac tgggcgctcc attgaggcct 3660
gtatacgtgg cactgggccg tgatgctgtt agaggcggac ccgctgaatt gagaggccct 3720
cgtcgtgaat tctgtgctag ggctctgctc gaacccgatg gagatgctcc tcctttggta 3780
ctccgtgacg acgccgatgc tggtcctccc ccacaaattc gctgggctag tgctgctgga 3840
cgtgctggta ctgtattggc tgctgctggc ggtggcgttg aagttgttgg tactgccgct 3900
ggactcgcta cacctccccg ccgtgaacct gtagacatgg atgctgaact cgaggatgat 3960
gacgacggat tgttcggaga gtaatag 3987

<210> SEQ ID NO 40
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40
atgaagttcc tcgtgaacgt ggccctggtg ttcatggtgg tgtacatcag ctacatctac 60
gccaaccgtt ggaagtacgc tctggctgac ccatccctga agatggctga ccccaaccgt 120
ttccgtggca agaacctgcc cgtgctggac cagctgaccg acccccctgg cgtgaagcgt 180
gtgtaccaca tccagccatc cctcgaagac cccttccagc ccccctccat ccccatcacc 240
gtgtactacg ctgtgctgga acgcgcttgc cgttccgtgc tgctgcacgc tccttccgag 300
gctccccaga tcgtgcgtgg tgcttccgac gaggctcgca agcacaccta caacctgact 360
atcgcttggt acaggatggg tgacaactgc gctatcccta tcaccgtcat ggaatacacc 420
gagtgcccct acaacaagtc cctgggcgtg tgccctatcc gtacccagcc ccgttggtcc 480
tactacgact ccttcagcgc tgtgtccgag gacaacctgg gtttcctgat gcacgctccc 540
gctttcgaga ctgctggcac ctacctgcgt ctggtcaaga tcaacgactg gaccgagatc 600
acccagttca tcctggaaca ccgtgctcgt gcttcgtgca agtacgccct gcccctgcgt 660
atccctcctg ctgcttgcct gacctccaag gcttaccagc agggcgtgac cgtggactcc 720
atcggcatgc tgccccgttt catccccgag aaccagcgta ccgtggctct gtactctctg 780
aagatcgctg gctggcacgg tcctaagccc ccctacacct ccactctgct gccccctgag 840

-continued ctgtccgaca ccaccaacgc tactcagccc gagttggtgc ctgaggaccc cgaggactcc 900
gctctgttgg aggaccccgc tggaaccgtg tcctcccaga tcccccccaa ctggcacatc 960
ccttccatcc aggacgtggc ccctcaccac gctccagctg ctccctccaa cccccgtcgt 1020
cgtgctcaga tggctcccaa gcgtctgcgt ctgccccaca tccgtgacga cgacgctcct 1080
ccatcccacc agcccctgtt ctaccaccac caccatcacc actaataa 1128

<210> SEQ ID NO 41
<211> LENGTH: 783
<212> TYPE: DNA
<213> ORGANISM: Human herpesvirus 2

<400> SEQUENCE: 41
atgtctcgtc gtcgtggtcc tcgtcgtcgt ggtcctcgtc gtcgtccgcg tccgggtgcg 60
ccggcggtac cacgcccggg tgcgccggca gtgccgcgtc caggcgcact gcctaccgcg 120
gactctcaaa tggtgccggc gtatgattct ggtactgccg tcgaatctgc tccggcagcg 180
agctccctgc tgcgtcgttg gctgctggtc cctcaggcgg acgattccga tgacgcagac 240
tacgcgggca acgacgacgc ggagtgggct aacagcccgc caagcgaggg tggtggcaaa 300
gcgccggagg ctccgcacgc agcgcctgcc gcagcgtgcc cgcctccgcc tcctcgtaaa 360
gaacgtggcc ctcaacgtcc tctgccgccg cacctggctc tgcgtctgcg tactaccact 420
gagtacctgg cgcgtctgtc tctgcgtcgt cgccgtccgc cggctagccc gccggccgat 480
gcaccgcgtg gcaaagtgtg cttctctcca cgtgttcaag ttcgtcacct ggtggcttgg 540
gaaacggctg cccgtctggc tcgccgtggc agctgggcac gtgagcgcgc agaccgtgac 600
cgcttccgtc gccgtgtggc ggctgctgaa gccgttatcg gcccgtgcct ggaacctgag 660
gctcgcgctc gcgcgcgtgc gcgcgctcgt gcccacgaag atggcggtcc agcagaggaa 720
gaagaggcag ctgcagcagc gcgcggtagc tccgcggctg cgggtccagg tcgtcgtgcc 780
gta 783

<210> SEQ ID NO 42
<211> LENGTH: 2523
<212> TYPE: DNA
<213> ORGANISM: Human herpesvirus 2

<400> SEQUENCE: 42
atgtcgtact accatcacca tcaccatcac atggagccac gtcctggtac ttcttctcgc 60
gctgatcctg gtcctgaacg tccgccacgc cagactccgg gcacccagcc ggccgcccct 120
cacgcttggg gcatgctgaa cgatatgcag tggctggcgt cctctgattc cgaagaggag 180
actgaggttg gtatcagcga tgatgatctg caccgcgact ctaccagcga agcaggttcc 240
actgacaccg aaatgtttga agcgggcctg atggatgccg cgaccccgcc ggctcgtccg 300
ccggctgaac gtcagggtag ccctacgcct gcggatgcgc aaggctcttg tggtggtggt 360
ccagtaggcg aagaggaggc tgaggccggt ggcggcggtg atgtgtgtgc ggtttgtacc 420
gatgaaatcg caccgccgct gcgttgtcag tctttcccgt gcctgcaccc gttttgcatt 480
ccgtgcatga aaacctggat cccgctgcgc aacacttgcc cgctgtgcaa cactccggtt 540
gcttatctga tcgttggtgt aaccgcatct ggttcctttt ctaccatccc gattgtcaac 600
gacccacgta cgcgtgttga ggcggaggcg gctgtacgtg cgggcaccgc ggtggacttt 660
atctggaccg gtaacccgcg caccgcgcca cgctccctgt ctctgggtgg ccataccgtt 720

```
cgtgctctga gcccgacccc accttggcca ggcaccgatg acgaagacga cgatctggct     780
gacgttgact atgttccgcc ggcaccgcgt cgcgcaccac gccgtggtgg cggtggcgcc     840
ggtgcgacgc gcggtacctc ccagccggca gcaactcgcc cagcaccgcc gggtgccccg     900
cgttctagca gctccggtgg cgcaccgctg cgtgctggcg tgggttctgg ttccggtggt     960
ggtccggccg tggcggctgt cgtcccgcgt gtggcttctc tgccaccggc agctggtggc    1020
ggtcgtgctc aagctcgtcg tgtcggcgag gacgcagcgg ctgctgaggg ccgtactcca    1080
ccggcccgtc aaccgcgcgc agcacaggaa ccgccgatcg tgatctccga ttccccgcca    1140
ccgagcccgc gtcgcccggc gggtccgggt ccgctgtctt ttgtatcctc cagctctgct    1200
caggtaagca gcggtcctgg cggtggcggc ctgccacagt cctctggtcg tgctgctcgt    1260
cctcgtgcgg cggttgctcc tcgtgtacgt tctccgccac gcgctgctgc cgcgccggtc    1320
gtttctgcct ctgctgacgc ggcaggtccg gctccgcctg cagttccggt tgatgcacac    1380
cgtgcaccgc gctctcgtat gacccaggcg cagactgata cccaggcaca atccctgggt    1440
cgcgcgggtg cgactgacgc tcgtggtagc ggtggtccgg gcgctgaagg tggcccgggt    1500
gttccacgcg gtactaacac tccgggcgct gcgccacacg cggctgaagg tgcggctgca    1560
cgtccgcgta aacgtcgtgg ttccgacagc ggtccggctg caagcagcag cgcgagctct    1620
tccgctgcgc ctcgcagccc gctggcgccg cagggtgttg gcgccaagcg tgctgctccg    1680
cgtcgtgcac cggactccga ttctggcgac cgcggtcacg gcccgctggc ccctgctagc    1740
gcaggcgctg cgccgccatc cgccagcccg tcttctcagg cagctgtggc tgcggcgtcc    1800
tcttcttccg ctagcagctc ttccgcctct tctagcagcg cgtcctctag cagcgcatct    1860
tcctcttctg cttcttcttc tagcgcttct agctcttccg cgtcctcttc cgctggcggt    1920
gcaggcggct ctgttgcttc cgccagcggc gcaggtgagc gtcgtgaaac gagcctgggc    1980
ccacgtgctg ctgcaccgcg tggcccgcgt aagtgtgcgc gcaagacccg ccacgctgaa    2040
ggcggtccgg agccgggtgc gcgtgatccg gctccgggtc tgacccgtta cctgccgatt    2100
gcgggtgtgt cctccgttgt ggcactggcg ccgtatgtga acaaaactgt cacgggcgat    2160
tgcctgcctg ttctggacat ggaaaccggt catatcggcg cttacgtcgt tctggttgac    2220
caaaccggca acgtggcgga tctgctgcgt gcggccgctc cggcttggtc ccgtcgtacc    2280
ctgctgccgg aacatgctcg caactgtgta cgcccaccgg attacccaac cccgccggcc    2340
tccgagtgga actccctgtg gatgaccccg gttggtaaca tgctgttcga ccagggcacg    2400
ctggttggtg ctctggactt tcacggcctg cgctcccgtc acccgtggtc ccgtgagcaa    2460
ggcgctccgg cccctgcggg cgatgccccg gctggccacg gcgagagtac tagaggatca    2520
taa                                                                  2523
```

<210> SEQ ID NO 43
<211> LENGTH: 2928
<212> TYPE: DNA
<213> ORGANISM: human herpesvirus 2

<400> SEQUENCE: 43

```
atgtcgtact accatcacca tcaccatcac gccgctcaac gtgctagggg atcctctgaa      60
cgctgggctg ctggtgtcga ggctgctttg gatagagtgg agaaccgtgc cgaattcgat     120
gttgtcgagc tgaggagact ccaagctttg gctggtactc acggctacaa ccctcgtgat     180
ttccgtaaac gtgccgaaca ggctttggcg gcaaacgctg aggccgtaac attggctctg     240
gacactgcct tcgctttcaa cccatacacg cccgaaaacc aacgtcatcc tatgctccca     300
```

-continued

```
cctctcgctg ctattcaccg cctgggatgg agcgctgctt tccatgctgc tgctgaaact    360
tacgccgaca tgttccgtgt cgatgccgaa ccactggcta gactgctccg tatcgctgag    420
ggactgctgg agatggctca agctggcgac ggattcatcg attaccatga ggctgtcggt    480
agactggccg atgatatgac ttctgtgccc ggattgaggc gctacgttcc tttcttccaa    540
catggctacg ccgattacgt ggaactgaga gatcgcctgg atgctattag ggccgacgtc    600
catagagcac tcggtggtgt tccgctggat ttggcggctg ctgccgaaca aatttccgct    660
gctcgtaacg atcctgaggc tactgctgaa ttggtccgta ctggtgtaac attgccttgc    720
cctagtgagg acgctctcgt ggcttgtgct gctgccctgg agagagtcga tcaatctccc    780
gtgaaaaaca cggcttacgc cgaatacgtt gccttcgtga cccgtcaaga cactgctgag    840
actaaagacg ctgtggtccg tgctaaacaa caacgtgctg aggccactga acgtgttatg    900
gctggcctga gagaggctct ggctgctaga gaacgtcgtg ctcaaattga ggctgaggga    960
ttggcaaacc tgaaaaccat gctcaaagtc gtggctgtac ccgctactgt tgctaaaact   1020
ctcgaccagg ctcgtagtgt tgccgaaatt gccgatcaag tcgaagtgtt gctggatcaa   1080
accgaaaaaa ctcgtgaact ggatgtgcct gctgtgatct ggctcgaaca cgcccaaaga   1140
acattcgaga cacacccttt gtctgccgct cgtggtgatg gtcctggacc cttggctcgt   1200
catgctggcc gcctcggtgc cctcttcgat actcgtcgta gagtagacgc cttgaggaga   1260
tccctggagg aggctgaggc tgaatgggac gaagtttggg gacgcttcgg tagagtgagg   1320
ggcggagcgt ggaaatctcc ggagggattc cgtgcaatgc atgagcaact gagggccctc   1380
caagacacaa caaacaccgt gtctggcctg agggctcaac ctgcttacga acgcttgtct   1440
gctcgctacc aaggagtact cggagcgaaa ggcgctgaga gagctgaggc tgttgaggaa   1500
ctcggtgctc gtgtcactaa acacaccgct ctgtgtgcta ggctgagaga tgaggtcgtc   1560
cgtagagtgc cttgggaaat gaacttcgat gctctgggag gattgttggc tgagttcgat   1620
gccgctgctg ccgatttggc accttgggct gtagaggaat tccgtggtgc tagagaactc   1680
attcaatacc gtatgggcct gtactctgcc tacgctagag ctggaggaca aactggtgct   1740
ggagctgaat ctgctcctgc tcctttgctc gtggatctga gggctttgga tgctcgtgct   1800
cgtgcttctt cttcccctga gggacatgaa gtggacccac aactgctgag gaggcgtgga   1860
gaggcttact tgagagctgg cggcgaccct ggacctctcg tgctccgtga agctgtttct   1920
gctttggacc tgccattcgc cacatctttc ttggcccccg atggaactcc cctccaatac   1980
gctttgtgct tccctgccgt aacggacaaa ctcggagctt tgctcatgag gcccgaggcc   2040
gcttgtgtta gacctccttt gcctaccgat gtgctggaat ctgccccaac tgtgactgcc   2100
atgtacgtac tcactgtggt caaccgcctc caactggcat tgagtgatgc tcaagcggca   2160
aacttccaac tgttcggtcg tttcgttcgt cataggcagg caacctgggg agcgtcaatg   2220
gatgccgccg ctgaattgta cgttgccctg gtggctacaa ctctcacacg tgaattcggt   2280
tgtcgctggg cacaattggg atgggctagt ggagctgctg ctcctagacc cccacctgga   2340
ccccgtggct cacaacgtca ctgtgtggca ttcaacgaga acgatgtcct cgtcgctttg   2400
gttgccggtg ttcccgaaca catctacaac ttctggcgcc tggacttggt ccgtcaacac   2460
gagtacatgc acctcacact ggagcgtgcc ttcgaggatg ctgccgagtc tatgctcttc   2520
gttcaacgcc tcactccaca tcccgacgct cgtattagag ttctgccgac cttcttggat   2580
ggtggtcctc ctacacgtgg tctgttgttc ggaacccgct tggcggactg gcgtcgtggt   2640
```

aaactgtctg aaaccgaccc attggcccca tggagatctg ctttggaact cggaacccaa 2700
cgtcgtgacg tgcctgcttt gggaaaactg tcccctgctc aagctttggc cgctgtgtcg 2760
gtactgggcc gtatgtgctt gccctcggct gccttggctg ctttgtggac ctgtatgttc 2820
cccgacgact acactgaata cgactcattc gacgccctct tggcggctcg cctggaatcg 2880
ggacaaacat tgggacctgc tggcggtaga gaggcttcat tgtaatag 2928

<210> SEQ ID NO 44
<211> LENGTH: 2646
<212> TYPE: DNA
<213> ORGANISM: human herpesvirus 2

<400> SEQUENCE: 44
atgtcgtact accatcacca tcaccatcac gaatacgact ccttcgacgc tttgttggct 60
gctagactgg aatctggtca aaccttggga cccgctggcg gtagagaggc ttctttgccc 120
gaggctcctc atgctttgta ccgtccaacc ggacaacatg ttgctgtgtt ggcggctgct 180
actcatagaa cccctgctgc tcgtgttact gctatggacc tggtcttggc ggccgttttg 240
ctgggcgctc ctgtggtggt cgctctgaga aacactactg ccttctcccg tgaatccgaa 300
ttggaactgt gcctcaccct gttcgattct cgtcccggcg gaccggatgc tgccctgaga 360
gatgtggtat cctccgacat tgaaacctgg gctgtgggct tgctccacac cgatttgaac 420
cctattgaga acgcttgctt ggcggctcaa ctgccacgct tgtctgccct cattgctgaa 480
cgtcctttgg ccgatggacc cccttgtttg gtgttggtgg acatttcgat gacacctgtc 540
gctgttttgt gggaggcccc tgaaccacct ggccctcccg atgttcgttt cgtcggtagc 600
gaggccactg aggaattgcc tttcgtggct actgctggtg atgttttggc ggcgagtgct 660
gccgatgccg atcctttctt cgctcgtgct atcctgggcc gtcctttcga tgcttctctg 720
ctcactggtg aactgttccc tggtcacccc gtttaccaac gtcccctggc ggatgaggct 780
ggtccttctg ctcctactgc cgctcgtgat cctagagatc tggctggagg cgacggtgga 840
tccggacctg aggatcccgc tgctccacct gctagacagg ccgatcctgg tgttttggct 900
cctactctgc tcaccgatgc tactactggc gaacctgtgc caccccgtat gtgggcttgg 960
attcatggac tggaggaact ggcttccgat gatgccggcg gtcctacccc aaaccctgcc 1020
ccggctttgc tgccccctcc tgctacggat caatctgtcc ccacttccca atacgcccct 1080
agaccaattg gcccggctgc cactgctaga gaaactcgtc cttccgttcc ccctcaacaa 1140
aacactggtc gtgtccctgt ggctccacgt gatgacccta gaccttcccc ccctactcct 1200
tccccccctg ccgatgctgc tttgccacct cctgccttct ctggttctgc tgctgctttc 1260
tccgctgctg ttccacgtgt tcgtcgttct aggcgtactc gtgccaaatc ccgtgcccct 1320
cgtgcttctg ccccacccga gggatggcgt ccccccgctt tgcctgcccc tgttgctcct 1380
gtggcggctt ctgctcgtcc ccccgatcaa cctcctactc ccgaatctgc tcccccggct 1440
tgggtttccg ctctgccatt gccacccgga cctgctagtg ctcgtggtgc tttccctgct 1500
ccaaccttgg cccctattcc cccacccccc gctgagggag ctgttgttcc cggtggtgat 1560
cgtagacgtg gtcgccgtca aacaactgct ggaccatccc ctacaccgcc acgtggcccg 1620
gctgctggtc ctcctcgtcg cctcactagg cctgctgttg ctagtctgtc cgcttctttg 1680
aactctctgc cttccccccg tgatcctgcc gatcatgctg ctgccgtttc tgctgccgcc 1740
gctgccgtac caccttcacc tggactggct cccccaactt ctgctgtcca aacctctcct 1800
cctcccttgg cgcctggtcc tgttgcccca tctgaacctt tgtgtggctg ggttgtgcct 1860
ggaggccctg ttgctagacg tcccccaccc caatctccgg ctactaaacc ggctgctcgt 1920
acccgtatta gggctcgttc tgtgccccaa ccacccttgc cccaacctcc actgcctcaa 1980 cccccccttgc ctcaaccccc tctcccccaa ccacctctgc ctcaacctcc gctgccccaa 2040
cctcctttgc cccaacctcc tttgccccaa cctcctttgc cccaacctcc gctgccccaa 2100
cctccgctgc cacctgttac tcgtacactc actccccaat ctcgtgactc tgtgcctaca 2160
cctgagtctc caactcacac aaacacccac ttgcccgtta gtgctgtgac ttcttgggct 2220
tcgtccctgg ctctccatgt ggattctgcc cctccccctg cttcattgct ccaaactctc 2280
cacatttcct ccgatgatga acactccgac gccgactcac tccgcttctc cgattccgat 2340
gacactgagg ctctcgatcc tttgcctcct gaacctcact tgccacctgc cgatgaaccc 2400
cccggacctc tggctgccga ccatctccaa tcacctcact cacaattcgg tcctttgccc 2460
gttcaagcga acgctgttct gtctcgtcgt tacgtgagat caactggccg ttctgccttg 2520
gctgtgctca ttagagcttg tcgccgtatc caacaacaac tccagcgtac taggagagca 2580
ctcttccaac gctcaaacgc cgtgctcaca tcactccacc atgtccgtat gctcttggga 2640
taatag 2646

<210> SEQ ID NO 45
<211> LENGTH: 261
<212> TYPE: DNA
<213> ORGANISM: Human herpesvirus 2

<400> SEQUENCE: 45
atgtcttggg ctctgaaaac caccgacatg ttcctggact cttctcgttg cacccaccgt 60
acctacggtg acgtttgcgc tgaaatccac aaacgtgaac gtgaagaccg tgaagctgct 120
cgtaccgctg ttaccgaccc ggaactgccg ctgctgtgcc cgccggacgt tcgttctgac 180
ccggcttctc gtaacccgac ccagcagacc cgtggttgcg ctcgttctaa cgaacgtcag 240
gaccgtgttc tggctccgtg a 261

<210> SEQ ID NO 46
<211> LENGTH: 993
<212> TYPE: DNA
<213> ORGANISM: human herpesvirus 2

<400> SEQUENCE: 46
atgaagttcc tcgtgaacgt ggccctggtg ttcatggtgg tgtacatcag ctacatctac 60
gctaaccgtt ggggttccgg cgtgccccggt cccatcaacc cccccaactc cgacgtggtg 120
ttccccggtg gttcccccgt ggctcagtac tgctacgctt acccccgtct ggacgaccct 180
ggtcccctgg gttctgctga cgctggtcgt caggacctgc cccgtcgtgt cgtgcgtcac 240
gagcccctgg gtcgtagctt cctgaccggt ggcctggtgc tgttggctcc ccctgtgcgc 300
ggtttcggtg ctcccaacgc tacctacgct gctcgtgtga cctactaccg tctgacccgt 360
gcttgccgtc agcccatcct gctgcgtcag tacggtggtt gccgtggtgg agagccccca 420
tcccccaaga cctgcggttc ttacacctac acctaccagg gtggtggtcc ccctacccgt 480
tacgctctgg tcaacgcttc cctgctggtg cccatctggg accgtgctgc tgagactttc 540
gagtaccaga tcgagctggg tggcgagctg cacgtgggtc tgctgtgggt ggaagtgggt 600
ggagagggtc ccggtcctac cgctcctcct caggctgctc gtgctgaggg tggtccttgc 660
gtgccacccg tgcctgctgg tcgtccttgg cgttccgtgc cccccgtgtg gtactccgct 720

-continued

```
cccaaccccg gtttccgcgg tctgcgtttc cgtgagcgtt gcctgcctcc ccagacccct    780

gctgctcctt ccgacctgcc tcgtgtggct ttcgctcccc agtccctgct cgtgggtatc    840

accggtcgta ccttcatccg tatggctcgt cccaccgagg acgtgggtgt cctgcctcct    900

cactgggctc caggtgctct ggacgacggt ccctacgctc ccttcccccc tcgtccccgt    960

ttccgtcgtc accaccacca tcaccactaa taa                                 993
```

```
<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Leu Ala His Val Ala Ala Ala Val
1               5


<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Ile Ser Gly Ser Val Ala Arg Ala
1               5


<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Tyr Ala Leu Ile Thr Arg Leu Leu
1               5


<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Tyr Asp Arg Ala Gln Lys Gly Phe
1               5


<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Tyr Ala Met Ala Ala Gly Arg Phe
1               5
```

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Pro Pro His Ala Asp Ala Pro Arg Leu
1 5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

Lys Pro Ala Ala Ala Ala Ala Pro Leu
1 5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Ser Glu Ala Ala Val Ala Ala Val
1 5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Phe Gly Trp Gly Leu Ala His Val
1 5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Tyr Ala Leu Ile Thr Arg Leu Leu Tyr
1 5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Ala Leu Pro Arg Ser Pro Arg Leu Leu
1 5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Asp Leu Leu Phe Gln Asn Gln Ser Leu
1 5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Ala Asp Leu Leu Phe Gln Asn Gln Ser
1 5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Ala Arg Asn Ser Ser Ser Phe Ile Ser
1 5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Gln Ala Cys Phe Arg Ile Ser Gly Ala
1 5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Phe Val Arg Asp Ala Leu Val Leu Met
1 5

<210> SEQ ID NO 63
<211> LENGTH: 9

<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Phe Asp Gly Asp Leu Ala Ala Val Pro
1 5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Gly Leu Gly Asp Ser Arg Pro Gly Leu
1 5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Trp Ala Pro Glu Leu Gly Asp Ala Ala
1 5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Glu Cys Leu Ala Ala Cys Arg Gly Ile
1 5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Arg Ala Trp Leu Arg Glu Leu Arg Phe
1 5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Ala Leu Ala Gly Ser Thr Leu Ala Val 1 5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Leu Leu Glu Asp Pro Ala Gly Thr Val
1 5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Val Ile Gly Gly Ile Ala Phe Trp Val
1 5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Thr Val Tyr Tyr Ala Val Leu Glu Arg
1 5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Lys Tyr Ala Leu Ala Asp Pro Ser Leu
1 5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Ala Phe Glu Thr Ala Gly Thr Tyr Leu
1 5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Ala Pro Ser Asn Pro Gly Leu Ile Ile
1 5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Ile Pro Ile Thr Val Tyr Tyr Ala Val
1 5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Ala Pro Pro Ser His Gln Pro Leu Phe
1 5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Phe Leu Met His Ala Pro Ala Phe Glu
1 5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Phe Ser Ala Val Ser Glu Asp Asn Leu
1 5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

Val Tyr Tyr Ala Val Leu Glu Arg
1 5

<210> SEQ ID NO 80

<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Ile Gly Met Leu Pro Arg Phe Ile
1 5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Tyr Thr Glu Cys Pro Tyr Asn Lys Ser
1 5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Phe Leu Met His Ala Pro Ala Phe Glu
1 5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Asn Leu Gly Phe Leu Met His Ala Pro
1 5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Val Ile Gly Gly Ile Ala Phe Trp Val
1 5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Gly Ile Ala Phe Trp Val Arg Arg Arg
1 5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Ser Glu Asp Asn Leu Gly Phe Leu Met
1 5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Arg Thr Gln Pro Arg Trp Ser Tyr Tyr
1 5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Ile Ala Phe Trp Val Arg Arg Arg Ala
1 5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Leu Val Ile Gly Gly Ile Ala Phe Trp
1 5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Phe Trp Val Arg Arg Arg Ala Gln Met
1 5

<210> SEQ ID NO 91
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 91

Pro Tyr Thr Ser Thr Leu Leu Pro Pro
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Val Gly Thr Ala Ala Leu Leu Val Val
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Ala Ala Leu Leu Val Val Ala Val
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Ser Thr Leu Leu Pro Pro Glu Leu
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Thr Val Ser Ser Gln Ile Pro Pro
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Ala Gly Thr Tyr Leu Arg Leu Val
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Gly Val Thr Val Asp Ser Ile Gly Met
1 5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Ala Phe Trp Val Arg Arg Arg Ala Gln
1 5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Arg Val Tyr His Ile Gln Pro Ser Leu
1 5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Ala Tyr Leu Val Asn Pro Phe Leu Phe
1 5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Pro Phe Leu Phe Ala Ala Gly Phe Leu
1 5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Thr Glu Tyr Val Leu Arg Ser Val Ile
1 5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Gly Ser Gln Ala Thr Glu Tyr Val Leu
1 5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Arg Ile Asp Gly Ile Phe Leu Arg Tyr
1 5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Phe Leu Glu Asp Leu Ser His Ser Val
1 5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Tyr Val Leu Arg Ser Val Ile Ala Lys
1 5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Tyr Val Leu Arg Ser Val Ile Ala Lys
1 5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 108

Ala Tyr Leu Val Asn Pro Phe Leu Phe
1 5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 109

Glu Thr Thr Thr Arg Arg Ala Leu Tyr
1 5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Arg Ile Asp Gly Ile Phe Leu Arg Tyr
1 5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Tyr Leu Val Asn Pro Phe Leu Phe Ala
1 5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Phe Val Cys Leu Phe Gly Leu Val Val
1 5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Leu Tyr Lys Glu Ile Arg Asp Ala Leu
1 5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Gly Leu Asp Thr Phe Leu Trp Asp Arg
1 5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

Arg Val Ser Pro Thr Arg Gly Arg Arg
1 5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

Gly Leu Asp Thr Phe Leu Trp Asp Arg
1 5

<210> SEQ ID NO 117
<211> LENGTH: 1221
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 117
atgtcgtact accatcacca tcaccatcac atggtgctgt acggcgggct gggcgacagc 60
cgccccggcc tctggggggc gcccgaggcg gaggaggcgc gggcccggtt cgaggcctcg 120
ggcgccccgg cgcccgtgtg ggcgcccgag ctgggcgacg cggcgcagca gtacgccctg 180
atcacgcggc tgctgtacac gccggacgcg gaggcgatgg ggtggctcca gaacccgcgc 240
gtggcgcccg gggacgtggc gctggaccag gcctgcttcc ggatctcggg cgcggcgcgc 300
aacagcagct ccttcatctc cggcagcgtg gcgcgggccg tgccccacct ggggtacgcc 360
atggcggcgg gccgcttcgg ctggggcctg gcgcacgtgg cggccgccgt ggccatgagc 420
cgccgctacg accgcgcgca gaagggcttc ctgctgacca gcctgcgccg cgcctacgcg 480
cccctgctgg cgcgcgagaa cgcggcgctg accggggcgc ggacccccga cgacggcggc 540
gacgccaacc gccgcgacgg cgacgacgcc cgcgggaagc ccgccgccgc cgccgccccg 600
ttgccgtcgg cggcggcgtc gccggccgac gagcgcgcgg tgcccgccgg ctacggcgcc 660
gcgggggtgc tcgccgccct ggggcgcctg agcgccgcgc ccgcctccgc gccggccggg 720
gccgacgacg acgacgacga cgacgacggc gccggcggtg gtggcggtgg tggcggtggt 780

-continued

```
ggcggcggcc ggcgcgcgga ggcgggccgc gtggccgtgg agtgcctggc cgcctgccgc    840

gggatcctgg aggcgctggc ggagggcttc gacggcgacc tggcggccgt gccggggctg    900

gccggagccc ggcccgccgc gcccccgcgc ccggggcccg cgggcgcggc cgccccgccg    960

cacgccgacg cgccccgcct gcgcgcctgg ctgcgcgagc tgcggttcgt gcgcgacgcg   1020

ctggtgctga tgcgcctgcg cggggacctg cgcgtggccg gcggcagcga ggccgccgtg   1080

gccgccgtgc gcgccgtgag cctggtcgcc ggggccctgg gcccggcgct gccgcggagc   1140

ccgcgcctgc tgagctccgc cgccgccgcc gccgcggacc tgctcttcca gaaccagagc   1200

ctgagtacta gaggatcata a                                             1221
```

<210> SEQ ID NO 118
<211> LENGTH: 705
<212> TYPE: DNA
<213> ORGANISM: Human herpesvirus 2

<400> SEQUENCE: 118

```
atgtcgtact accatcacca tcaccatcac atggggttcg tctgtctgtt tgggcttgtc     60

gttatgggag cctgggggc gtggggtggg tcacaggcaa ccgaatatgt tcttcgtagt    120

gttattgcca aagaggtggg ggacatacta agagtgcctt gcatgcggac ccccgcggac    180

gatgtttctt ggcgctacga ggccccgtcc gttattgact atgcccgcat agacggaata    240

tttcttcgct atcactgccc ggggttggac acgtttttgt gggataggca cgcccagagg    300

gcgtatcttg ttaacccctt tctctttgcg gcgggatttt tggaggactt gagtcactct    360

gtgtttccgg ccgacaccca ggaaacaacg acgcgccggg ccctttataa agagatacgc    420

gatgcgttgg gcagtcgaaa acaggccgtc agccacgcac ccgtcagggc cgggtgtgta    480

aactttgact actcacgcac tcgccgctgc gtcgggcgac gcgatttacg gcctgccaac    540

accacgtcaa cgtgggaacc gcctgtgtcg tcggacgatg aagcgagctc gcagtcgaag    600

cccctcgcca cccagccgcc cgtcctcgcc ctttcgaacg cccccccacg gcgggtctcc    660

ccgacgcgag gtcggcgccg gcatactcgc ctccgacgca actga                   705
```

<210> SEQ ID NO 119
<211> LENGTH: 762
<212> TYPE: DNA
<213> ORGANISM: Human herpesvirus 2

<400> SEQUENCE: 119

```
atgaagttcc tcgtgaacgt ggccctggtg ttcatggtgg tgtacatcag ctacatctac     60

gccaaccgtt gggggttcgt ctgtctgttt gggcttgtcg ttatgggagc ctgggggcg    120

tggggtgggt cacaggcaac cgaatatgtt cttcgtagtg ttattgccaa agaggtgggg    180

gacatactaa gagtgccttg catgcggacc cccgcggacg atgtttcttg gcgctacgag    240

gccccgtccg ttattgacta tgcccgcata gacggaatat ttcttcgcta tcactgcccg    300

gggttggaca cgtttttgtg ggataggcac gcccagaggg cgtatcttgt taaccccttt    360

ctctttgcgg cgggattttt ggaggacttg agtcactctg tgtttccggc cgacacccag    420

gaaacaacga cgcgccgggc cctttataaa gagatacgcg atgcgttggg cagtcgaaaa    480

caggccgtca gccacgcacc cgtcagggcc gggtgtgtaa actttgacta ctcacgcact    540

cgccgctgcg tcgggcgacg cgatttacgg cctgccaaca ccacgtcaac gtgggaaccg    600

cctgtgtcgt cggacgatga agcgagctcg cagtcgaagc ccctcgccac ccagccgccc    660

gtcctcgccc tttcgaacgc ccccccacgg cgggtctccc cgacgcgagg tcggcgccgg    720
```

catactcgcc tccgacgcaa ccatcaccat caccatcact ga 762

<210> SEQ ID NO 120
<211> LENGTH: 4155
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 120
atgtcgtact accatcacca tcaccatcac atggccgctc ctgcccgcga ccccccgggt 60
taccggtacg ccgcggccat ggtgcccacc ggctccatcc tgagtacgat cgaggtggcg 120
tcccaccgca gactctttga ttttttcgcc cgcgtgcgct ccgacgaaaa cagcctgtat 180
gacgtagagt ttgacgccct gctggggtcc tactgcaaca ccctgtcgct cgtgcgcttt 240
ctggagctcg gcctgtccgt ggcgtgcgtg tgcaccaagt tcccggagct ggcttacatg 300
aacgaagggc gtgtgcagtt cgaggtccac cagcccctca tcgcccgcga cggcccgcac 360
cccgtcgagc agcccgtgca taattacatg acgaaggtca tcgaccgccg ggccctgaac 420
gccgccttca gcctggccac cgaggccatt gccctgctca cgggggaggc cctggacggg 480
acgggcatta gcctgcatcg ccagctgcgc gccatccagc agctcgcgcg caacgtccag 540
gccgtcctgg gggcgtttga gcgcggcacg gccgaccaga tgctgcacgt gctgttggag 600
aaggcgcctc ccctggccct gctgttgccc atgcaacgat atctcgacaa cgggcgcctg 660
gcgaccaggg ttgcccgggc gaccctggtc gccgagctga agcggagctt ttgcgacacg 720
agcttcttcc tgggcaaggc gggccatcgc cgcgaggcca tcgaggcctg gctcgtggac 780
ctgaccacgg cgacgcagcc gtccgtggcc gtgccccgcc tgacgcacgc cgacacgcgc 840
gggcggccgg tcgacggggt gctggtcacc accgccgcca tcaaacagcg cctcctgcag 900
tccttcctga aggtggagga caccgaggcc gacgtgccgg tgacctacgg cgagatggtc 960
ttgaacgggg ccaacctcgt cacggcgctg gtgatgggca aggccgtgcg gagcctggac 1020
gacgtgggcc gccacctgct ggagatgcag gaggagcaac tcgaggcgaa ccgggagacg 1080
ctggatgaac tcgaaagcgc cccccagaca acgcgcgtgc gcgcggatct ggtggccata 1140
ggcgacaggc tggtcttcct ggaggccctg gagaagcgca tctacgccgc caccaacgtg 1200
ccctaccccc tggtgggcgc catggacctg acgttcgtcc tgcccctggg gctgttcaac 1260
ccggccatgg agcgcttcgc cgcgcacgcc ggggacctgg tgcccgcccc cggccacccg 1320
gagccccgcg cgttccctcc ccggcagctg ttttttttggg gaaaggacca ccaggttctg 1380
cggctgtcca tggagaacgc ggtcgggacc gtgtgtcatc cttcgctcat gaacatcgac 1440
gcggccgtcg gggggcgtgaa ccacgacccc gtcgaggccg cgaatccgta cggggcgtac 1500
gtcgcggccc cggccggccc cggcgcggac atgcagcagc gttttctgaa cgcctggcgg 1560
cagcgcctcg cccacggccg ggtccggtgg gtcgccgagt gccagatgac cgcggagcag 1620
ttcatgcagc ccgacaacgc caacctggct ctggagctgc accccgcgtt cgacttcttc 1680
gcgggcgtgg ccgacgtcga gcttcccggc ggcgaagtcc ccccggccgg tccgggggcg 1740
atccaggcca cctggcgcgt ggtcaacggc aacctgcccc tggcgctgtg tccggtggcg 1800
tttcgtgacg cccggggcct ggagctcggc gttggccgcc acgccatggc gccggctacc 1860
atagccgccg tccgcggggc gttcgaggac cgcagctacc cggcggtgtt ctacctgctg 1920
caagccgcga ttcacggcag cgagcacgtg ttctgcgccc tggcgcggct cgtgactcag 1980

```
tgcatcacca gctactggaa caacacgcga tgcgcggcgt tcgtgaacga ctactcgctg   2040
gtctcgtaca tcgtgaccta cctcgggggc gacctccccg aggagtgcat ggccgtgtat   2100
cgggacctgg tggcccacgt cgaggccctg gcccagctgg tggacgactt taccctgccg   2160
ggcccggagc tgggcgggca ggctcaggcc gagctgaatc acctgatgcg cgacccggcg   2220
ctgctgccgc ccctcgtgtg ggactgcgac ggccttatgc gacacgcggc cctggaccgc   2280
caccgagact gccggattga cgcgggggag cacgagcccg tctacgcggc ggcgtgcaac   2340
gtggcgacgg ccgactttaa ccgcaacgac ggccggctgc tgcacaacac ccaggcccgc   2400
gcggccgacg ccgccgacga ccggccgcac cggccggccg actggaccgt ccaccacaaa   2460
atctactatt acgtgctggt gccggccttc tcgcgggggc gctgctgcac cgcgggggtc   2520
cgcttcgacc gcgtgtacgc cacgctgcag aacatggtgg tcccggagat cgcccccggc   2580
gaggagtgcc cgagcgatcc cgtgaccgac cccgcccacc cgctgcatcc cgccaatctg   2640
gtggccaaca cggtcaacgc catgttccac aacgggcgcg tcgtcgtcga cgggcccgcc   2700
atgctcacgc tgcaggtgct ggcgcacaac atggccgagc gcacgacggc gctgctgtgc   2760
tccgcggcgc ccgacgcggg cgccaacacc gcgtcgacgg ccaacatgcg catcttcgac   2820
ggggcgctgc acgccggcgt gctgctcatg gccccccagc acctggacca caccatccaa   2880
aatggcgaat acttctacgt cctgcccgtc cacgcgctgt ttgcgggcgc cgaccacgtg   2940
gccaacgcgc ccaacttccc cccggccctg cgcgacctgg cgcgccacgt ccccctggtc   3000
cccccggccc tgggggccaa ctacttctcc tccatccgcc agcccgtggt gcagcacgcc   3060
cgcgagagcg cggcggggga gaacgcgctg acctacgcgc tcatggcggg gtacttcaag   3120
atgagccccg tggccctgta tcaccagctc aagacgggcc tccaccccgg gttcgggttc   3180
accgtcgtgc ggcaggaccg cttcgtgacc gagaacgtgc tgttttccga gcgcgcgtcg   3240
gaggcgtact ttctgggcca gctccaggtg gcccgccacg aaacgggcgg gggggtcagc   3300
ttcacgctca cccagccgcg cggaaacgtg gacctgggtg tgggctacac cgccgtcgcg   3360
gccacggcca ccgtccgcaa ccccgttacg gacatgggca acctccccca aaacttttac   3420
ctcggccgcg gggccccccc gctgctagac aacgcggccg ccgtgtacct gcgcaacgcg   3480
gtcgtggcgg gaaaccggct ggggccggcc cagcccctcc cggtctttgg ctgcgcccag   3540
gtgccgcggc gcgccggcat ggaccacggg caggatgccg tgtgtgagtt catcgccacc   3600
cccgtggcca cggacatcaa ctactttcgc cggccctgca acccgcgggg acgcgcggcc   3660
ggcggcgtgt acgcggggga caaggagggg gacgtcatag ccctcatgta cgaccacggc   3720
cagagcgacc cggcgcggcc cttcgcggcc acggccaacc cgtgggcgtc gcagcggttc   3780
tcgtacgggg acctgctgta caacggggcc tatcacctca acggggcctc gcccgtcctc   3840
agcccctgct tcaagttctt caccgcggcc gacatcacgg ccaaacatcg ctgcctggag   3900
cgtcttatcg tggaaacggg atcggcggta tccacggcca ccgctgccag cgacgtgcag   3960
tttaagcgcc cgccggggtg ccgcgagctc gtggaagacc cgtgcggcct gtttcaggaa   4020
gcctacccga tcacctgcgc cagcgacccc gccctgctac gcagcgcccg cgatggggag   4080
gcccacgcgc gagagaccca ctttacgcag tatctcatct acgacgcctc cccgctaaag   4140
ggcctgtctc tgtaa                                                    4155
```

<210> SEQ ID NO 121
<211> LENGTH: 1200
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 121
atgagtgccg aacagcgtaa aaagaaaaaa accaccacca cgacccaagg acgtggagct 60
gaagttgcta tggcggatga ggatggaggc cgcttgagag ctgctgctga gactactgga 120
ggacctggat caccggaccc tgccgatgga cccccccccta caccaaaccc cgatcgtaga 180
ccggctgcta gacctggatt cggatggcat ggaggacccg aggaaaacga ggacgaggcg 240
gacgacgccg ctgccgacgc cgacgccgat gaggctgccc ctgcttctgg agaggcggta 300
gacgaacctg ctgccgatgg agttgttagc cctaggcaat tggctttgtt ggcgagcatg 360
gtagacgagg ctgtgagaac aatcccttcc cctccccctg aacgtgatgg agcacaagag 420
gaggcggcta ggagtccctc accaccccgt acaccttcta tgagagcgga ttacggcgag 480
gaaaacgacg acgacgacga tgatgatgac gacgatgatc gtgatgccgg acgctgggtt 540
aggggacctg aaaccacttc tgctgtccgt ggagcatacc ccgatcctat ggcgagtttg 600
agccctagac cacctgcccc gaggagacac caccaccacc accatcatag gcgtagacgt 660
gctcctagac gtcgttctgc cgctagtgac tcttccaaat ctggctcttc ttcatctgcc 720
tcttccgctt catcttcggc ctcatcgtcc tcttcggcat ccgcttcgag tagtgatgat 780
gatgatgacg acgacgctgc tagagccccc gcttctgctg ccgaccacgc tgctggcgga 840
actttgggag ccgacgacga ggaggcggga gttcctgctc gtgccccggg agctgctccg 900
aggccttctc caccccgtgc tgaacctgct ccggctagaa caccggccgc tactgctggt 960
agactggagc gtagacgtgc ccgtgctgct gtggctggta gagatgctac tggccgcttc 1020
actgctggcc gtcctagacg tgttgaactg gacgccgatg ctgcttctgg tgctttctac 1080
gcccgttacc gtgatggtta cgtgtctggt gaaccttggc ctggcgctgg tccacctccg 1140
cccggacgtg tactctacgg tggattgggc gattctcgcc ctggtctgtg gggcgctccg 1200

<210> SEQ ID NO 122
<211> LENGTH: 825
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 122
tcgagtgccg ccgctgctgc cgccgatttg ttgttccaaa accaatccct ccgccctctg 60
ctcgccgaca ctgttgccgc tgccgattct ctggctgctc cggcttctgc cccacgtgaa 120
gctcgtaaac gtaaatcacc cgctccggct cgtgctcccc ctggtggcgc ccctagaccc 180
cctaaaaaat cccgtgccga tgcccctaga cctgctgctg ctccccccgc tggtgctgct 240
ccccccgctc cccctactcc ccccccacgc ccacctcgtc ccgctgccct cacacgccgt 300
cctgctgagg gacccgatcc acaaggcggc tggcgtagac aacctcctgg cccatcccat 360
acaccggcac catctgccgc tgctttggag gcttactgtg ctcctcgtgc tgtggctgaa 420
ctcaccgatc atccgctgtt ccctgctccc tggcgtcccg ccctcatgtt cgatcctaga 480
gctttggctt ccttggccgc tcgttgtgct gcccctcccc ctggcggtgc tccggctgct 540
ttcggtcctc tccgtgcctc tggtccactc cgccgtgccg ctgcctggat gagacaagtt 600
cccgaccctg aggatgttag agttgtgatc ttgtactcgc ccttgcctgg cgaggatttg 660

```
gccgctggta gagctggcgg tggcccccct cctgaatggt ctgctgaacg tggtggtttg    720

tcttgcttgt tggccgccct gggaaaccgt ctgtgtggtc ctgctactgc tgcttgggct    780

ggaaactgga ctggcgctcc cgatgtttct gctctcggtg ctcaa                    825
```

<210> SEQ ID NO 123
<211> LENGTH: 933
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
tgggctggaa actggactgg cgctcccgat gtttctgctc tcggtgctca aggagttttg     60

ctgctctcta ctcgtgactt ggcattcgct ggagctgttg aattcctggg actcttggct    120

ggcgcttgtg ataggagact catcgtcgta aacgctgtga gagctgccga ttggcctgcc    180

gatggtcctg ttgtgtctcg tcaacacgct tacttggctt gtgaagtgtt gcccgctgtc    240

caatgtgctg ttcgctggcc tgctgctcgt gatctgaggc gtactgttct ggctagtggt    300

cgtgttttcg gacctggtgt tttcgctcgt gtcgaagctg ctcacgctag actgtacccc    360

gatgccccac ccctccgttt gtgtcgtgga gcaaacgttc gctaccgtgt ccgtactcgt    420

ttcggacccg atactctggt tccaatgtcc cctcgtgaat accgtcgtgc tgttctgcct    480

gccctcgatg gacgtgctgc cgcttctggc gctggtgacg ctatggctcc tggcgctccg    540

gacttctgtg aggatgaggc tcactcacat cgtgcctgtg cccgctgggg actgggcgct    600

ccattgaggc ctgtatacgt ggcactgggc cgtgatgctg ttagaggcgg acccgctgaa    660

ttgagaggcc ctcgtcgtga attctgtgct agggctctgc tcgaacccga tggagatgct    720

cctcctttgg tactccgtga cgacgccgat gctggtcctc ccccacaaat tcgctgggct    780

agtgctgctg gacgtgctgg tactgtattg gctgctgctg gcggtggcgt tgaagttgtt    840

ggtactgccg ctggactcgc tacacctccc cgccgtgaac ctgtagacat ggatgctgaa    900

ctcgaggatg atgacgacgg attgttcgga gag                                 933
```

<210> SEQ ID NO 124
<211> LENGTH: 1707
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 124

```
tcgagtgccg ccgctgctgc cgccgatttg ttgttccaaa accaatccct ccgccctctg     60

ctcgccgaca ctgttgccgc tgccgattct ctggctgctc cggcttctgc cccacgtgaa    120

gctcgtaaac gtaaatcacc cgctccggct cgtgctcccc ctggtggcgc ccctagaccc    180

cctaaaaaat cccgtgccga tgcccctaga cctgctgctg ctccccccgc tggtgctgct    240

ccccccgctc cccctactcc ccccccacgc ccacctcgtc ccgctgccct cacacgccgt    300

cctgctgagg gacccgatcc acaaggcggc tggcgtagac aacctcctgg cccatcccat    360

acaccggcac catctgccgc tgctttggag gcttactgtg ctcctcgtgc tgtggctgaa    420

ctcaccgatc atccgctgtt ccctgctccc tggcgtcccg ccctcatgtt cgatcctaga    480

gctttggctt ccttggccgc tcgttgtgct gcccctcccc ctggcggtgc tccggctgct    540
```

ttcggtcctc tccgtgcctc tggtccactc cgccgtgccg ctgcctggat gagacaagtt 600
cccgaccctg aggatgttag agttgtgatc ttgtactcgc ccttgcctgg cgaggatttg 660
gccgctggta gagctggcgg tggccccccct cctgaatggt ctgctgaacg tggtggtttg 720
tcttgcttgt tggccgccct gggaaaccgt ctgtgtggtc ctgctactgc tgcttgggct 780
ggaaactgga ctggcgctcc cgatgtttct gctctcggtg ctcaaggagt tttgctgctc 840
tctactcgtg acttggcatt cgctggagct gttgaattcc tgggactctt ggctggcgct 900
tgtgatagga gactcatcgt cgtaaacgct gtgagagctg ccgattggcc tgccgatggt 960
cctgttgtgt ctcgtcaaca cgcttacttg gcttgtgaag tgttgcccgc tgtccaatgt 1020
gctgttcgct ggcctgctgc tcgtgatctg aggcgtactg ttctggctag tggtcgtgtt 1080
ttcggacctg gtgttttcgc tcgtgtcgaa gctgctcacg ctagactgta ccccgatgcc 1140
ccacccctcc gtttgtgtcg tggagcaaac gttcgctacc gtgtccgtac tcgtttcgga 1200
cccgatactc tggttccaat gtcccctcgt gaataccgtc gtgctgttct gcctgccctc 1260
gatggacgtg ctgccgcttc tggcgctggt gacgctatgg ctcctggcgc tccggacttc 1320
tgtgaggatg aggctcactc acatcgtgcc tgtgcccgct ggggactggg cgctccattg 1380
aggcctgtat acgtggcact gggccgtgat gctgttagag gcggacccgc tgaattgaga 1440
ggccctcgtc gtgaattctg tgctagggct ctgctcgaac ccgatggaga tgctcctcct 1500
ttggtactcc gtgacgacgc cgatgctggt cctcccccac aaattcgctg ggctagtgct 1560
gctggacgtg ctggtactgt attggctgct gctggcggtg gcgttgaagt tgttggtact 1620
gccgctggac tcgctacacc tccccgccgt gaacctgtag acatggatgc tgaactcgag 1680
gatgatgacg acggattgtt cggagag 1707

<210> SEQ ID NO 125
<211> LENGTH: 1629
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 125
actgctggcc gtcctagacg tgttgaactg gacgccgatg ctgcttctgg tgctttctac 60
gcccgttacc gtgatggtta cgtgtctggt gaaccttggc ctggcgctgg tccacctccg 120
cccggacgtg tactctacgg tggattgggc gattctcgcc ctggtctgtg gggcgctccg 180
gaggctgagg aggctagagc ccgtttcgag gcttctggtg cccctgctcc tgtttgggct 240
cctgaattgg gcgacgctgc tcaacaatac gccctcatca cacgcttgct gtacactccc 300
gacgccgagg ctatgggatg gctccaaaac cctagagttg cccctggtga tgttgctctg 360
gatcaggctt gtttccgtat ctccggcgct gctcgtaact cttcttcgtt catctccggt 420
tctgtggcta gagctgtgcc tcacttggga tacgccatgg ccgctggacg tttcggctgg 480
ggactggctc atgttgctgc cgctgtagca atgtctagac gctacgaccg tgctcaaaaa 540
ggattcttgc tcacgtcact gaggcgtgct tacgcccctt tgttggcccg tgaaaacgct 600
gccctcactg gcgcccgtac ccccgatgac ggtggcgacg ccaaccgcca cgatggtgat 660
gatgctagag gcaaacccgc tgccgctgct gctcctttgc cctctgccgc cgcttcccct 720
gccgatgaac gtgctgttcc tgccggttac ggtgccgctg gtgtgttggc tgctttggga 780
cgcttgagtg ctgccccggc tagtgccccc gctggtgccg atgacgatga cgatgacgat 840

-continued ggtgctggcg gaggcggtgg cggtagacgt gctgaggctg gacgtgttgc tgttgaatgc 900
ctggctgcct gtagaggaat cttggaggct ctggccgagg gattcgacgg agacttggcg 960
gctgtaccgg gactggcggg agcgaggcct gccgctccac ctcgccccgg tcctgctggt 1020
gctgccgctc ctcctcatgc cgacgctcct agactccgtg cttggctccg tgaactccgt 1080
ttcgttcgtg acgctttggt tctgatgaga ctgagaggcg acttgagagt ggctggagga 1140
tccgaggctg ctgttgctgc tgtccgtgct gtttctttgg ttgctggtgc tttgggccct 1200
gctttgccga gatctccccg tttgttgtcg agtgccgccg ctgctgccgc cgatttgttg 1260
ttccaaaacc aatccctccg ccctctgctc gccgacactg ttgccgctgc cgattctctg 1320
gctgctccgg cttctgcccc acgtgaagct cgtaaacgta aatcacccgc tccggctcgt 1380
gctccccctg gtggcgcccc tagaccccct aaaaaatccc gtgccgatgc ccctagacct 1440
gctgctgctc cccccgctgg tgctgctccc cccgctcccc ctactccccc cccacgccca 1500
cctcgtcccg ctgccctcac acgccgtcct gctgagggac ccgatccaca aggcggctgg 1560
cgtagacaac ctcctggccc atcccataca ccggcaccat ctgccgctgc tttggaggct 1620
tactgtgct 1629

<210> SEQ ID NO 126
<211> LENGTH: 1632
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
gccgctgccg attctctggc tgctccggct tctgccccac gtgaagctcg taaacgtaaa 60
tcacccgctc cggctcgtgc tccccctggt ggcgccccta gaccccctaa aaaatcccgt 120
gccgatgccc ctagacctgc tgctgctccc cccgctggtg ctgctccccc cgctccccct 180
actccccccc cacgcccacc tcgtcccgct gccctcacac gccgtcctgc tgagggaccc 240
gatccacaag gcggctggcg tagacaacct cctggcccat cccatacacc ggcaccatct 300
gccgctgctt tggaggctta ctgtgctcct cgtgctgtgg ctgaactcac cgatcatccg 360
ctgttccctg ctccctggcg tcccgccctc atgttcgatc ctagagcttt ggcttccttg 420
gccgctcgtt gtgctgcccc tccccctggc ggtgctccgg ctgctttcgg tcctctccgt 480
gcctctggtc cactccgccg tgccgctgcc tggatgagac aagttcccga ccctgaggat 540
gttagagttg tgatcttgta ctcgcccttg cctggcgagg atttggccgc tggtagagct 600
ggcggtggcc cccctcctga atggtctgct gaacgtggtg gtttgtcttg cttgttggcc 660
gccctgggaa accgtctgtg tggtcctgct actgctgctt gggctggaaa ctggactggc 720
gctcccgatg tttctgctct cggtgctcaa ggagttttgc tgctctctac tcgtgacttg 780
gcattcgctg gagctgttga attcctggga ctcttggctg gcgcttgtga taggagactc 840
atcgtcgtaa acgctgtgag agctgccgat tggcctgccg atggtcctgt tgtgtctcgt 900
caacacgctt acttggcttg tgaagtgttg cccgctgtcc aatgtgctgt tcgctggcct 960
gctgctcgtg atctgaggcg tactgttctg gctagtggtc gtgttttcgg acctggtgtt 1020
ttcgctcgtg tcgaagctgc tcacgctaga ctgtaccccg atgccccacc cctccgtttg 1080
tgtcgtggag caaacgttcg ctaccgtgtc cgtactcgtt tcggacccga tactctggtt 1140
ccaatgtccc ctcgtgaata ccgtcgtgct gttctgcctg ccctcgatgg acgtgctgcc 1200

-continued gcttctggcg ctggtgacgc tatggctcct ggcgctccgg acttctgtga ggatgaggct 1260
cactcacatc gtgcctgtgc ccgctgggga ctgggcgctc cattgaggcc tgtatacgtg 1320
gcactgggcc gtgatgctgt tagaggcgga cccgctgaat tgagaggccc tcgtcgtgaa 1380
ttctgtgcta gggctctgct cgaacccgat ggagatgctc ctcctttggt actccgtgac 1440
gacgccgatg ctggtcctcc cccacaaatt cgctgggcta gtgctgctgg acgtgctggt 1500
actgtattgg ctgctgctgg cggtggcgtt gaagttgttg gtactgccgc tggactcgct 1560
acacctcccc gccgtgaacc tgtagacatg gatgctgaac tcgaggatga tgacgacgga 1620
ttgttcggag ag 1632

<210> SEQ ID NO 127
<211> LENGTH: 3330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127
caccaccacc accaccatca taggcgtaga cgtgctccta gacgtcgttc tgccgctagt 60
gactcttcca aatctggctc ttcttcatct gcctcttccg cttcatcttc ggcctcatcg 120
tcctcttcgg catccgcttc gagtagtgat gatgatgatg acgacgacgc tgctagagcc 180
cccgcttctg ctgccgacca cgctgctggc ggaactttgg gagccgacga cgaggaggcg 240
ggagttcctg ctcgtgcccc gggagctgct ccgaggcctt ctccaccccg tgctgaacct 300
gctccggcta gaacaccggc cgctactgct ggtagactgg agcgtagacg tgcccgtgct 360
gctgtggctg gtagagatgc tactggccgc ttcactgctg gccgtcctag acgtgttgaa 420
ctggacgccg atgctgcttc tggtgctttc tacgcccgtt accgtgatgg ttacgtgtct 480
ggtgaacctt ggcctggcgc tggtccacct ccgcccggac gtgtactcta cggtggattg 540
ggcgattctc gccctggtct gtggggcgct ccggaggctg aggaggctag agcccgtttc 600
gaggcttctg gtgcccctgc tcctgtttgg gctcctgaat tgggcgacgc tgctcaacaa 660
tacgccctca tcacacgctt gctgtacact cccgacgccg aggctatggg atggctccaa 720
aaccctagag ttgcccctgg tgatgttgct ctggatcagg cttgtttccg tatctccggc 780
gctgctcgta actcttcttc gttcatctcc ggttctgtgg ctagagctgt gcctcacttg 840
ggatacgcca tggccgctgg acgtttcggc tggggactgg ctcatgttgc tgccgctgta 900
gcaatgtcta gacgctacga ccgtgctcaa aaaggattct tgctcacgtc actgaggcgt 960
gcttacgccc ctttgttggc ccgtgaaaac gctgccctca ctggcgcccg tacccccgat 1020
gacggtggcg acgccaaccg ccacgatggt gatgatgcta gaggcaaacc cgctgccgct 1080
gctgctcctt tgccctctgc cgccgcttcc cctgccgatg aacgtgctgt tcctgccggt 1140
tacggtgccg ctggtgtgtt ggctgctttg ggacgcttga gtgctgcccc ggctagtgcc 1200
cccgctggtg ccgatgacga tgacgatgac gatggtgctg gcggaggcgg tggcggtaga 1260
cgtgctgagg ctggacgtgt tgctgttgaa tgcctggctg cctgtagagg aatcttggag 1320
gctctggccg agggattcga cggagacttg gcggctgtac cgggactggc gggagcgagg 1380
cctgccgctc cacctcgccc cggtcctgct ggtgctgccg ctcctcctca tgccgacgct 1440
cctagactcc gtgcttggct ccgtgaactc cgtttcgttc gtgacgcttt ggttctgatg 1500
agactgagag gcgacttgag agtggctgga ggatccgagg ctgctgttgc tgctgtccgt 1560

-continued gctgtttctt tggttgctgg tgctttgggc cctgctttgc cgagatctcc ccgtttgttg 1620
tcgagtgccg ccgctgctgc cgccgatttg ttgttccaaa accaatccct ccgccctctg 1680
ctcgccgaca ctgttgccgc tgccgattct ctggctgctc cggcttctgc cccacgtgaa 1740
gctcgtaaac gtaaatcacc cgctccggct cgtgctcccc ctggtggcgc ccctagaccc 1800
cctaaaaaat cccgtgccga tgcccctaga cctgctgctg ctccccccgc tggtgctgct 1860
ccccccgctc cccctactcc ccccccacgc ccacctcgtc ccgctgccct cacacgccgt 1920
cctgctgagg gacccgatcc acaaggcggc tggcgtagac aacctcctgg cccatcccat 1980
acaccggcac catctgccgc tgctttggag gcttactgtg ctcctcgtgc tgtggctgaa 2040
ctcaccgatc atccgctgtt ccctgctccc tggcgtcccg ccctcatgtt cgatcctaga 2100
gctttggctt ccttggccgc tcgttgtgct gcccctcccc ctggcggtgc tccggctgct 2160
ttcggtcctc tccgtgcctc tggtccactc cgccgtgccg ctgcctggat gagacaagtt 2220
cccgaccctg aggatgttag agttgtgatc ttgtactcgc ccttgcctgg cgaggatttg 2280
gccgctggta gagctggcgg tggccccccct cctgaatggt ctgctgaacg tggtggtttg 2340
tcttgcttgt tggccgccct gggaaaccgt ctgtgtggtc ctgctactgc tgcttgggct 2400
ggaaactgga ctggcgctcc cgatgtttct gctctcggtg ctcaaggagt tttgctgctc 2460
tctactcgtg acttggcatt cgctggagct gttgaattcc tgggactctt ggctggcgct 2520
tgtgatagga gactcatcgt cgtaaacgct gtgagagctg ccgattggcc tgccgatggt 2580
cctgttgtgt ctcgtcaaca cgcttacttg gcttgtgaag tgttgcccgc tgtccaatgt 2640
gctgttcgct ggcctgctgc tcgtgatctg aggcgtactg ttctggctag tggtcgtgtt 2700
ttcggacctg gtgttttcgc tcgtgtcgaa gctgctcacg ctagactgta ccccgatgcc 2760
ccacccctcc gtttgtgtcg tggagcaaac gttcgctacc gtgtccgtac tcgtttcgga 2820
cccgatactc tggttccaat gtcccctcgt gaataccgtc gtgctgttct gcctgccctc 2880
gatggacgtg ctgccgcttc tggcgctggt gacgctatgg ctcctggcgc tccggacttc 2940
tgtgaggatg aggctcactc acatcgtgcc tgtgcccgct ggggactggg cgctccattg 3000
aggcctgtat acgtggcact gggccgtgat gctgttagag gcggacccgc tgaattgaga 3060
ggccctcgtc gtgaattctg tgctagggct ctgctcgaac ccgatggaga tgctcctcct 3120
ttggtactcc gtgacgacgc cgatgctggt cctccccccac aaattcgctg ggctagtgct 3180
gctggacgtg ctggtactgt attggctgct gctggcggtg gcgttgaagt tgttggtact 3240
gccgctggac tcgctacacc tccccgccgt gaacctgtag acatggatgc tgaactcgag 3300
gatgatgacg acggattgtt cggagagtaa 3330

<210> SEQ ID NO 128
<211> LENGTH: 3492
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 128
atgagtgccg aacagcgtaa aaagaaaaaa accaccacca cgacccaagg acgtggagct 60
gaagttgcta tggcggatga ggatggaggc cgcttgagag ctgctgctga gactactgga 120
ggacctggat caccggaccc tgccgatgga ccccccccta caccaaaccc cgatcgtaga 180
ccggctgcta gacctggatt cggatggcat ggaggacccg aggaaaacga ggacgaggcg 240

-continued gacgacgccg ctgccgacgc cgacgccgat gaggctgccc ctgcttctgg agaggcggta 300
gacgaacctg ctgccgatgg agttgttagc cctaggcaat tggctttgtt ggcgagcatg 360
gtagacgagg ctgtgagaac aatcccttcc cctccccctg aacgtgatgg agcacaagag 420
gaggcggcta ggagtccctc accaccccgt acaccttcta tgagagcgga ttacggcgag 480
gaaaacgacg acgacgacga tgatgatgac gacgatgatc gtgatgccgg acgctgggtt 540
aggggacctg aaaccacttc tgctgtccgt ggagcatacc ccgatcctat ggcgagtttg 600
agccctagac cacctgcccc gaggagacac caccaccacc accatcatag gcgtagacgt 660
gctcctagac gtcgttctgc cgctagtgac tcttccaaat ctggctcttc ttcatctgcc 720
tcttccgctt catcttcggc ctcatcgtcc tcttcggcat ccgcttcgag tagtgatgat 780
gatgatgacg acgacgctgc tagagccccc gcttctgctg ccgaccacgc tgctggcgga 840
actttgggag ccgacgacga ggaggcggga gttcctgctc gtgcccccggg agctgctccg 900 aggccttctc caccccgtgc tgaacctgct ccggctagaa caccggccgc tactgctggt 960
agactggagc gtagacgtgc ccgtgctgct gtggctggta gagatgctac tggccgcttc 1020
actgctggcc gtcctagacg tgttgaactg gacgccgatg ctgcttctgg tgctttctac 1080
gcccgttacc gtgatggtta cgtgtctggt gaaccttggc ctggcgctgg tccacctccg 1140
cccggacgtg tactctacgg tggattgggc gcccgtaccc ccgatgacgg tggcgacgcc 1200
aaccgccacg atggtgatga tgctagaggc aaacccgctg ccgctgctgc tcctttgccc 1260
tctgccgccg cttcccctgc cgatgaacgt gctgttcctg ccggttacgg tgccgctggt 1320
gtgttggctg ctttgggacg cttgagtgct gccccggcta gtgcccccgc tggtgccgat 1380
gacgatgacg atgacgatgg tgctggcgga ggcggtggcg gtagacgtgc tgaggctgga 1440
cgtgttgctg ttgaatgcct ggctgcctgt agaggaatct tggaggctct ggccgaggga 1500
ttcgacggag acttggcggc tgtaccggga ctggcgggag cgaggcctgc cgctccacct 1560
cgccccggtc ctgctggtgc tgccgctcct cctcatgccg acgctcctag actccgtgct 1620
tggctccgtg aactccgttt cgttcgtgac gctttggttc tgatgagact gagaggcgac 1680
ttgagagtgg ctggaggatc cgaggctgct gttgctgctg tccgtgctgt ttctttggtt 1740
gctggtgctt tgggccctgc tttgccgaga tctccccgtt tgttgtcgag tgccgccgct 1800
gctgccgccg atttgttgtt ccaaaaccaa tccctccgcc ctctgctcgc cgacactgtt 1860
gccgctgccg attctctggc tgctccggct tctgccccac gtgaagctcg taaacgtaaa 1920
tcacccgctc cggctcgtgc tccccctggt ggcgccccta gaccccctaa aaaatcccgt 1980
gccgatgccc ctagacctgc tgctgctccc cccgctggtg ctgctccccc cgctccccct 2040
actccccccc cacgcccacc tcgtcccgct gccctcacac gccgtcctgc tgagggaccc 2100
gatccacaag gcggctggcg tagacaacct cctggcccat cccatacacc ggcaccatct 2160
gccgctgctt tggaggctta ctgtgctcct cgtgctgtgg ctgaactcac cgatcatccg 2220
ctgttccctg ctccctggcg tcccgccctc atgttcgatc ctagagcttt ggcttccttg 2280
gccgctcgtt gtgctgcccc tccccctggc ggtgctccgg ctgctttcgg tcctctccgt 2340
gcctctggtc cactccgccg tgccgctgcc tggatgagac aagttcccga ccctgaggat 2400
gttagagttg tgatcttgta ctcgcccttg cctggcgagg atttggccgc tggtagagct 2460
ggcggtggcc cccctcctga atggtctgct gaacgtggtg gtttgtcttg cttgttggcc 2520
gccctgggaa accgtctgtg tggtcctgct actgctgctt gggctggaaa ctggactggc 2580
gctcccgatg tttctgctct cggtgctcaa ggagttttgc tgctctctac tcgtgacttg 2640
gcattcgctg gagctgttga attcctggga ctcttggctg gcgcttgtga taggagactc 2700
atcgtcgtaa acgctgtgag agctgccgat tggcctgccg atggtcctgt tgtgtctcgt 2760
caacacgctt acttggcttg tgaagtgttg cccgctgtcc aatgtgctgt tcgctggcct 2820
gctgctcgtg atctgaggcg tactgttctg gctagtggtc gtgttttcgg acctggtgtt 2880
ttcgctcgtg tcgaagctgc tcacgctaga ctgtaccccg atgccccacc cctccgtttg 2940
tgtcgtggag caaacgttcg ctaccgtgtc cgtactcgtt tcggacccga tactctggtt 3000
ccaatgtccc ctcgtgaata ccgtcgtgct gttctgcctg ccctcgatgg acgtgctgcc 3060
gcttctggcg ctggtgacgc tatggctcct ggcgctccgg acttctgtga ggatgaggct 3120
cactcacatc gtgcctgtgc ccgctgggga ctgggcgctc cattgaggcc tgtatacgtg 3180
gcactgggcc gtgatgctgt tagaggcgga cccgctgaat tgagaggccc tcgtcgtgaa 3240
ttctgtgcta gggctctgct cgaacccgat ggagatgctc ctcctttggt actccgtgac 3300
gacgccgatg ctggtcctcc cccacaaatt cgctgggcta gtgctgctgg acgtgctggt 3360
actgtattgg ctgctgctgg cggtggcgtt gaagttgttg gtactgccgc tggactcgct 3420
acacctcccc gccgtgaacc tgtagacatg gatgctgaac tcgaggatga tgacgacgga 3480
ttgttcggag ag 3492

<210> SEQ ID NO 129
<211> LENGTH: 3702
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 129
atgagtgccg aacagcgtaa aaagaaaaaa accaccacca cgacccaagg acgtggagct 60
gaagttgcta tggcggatga ggatggaggc cgcttgagag ctgctgctga gactactgga 120
ggacctggat caccggaccc tgccgatgga ccccccccta caccaaaccc cgatcgtaga 180
ccggctgcta gacctggatt cggatggcat ggaggacccg aggaaaacga ggacgaggcg 240
gacgacgccg ctgccgacgc cgacgccgat gaggctgccc ctgcttctgg agaggcggta 300
gacgaacctg ctgccgatgg agttgttagc cctaggcaat tggctttgtt ggcgagcatg 360
gtagacgagg ctgtgagaac aatcccttcc cctccccctg aacgtgatgg agcacaagag 420
gaggcggcta ggagtccctc accaccccgt acaccttcta tgagagcgga ttacggcgag 480
gaaaacgacg acgacgacga tgatgatgac gacgatgatc gtgatgccgg acgctgggtt 540
aggggacctg aaaccacttc tgctgtccgt ggagcatacc ccgatcctat ggcgagtttg 600
agccctagac cacctgcccc gaggagacac caccaccacc accatcatag gcgtagacgt 660
gctcctagac gtcgttctgc cgctagtgac tcttccaaat ctggctcttc ttcatctgcc 720
tcttccgctt catcttcggc ctcatcgtcc tcttcggcat ccgcttcgag tagtgatgat 780
gatgatgacg acgacgctgc tagagccccc gcttctgctg ccgaccacgc tgctggcgga 840
actttgggag ccgacgacga ggaggcggga gttcctgctc gtgccccggg agctgctccg 900
aggccttctc caccccgtgc tgaacctgct ccggctagaa caccggccgc tactgctggt 960
agactggagc gtagacgtgc ccgtgctgct gtggctggta gagatgctac tggccgcttc 1020
actgctggcc gtcctagacg tgttgaactg gacgccgatg ctgcttctgg tgctttctac 1080
gcccgttacc gtgatggtta cgtgtctggt gaaccttggc ctggcgctgg tccacctccg 1140

-continued

```
cccggacgtg tactctacgg tggattgggc gattctcgcc ctggtctgtg gggcgctccg   1200
gaggctgagg aggctagagc ccgtttcgag gcttctggtg cccctgctcc tgtttgggct   1260
cctgaattgg gcgacgctgc tcaacaatac gccctcatca cacgcttgct gtacactccc   1320
gacgccgagg ctatgggatg gctccaaaac cctagagttg cccctggtga tgttgctctg   1380
gatcaggctt gtttccgtat ctccggcgct gctcgtaact cttcttcgtt catctccggt   1440
tctgtggcta gagctgtgcc tcacttggga tacgccatgg ccgctggacg tttcggctgg   1500
ggactggctc atgttgctgc cgctgtagca atgtctagac gctacgaccg tgctcaaaaa   1560
ggattcttgc tcacgtcact gaggcgtgct tacgcccctt tgttggcccg tgaaaacgct   1620
gccctcactg gcgcccgtac cccgatgac ggtggcgacg ccaaccgcca cgatggtgat    1680
gatgctagag gcaaacccgc tgccgctgct gctcctttgc cctctgccgc cgcttcccct   1740
gccgatgaac gtgctgttcc tgccggttac ggtgccgctg gtgtgttggc tgctttggga   1800
cgcttgagtg ctgccccggc tagtgccccc gctggtgccg atgacgatga cgatgacgat   1860
ggtgctggcg gaggcggtgg cggtagacgt gctgaggctg gacgtgttgc tgttgaatgc   1920
ctggctgcct gtagaggaat cttggaggct ctggccgagg gattcgacgg agacttggcg   1980
gctgtaccgg gactggcggg agcgaggcct gccgctccac ctcgccccgg tcctgctggt   2040
gctgccgctc ctcctcatgc cgacgctcct agactccgtg cttggctccg tgaactccgt   2100
ttcgttcgtg acgctttggt tctgatgaga ctgagaggcg acttgagagt ggctggagga   2160
tccgaggctg ctgttgctgc tgtccgtgct gtttctttgg ttgctggtgc tttgggccct   2220
gctttgccga gatctccccg tttgttgtcg agtgccgccg ctgctgccgc cgatttgttg   2280
ttccaaaacc aatccctccg ccctctgctc gccgacactg ttgccgctgc cgattctctg   2340
gctgctccgg cttctacacc ggcaccatct gccgctgctt tggaggctta ctgtgctcct   2400
cgtgctgtgg ctgaactcac cgatcatccg ctgttccctg ctccctggcg tcccgccctc   2460
atgttcgatc ctagagcttt ggcttccttg gccgctcgtt gtgctgcccc tcccccctggc   2520
ggtgctccgg ctgctttcgg tcctctccgt gcctctggtc cactccgccg tgccgctgcc   2580
tggatgagac aagttcccga ccctgaggat gttagagttg tgatcttgta ctcgcccttg   2640
cctggcgagg atttggccgc tggtagagct ggcggtggcc cccctcctga atggtctgct   2700
gaacgtggtg gtttgtcttg cttgttggcc gccctgggaa accgtctgtg tggtcctgct   2760
actgctgctt gggctggaaa ctggactggc gctcccgatg tttctgctct cggtgctcaa   2820
ggagttttgc tgctctctac tcgtgacttg gcattcgctg gagctgttga attcctggga   2880
ctcttggctg gcgcttgtga taggagactc atcgtcgtaa acgctgtgag agctgccgat   2940
tggcctgccg atggtcctgt tgtgtctcgt caacacgctt acttggcttg tgaagtgttg   3000
cccgctgtcc aatgtgctgt tcgctggcct gctgctcgtg atctgaggcg tactgttctg   3060
gctagtggtc gtgttttcgg acctggtgtt ttcgctcgtg tcgaagctgc tcacgctaga   3120
ctgtaccccg atgccccacc cctccgtttg tgtcgtggag caaacgttcg ctaccgtgtc   3180
cgtactcgtt tcggacccga tactctggtt ccaatgtccc ctcgtgaata ccgtcgtgct   3240
gttctgcctg ccctcgatgg acgtgctgcc gcttctggcg ctggtgacgc tatggctcct   3300
ggcgctccgg acttctgtga ggatgaggct cactcacatc gtgcctgtgc ccgctgggga   3360
ctgggcgctc cattgaggcc tgtatacgtg gcactgggcc gtgatgctgt tagaggcgga   3420
cccgctgaat tgagaggccc tcgtcgtgaa ttctgtgcta gggctctgct cgaacccgat   3480
```

```
ggagatgctc ctcctttggt actccgtgac gacgccgatg ctggtcctcc cccacaaatt   3540

cgctgggcta gtgctgctgg acgtgctggt actgtattgg ctgctgctgg cggtggcgtt   3600

gaagttgttg gtactgccgc tggactcgct acacctcccc gccgtgaacc tgtagacatg   3660

gatgctgaac tcgaggatga tgacgacgga ttgttcggag ag                      3702


<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 130

His His His His His His
1               5


<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Met Ser Tyr Tyr His His His His His His
1               5                   10


<210> SEQ ID NO 132
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Met Lys Phe Leu Val Asn Val Ala Leu Val Phe Met Val Val Tyr Ile
1               5                   10                  15

Ser Tyr Ile Tyr Ala
            20


<210> SEQ ID NO 133
<211> LENGTH: 294
<212> TYPE: DNA
<213> ORGANISM: Human herpesvirus 2

<400> SEQUENCE: 133

atgtcgtact accatcacca tcaccatcac atgacgggga aacccgcaag actgggccgc     60

tgggtggtgc tgttgttcgt cgcgctcgtc gcgggcgtgc ccggggagcc gccgaacgcg    120

gcaggcgcac gcggcgttat cggggacgcg caatgccggg gcgacagcgc cggtgtggtg    180

tccgtcccgg gggtcctggt gcccttttat ctaggcatga cctcgatggg cgtatgtatg    240

atcgcgcacg tgtatcagat atgccagcgg gcactggccg ccgggtcagc ctga          294


<210> SEQ ID NO 134
<211> LENGTH: 1404
<212> TYPE: DNA
<213> ORGANISM: Human herpesvirus 2

<400> SEQUENCE: 134
```

-continued

```
atgggacgcc gggcccccag gggatccccc gaggccgcgc cgggcgccga cgtcgcgccc      60

ggggcgcggg cggcgtggtg ggtctggtgt gtgcaggtgg cgacgttcat cgtctcggcc     120

atctgcgtcg tggggctcct ggtgctggcc tctgtgttcc gggacaggtt tccctgcctt     180

tacgcccccg cgacctctta tgcgaaggcg aacgccacgg tcgaggtgcg cgggggtgta     240

gccgtccccc tccggttgga cacgcagagc ctgctggcca cgtacgcaat tacgtctacg     300

ctgttgctgg cggcggccgt gtacgccgcg gtgggcgcgg tgacctcgcg ctacgagcgc     360

gcgctggatg cggcccgtcg cctggcggcg gcccgtatgg cgatgccaca cgccacgcta     420

atcgccggaa acgtctgcgc gtggctgttg cagatcacag tcctgctgct ggcccaccgc     480

atcagccagc tggcccacct tatctacgtc ctgcactttg cgtgcctcgt gtatctcgcg     540

gcccattttt gcaccagggg ggtcctgagc gggacgtacc tgcgtcaggt tcacggcctg     600

attgacccgg cgccgacgca ccatcgtatc gtcggtccgg tgcgggcagt aatgacaaac     660

gccttattac tgggcaccct cctgtgcacg gccgccgccg cggtctcgtt gaacacgatc     720

gccgccctga acttcaactt ttccgccccg agcatgctca tctgcctgac gacgctgttc     780

gccctgcttg tcgtgtcgct gttgttggtg gtcgaggggg tgctgtgtca ctacgtgcgc     840

gtgttggtgg gcccccacct cggggccatc gccgccaccg gcatcgtcgg cctggcctgc     900

gagcactacc acaccggtgg ttactacgtg gtggagcagc agtggccggg ggcccagacg     960

ggagtccgcg tcgccctggc gctcgtcgcc gcctttgccc tcgccatggc cgtgcttcgg    1020

tgcacgcgcg cctacctgta tcaccggcga caccacacta aatttttcgt gcgcatgcgc    1080

gacacccggc accgcgccca ttcggcgctt cgacgcgtac gcagctccat gcgcggttct    1140

aggcgtggcg ggccgcccgg agacccgggc tacgcggaaa ccccctacgc gagcgtgtcc    1200

caccacgccg agatcgaccg gtatggggat tccgacgggg acccgatcta cgacgaagtg    1260

gcccccgacc acgaggccga gctctacgcc cgagtgcaac gccccgggcc tgtgcccgac    1320

gccgagccca tttacgacac cgtggagggg tatgcgccaa ggtccgcggg ggagccggtg    1380

tacagcaccg ttcggcgatg gtag                                           1404
```

```
<210> SEQ ID NO 135
<211> LENGTH: 334
<212> TYPE: PRT
<213> ORGANISM: human herpesvirus 2

<400> SEQUENCE: 135

Met Lys Arg Ala Arg Ser Arg Ser Pro Ser Pro Pro Ser Arg Pro Ser
1               5                   10                  15

Ser Pro Phe Arg Thr Pro Pro His Gly Gly Ser Pro Arg Arg Glu Val
            20                  25                  30

Gly Ala Gly Ile Leu Ala Ser Asp Ala Thr Ser His Val Cys Ile Ala
        35                  40                  45

Ser His Pro Gly Ser Gly Ala Gly Gln Pro Thr Arg Leu Ala Ala Gly
    50                  55                  60

Ser Ala Val Gln Arg Arg Arg Pro Arg Gly Cys Pro Pro Gly Val Met
65                  70                  75                  80

Phe Ser Ala Ser Thr Thr Pro Glu Gln Pro Leu Gly Leu Ser Gly Asp
                85                  90                  95

Ala Thr Pro Pro Leu Pro Thr Ser Val Pro Leu Asp Trp Ala Ala Phe
            100                 105                 110

Arg Arg Ala Phe Leu Ile Asp Asp Ala Trp Arg Pro Leu Leu Glu Pro
        115                 120                 125
```

```
Glu Leu Ala Asn Pro Leu Thr Ala Arg Leu Leu Ala Glu Tyr Asp Arg
    130                 135                 140

Arg Cys Gln Thr Glu Glu Val Leu Pro Pro Arg Glu Asp Val Phe Ser
145                 150                 155                 160

Trp Thr Arg Tyr Cys Thr Pro Asp Asp Val Arg Val Val Ile Ile Gly
                165                 170                 175

Gln Asp Pro Tyr His His Pro Gly Gln Ala His Gly Leu Ala Phe Ser
            180                 185                 190

Val Arg Ala Asp Val Pro Val Pro Pro Ser Leu Arg Asn Val Leu Ala
        195                 200                 205

Ala Val Lys Asn Cys Tyr Pro Asp Ala Arg Met Ser Gly Arg Gly Cys
    210                 215                 220

Leu Glu Lys Trp Ala Arg Asp Gly Val Leu Leu Leu Asn Thr Thr Leu
225                 230                 235                 240

Thr Val Lys Arg Gly Ala Ala Ala Ser His Ser Lys Leu Gly Trp Asp
                245                 250                 255

Arg Phe Val Gly Gly Val Val Gln Arg Leu Ala Ala Arg Arg Pro Gly
            260                 265                 270

Leu Val Phe Met Leu Trp Gly Ala His Ala Gln Asn Ala Ile Arg Pro
        275                 280                 285

Asp Pro Arg Gln His Tyr Val Leu Lys Phe Ser His Pro Ser Pro Leu
    290                 295                 300

Ser Lys Val Pro Phe Gly Thr Cys Gln His Phe Leu Ala Ala Asn Arg
305                 310                 315                 320

Tyr Leu Glu Thr Arg Asp Ile Met Pro Ile Asp Trp Ser Val
                325                 330
```

<210> SEQ ID NO 136
<211> LENGTH: 206
<212> TYPE: PRT
<213> ORGANISM: human herpesvirus 2

<400> SEQUENCE: 136

```
Ala Gly Ser Gln Ala Thr Glu Tyr Val Leu Arg Ser Val Ile Ala Lys
1               5                   10                  15

Glu Val Gly Asp Ile Leu Arg Val Pro Cys Met Arg Thr Pro Ala Asp
            20                  25                  30

Asp Val Ser Trp Arg Tyr Glu Ala Pro Ser Val Ile Asp Tyr Ala Arg
        35                  40                  45

Ile Asp Gly Ile Phe Leu Arg Tyr His Cys Pro Gly Leu Asp Thr Phe
    50                  55                  60

Leu Trp Asp Arg His Ala Gln Arg Ala Tyr Leu Val Asn Pro Phe Leu
65                  70                  75                  80

Phe Ala Ala Gly Phe Leu Glu Asp Leu Ser His Ser Val Phe Pro Ala
                85                  90                  95

Asp Thr Gln Glu Thr Thr Thr Arg Arg Ala Leu Tyr Lys Glu Ile Arg
            100                 105                 110

Asp Ala Leu Gly Ser Arg Lys Gln Ala Val Ser His Ala Pro Val Arg
        115                 120                 125

Ala Gly Cys Val Asn Phe Asp Tyr Ser Arg Thr Arg Arg Cys Val Gly
    130                 135                 140

Arg Arg Asp Leu Arg Pro Ala Asn Thr Thr Ser Thr Trp Glu Pro Pro
145                 150                 155                 160

Val Ser Ser Asp Asp Glu Ala Ser Ser Gln Ser Lys Pro Leu Ala Thr
```

```
            165                 170                 175

Gln Pro Pro Val Leu Ala Leu Ser Asn Ala Pro Pro Arg Arg Val Ser
        180                 185                 190

Pro Thr Arg Gly Arg Arg Arg His Thr Arg Leu Arg Arg Asn
    195                 200                 205


<210> SEQ ID NO 137
<211> LENGTH: 702
<212> TYPE: DNA
<213> ORGANISM: human herpesvirus 2

<400> SEQUENCE: 137

atgaagttcc tcgtgaacgt ggccctggtg ttcatggtgg tgtacatcag ctacatctac      60

gccgccgggt cacaggcaac cgaatatgtt cttcgtagtg ttattgccaa agaggtgggg     120

gacatactaa gagtgccttg catgcggacc cccgcggacg atgtttcttg gcgctacgag     180

gccccgtccg ttattgacta tgcccgcata gacggaatat ttcttcgcta tcactgcccg     240

gggttggaca cgtttttgtg ggataggcac gcccagaggg cgtatcttgt taacccccttt    300

ctctttgcgg cgggattttt ggaggacttg agtcactctg tgtttccggc cgacacccag     360

gaaacaacga cgcgccgggc cctttataaa gagatacgcg atgcgttggg cagtcgaaaa     420

caggccgtca gccacgcacc cgtcagggcc gggtgtgtaa actttgacta ctcacgcact     480

cgccgctgcg tcgggcgacg cgatttacgg cctgccaaca ccacgtcaac gtgggaaccg     540

cctgtgtcgt cggacgatga agcgagctcg cagtcgaagc ccctcgccac ccagccgccc     600

gtcctcgccc tttcgaacgc ccccccacgg cgggtctccc cgacgcgagg tcggcgccgg     660

catactcgcc tccgacgcaa ccatcaccat caccatcact ga                        702


<210> SEQ ID NO 138
<211> LENGTH: 1128
<212> TYPE: PRT
<213> ORGANISM: human herpesvirus 2

<400> SEQUENCE: 138

Met Ser Ala Glu Gln Arg Lys Lys Lys Lys Thr Thr Thr Thr Thr Gln
1               5                   10                  15

Gly Arg Gly Ala Glu Val Ala Met Ala Asp Glu Asp Gly Gly Arg Leu
            20                  25                  30

Arg Ala Ala Ala Glu Thr Thr Gly Gly Pro Gly Ser Pro Asp Pro Ala
        35                  40                  45

Asp Gly Pro Pro Pro Thr Pro Asn Pro Asp Arg Arg Pro Ala Ala Arg
    50                  55                  60

Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Ala Pro Ala Ser
                85                  90                  95

Gly Glu Ala Val Asp Glu Pro Ala Ala Asp Gly Val Val Ser Pro Arg
            100                 105                 110

Gln Leu Ala Leu Leu Ala Ser Met Val Asp Glu Ala Val Arg Thr Ile
        115                 120                 125

Pro Ser Pro Pro Pro Glu Arg Asp Gly Ala Gln Glu Glu Ala Ala Arg
    130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Asp Asp Arg Asp Ala
```

-continued

```
                165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Pro Ala Pro Arg
        195                 200                 205

Arg His His His His His His His Arg Arg Arg Arg Ala Pro Arg Arg
    210                 215                 220

Arg Ser Ala Ala Ser Asp Ser Ser Lys Ser Gly Ser Ser Ser Ser Ala
225                 230                 235                 240

Ser Ser Ala Ser Ser Ser Ala Ser Ser Ser Ser Ser Ala Ser Ala Ser
                245                 250                 255

Ser Ser Asp Asp Asp Asp Asp Asp Asp Ala Ala Arg Ala Pro Ala Ser
            260                 265                 270

Ala Ala Asp His Ala Ala Gly Gly Thr Leu Gly Ala Asp Asp Glu Glu
        275                 280                 285

Ala Gly Val Pro Ala Arg Ala Pro Gly Ala Ala Pro Arg Pro Ser Pro
    290                 295                 300

Pro Arg Ala Glu Pro Ala Pro Ala Arg Thr Pro Ala Ala Thr Ala Gly
305                 310                 315                 320

Arg Leu Glu Arg Arg Arg Ala Arg Ala Ala Val Ala Gly Arg Asp Ala
                325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
        355                 360                 365

Ser Gly Glu Pro Trp Pro Gly Ala Gly Pro Pro Pro Pro Gly Arg Val
    370                 375                 380

Leu Tyr Gly Gly Leu Gly Arg Thr Pro Asp Asp Gly Gly Asp Ala Asn
385                 390                 395                 400

Arg His Asp Gly Asp Asp Ala Arg Gly Lys Pro Ala Ala Ala Ala Ala
                405                 410                 415

Pro Leu Pro Ser Ala Ala Ala Ser Pro Ala Asp Glu Arg Ala Val Pro
            420                 425                 430

Ala Gly Tyr Gly Ala Ala Gly Val Leu Ala Ala Leu Gly Arg Leu Ser
        435                 440                 445

Ala Ala Pro Ala Ser Ala Pro Ala Gly Ala Asp Asp Asp Asp Asp Asp
    450                 455                 460

Asp Gly Ala Gly Gly Gly Gly Gly Gly Arg Arg Ala Glu Ala Gly Arg
465                 470                 475                 480

Val Ala Val Glu Cys Leu Ala Ala Cys Arg Gly Ile Leu Glu Ala Leu
                485                 490                 495

Ala Glu Gly Phe Asp Gly Asp Leu Ala Ala Val Pro Gly Leu Ala Gly
            500                 505                 510

Ala Arg Pro Ala Ala Pro Pro Arg Pro Gly Pro Ala Gly Ala Ala Ala
        515                 520                 525

Pro Pro His Ala Asp Ala Pro Arg Leu Arg Ala Trp Leu Arg Glu Leu
    530                 535                 540

Arg Phe Val Arg Asp Ala Leu Val Leu Met Arg Leu Arg Gly Asp Leu
545                 550                 555                 560

Arg Val Ala Gly Gly Ser Glu Ala Ala Val Ala Ala Val Arg Ala Val
                565                 570                 575

Ser Leu Val Ala Gly Ala Leu Gly Pro Ala Leu Pro Arg Ser Pro Arg
            580                 585                 590
```

-continued

```
Leu Leu Ser Ser Ala Ala Ala Ala Ala Ala Asp Leu Leu Phe Gln Asn
        595                 600                 605

Gln Ser Leu Arg Pro Leu Leu Ala Asp Thr Val Ala Ala Ala Asp Ser
    610                 615                 620

Leu Ala Ala Pro Ala Ser Ala Ala Ala Pro Pro Ala Gly Ala Ala Pro
625                 630                 635                 640

Pro Ala Pro Pro Thr Pro Pro Pro Arg Pro Pro Arg Pro Ala Ala Leu
                645                 650                 655

Thr Arg Arg Pro Ala Glu Gly Pro Asp Pro Gln Gly Gly Trp Arg Arg
            660                 665                 670

Gln Pro Pro Gly Pro Ser His Thr Pro Ala Pro Ser Ala Ala Ala Leu
        675                 680                 685

Glu Ala Tyr Cys Ala Pro Arg Ala Val Ala Glu Leu Thr Asp His Pro
    690                 695                 700

Leu Phe Pro Ala Pro Trp Arg Pro Ala Leu Met Phe Asp Pro Arg Ala
705                 710                 715                 720

Leu Ala Ser Leu Ala Ala Arg Cys Ala Ala Pro Pro Pro Gly Gly Ala
                725                 730                 735

Pro Ala Ala Phe Gly Pro Leu Arg Ala Ser Gly Pro Leu Arg Arg Ala
            740                 745                 750

Ala Ala Trp Met Arg Gln Val Pro Asp Pro Glu Asp Val Arg Val Val
        755                 760                 765

Ile Leu Tyr Ser Pro Leu Pro Gly Glu Asp Leu Ala Ala Gly Arg Ala
    770                 775                 780

Gly Gly Gly Pro Pro Pro Glu Trp Ser Ala Glu Arg Gly Gly Leu Ser
785                 790                 795                 800

Cys Leu Leu Ala Ala Leu Gly Asn Arg Leu Cys Gly Pro Ala Thr Ala
                805                 810                 815

Ala Trp Ala Gly Asn Trp Thr Gly Ala Pro Asp Val Ser Ala Leu Gly
            820                 825                 830

Ala Gln Gly Val Leu Leu Leu Ser Thr Arg Asp Leu Ala Phe Ala Gly
        835                 840                 845

Ala Val Glu Phe Leu Gly Leu Leu Ala Gly Ala Cys Asp Arg Arg Leu
    850                 855                 860

Ile Val Val Asn Ala Val Arg Ala Ala Asp Trp Pro Ala Asp Gly Pro
865                 870                 875                 880

Val Val Ser Arg Gln His Ala Tyr Leu Ala Cys Glu Val Leu Pro Ala
                885                 890                 895

Val Gln Cys Ala Val Arg Trp Pro Ala Ala Arg Asp Leu Arg Arg Thr
            900                 905                 910

Val Leu Ala Ser Gly Arg Val Phe Gly Pro Gly Val Phe Ala Arg Val
        915                 920                 925

Glu Ala Ala His Ala Arg Leu Tyr Pro Asp Ala Pro Pro Leu Arg Leu
    930                 935                 940

Cys Arg Gly Ala Asn Val Arg Tyr Arg Val Arg Thr Arg Phe Gly Pro
945                 950                 955                 960

Asp Thr Leu Val Pro Met Ser Pro Arg Glu Tyr Arg Arg Ala Val Leu
                965                 970                 975

Pro Ala Leu Asp Gly Arg Ala Ala Ala Ser Gly Ala Gly Asp Ala Met
            980                 985                 990

Ala Pro Gly Ala Pro Asp Phe Cys  Glu Asp Glu Ala His  Ser His Arg
        995                 1000                1005
```

```
Ala Cys  Ala Arg Trp Gly Leu  Gly Ala Pro Leu Arg  Pro Val Tyr
    1010                1015                1020

Val Ala  Leu Gly Arg Asp Ala  Val Arg Gly Gly Pro  Ala Glu Leu
    1025                1030                1035

Arg Gly  Pro Arg Arg Glu Phe  Cys Ala Arg Ala Leu  Leu Glu Pro
    1040                1045                1050

Asp Gly  Asp Ala Pro Pro Leu  Val Leu Arg Asp Asp  Ala Asp Ala
    1055                1060                1065

Gly Pro  Pro Pro Gln Ile Arg  Trp Ala Ser Ala Ala  Gly Arg Ala
    1070                1075                1080

Gly Thr  Val Leu Ala Ala Ala  Gly Gly Gly Val Glu  Val Val Gly
    1085                1090                1095

Thr Ala  Ala Gly Leu Ala Thr  Pro Pro Arg Arg Glu  Pro Val Asp
    1100                1105                1110

Met Asp  Ala Glu Leu Glu Asp  Asp Asp Asp Gly Leu  Phe Gly Glu
    1115                1120                1125


<210> SEQ ID NO 139
<211> LENGTH: 1164
<212> TYPE: PRT
<213> ORGANISM: human herpesvirus 2

<400> SEQUENCE: 139

Met Ser Ala Glu Gln Arg Lys Lys Lys Lys Thr Thr Thr Thr Thr Gln
1               5                   10                  15

Gly Arg Gly Ala Glu Val Ala Met Ala Asp Glu Asp Gly Gly Arg Leu
            20                  25                  30

Arg Ala Ala Ala Glu Thr Thr Gly Gly Pro Gly Ser Pro Asp Pro Ala
        35                  40                  45

Asp Gly Pro Pro Pro Thr Pro Asn Pro Asp Arg Arg Pro Ala Ala Arg
    50                  55                  60

Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Ala Pro Ala Ser
                85                  90                  95

Gly Glu Ala Val Asp Glu Pro Ala Ala Asp Gly Val Val Ser Pro Arg
            100                 105                 110

Gln Leu Ala Leu Leu Ala Ser Met Val Asp Glu Ala Val Arg Thr Ile
        115                 120                 125

Pro Ser Pro Pro Pro Glu Arg Asp Gly Ala Gln Glu Glu Ala Ala Arg
    130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Asp Asp Arg Asp Ala
                165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Pro Ala Pro Arg
        195                 200                 205

Arg His His His His His His His Arg Arg Arg Arg Ala Pro Arg Arg
    210                 215                 220

Arg Ser Ala Ala Ser Asp Ser Ser Lys Ser Gly Ser Ser Ser Ser Ala
225                 230                 235                 240

Ser Ser Ala Ser Ser Ser Ala Ser Ser Ser Ser Ser Ala Ser Ala Ser
                245                 250                 255
```

-continued

```
Ser Ser Asp Asp Asp Asp Asp Asp Asp Ala Ala Arg Ala Pro Ala Ser
            260                 265                 270

Ala Ala Asp His Ala Ala Gly Gly Thr Leu Gly Ala Asp Asp Glu Glu
        275                 280                 285

Ala Gly Val Pro Ala Arg Ala Pro Gly Ala Ala Pro Arg Pro Ser Pro
    290                 295                 300

Pro Arg Ala Glu Pro Ala Pro Ala Arg Thr Pro Ala Ala Thr Ala Gly
305                 310                 315                 320

Arg Leu Glu Arg Arg Arg Ala Arg Ala Ala Val Ala Gly Arg Asp Ala
                325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
        355                 360                 365

Ser Gly Glu Pro Trp Pro Gly Ala Gly Pro Pro Pro Pro Gly Arg Val
    370                 375                 380

Leu Tyr Gly Gly Leu Gly Ala Met Ser Arg Arg Tyr Asp Arg Ala Gln
385                 390                 395                 400

Lys Gly Phe Leu Leu Thr Ser Leu Arg Arg Ala Tyr Ala Pro Leu Leu
                405                 410                 415

Ala Arg Glu Asn Ala Ala Leu Thr Gly Ala Arg Thr Pro Asp Asp Gly
            420                 425                 430

Gly Asp Ala Asn Arg His Asp Gly Asp Asp Ala Arg Gly Lys Pro Ala
        435                 440                 445

Ala Ala Ala Ala Pro Leu Pro Ser Ala Ala Ala Ser Pro Ala Asp Glu
    450                 455                 460

Arg Ala Val Pro Ala Gly Tyr Gly Ala Ala Gly Val Leu Ala Ala Leu
465                 470                 475                 480

Gly Arg Leu Ser Ala Ala Pro Ala Ser Ala Pro Ala Gly Ala Asp Asp
                485                 490                 495

Asp Asp Asp Asp Asp Gly Ala Gly Gly Gly Gly Gly Gly Arg Arg Ala
            500                 505                 510

Glu Ala Gly Arg Val Ala Val Glu Cys Leu Ala Ala Cys Arg Gly Ile
        515                 520                 525

Leu Glu Ala Leu Ala Glu Gly Phe Asp Gly Asp Leu Ala Ala Val Pro
    530                 535                 540

Gly Leu Ala Gly Ala Arg Pro Ala Ala Pro Pro Arg Pro Gly Pro Ala
545                 550                 555                 560

Gly Ala Ala Ala Pro Pro His Ala Asp Ala Pro Arg Leu Arg Ala Trp
                565                 570                 575

Leu Arg Glu Leu Arg Phe Val Arg Asp Ala Leu Val Leu Met Arg Leu
            580                 585                 590

Arg Gly Asp Leu Arg Val Ala Gly Gly Ser Glu Ala Ala Val Ala Ala
        595                 600                 605

Val Arg Ala Val Ser Leu Val Ala Gly Ala Leu Gly Pro Ala Leu Pro
    610                 615                 620

Arg Ser Pro Arg Leu Leu Ser Ser Ala Ala Ala Ala Ala Ala Asp Leu
625                 630                 635                 640

Leu Phe Gln Asn Gln Ser Leu Arg Pro Leu Leu Ala Asp Thr Val Ala
                645                 650                 655

Ala Ala Asp Ser Leu Ala Ala Pro Ala Ser Ala Ala Ala Pro Pro Ala
            660                 665                 670
```

-continued

```
Gly Ala Ala Pro Pro Ala Pro Pro Thr Pro Pro Pro Arg Pro Pro Arg
        675                 680                 685

Pro Ala Ala Leu Thr Arg Arg Pro Ala Glu Gly Pro Asp Pro Gln Gly
    690                 695                 700

Gly Trp Arg Arg Gln Pro Pro Gly Pro Ser His Thr Pro Ala Pro Ser
705                 710                 715                 720

Ala Ala Ala Leu Glu Ala Tyr Cys Ala Pro Arg Ala Val Ala Glu Leu
                725                 730                 735

Thr Asp His Pro Leu Phe Pro Ala Pro Trp Arg Pro Ala Leu Met Phe
            740                 745                 750

Asp Pro Arg Ala Leu Ala Ser Leu Ala Ala Arg Cys Ala Ala Pro Pro
        755                 760                 765

Pro Gly Gly Ala Pro Ala Ala Phe Gly Pro Leu Arg Ala Ser Gly Pro
    770                 775                 780

Leu Arg Arg Ala Ala Ala Trp Met Arg Gln Val Pro Asp Pro Glu Asp
785                 790                 795                 800

Val Arg Val Val Ile Leu Tyr Ser Pro Leu Pro Gly Glu Asp Leu Ala
                805                 810                 815

Ala Gly Arg Ala Gly Gly Gly Pro Pro Pro Glu Trp Ser Ala Glu Arg
            820                 825                 830

Gly Gly Leu Ser Cys Leu Leu Ala Ala Leu Gly Asn Arg Leu Cys Gly
        835                 840                 845

Pro Ala Thr Ala Ala Trp Ala Gly Asn Trp Thr Gly Ala Pro Asp Val
    850                 855                 860

Ser Ala Leu Gly Ala Gln Gly Val Leu Leu Leu Ser Thr Arg Asp Leu
865                 870                 875                 880

Ala Phe Ala Gly Ala Val Glu Phe Leu Gly Leu Leu Ala Gly Ala Cys
                885                 890                 895

Asp Arg Arg Leu Ile Val Val Asn Ala Val Arg Ala Ala Asp Trp Pro
            900                 905                 910

Ala Asp Gly Pro Val Val Ser Arg Gln His Ala Tyr Leu Ala Cys Glu
        915                 920                 925

Val Leu Pro Ala Val Gln Cys Ala Val Arg Trp Pro Ala Ala Arg Asp
    930                 935                 940

Leu Arg Arg Thr Val Leu Ala Ser Gly Arg Val Phe Gly Pro Gly Val
945                 950                 955                 960

Phe Ala Arg Val Glu Ala Ala His Ala Arg Leu Tyr Pro Asp Ala Pro
                965                 970                 975

Pro Leu Arg Leu Cys Arg Gly Ala Asn Val Arg Tyr Arg Val Arg Thr
            980                 985                 990

Arg Phe Gly Pro Asp Thr Leu Val  Pro Met Ser Pro Arg  Glu Tyr Arg
        995                 1000                 1005

Arg Ala  Val Leu Pro Ala Leu  Asp Gly Arg Ala Ala  Ala Ser Gly
    1010                 1015                 1020

Ala Gly  Asp Ala Met Ala Pro  Gly Ala Pro Asp Phe  Cys Glu Asp
    1025                 1030                 1035

Glu Ala  His Ser His Arg Ala  Cys Ala Arg Trp Gly  Leu Gly Ala
    1040                 1045                 1050

Pro Leu  Arg Pro Val Tyr Val  Ala Leu Gly Arg Asp  Ala Val Arg
    1055                 1060                 1065

Gly Gly  Pro Ala Glu Leu Arg  Gly Pro Arg Arg Glu  Phe Cys Ala
    1070                 1075                 1080

Arg Ala  Leu Leu Glu Pro Asp  Gly Asp Ala Pro Pro  Leu Val Leu
```

-continued

```
    1085                1090                1095

Arg Asp  Asp Ala Asp Ala Gly  Pro Pro Pro Gln Ile  Arg Trp Ala
    1100                1105                1110

Ser Ala  Ala Gly Arg Ala Gly  Thr Val Leu Ala Ala  Ala Gly Gly
    1115                1120                1125

Gly Val  Glu Val Val Gly Thr  Ala Ala Gly Leu Ala  Thr Pro Pro
    1130                1135                1140

Arg Arg  Glu Pro Val Asp Met  Asp Ala Glu Leu Glu  Asp Asp Asp
    1145                1150                1155

Asp Gly  Leu Phe Gly Glu
    1160
```

<210> SEQ ID NO 140
<211> LENGTH: 3384
<212> TYPE: DNA
<213> ORGANISM: human herpesvirus 2

<400> SEQUENCE: 140

```
atgagtgccg aacagcgtaa aaagaaaaaa accaccacca cgacccaagg acgtggagct     60

gaagttgcta tggcggatga ggatggaggc cgcttgagag ctgctgctga gactactgga    120

ggacctggat caccggaccc tgccgatgga cccccccccta caccaaaccc cgatcgtaga    180

ccggctgcta gacctggatt cggatggcat ggaggacccg aggaaaacga ggacgaggcg    240

gacgacgccg ctgccgacgc cgacgccgat gaggctgccc ctgcttctgg agaggcggta    300

gacgaacctg ctgccgatgg agttgttagc cctaggcaat tggctttgtt ggcgagcatg    360

gtagacgagg ctgtgagaac aatcccttcc cctccccctg aacgtgatgg agcacaagag    420

gaggcggcta ggagtccctc accaccccgt acaccttcta tgagagcgga ttacggcgag    480

gaaaacgacg acgacgacga tgatgatgac gacgatgatc gtgatgccgg acgctgggtt    540

aggggacctg aaaccacttc tgctgtccgt ggagcatacc ccgatcctat ggcgagtttg    600

agccctagac cacctgcccc gaggagacac caccaccacc accatcatag gcgtagacgt    660

gctcctagac gtcgttctgc cgctagtgac tcttccaaat ctggctcttc ttcatctgcc    720

tcttccgctt catcttcggc ctcatcgtcc tcttcggcat ccgcttcgag tagtgatgat    780

gatgatgacg acgacgctgc tagagccccc gcttctgctg ccgaccacgc tgctggcgga    840

actttgggag ccgacgacga ggaggcggga gttcctgctc gtgccccggg agctgctccg    900

aggccttctc caccccgtgc tgaacctgct ccggctagaa caccggccgc tactgctggt    960

agactggagc gtagacgtgc ccgtgctgct gtggctggta gagatgctac tggccgcttc   1020

actgctggcc gtcctagacg tgttgaactg gacgccgatg ctgcttctgg tgctttctac   1080

gcccgttacc gtgatggtta cgtgtctggt gaaccttggc ctggcgctgg tccacctccg   1140

cccggacgtg tactctacgg tggattgggc cgtacccccg atgacggtgg cgacgccaac   1200

cgccacgatg gtgatgatgc tagaggcaaa cccgctgccg ctgctgctcc tttgccctct   1260

gccgccgctt cccctgccga tgaacgtgct gttcctgccg gttacggtgc cgctggtgtg   1320

ttggctgctt tgggacgctt gagtgctgcc ccggctagtg cccccgctgg tgccgatgac   1380

gatgacgatg acgatggtgc tggcggaggc ggtggcggta gacgtgctga ggctggacgt   1440

gttgctgttg aatgcctggc tgcctgtaga ggaatcttgg aggctctggc cgagggattc   1500

gacggagact tggcggctgt accgggactg gcgggagcga ggcctgccgc tccacctcgc   1560

cccggtcctg ctggtgctgc cgctcctcct catgccgacg ctcctagact ccgtgcttgg   1620
```

ctccgtgaac tccgtttcgt tcgtgacgct ttggttctga tgagactgag aggcgacttg 1680
agagtggctg gaggatccga ggctgctgtt gctgctgtcc gtgctgtttc tttggttgct 1740
ggtgctttgg gccctgcttt gccgagatct ccccgtttgt tgtcgagtgc cgccgctgct 1800
gccgccgatt tgttgttcca aaaccaatcc ctccgccctc tgctcgccga cactgttgcc 1860
gctgccgatt ctctggctgc tccggcttct gctgctgctc cccccgctgg tgctgctccc 1920
cccgctcccc ctactccccc cccacgccca cctcgtcccg ctgccctcac acgccgtcct 1980
gctgagggac ccgatccaca aggcggctgg cgtagacaac ctcctggccc atcccataca 2040
ccggcaccat ctgccgctgc tttggaggct tactgtgctc ctcgtgctgt ggctgaactc 2100
accgatcatc cgctgttccc tgctccctgg cgtcccgccc tcatgttcga tcctagagct 2160
ttggcttcct tggccgctcg ttgtgctgcc cctccccctg gcggtgctcc ggctgctttc 2220
ggtcctctcc gtgcctctgg tccactccgc cgtgccgctg cctggatgag acaagttccc 2280
gaccctgagg atgttagagt tgtgatcttg tactcgccct tgcctggcga ggatttggcc 2340
gctggtagag ctggcggtgg ccccccctcct gaatggtctg ctgaacgtgg tggtttgtct 2400
tgcttgttgg ccgccctggg aaaccgtctg tgtggtcctg ctactgctgc ttgggctgga 2460
aactggactg gcgctcccga tgtttctgct ctcggtgctc aaggagtttt gctgctctct 2520
actcgtgact tggcattcgc tggagctgtt gaattcctgg gactcttggc tggcgcttgt 2580
gataggagac tcatcgtcgt aaacgctgtg agagctgccg attggcctgc cgatggtcct 2640
gttgtgtctc gtcaacacgc ttacttggct tgtgaagtgt tgcccgctgt ccaatgtgct 2700
gttcgctggc ctgctgctcg tgatctgagg cgtactgttc tggctagtgg tcgtgttttc 2760
ggacctggtg ttttcgctcg tgtcgaagct gctcacgcta gactgtaccc cgatgcccca 2820
cccctccgtt tgtgtcgtgg agcaaacgtt cgctaccgtg tccgtactcg tttcggaccc 2880
gatactctgg ttccaatgtc ccctcgtgaa taccgtcgtg ctgttctgcc tgccctcgat 2940
ggacgtgctg ccgcttctgg cgctggtgac gctatggctc ctggcgctcc ggacttctgt 3000
gaggatgagg ctcactcaca tcgtgcctgt gcccgctggg gactgggcgc tccattgagg 3060
cctgtatacg tggcactggg ccgtgatgct gttagaggcg gacccgctga attgagaggc 3120
cctcgtcgtg aattctgtgc tagggctctg ctcgaacccg atggagatgc tcctcctttg 3180
gtactccgtg acgacgccga tgctggtcct cccccacaaa ttcgctgggc tagtgctgct 3240
ggacgtgctg gtactgtatt ggctgctgct ggcggtggcg ttgaagttgt tggtactgcc 3300
gctggactcg ctacacctcc ccgccgtgaa cctgtagaca tggatgctga actcgaggat 3360
gatgacgacg gattgttcgg agag 3384

<210> SEQ ID NO 141
<211> LENGTH: 3492
<212> TYPE: DNA
<213> ORGANISM: human herpesvirus 2

<400> SEQUENCE: 141
atgagtgccg aacagcgtaa aaagaaaaaa accaccacca cgacccaagg acgtggagct 60
gaagttgcta tggcggatga ggatggaggc cgcttgagag ctgctgctga gactactgga 120
ggacctggat caccggaccc tgccgatgga cccccccccta caccaaaccc cgatcgtaga 180
ccggctgcta gacctggatt cggatggcat ggaggacccg aggaaaacga ggacgaggcg 240
gacgacgccg ctgccgacgc cgacgccgat gaggctgccc ctgcttctgg agaggcggta 300
gacgaacctg ctgccgatgg agttgttagc cctaggcaat tggctttgtt ggcgagcatg 360

```
gtagacgagg ctgtgagaac aatcccttcc cctccccctg aacgtgatgg agcacaagag    420
gaggcggcta ggagtccctc accaccccgt acaccttcta tgagagcgga ttacggcgag    480
gaaaacgacg acgacgacga tgatgatgac gacgatgatc gtgatgccgg acgctgggtt    540
aggggacctg aaaccacttc tgctgtccgt ggagcatacc ccgatcctat ggcgagtttg    600
agccctagac cacctgcccc gaggagacac caccaccacc accatcatag gcgtagacgt    660
gctcctagac gtcgttctgc cgctagtgac tcttccaaat ctggctcttc ttcatctgcc    720
tcttccgctt catcttcggc ctcatcgtcc tcttcggcat ccgcttcgag tagtgatgat    780
gatgatgacg acgacgctgc tagagccccc gcttctgctg ccgaccacgc tgctggcgga    840
actttgggag ccgacgacga ggaggcggga gttcctgctc gtgccccggg agctgctccg    900
aggccttctc caccccgtgc tgaacctgct ccggctagaa caccggccgc tactgctggt    960
agactggagc gtagacgtgc ccgtgctgct gtggctggta gagatgctac tggccgcttc   1020
actgctggcc gtcctagacg tgttgaactg gacgccgatg ctgcttctgg tgctttctac   1080
gcccgttacc gtgatggtta cgtgtctggt gaaccttggc ctggcgctgg tccacctccg   1140
cccggacgtg tactctacgg tggattgggc gcaatgtcta gacgctacga ccgtgctcaa   1200
aaaggattct tgctcacgtc actgaggcgt gcttacgccc ctttgttggc ccgtgaaaac   1260
gctgccctca ctggcgcccg tacccccgat gacggtggcg acgccaaccg ccacgatggt   1320
gatgatgcta gaggcaaacc cgctgccgct gctgctcctt tgccctctgc cgccgcttcc   1380
cctgccgatg aacgtgctgt tcctgccggt tacggtgccg ctggtgtgtt ggctgctttg   1440
ggacgcttga gtgctgcccc ggctagtgcc cccgctggtg ccgatgacga tgacgatgac   1500
gatggtgctg gcggaggcgg tggcggtaga cgtgctgagg ctggacgtgt tgctgttgaa   1560
tgcctggctg cctgtagagg aatcttggag gctctggccg agggattcga cggagacttg   1620
gcggctgtac cgggactggc gggagcgagg cctgccgctc cacctcgccc cggtcctgct   1680
ggtgctgccg ctcctcctca tgccgacgct cctagactcc gtgcttggct ccgtgaactc   1740
cgtttcgttc gtgacgcttt ggttctgatg agactgagag gcgacttgag agtggctgga   1800
ggatccgagg ctgctgttgc tgctgtccgt gctgtttctt tggttgctgg tgctttgggc   1860
cctgctttgc cgagatctcc ccgtttgttg tcgagtgccg ccgctgctgc cgccgatttg   1920
ttgttccaaa accaatccct ccgccctctg ctcgccgaca ctgttgccgc tgccgattct   1980
ctggctgctc cggcttctgc tgctgctccc cccgctggtg ctgctccccc cgctccccct   2040
actccccccc cacgcccacc tcgtcccgct gccctcacac gccgtcctgc tgagggaccc   2100
gatccacaag gcggctggcg tagacaacct cctggcccat cccatacacc ggcaccatct   2160
gccgctgctt tggaggctta ctgtgctcct cgtgctgtgg ctgaactcac cgatcatccg   2220
ctgttccctg ctccctggcg tcccgccctc atgttcgatc ctagagcttt ggcttccttg   2280
gccgctcgtt gtgctgcccc tccccctggc ggtgctccgg ctgctttcgg tcctctccgt   2340
gcctctggtc cactccgccg tgccgctgcc tggatgagac aagttcccga ccctgaggat   2400
gttagagttg tgatcttgta ctcgcccttg cctggcgagg atttggccgc tggtagagct   2460
ggcggtggcc cccctcctga atggtctgct gaacgtggtg gtttgtcttg cttgttggcc   2520
gccctgggaa accgtctgtg tggtcctgct actgctgctt gggctggaaa ctggactggc   2580
gctcccgatg tttctgctct cggtgctcaa ggagttttgc tgctctctac tcgtgacttg   2640
gcattcgctg gagctgttga attcctggga ctcttggctg gcgcttgtga taggagactc   2700
```

-continued

```
atcgtcgtaa acgctgtgag agctgccgat tggcctgccg atggtcctgt tgtgtctcgt   2760

caacacgctt acttggcttg tgaagtgttg cccgctgtcc aatgtgctgt tcgctggcct   2820

gctgctcgtg atctgaggcg tactgttctg gctagtggtc gtgttttcgg acctggtgtt   2880

ttcgctcgtg tcgaagctgc tcacgctaga ctgtaccccg atgccccacc cctccgtttg   2940

tgtcgtggag caaacgttcg ctaccgtgtc cgtactcgtt tcggacccga tactctggtt   3000

ccaatgtccc ctcgtgaata ccgtcgtgct gttctgcctg ccctcgatgg acgtgctgcc   3060

gcttctggcg ctggtgacgc tatggctcct ggcgctccgg acttctgtga ggatgaggct   3120

cactcacatc gtgcctgtgc ccgctgggga ctgggcgctc cattgaggcc tgtatacgtg   3180

gcactgggcc gtgatgctgt tagaggcgga cccgctgaat tgagaggccc tcgtcgtgaa   3240

ttctgtgcta gggctctgct cgaacccgat ggagatgctc ctcctttggt actccgtgac   3300

gacgccgatg ctggtcctcc cccacaaatt cgctgggcta gtgctgctgg acgtgctggt   3360

actgtattgg ctgctgctgg cggtggcgtt gaagttgttg gtactgccgc tggactcgct   3420

acacctcccc gccgtgaacc tgtagacatg gatgctgaac tcgaggatga tgacgacgga   3480

ttgttcggag ag                                                       3492


<210> SEQ ID NO 142
<211> LENGTH: 9
<212> TYPE: PRT
<213> ORGANISM: human herpesvirus 2

<400> SEQUENCE: 142

Tyr Val Leu Arg Ser Val Ile Ala Lys
1               5


<210> SEQ ID NO 143
<211> LENGTH: 9
<212> TYPE: PRT
<213> ORGANISM: human herpesvirus 2

<400> SEQUENCE: 143

Asp Ile Leu Arg Val Pro Cys Met Arg
1               5


<210> SEQ ID NO 144
<211> LENGTH: 9
<212> TYPE: PRT
<213> ORGANISM: human herpesvirus 2

<400> SEQUENCE: 144

Asp Arg His Ala Gln Arg Ala Tyr Leu
1               5
```

VACCINES AGAINST HERPES SIMPLEX VIRUS TYPE 2: COMPOSITIONS AND METHODS FOR ELICITING AN IMMUNE RESPONSE

CROSS REFERENCE TO RELATED APPLICATIONS

This application is the National Stage of International Application No. PCT/US11/62120, filed Nov. 23, 2011, which claims the benefit of U.S. Provisional Patent Application Ser. No. 61/417,089, filed Nov. 24, 2010; the entire contents of all of which are incorporated herein by reference.

SEQUENCE LISTING

In accordance with 37 CFR 1.52(e)(5), a Sequence Listing in the form of an ASCII text file (entitled "Sequence_Listing.txt," created on May 20, 2013, and 323 KB in size) is incorporated herein by reference in its entirety.

BACKGROUND

Herpes simplex virus type 2 (HSV-2) is the leading cause of genital herpes. HSV-2 is most often transmitted by sexual contact, and infection with the virus typically leads to recurring outbreaks of lesions on the genitals and perianal regions, combined with shedding of virus into the genital tract. Viral shedding can also occur in the absence of lesions or other symptoms. HSV-2 also establishes latency in sensory ganglia. HSV-2 infection causes physical discomfort and psychosexual morbidity in affected patients, and introduces additional health risks. In particular, patients infected with HSV-2 are at increased risk for contracting HIV, and pregnant mothers infected with HSV-2 can vertically transmit HSV-2 to their fetuses. In immunocompromised individuals or in neonates, HSV-2 infections can be fatal. Currently, there is no cure for HSV-2 infection.

HSV-2 infection is widespread, with one study estimating that nearly 20% of the population worldwide is infected (Looker et al., 2008, Bulletin of the World Health Organization, October 2008, 86(10)). More women than men are infected, and the prevalence of the disease increases with age. High numbers of adolescents diagnosed with HSV-2 indicate that the prevalence across the population will continue to rise, as HSV-2 infection is lifelong.

Treatment options for HSV-2 symptoms are limited. Antiviral therapy, using compounds such as famciclovir, valaciclovir, or aciclovir, limits the duration of symptoms and, in some cases, speeds healing of lesions and reduces incidence of viral shedding. Antiviral drugs are not curative, however, and do not prevent recurrence of outbreaks or clear the virus completely. In addition, use of antiviral drugs requires patients to recognize symptoms of HSV-2 infection, then obtain a confirmative diagnosis, and ultimately, comply with the antiviral regimen. These requirements may be untenable in regions of the world where antiviral drugs are not readily available. In addition, patients are often unaware that they are infected, either because they do not present symptoms, or because the symptoms of the initial infection subside, suggesting recovery from the disease.

To address the medical and social problems associated with HSV-2, it is highly desirable to develop pharmaceutical compositions to inhibit or counteract infection by HSV-2. An effective composition may be used to elicit an enhanced immune response against HSV-2, thereby preventing initial infection, blocking the ability of the virus to establish latency in sensory ganglia, eliminating recurrence of outbreaks, and/or preventing viral shedding. The immune system is known to mount a defense against HSV-2, as evidenced by recurrent infections which manifest with fewer, less intense symptoms and decreased frequency over time.

While the ultimate goal of an HSV vaccine would be long-lasting protection from viral infection, the suppression of disease symptoms would also provide significant health benefits. One of the current goals for either a prophylactic or therapeutic vaccine is to reduce clinical episodes and viral shedding from primary and latent infections. Three categories of prophylactic vaccines have been tested in clinical trials with disappointing results: i) whole virus, ii) protein subunit, and iii) gene-based subunit vaccines (Stanberry et al., Clinical Infect. Dis., 30(3):549-566, 2000). In the 1970s a number of killed virus vaccines were explored, none of which were efficacious. More recently an attenuated HSV was found to be poorly immunogenic. Subunit vaccines based on two recombinant glycoproteins have been clinically evaluated in combination with different adjuvant formulations. One developed by Chiron contains truncated forms of both glycoprotein D (gD2) and glycoprotein B (gB2) of HSV-2, purified from transfected Chinese Hamster Ovary (CHO) cells and formulated with adjuvants alum and MF59. Another developed by Glaxo-Smithkline (GSK) contains a truncated gD2 formulated with adjuvants alum and 3-O-deacylated monophosphoryl lipid A (MPL). Both vaccines were immunogenic and well tolerated in phase I/II trials. However in phase III analyses, the Chiron vaccine showed no overall efficacy against HSV-2 seroconversion and work was discontinued. The GSK vaccine showed significant efficacy (73-74%) in HSV-1, HSV-2 seronegative women volunteers but no efficacy in men.

While even limited vaccine efficacy would beneficially impact HSV sufferers, these trials are testing only a small number of vaccine possibilities. This is because the vaccine discovery has not been systematic. Pursuance of a whole-virus vaccine assumes that presentation of the pathogen itself to the immune system will generate optimal immunity. Indeed the breadth and duration of immune responses to whole pathogen vaccines historically have been better than subunit vaccines. However, pathogenicity of the vaccine strain must be considered. Subunit vaccines, to date, have been selected for vaccine testing based on their assumed importance in disease pathogenesis and immunogenicity during infection. These approaches have identified one candidate against HSV with limited efficacy in some but no efficacy in other formulations. Thus, new and improved methodologies for herpesvirus vaccine discovery are needed to protect against herpes diseases.

SUMMARY

Infection and transmission of HSV-2 is a major health concern. The present disclosure provides, inter alia, certain highly effective vaccines against HSV-2. Such vaccines can be used either therapeutically or prophylactically. The present disclosure also provides specific antigens and methods for using the antigens to elicit an immune response against HSV-2.

In one aspect, the present disclosure describes a vaccine formulation comprising a pharmaceutically-acceptable carrier and at least one polypeptide consisting of SEQ ID NO: 136 or an immunogenic fragment thereof, The vaccine formulation may comprise a first polypeptide consisting of the above SEQ ID NO, a second polypeptide consisting of SEQ ID NO: 1 or SEQ ID NO: 4 and optionally a third polypeptide consisting of the other of SEQ ID NOS: 1 and 4. In some embodiments, the second or third polypeptide consists of polypeptide fragments of SEQ ID NO: 1, such as the polypeptides of SEQ ID NOS: 2, 8-16, 138 and 139, or immunogenic fragments thereof. In some embodiments, the vaccine formulation may comprise a first polypeptide consisting of SEQ ID NO: 136, a second polypeptide consisting of SEQ ID NO: 4 or SEQ ID NO: 5, a third polypeptide selected from the group consisting of SEQ ID NOS: 2, 8-16, 138 and 139, and optionally a fourth polypeptide selected from the group consisting of SEQ ID NOS: 2, 8-16, 138 and 139, or immunogenic fragments thereof.

Another aspect of the present invention provides a vaccine formulation comprising a pharmaceutically acceptable carrier, an adjuvant comprising one or more purified fractions of *Quillaja saponins*, and at least one polypeptide comprising any of SEQ ID NOS: 1, 4, 5, and 136 or an immunogenic fragment thereof. In certain embodiments, at least one polypeptide comprises one or more polypeptide fragments of SEQ ID NO: 1, such as the polypeptides of SEQ ID NOS: 2, 8-16, 138 and 139.

In still a further aspect, the present invention provides a vaccine formulation where a polypeptide comprising SEQ ID NO: 5 is present in place of a polypeptide of SEQ ID NO: 4, wherein the polypeptide lacks all or at least an 8 contiguous amino acid residue portion of the transmembrane domain spanning residues 340-363. The polypeptide may be glycosylated, or may be unglycosylated.

In some embodiments, polypeptides in the vaccine formulations may be conjugated to an immunogenic carrier, for example keyhole limpet hemocyanin. In other embodiments, the vaccine formulations further comprise an adjuvant. The adjuvant may be one or more purified fractions of *Quillaja saponins*, or the adjuvant may comprise a cytokine, or the adjuvant may comprise a cationic peptide with TLR agonist.

The invention provides methods of treating a subject suffering from or susceptible to HSV-2 infection by administering an effective amount of a vaccine formulation disclosed herein. In some embodiments, the method inhibits HSV-2 symptoms, for example by reducing the number of herpetic lesions, reducing the number of days a subject experiences herpetic lesions, reducing infection by HSV-2 in an uninfected subject, increasing the IgG titer and/or T cell response to one or more HSV-2 antigens, and/or reducing the number of herpetic lesions at the onset of HSV-2 infection.

One aspect of the present invention provides pharmaceutical compositions comprising two, three, four, or more isolated polypeptides selected from polypeptides having an amino acid sequence of at least one of SEQ ID NOS: 1-38, 135, 136, 138 and 139, or an immunogenic fragment thereof.

In another aspect, the invention provides vaccine formulations that include a pharmaceutically-acceptable carrier and a polypeptide comprising at least one of SEQ ID NOS: 1-38, 135, 136, 138 and 139, or an immunogenic fragment thereof. In certain embodiments, the polypeptide consists of at least one of SEQ ID NOS: 1-38, 135, 136, 138 and 139.

Another aspect of the present invention provides pharmaceutical compositions comprising two, three, four, or more isolated nucleic acids having a nucleotide sequence that encodes at least one of SEQ ID NOS: 1-38, 135, 136, 138 and 139, or an immunogenic fragment thereof. In certain embodiments, the nucleic acids encode at least one of SEQ ID NOS: 1, 3, 5, 38 or an immunogenic fragment thereof. For example, the nucleic acids may include at least one of SEQ ID NOS: 39-45, 117-129, 137, 140 and 141, or a fragment thereof that encodes an immunogenic polypeptide.

In another aspect, the invention provides vaccine formulations that include a pharmaceutically-acceptable carrier and a nucleic acid having a nucleotide sequence that encodes at least one of SEQ ID NOS: 1, 3, 5, 38, 136 or 138, or an immunogenic fragment thereof. For example, the nucleic acids can have a nucleotide sequence comprising at least one of SEQ ID NOS: 39, 46, 118, 137 or 140, or a fragment thereof that encodes an immunogenic polypeptide.

Another aspect of the present invention provides a method of inducing an immune response in a subject, comprising administering to said subject an effective amount of a vaccine formulation or a pharmaceutical composition as described herein.

Yet another aspect of the present invention provides a method of reducing one or more symptoms of HSV-2 infection in a subject, comprising administering to said subject an effective amount of a vaccine formulation or a pharmaceutical composition as described herein. In some embodiments, the symptoms of HSV-2 infection comprise one or more of lesion formation, pain, irritation, itching, fever, malaise, headache, viral shedding, and prodrome.

A further aspect of the present invention provides a method of inhibiting the onset of HSV-2 infection, comprising administering an effective amount of a vaccine formulation or a composition as described herein.

Applicants disclose another aspect of the present invention, which provides a method of inhibiting development of a latent HSV-2 infection in a subject exposed to HSV-2, comprising administering an effective amount of a vaccine formulation or a composition as described herein.

In a related aspect, the present invention provides a method of reducing viral shedding in a subject infected with HSV-2, comprising administering an effective amount of a vaccine formulation or a composition as described herein.

Further, an aspect of the present invention provides a method of reducing recurrence of outbreaks in a subject infected with HSV-2, comprising administering an effective amount of a vaccine formulation or a composition as described herein.

An additional aspect of the present invention provides a method of producing any of the pharmaceutical compositions described above, comprising expressing said two or more polypeptides; and isolating said two or more polypeptides.

Applicants further disclose an aspect of the present invention which provides a method for diagnosing severity of symptoms in a subjected infected with HSV-2, comprising (i) measuring activation of T cells in response to autologous antigen presenting cells (APCs) pulsed with one or more isolated HSV-2 polypeptides as described herein, and (ii) comparing said levels to reference levels obtained from infected subjects experiencing frequent outbreaks; whereby a significant increase in said responses relative to reference levels indicates that said subject has less severe symptoms (e.g., the subject is asymptomatic). A significant increase in response can, for example, comprise a 1.5-fold or greater, 2-fold or greater, 3-fold or greater, 5-fold or greater, 10-fold or greater or even 20-fold or greater increase.

Another aspect of the present invention provides a method for diagnosing severity of symptoms in a subject infected with HSV-2, comprising (i) measuring activation of T cells from naturally infected or virus-exposed subjects in response to APCs presenting one or more isolated HSV-2 polypeptides selected from polypeptides as described herein, or an immunogenic fragment thereof, and (ii) comparing said levels to reference levels obtained from infected subjects experiencing frequent outbreaks; whereby a significant decrease in said activation relative to reference levels indicates that said subject has more severe symptoms (e.g., frequent outbreaks).

Another aspect of the present invention provides pharmaceutical compositions comprising an antibody that binds to one or more isolated HSV polypeptides selected from the list as described herein, or an immunogenic fragment thereof.

Moreover, a different aspect of the present invention provides a method of identifying immunogenic compositions for HSV-2 by testing two, three, four, or more polypeptides selected from polypeptides having an amino acid sequence as described herein, or an immunogenic fragment thereof, for ability to promote cytokine production in a mammalian T cell, wherein an immunogenic composition is one that elevates levels of a cytokine significantly above the levels of that cytokine produced by a naïve mammalian T cell. A significant increase in cytokine levels is typically one that is at least 1.5-fold, 2-fold, 3-fold, 5-fold, 10-fold or even 20-fold the level produced by a naïve cell.

Still another aspect of the present invention provides a method of detecting HSV-2 in a sample from a subject, said method comprising (i) contacting said sample with one or more antibodies raised against one or more polypeptides having an amino acid sequence as described herein or an immunogenic fragment thereof, and (ii) detecting said one or more antibodies bound to said one or more HSV-2 polypeptide from the sample.

Finally, one aspect of the present invention provides pharmaceutical compositions comprising two or more isolated polynucleotides, encoding polypeptides as described herein, or fragments encoding immunogenic peptides thereof.

BRIEF DESCRIPTION OF THE DRAWINGS

The Figures described below, that together make up the Drawing, are for illustration purposes only, not for limitation.

FIG. 5 illustrates IgG1 and IgG2c antibody titers against gL2s v.2, UL40 protein, and gL2s v.2 plus UL40 protein.

DETAILED DESCRIPTION OF THE INVENTION

Figure 1A:
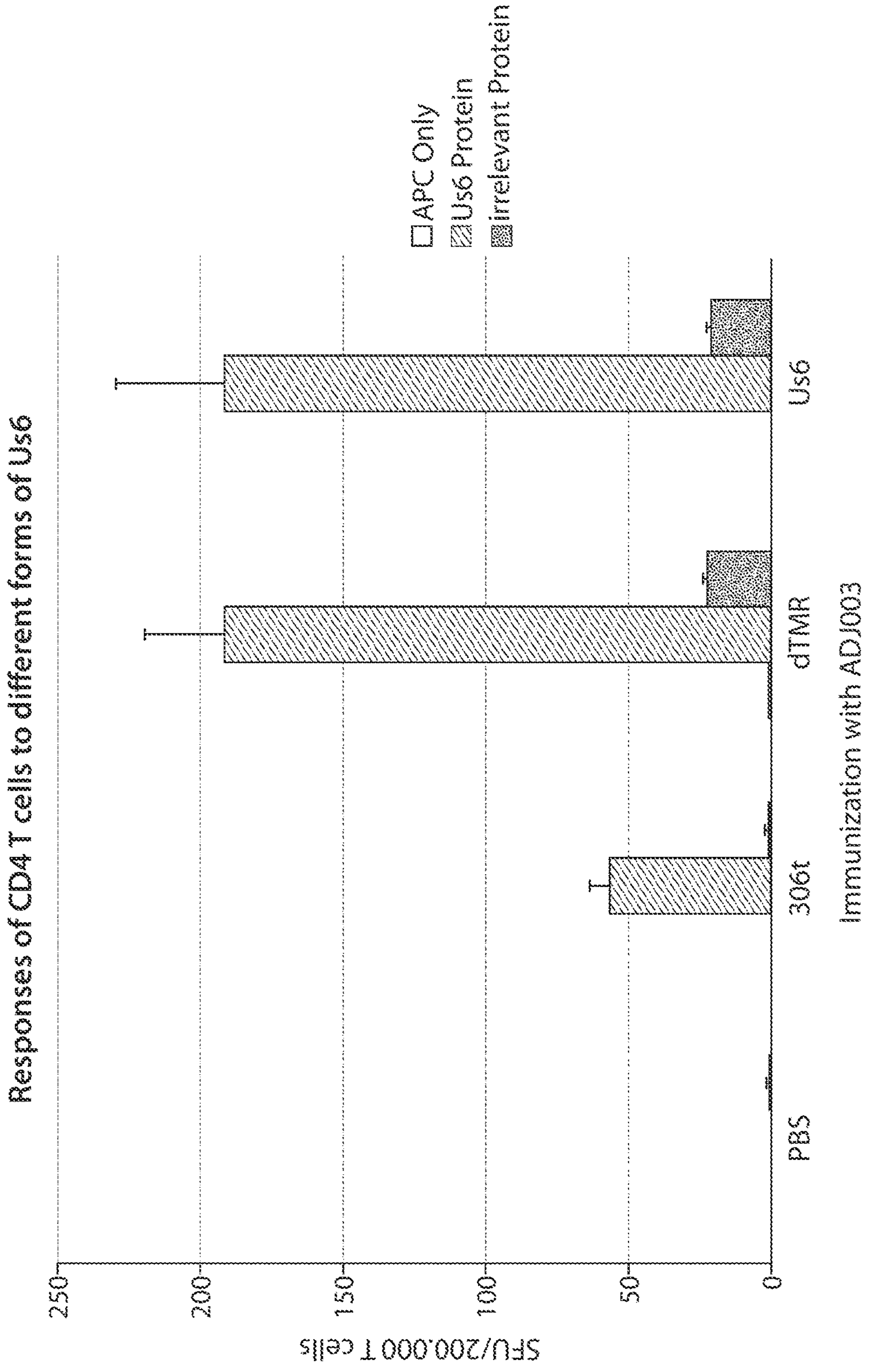
FIGS. 1A and B depict exemplary graphs illustrating, respectively, $CD4^+$ and $CD8^+$ T cell responses following immunization with gD2 full-length protein, gD2ΔTMR, or gD2 truncated immediately upstream of the transmembrane domain (denoted 306t).

This application describes vaccines and immunogenic compositions against HSV-2. Vaccine formulations may include a polypeptide comprising a sequence from Table 1 or an immunogenic fragment thereof, or a combination of at least two polypeptides comprising sequences from Table 1 or immunogenic fragments thereof. In certain embodiments, the polypeptide(s) of the vaccines comprise the entire sequence of at least one of SEQ ID NOS: 1-26, 135, 136, 138 and 139, or consist of the entire sequence of any one of SEQ ID NOS: 1-26, 135, 136, 138 and 139. Immunogenic compositions may include a polypeptide comprising a sequence from Table 1 or Table 2 or an immunogenic fragment thereof or a combination of at least two polypeptides comprising sequences from Table 1 or Table 2, or immunogenic fragments thereof. In certain embodiments, the polypeptide(s) of the immunogenic compositions comprise the entire sequence of any one of SEQ ID NOS: 1-38, 135, 136, 138 and 139 or consist of the entire sequence of any one of SEQ ID NO: 1-38, 135, 136, 138 and 139. The polypeptides in Tables 1 or 2 may be encoded by SEQ ID NOS: 39-46 and 117-134, 137, 140 and 141 as indicated and/or by cDNA sequences publically available on the world wide web at the hypertext protocol transfer address of "ncbi.nlm.nih.gov/sites/entrez". cDNA and protein sequences may also be obtained from any known strains of HSV-2, including HG52, 333, and Strain G. Accordingly, cDNA sequences may be accessed by gene or protein name from genomic sequence at NC_001798.1, and may be approximately 97% conserved with sequences disclosed at NC 001798.1. As described herein, the polypeptides may be referred to by protein name, by SEQ ID NO, and/or by the name of the gene encoding the protein.

The polypeptides can be prepared in a variety of expression systems. Suitable expression systems include *E. coli* and Baculovirus-based expression systems (e.g., in insect cells). Polypeptides prepared using *E. coli* are typically full-length and unglycosylated, although truncated variants can be prepared. In certain embodiments, these truncated variants retain all or part of the signal domain. Polypeptides prepared using a Baculovirus system typically lack the N-terminal signal sequence, but are fully or partially glycosylated.

In some embodiments, the polypeptides are prepared in non-mammalian cell systems. When an exogenous signal sequence is used, polypeptides may contain one or more amino acids at the N-terminal end which correspond to the exogenous signal sequence. An exogenous signal sequence commonly used in insect expression systems is the honey bee mellitin signal sequence. In other embodiments, the polypeptides may contain one or more amino acids corresponding to a signal sequence that has been cleaved. Exemplary polypeptides may contain one or more amino acids from a mammalian signal sequence that has been left intact or cleaved off, depending on the system used to prepare the polypeptides.

TABLE 1

HSV-2 antigens for vaccines or immunogenic compositions

| Protein SEQ ID No. | DNA SEQ ID No. | Gene or Construct Name<br>Protein Name | GeneID No. | GenBank Accession Nos. |
|---|---|---|---|---|
| 1 | 39 | RS1<br>ICP4 | 1487291 (duplicated in HSV-2 genome: also 1487290) | NP_044530.1 (duplicated in HSV-2 genome: also NP_044544.1) |
| 2 | 117 | RS1.2<br>ICP4 internal fragment (ICP4.2) | 1487291 | NP_044530.1<br>RS1.2 corresponds to amino acid residues 383-766 or nucleotides 1150-2398 of the RS1 sequence |
| 3 | 118 | UL1<br>gL2 cytoplasmic | 1487292 | NP_044470.1 |
| 4 | 40 | US6ΔTMR<br>gD2 internal deletion (gD2ΔTMR) | 1487358 | NP_044536.1<br>US6ΔTMR corresponds to gD2 will a deletion of amino acids 341-363 |
| 5 | | US6<br>gD2 | 1487358 | NP_044536.1 |
| 6 | 41 | RL1<br>ICP34.5 | 1487287 | NP_044529.1 |
| 7 | 42 | RL2<br>ICP0 | 1487289 | NP_044528.2 |
| 8 | 121 | RS1.1<br>ICP4 internal fragment | 1487291 | NP_044530.1<br>RS1.1 corresponds to residues 1-400 of RS1 |
| 9 | 122 | RS1.3.1<br>ICP4 internal fragment | 1487291 | NP_044530.1<br>RS1.3.1 corresponds to residues 750-1024 of RS1 |
| 10 | 123 | RS1.3.2<br>ICP4 internal fragment | 1487291 | NP_044530.1<br>RS1.3.2 corresponds to residues 1008-1319 of RS1 |
| 11 | 124 | RS1.3<br>ICP4 internal fragment | 1487291 | NP_044530.1<br>RS1.3 corresponds to residues 750-1319_of RS1 |
| 12 | 125 | RS1.4<br>ICP4 internal fragment | 1487291 | NP_044530.1<br>RS1.4 corresponds to residues 341-883 of RS1 |
| 13 | 126 | RS1.5<br>ICP4 internal fragment | 1487291 | NP_044530.1<br>RS1.5 corresponds to residues 775-1318 of RS1 |
| 14 | 127 | RS1.6<br>ICP4 internal fragment | 1487291 | NP_044530.1<br>RS1.6 corresponds to residues 210-1318 of RS1 |
| 15 | 128 | RS1.7<br>ICP4 internal fragment | 1487291 | NP_044530.1<br>RS1.7 has a deletion of residues 391-544 of RS1 |
| 16 | 129 | RS1.8<br>ICP4 internal fragment | 1487291 | NP_044530.1<br>RS1.8 has a deletion of residues 786-868 of RS1 |
| 17 | | UL2 v.1<br>uracil DNA glycosylase | 1487303 | NP_044471.2 |
| 135 | | UL2 v.2<br>uracil DNA glycosylase | 1487303 | NP_044471.2 |
| 18 | | UL11<br>myristylated tegument protein | 1487294 | NP_044480.1 |

TABLE 1-continued

HSV-2 antigens for vaccines or immunogenic compositions

| Protein SEQ ID No. | DNA SEQ ID No. | Gene or Construct Name Protein Name | GeneID No. | GenBank Accession Nos. |
|---|---|---|---|---|
| 19 | 119 | UL1s v.1 gL2 secreted | 1487292 | NP_044470.1 |
| 136 | 137 | UL1s v.2 gL2 secreted | 1487292 | NP_044470.1 |
| 20 | | UL19a VP5 | 1487302 | NP_044488.1 |
| 21 | 120 | UL19ΔTEV VP5 | 1487302 | NP_044488.1 |
| 22 | | UL36 ICP1/2 | 1487322 | NP_044506.1 |
| 23 | 43 | UL36.3.4.1 ICP1/2 internal fragment | 1487322 | NP_044506.1 UL 36.3.4.1 corresponds to residues 1318-2280 of UL36 |
| 24 | 44 | UL36.4.2.5 ICP1/2 internal fragment | 1487322 | NP_044506.1 UL 36.4.2.5 corresponds to residues 2253-3122 of UL36 |
| 25 | | UL40 ribonucleoside reductase | 1487327 | NP_044510.1 |
| 26 | 45 | US12 ICP47 | 1487353 | NP_044543.1 |
| 138 | 140 | RS1.9 ICP4 internal fragment | 1487291 | NP_044530.1 RS1.9 has a deletion of residues 391-544 and 786-821 of RS1 |
| 139 | 141 | RS1.10 ICP4 internal fragment | 1487291 | NP_044530.1 RS1.10 has a deletion of residues 391-508 and 786-821 of RS1 |

TABLE 2

Additional HSV-2 antigens for immunogenic compositions

| Protein SEQ ID No. | DNA SEQ ID No. | Gene or Construct Name Protein Name | GeneID No. | GenBank Accession Nos. |
|---|---|---|---|---|
| 27 | 134 | UL10 gM2 | 1487293 | NP_044479.1 |
| 28 | | UL15 DNA cleavage/packaging protein | 1487298 | NP_044484.1 |
| 29 | | UL26.5 ICP35 | 1487311 | NP_044496.1 |
| 30 | | UL30 DNA-directed polymerase | 1487316 | NP_044500.1 |
| 31 | | UL5 DNA helicase/primase complex | 1487338 | NP_044474.1 |
| 32 | | UL8 DNA helicase/primase complex | 1487348 | NP_044477.1 |
| 33 | | UL15.5 unknown | 1487298 | NP_044484.1 UL15.5 is an alternate translation of UL15 |
| 34 | | UL32 cleavage/packaging protein | 1487318 | NP_044502.1 |
| 35 | | UL36.4.2 ICP1/2 fragment | 1487322 | NP_044506.1 |
| 36 | | UL54 ICP27 | 1487343 | NP_044525.1 |
| 37 | 133 | UL49.5 membrane-associated virion protein | 1487337 | NP_044520.1 |
| 38 | 46 | US4 gG2 | 1487356 | NP_044534.1 |

Immunogenic HSV-2 Polypeptides

Immunogenic polypeptides or polynucleotides as indicated in Table 1 and/or Table 2 may be used in pharmaceutical compositions. The invention provides pharmaceutical compositions containing immunogenic polypeptides or polynucleotides encoding these immunogenic polypeptides together with a pharmaceutical carrier. Antigens from HSV-2 may be identified by screening immune cells from patients exposed to or infected with HSV-2. Briefly, a library of HSV-2 antigens was expressed by bacteria and mixed with APCs. The APCs, in turn, processed and presented HSV-2-derived peptides to lymphocytes that had been isolated from human patients exposed to or infected with HSV-2. The patients belonged to several populations: (1) exposed to HSV-2 but seronegative for infection, (2) infected with HSV-2 but asymptomatic, (3) infected with HSV-2 and experiencing infrequent outbreaks, (4) infected with HSV-2 and experiencing frequent outbreaks, (5) naïve and (6) seronegative for HSV-2 (HSV-2-) but seropositive for HSV-1 (HSV-1+). Lymphocyte responses from each population were compared for reactivity to HSV-2-derived polypeptides, and the screen detected antigens that induced reactive lymphocytes with greater frequency in one patient population as compared to the others. Infected but asymptomatic, and exposed but seronegative patients may activate protective immune responses that patients who experience frequent outbreaks do not; in particular, exposed but seronegative patients are presumed to have mounted sterilizing immunity to HSV-2 infection. It is believed that a unique set of polypeptides will activate lymphocytes from these patient populations. Thus, the present invention contemplates compositions of the specific HSV-2 polypeptides that activate the lymphocytes of infected but asymptomatic, or exposed but seronegative patients or a combination of these polypeptides for inhibiting or counteracting infection by HSV-2.

Antigens identified on the basis of their immunogenicity in infected but asymptomatic, or exposed but seronegative patients, are similarly expected to be immunogenic in any subject.

In some embodiments, a polypeptide may induce an innate immune response, a humoral immune response, or a cell-mediated immune response. The cell-mediated immune response may involve CD4+ and/or CD8+ T cells, and in certain embodiments, the immune response involving CD4+ T cells is an immune response in which TH1 cells are activated. In some embodiments, an immunogenic polypeptide avoids induction of TH2 cytokines. In some embodiments, the immune response involving CD4+ T cells is an immune response in which TH17 cells are activated.

Polypeptides (or immunogenic fragments thereof) in compositions of the invention may induce T cell responses in multiple individuals, regardless of the HLA haplotype of the individuals. Specifically, epitopes in the polypeptides may induce T cell responses in individuals with one or more of the following HLA supertypes: HLA-A2, -A3, -A24, -A1, -B7, -B8, -B27, -B44, -B58, and B62, and HLA-DQB01, -DQB02, -DQB03, -DQB-04, and -DQB05.

In some embodiments, one or more, e.g. two, three, four, or more polypeptides from Table 1 and/or Table 2 (or immunogenic fragments thereof) are provided in a composition of the invention. In some embodiments, two polypeptides from Table 1 and/or Table 2 are provided in a composition of the invention. In other embodiments, three polypeptides from Table 1 and/or Table 2 are provided in a composition of the invention. In other embodiments, four polypeptides from Table 1 and/or Table 2 are provided in a composition of the invention.

In some embodiments, two, three, four, or more polypeptides from Table 1 and/or Table 2 (or immunogenic fragments thereof) are provided together as a conjugate. In some embodiments, two polypeptides from Table 1 and/or Table 2, or three polypeptides from Table 1 and/or Table 2, or four polypeptides from Table 1 and/or Table 2, are provided as a conjugate. In some embodiments, two, three, four, or more polypeptides from Table 1 and/or Table 2 are covalently bound to each other, e.g., as a fusion protein. In some embodiments, two polypeptides from Table 1 and/or Table 2, or three polypeptides from Table 1 and/or Table 2, or four polypeptides from Table 1 and/or Table 2, are covalently bound to each other, e.g. as a fusion protein.

In some embodiments, the compositions comprise two, three, four, or more polypeptides selected from the group consisting of SEQ ID NOS: 1-38, 135, 136, 138 and 139, and may contain or may not contain any other HSV-2 polypeptides.

In certain embodiments, Applicants provide polypeptides that are at least 70%, 80%, 90%, 95%, 96%, 97%, 98%, 99%, or 100% identical to a polypeptide encoded by a gene in Table 1 and/or Table 2, or a portion of said polypeptide. In certain embodiments, the homologous polypeptide is at least 8, 10, 15, 20, 30, 40, 50, 60, 80, 100, 120, 140, 160, 180, 200, 220, 240, 260, 280, 300, 350, 400, 450, or 500 amino acids in length. In some embodiments, such as those described immediately above, the polypeptide is no more than 300, 350, 400, 450, or 500 amino acids in length.

An immunogenic composition may also comprise portions of said polypeptides and genes, for example deletion mutants, truncation mutants, oligonucleotides, and peptide fragments. In some embodiments, the portions of said proteins are immunogenic.

The immunogenicity of a portion of a protein or a homolog thereof can be readily determined using the same assays that are used to determine the immunogenicity of the full-length protein. In some embodiments, the portion of the protein has substantially the same immunogenicity as the full-length proteins. In some embodiments, the immunogenicity is no more than 10%, 20%, 30%, 40%, or 50% less than that of the full-length protein. The protein fragments may be, for example, linear, circular, or branched. In some embodiments, a protein or protein fragment comprises one or more non-natural amino acids (e.g. an amino acid other than the 20 typically found in natural proteins). A non-natural amino acid may have an atypical side chain. In addition, peptidomimetics may be used; these may incorporate alterations to the peptide backbone.

Some embodiments of the polypeptide composition described herein include an immunogenic polypeptide that contains a membrane translocating sequence (MTS), to facilitate introduction of the polypeptide into the mammalian cell and subsequent stimulation of the cell-mediated immune response. Exemplary membrane translocating sequences include hydrophobic region in the signal sequence of Kaposi fibroblast growth factor, the MTS of α-synuclein, β-synuclein, or γ-synuclein, the third helix of the Antennapedia homeodomain, SN50, integrin β3 h-region, HIV Tat, pAntp, PR-39, abaecin, apidaecin, BacS, Bac7, *P. berghei* CS protein, and those MTSs described in U.S. Pat. Nos. 6,248,558, 6,432,680 and 6,248,558.

In certain embodiments, the immunogenic polypeptide is conjugated (i.e. covalently bound) to another molecule. This may, for example, increase the half-life, solubility, bioavailability, or immunogenicity of the antigen. Molecules that may be conjugated to an immunogenic polypeptide include a carbohydrate, biotin, poly(ethylene glycol) (PEG), polysialic acid, N-propionylated polysialic acid, nucleic acids, polysaccharides, and PLGA. There are many different types of PEG, ranging from molecular weights of below 300 g/mol to over 10,000,000 g/mol. PEG chains can be linear, branched, or with comb or star geometries.

Immunogenic HSV-2 polypeptides and nucleic acids for use in vaccines

In certain embodiments, one or more, e.g. two, three, four, or more immunogenic fragments or variants thereof are provided in a mixture. For example, a vaccine formulation may comprise any one or more of SEQ ID NOS: 1-26, 136, 138 or 139.

In certain embodiments, a vaccine formulation may comprise any one, two, three, or four of ICP4, ICP4.2, ICP4.5, ICP4.9, ICP4.10, gL2, gL2s v.2, gD2ΔTMR and gD2 (SEQ ID NOS: 1-5, 13, 136, 138 and 139), or immunogenic fragment(s) thereof. In certain embodiments, combinations contain polypeptides or immunogenic fragments from only one of ICP4 (SEQ ID NO: 1), ICP4.2 (SEQ ID NO: 2), ICP4.5 (SEQ ID NO: 13), ICP4.9 (SEQ ID NO: 138) and ICP4.10 (SEQ ID NO: 139). In other embodiments, combinations contain polypeptides or immunogenic fragments from only one of gD2ΔTMR (SEQ ID NO: 4) and gD2 (SEQ ID NO: 5). In yet other embodiments, combinations contain polypeptides or immunogenic fragments from only one of gL2 (SEQ ID NO: 3) and gL2s v.2s (SEQ ID NO: 136). In some embodiments, combinations contain polypeptides or immunogenic fragments from any two of ICP4.2 (SEQ ID NO: 2), ICP4.5 (SEQ ID NO: 13), ICP4.9 (SEQ ID NO: 138) and ICP4.10 (SEQ ID NO: 139).

In some embodiments, the vaccine formulation may comprise at least one polypeptide fragment of SEQ ID NO: 1, such as the polypeptides of SEQ ID NOS: 2, 8-16, 138 and 139. In some embodiments, the vaccine formulation may comprise at least two polypeptide fragments of SEQ ID NO: 1, such as the polypeptides of SEQ ID NOS: 2, 8-16, 138 and 139. One or more polypeptide fragments of SEQ ID NO: 1 may replace SEQ ID NO: 1 in any of the vaccine formulations or immunogenic compositions as described herein.

Exemplary combinations of ICP4, ICP4.2, ICP4.5, ICP4.9, ICP4.10, gL2, gL2s v.2, gD2ΔTMR and gD2 include:

| Two antigen combinations | |
|---|---|
| ICP4 | gL2 or gL2s v.2 |
| SEQ ID NO: 1 | SEQ ID NO: 3 or SEQ ID NO: 136 |
| ICP4 | gD2ΔTMR |
| SEQ ID NO: 1 | SEQ ID NO: 4 |
| ICP4 | gD2 |
| SEQ ID NO: 1 | SEQ ID NO: 5 |
| ICP4.2 | gL2 or gL2s v.2 |
| SEQ ID NO: 2 | SEQ ID NO: 3 or SEQ ID NO: 136 |
| ICP4.2 | gD2ΔTMR |
| SEQ ID NO: 2 | SEQ ID NO: 4 |
| ICP4.2 | gD2 |
| SEQ ID NO: 2 | SEQ ID NO: 5 |
| gL2 or gL2s v.2 | gD2ΔTMR |
| SEQ ID NO: 3 or SEQ ID NO: 136 | SEQ ID NO: 4 |
| gL2 or gL2s v.2 | gD2 |
| SEQ ID NO: 3 or SEQ ID NO: 136 | SEQ ID NO: 5 |
| ICP4.5 | gL2 or gL2s v.2 |
| SEQ ID NO: 13 | SEQ ID NO: 3 or SEQ ID NO: 136 |
| ICP4.5 | gD2ΔTMR |
| SEQ ID NO: 13 | SEQ ID NO: 4 |
| ICP4.5 | gD2 |
| SEQ ID NO: 13 | SEQ ID NO: 5 |
| ICP4.9 | gL2 or gL2s v.2 |
| SEQ ID NO: 138 | SEQ ID NO: 3 or SEQ ID NO: 136 |
| ICP4.9 | gD2ΔTMR |
| SEQ ID NO: 138 | SEQ ID NO: 4 |
| ICP4.9 | gD2 |
| SEQ ID NO: 138 | SEQ ID NO: 5 |
| ICP4.10 | gL2 or gL2s v.2 |
| SEQ ID NO: 139 | SEQ ID NO: 3 or SEQ ID NO: 136 |
| ICP4.10 | gD2ΔTMR |
| SEQ ID NO: 139 | SEQ ID NO: 4 |
| ICP4.10 | gD2 |
| SEQ ID NO: 139 | SEQ ID NO: 5 |

-continued

| Three antigen combinations | | |
|---|---|---|
| ICP4 | gL2 | gD2ΔTMR |
| SEQ ID NO: 1 | SEQ ID NO: 3 | SEQ ID NO: 4 |
| ICP4.2 | gL2 | gD2ΔTMR |
| SEQ ID NO: 2 | SEQ ID NO: 3 | SEQ ID NO: 4 |
| ICP4.5 | gL2 | gD2ΔTMR |
| SEQ ID NO: 13 | SEQ ID NO: 3 | SEQ ID NO: 4 |
| ICP4.9 | gL2 | gD2ΔTMR |
| SEQ ID NO: 138 | SEQ ID NO: 3 | SEQ ID NO: 4 |
| ICP4.10 | gL2 | gD2ΔTMR |
| SEQ ID NO: 139 | SEQ ID NO: 3 | SEQ ID NO: 4 |
| ICP4 | gL2 | gD2 |
| SEQ ID NO: 1 | SEQ ID NO: 3 | SEQ ID NO: 5 |
| ICP4.2 | gL2 | gD2 |
| SEQ ID NO: 2 | SEQ ID NO: 3 | SEQ ID NO: 5 |
| ICP4.5 | gL2 | gD2 |
| SEQ ID NO: 13 | SEQ ID NO: 3 | SEQ ID NO: 5 |
| ICP4.9 | gL2 | gD2 |
| SEQ ID NO: 138 | SEQ ID NO: 3 | SEQ ID NO: 5 |
| ICP4.10 | gL2 | gD2 |
| SEQ ID NO: 139 | SEQ ID NO: 3 | SEQ ID NO: 5 |
| ICP4 | gL2s v.2 | gD2ΔTMR |
| SEQ ID NO: 1 | SEQ ID NO: 136 | SEQ ID NO: 4 |
| ICP4.2 | gL2s v.2 | gD2ΔTMR |
| SEQ ID NO: 2 | SEQ ID NO: 136 | SEQ ID NO: 4 |
| ICP4.5 | gL2s v.2 | gD2ΔTMR |
| SEQ ID NO: 13 | SEQ ID NO: 136 | SEQ ID NO: 4 |
| ICP4.9 | gL2s v.2 | gD2ΔTMR |
| SEQ ID NO: 138 | SEQ ID NO: 136 | SEQ ID NO: 4 |
| ICP4.10 | gL2s v.2 | gD2ΔTMR |
| SEQ ID NO: 139 | SEQ ID NO: 136 | SEQ ID NO: 4 |
| ICP4 | gL2s v.2 | gD2 |
| SEQ ID NO: 1 | SEQ ID NO: 136 | SEQ ID NO: 5 |
| ICP4.2 | gL2s v.2 | gD2 |
| SEQ ID NO: 2 | SEQ ID NO: 136 | SEQ ID NO: 5 |
| ICP4.5 | gL2s v.2 | gD2 |
| SEQ ID NO: 13 | SEQ ID NO: 136 | SEQ ID NO: 5 |
| ICP4.9 | gL2s v.2 | gD2 |
| SEQ ID NO: 138 | SEQ ID NO: 136 | SEQ ID NO: 5 |
| ICP4.10 | gL2s v.2 | gD2 |
| SEQ ID NO: 139 | SEQ ID NO: 136 | SEQ ID NO: 5 |

| Four antigen combinations | | | |
|---|---|---|---|
| ICP4.2 | ICP4.5 | gL2 | gD2ΔTMR |
| SEQ ID NO: 2 | SEQ ID NO: 13 | SEQ ID NO: 3 | SEQ ID NO: 4 |
| ICP4.2 | ICP4.9 | gL2 | gD2ΔTMR |
| SEQ ID NO: 2 | SEQ ID NO: 138 | SEQ ID NO: 3 | SEQ ID NO: 4 |
| ICP4.2 | ICP4.10 | gL2 | gD2ΔTMR |
| SEQ ID NO: 2 | SEQ ID NO: 139 | SEQ ID NO: 3 | SEQ ID NO: 4 |
| ICP4.2 | ICP4.5 | gL2 | gD2 |
| SEQ ID NO: 2 | SEQ ID NO: 13 | SEQ ID NO: 3 | SEQ ID NO: 5 |
| ICP4.2 | ICP4.9 | gL2 | gD2 |
| SEQ ID NO: 2 | SEQ ID NO: 138 | SEQ ID NO: 3 | SEQ ID NO: 5 |
| ICP4.2 | ICP4.10 | gL2 | gD2 |
| SEQ ID NO: 2 | SEQ ID NO: 139 | SEQ ID NO: 3 | SEQ ID NO: 5 |
| ICP4.2 | ICP4.5 | gL2s v.2 | gD2ΔTMR |
| SEQ ID NO: 2 | SEQ ID NO: 13 | SEQ ID NO: 136 | SEQ ID NO: 4 |
| ICP4.2 | ICP4.9 | gL2s v.2 | gD2ΔTMR |
| SEQ ID NO: 2 | SEQ ID NO: 138 | SEQ ID NO: 136 | SEQ ID NO: 4 |

-continued

| Four antigen combinations | | | |
|---|---|---|---|
| ICP4.2<br>SEQ ID NO: 2 | ICP4.10<br>SEQ ID NO: 139 | gL2s v.2<br>SEQ ID NO: 136 | gD2ΔTMR<br>SEQ ID NO: 4 |
| ICP4.2<br>SEQ ID NO: 2 | ICP4.5<br>SEQ ID NO: 13 | gL2s v.2<br>SEQ ID NO: 136 | gD2<br>SEQ ID NO: 5 |
| ICP4.2<br>SEQ ID NO: 2 | ICP4.9<br>SEQ ID NO: 138 | gL2s v.2<br>SEQ ID NO: 136 | gD2<br>SEQ ID NO: 5 |
| ICP4.2<br>SEQ ID NO: 2 | ICP4.10<br>SEQ ID NO: 139 | gL2s v.2<br>SEQ ID NO: 136 | gD2<br>SEQ ID NO: 5 |

The individual antigens and combinations described above can also include additional peptides from or derived from HSV-2, such as polypeptides comprising sequences selected from SEQ ID NOS: 6-12, 14-26, and SEQ ID NO: 135, or immunogenic fragments thereof.

In some embodiments, the individual antigens and combinations described above are provided as isolated nucleic acids. In certain aspects, the nucleic acids have the nucleotide sequence of at least one of SEQ ID NOS: 39-45, 117-129, 137, 140, 141, or an immunogenic fragment thereof. Nucleic acids can be present in compositions of the invention singly or in combinations. Exemplary combinations include nucleic acids encoding for two or more of ICP4 (SEQ ID NO: 1), ICP4.9 (SEQ ID NO: 138), gL2 (SEQ ID NO: 3), gG2 (SEQ ID NO: 38) and gD2 (SEQ ID NO: 5).

ICP4 (SEQ ID NO: 1) Encoded by RS1

RS1 encodes ICP4, a transcriptional transactivator that may interact with and recruit specific components of the general transcription machinery to viral promoters and stabilize their formation for transcription initiation. ICP4 contains distinct domains for transactivation/phosphorylation (approximately spanning amino acid residues 150-200 of SEQ ID NO: 1), DNA binding (approximately spanning residues 380-540 of SEQ ID NO: 1), nuclear localization (approximately spanning residues 630-730 of SEQ ID NO: 1), and late regulatory transactivation (approximately spanning residues 1220-1319 of SEQ ID NO: 1). The DNA and protein sequence of RS1 may be found by searching for RS1 in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In some embodiments, vaccines against HSV-2 include a polypeptide containing at least 20 consecutive amino acid residues selected from residues 383-766 of ICP4 (SEQ ID NO: 1), but no more than 1000 amino acids of ICP4 (SEQ ID NO: 1). The polypeptide may also be a variant of the at least 20 residue fragment.

In certain embodiments, the polypeptide includes no more than 950, 900, 850, 800, 750, 700, 650, 600, 550, 500, 450 or even 400 consecutive amino acids from ICP4. Exemplary polypeptides correspond approximately to amino acids residues of full-length ICP4 as follows: 383-766 (RS1.2); 1-400 (RS1.1); 750-1024 (RS1.3.1); 1008-1319 (RS1.3.2); 750-1319 (RS1.3); 280-785 (RS1.4 comprising the full DNA binding region); 680-1319 (RS1.5 comprising the glycosylase/C-terminal region); 208-1319 (RS1.6 which may also comprise a Met residue at the N-term end); 1-380 plus 545-1319 (RS1.7, in which a region spanning approximately residues 381-544 is deleted, removing the DNA binding regions); 1-785 plus 870-1319 (RS1.8, in which a region spanning approximately residues 786-869 is deleted, removing the nuclear localization domain), or 1-766, 383-1318, 100-750, 400-1300, 250-766, 383-900 of ICP4 (SEQ ID NO: 1) and the like.

ICP4 Internal Fragment ICP4.2 (SEQ ID NO: 2) Encoded by RS1.2

RS1.2 encodes a 3913-84 amino acid fragment of ICP4 denoted ICP4.2. The DNA and protein sequences of RS1.2 may be found by searching for RS1 in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In specific embodiments, vaccines against HSV-2 include a polypeptide containing from 50 to all 391 amino acids residues of ICP4.2 (SEQ ID NO: 2), such as from 100 to 391, 200 to 391 or 250 to 350 residues. In particular embodiments, the polypeptide includes all of ICP4.2 (SEQ ID NO: 2) or is ICP4.2 (SEQ ID NO: 2) itself. These polypeptides may, for example, include the full length or fragments of ICP4.2 (SEQ ID NO: 2) described herein with amino acid residues 1-382 or 767-1318 of ICP4 (SEQ ID NO: 1) or fragments thereof, which, in certain embodiments, are consecutive with the amino acid residues of ICP4.2 being used. Exemplary fragments that combine the residues of SEQ ID NO: 2 with select residues from 1-382 or 767-1318 of SEQ ID NO: 1 are described above.

An immunogenic fragment of ICP4.2 comprises at least one immunogenic portion, as measured experimentally or identified by algorithm. Peptides identified by such methods include the following:

```
                    (SEQ ID NO: 47)
GLAHVAAAV

                    (SEQ ID NO: 48)
FISGSVARA

                    (SEQ ID NO: 49)
QYALITRLL

                    (SEQ ID NO: 50)
RYDRAQKGF

                    (SEQ ID NO: 51)
GYAMAAGRF

                    (SEQ ID NO: 52)
PPHADAPRL

                    (SEQ ID NO: 53)
KPAAAAAPL

                    (SEQ ID NO: 54)
SEAAVAAV

                    (SEQ ID NO: 55)
FGWGLAHV

                    (SEQ ID NO: 56)
YALITRLLY

                    (SEQ ID NO: 57)
ALPRSPRLL

                    (SEQ ID NO: 58)
DLLFQNQSL

                    (SEQ ID NO: 59)
ADLLFQNQS

                    (SEQ ID NO: 60)
ARNSSSFIS
```

-continued (SEQ ID NO: 61)
QACFRISGA (SEQ ID NO: 62)
FVRDALVLM (SEQ ID NO: 63)
FDGDLAAVP (SEQ ID NO: 64)
GLGDSRPGL (SEQ ID NO: 65)
WAPELGDAA (SEQ ID NO: 66)
ECLAACRGI (SEQ ID NO: 67)
RAWLRELRF.

Thus, in some aspects, this application provides an immunogenic fragment of ICP4.2. The fragments, in some instances, are close in size to the full-length polypeptide. For example, they may lack at most one, two, three, four, five, ten, or twenty amino acids from one or both termini. In other embodiments, the fragment is 100-391 amino acids in length, or 150-391, or 200-391, or 250-391 amino acids in length. Other exemplary fragments are amino acid residues 1-350, 1-300, 1-250, 1-200, 1-150, 1-100, 1-50, 50-391, 50-350, 50-300, 50-250, 50-200, 50-150, 50-100, 100-391, 100-350, 100-300, 100-250, 100-200, 100-150, 150-391, 150-350, 150-300, 150-250, 150-200, 200-391, 200-350, 200-300, 200-250, 250-391, 250-350, 250-300, 300-391 and 350-391. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In certain aspects, this application provides immunogenic polypeptides with at least 90%, 95%, 97%, 98%, 99%, or 99.5% identity to ICP4.2 or an immunogenic fragment thereof.

Glycoprotein L-2 (SEQ ID NO: 3 or SEQ ID NO: 136) Encoded by UL1

UL1 encodes Glycoprotein L-2 (gL2), a heterodimer glycoprotein that is required for the fusion of viral and cellular membranes and enables the virus to enter the host cell. The DNA and protein sequence of UL1 may be found by searching in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In some embodiments, the polypeptide may be a cytoplasmic form of UL1 (SEQ ID NO:3). In other embodiments, the polypeptide may be a secreted form of UL1, which lacks one or more amino acids of the signal sequence. An exemplary polypeptide of the secreted form of UL1 is the polypeptide of SEQ ID NO: 136. In certain embodiments, this polypeptide will not form an aggregate after it is substantially purified. In some embodiments, the polypeptide will contain one or more amino acids corresponding to a signal sequence that has been cleaved. The signal sequence may be a mammalian signal sequence or may be a non-mammalian signal sequence, depending on the system from which the polypeptide was purified.

In some embodiments, vaccines against HSV-2 include a polypeptide containing at least 20 consecutive amino acid residues selected from residues 1-224 or 1-200 of gL2 (SEQ ID NO: 3 or SEQ ID NO: 136), but no more than 224 or 200 amino acids of gL2 (SEQ ID NO: 3 or SEQ ID NO: 136). The polypeptide may also be a variant of the at least 20 residue fragment.

In some embodiments, the polypeptide is at least 85% identical to a fragment of 150-200 or 200-250 amino acids of SEQ ID NO: 3 or SEQ ID NO: 136.

In certain embodiments, the polypeptide includes no more than 200 or 100 consecutive amino acids from gL2. Exemplary polypeptides are amino acids residues 1-20, 21-40, 41-60, of 61-80, 81-100, 101-120, 121-140, 141-160, 161-180, 181-200, 201-221 of gL2 (SEQ ID NO: 3 or amino acids residues 1-20, 21-40, 41-60, of 61-80, 81-100, 101-120, 121-140, 141-160, 161-180, or 181-200 SEQ ID NO: 136) and the like.

In other aspects, this application provides an immunogenic fragment of gL2. An immunogenic fragment of gL2 comprises at least one immunogenic portion, as measured experimentally or identified by algorithm. Peptides identified by such methods include the following:

(SEQ ID NO: 100)
AYLVNPFLF (SEQ ID NO: 101)
PFLFAAGFL (SEQ ID NO: 102)
TEYVLRSVI (SEQ ID NO: 103)
GSQATEYVL (SEQ ID NO: 104)
RIDGIFLRY (SEQ ID NO: 105)
FLEDLSHSV (SEQ ID NO: 106)
YVLRSVIAK (SEQ ID NO: 107)
YVLRSVIAK (SEQ ID NO: 108)
AYLVNPFLF (SEQ ID NO: 109)
ETTTRRALY (SEQ ID NO: 110)
RIDGIFLRY (SEQ ID NO: 111)
YLVNPFLFA (SEQ ID NO: 112)
FVCLFGLVV (SEQ ID NO: 113)
LYKEIRDAL (SEQ ID NO: 114)
GLDTFLWDR (SEQ ID NO: 115)
RVSPTRGRR (SEQ ID NO: 115)
YVLRSVIAK

-continued

```
                            (SEQ ID NO: 116)
GLDTFLWDR

                            (SEQ ID NO: 117)
DILRVPCMR

                            (SEQ ID NO: 118)
DRHAQRAYL
```

Glycoprotein D-2 (SEQ ID NO: 5) Encoded by US6 and Internally-Deleted Glycoprotein D-2 (SEQ ID NO: 4) Encoded by US6ΔTMR US6 encodes envelope glycoprotein D-2 (gD2), an envelope glycoprotein that binds to host cell entry receptors and may trigger fusion of the virus with the host membrane. The gD2 protein has several distinct domains, including a signal domain (amino acid residues 1-25) which is cleaved from the mature protein, and a transmembrane domain (spanning approximately amino acids residues 340-363). The DNA and protein sequence of US6 may be found by searching in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In some embodiments, vaccines against HSV-2 include a polypeptide comprising gD2 that is missing all or part of the transmembrane domain (which spans approximately amino acids residues 340-363 inclusive) as well as the signal sequence. In other embodiments, the deleted region may additionally include 5-10 amino acids of the sequence flanking the transmembrane domain. The deleted region may also comprise a portion of the transmembrane domain, for example at least 3 amino acids between residues 340-363. In some embodiments, at least one residue in the transmembrane domain has been modified, deleted or substituted, such that the transmembrane domain is no longer functional. For example, a variant may have its internal deletion begin at amino acid residue 336, 337, 338, 339, 340, 341, 342, 343, 344, 345 or 346 and end at amino acid residue 358, 359, 360, 361, 362, 363, 364, 365, 366, 367 or 368.

A construct encoding gD2 which is missing amino acid residues 340-363 (the transmembrane domain) is called US6ΔTMR (SEQ ID NO: 40). The corresponding protein is denoted gD2ΔTMR (SEQ ID NO: 4). In other embodiments, an immunogenic fragment of gD2 or gD2ΔTMR may comprise a deletion in a portion of the transmembrane domain, and/or may comprise a deletion in the flanking sequence outside of the transmembrane domain.

In other aspects, this application provides an immunogenic fragment of gD2 or gD2ΔTMR. An immunogenic fragment of gD2 or gD2ΔTMR comprises at least one immunogenic portion, as measured experimentally or identified by algorithm. Peptides identified by such methods include the following:

```
                           (SEQ ID NO: 68)
ALAGSTLAV

                           (SEQ ID NO: 69)
LLEDPAGTV

                           (SEQ ID NO: 70)
VIGGIAFWV

                           (SEQ ID NO: 71)
TVYYAVLER
```

-continued

```
                           (SEQ ID NO: 72)
KYALADPSL

                           (SEQ ID NO: 73)
AFETAGTYL

                           (SEQ ID NO: 74)
APSNPGLII

                           (SEQ ID NO: 75)
IPITVYYAV

                           (SEQ ID NO: 76)
APPSHQPLF

                           (SEQ ID NO: 77)
FLMHAPAFE

                           (SEQ ID NO: 78)
FSAVSEDNL

                           (SEQ ID NO: 79)
VYYAVLER

                           (SEQ ID NO: 80)
IGMLPRFI

                           (SEQ ID NO: 81)
YTECPYNKS

                           (SEQ ID NO: 82)
FLMHAPAFE

                           (SEQ ID NO: 83)
NLGFLMHAP

                           (SEQ ID NO: 84)
VIGGIAFWV

                           (SEQ ID NO: 85)
GIAFWVRRR

                           (SEQ ID NO: 86)
SEDNLGFLM

                           (SEQ ID NO: 87)
RTQPRWSYY

                           (SEQ ID NO: 88)
IAFWVRRRA

                           (SEQ ID NO: 89)
LVIGGIAFW

                           (SEQ ID NO: 90)
FWVRRRAQM

                           (SEQ ID NO: 91)
PYTSTLLPP

                           (SEQ ID NO: 92)
VGTAALLVV

                           (SEQ ID NO: 93)
TAALLVVAV

                           (SEQ ID NO: 94)
TSTLLPPEL

                           (SEQ ID NO: 95)
GTVSSQIPP

                           (SEQ ID NO: 96)
TAGTYLRLV

                           (SEQ ID NO: 97)
GVTVDSIGM

                           (SEQ ID NO: 98)
AFWVRRRAQ
```

-continued (SEQ ID NO: 99)

RVYHIQPSL

Thus, in some aspects, this application provides an immunogenic fragment of gD2 (SEQ ID NO: 5) or gD2ΔTMR (SEQ ID NO: 4). The fragments, in some instances, are close in size to the full-length polypeptide. For example, they may lack at most one, two, three, four, five, ten, or twenty amino acids from one or both termini. In other embodiments, the fragment is 100-393 amino acids in length, or 150-393, or 200-393, or 250-393 amino acids in length. Other exemplary fragments are amino acid residues 1-350, 1-300, 1-250, 1-200, 1-150, 1-100, 1-50, 50-393, 50-350, 50-300, 50-250, 50-200, 50-150, 50-100, 100-393, 100-350, 100-300, 100-250, 100-200, 100-150, 150-393, 150-350, 150-300, 150-250, 150-200, 200-393, 200-350, 200-300, 200-250, 250-393, 250-350, 250-300, 300-393 and 350-393. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In other embodiments, the polypeptide comprises the entire sequence of SEQ ID NO: 4 or SEQ ID NO: 5, or consists of the entire sequence of SEQ ID NO: 4 or SEQ ID NO: 5. In certain embodiments, an immunogenic fragment of gD2 retains all or part of the signal domain (amino acid residues 1-25) and/or the transmembrane domain (amino acids residues 340-363).

In certain embodiments, polypeptides have less than 20%, 30%, 40%, 50%, 60% or 70% homology with human autoantigens. Examples of such autoantigens include UL6 from HSV-1 and gK or UL53 from HSV-2.

In certain aspects, this application provides immunogenic polypeptides with at least 90%, 95%, 97%, 98%, 99%, or 99.5% identity to gD2ΔTMR, or an immunogenic fragment thereof.

ICP4 Internal Fragment ICP4.5 (SEQ ID NO: 13) Encoded by RS1.5

RS1.5 encodes a 544 amino acid fragment corresponding to residues 775-1318 of ICP4, denoted ICP4.5. The DNA and protein sequences of RS1.5 may be found by searching for RS1 in the publicly available database, Entrez Gene (on the NCBI NIH web site on the World Wide Web, at the hypertext protocol transfer address of "ncbi.nlm.nih.gov/sites/entrez?db=gene"), in the Human herpes virus 2 complete genome.

In specific embodiments, vaccines against HSV-2 include a polypeptide containing from 50 to all 544 amino acids residues of ICP4.5 (SEQ ID NO: 13), such as 50, 100, 150, 200, 250, 300, 350, 400, 450, 500, or 544 residues. In particular embodiments, the polypeptide includes all of ICP4.5 (SEQ ID NO: 13) or is ICP4.5 (SEQ ID NO: 13) itself. These polypeptides may, for example, include the full length or fragments of ICP4.5 (SEQ ID NO: 13) described herein with amino acid residues 1-774 of ICP4 (SEQ ID NO: 1) or fragments thereof, which, in certain embodiments, are consecutive with the amino acid residues of ICP4.5 being used. Exemplary fragments that combine the residues of SEQ ID NO: 13 with select residues from 1-774 of SEQ ID NO: 1 are described above.

An immunogenic fragment of ICP4.5 comprises at least one immunogenic portion, as measured experimentally or identified by algorithm. Thus, in some aspects, this application provides an immunogenic fragment of ICP4.5. The fragments, in some instances, are close in size to the full-length polypeptide. For example, they may lack at most one, two, three, four, five, ten, or twenty amino acids from one or both termini. In other embodiments, the fragment is 50-544 amino acids in length, or 100-544, or 150-544, or 200-544, or 250-544, or 300-544, or 350-544, or 400-544, or 450-544, or 500-544 amino acids in length. Other exemplary fragments are amino acid residues 1-500, 1-450, 1-400, 1-350, 1-300, 1-250, 1-200, 1-150, 1-100, 1-50, 50-544, 50-500, 50-450, 50-400, 50-350, 50-300, 50-250, 50-200, 50-150, 50-100, 100-544, 100-500, 100-450, 100-400, 100-350, 100-300, 100-250, 100-200, 100-150, 150-544, 150-500, 150-450, 150-400, 150-350, 150-300, 150-250, 150-200, 200-544, 200-500, 200-450, 200-400, 200-350, 200-300, 200-250, and so forth. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In certain aspects, this application provides immunogenic polypeptides with at least 90%, 95%, 97%, 98%, 99%, or 99.5% identity to ICP4.5 or an immunogenic fragment thereof.

ICP4 Fragment ICP4.9 (SEQ ID NO: 138) Encoded by RS1.9, and ICP4 Fragment ICP4.10 (SEQ ID NO: 139) Encoded by RS1.10

RS1.9 encodes a 1130 amino acid fragment of ICP4, carrying a double internal deletion of residues 391-544 and residues 786-821 of ICP4, denoted ICP4.9. RS1.10 encodes a 1166 amino acid fragment of ICP4, carrying a double internal deletion of residues 391-508 and residues 786-821 of ICP4, denoted ICP4.10. The DNA and protein sequences of RS1.9 and RS1.10 may be found by searching for RS1 in the publicly available database, Entrez Gene (on the NCBI NIH web site on the World Wide Web, at the hypertext protocol transfer address of "ncbi.nlm.nih.gov/sites/entrez?db=gene"), in the Human herpesvirus 2 complete genome.

In specific embodiments, vaccines against HSV-2 include a polypeptide containing from 50 to all 1130 or 1166 amino acids residues of ICP4.9 (SEQ ID NO: 138) or ICP4.10 (SEQ ID NO: 139), such as 50, 100, 150, 200, 250, 300, 350, 400, 450, 500, 550, 600, 650, 700, 750, 800, 850, 900, 950, 1000, 1050, 1100, 1130 or 1166 residues. In particular embodiments, the polypeptide includes all of ICP4.9 (SEQ ID NO: 138) or ICP4.10 (SEQ ID NO: 139), or is ICP4.9 (SEQ ID NO: 138) or ICP4.10 (SEQ ID NO: 139) itself. These polypeptides may, for example, include the full length or fragments of ICP4.9 (SEQ ID NO: 138) or ICP4.10 (SEQ ID NO: 139) described herein.

An immunogenic fragment of ICP4.9 or ICP4.10 comprises at least one immunogenic portion, as measured experimentally or identified by algorithm. Thus, in some aspects, this application provides an immunogenic fragment of ICP4.9 or ICP4.10. The fragments, in some instances, are close in size to the full-length polypeptide. For example, they may lack at most one, two, three, four, five, ten, or twenty amino acids from one or both termini. In other embodiments, the fragment is 50-1130 amino acids in length, or 100-1130, 150-1130, or 200-1130, or 250-1130, or 300-1130, or 400-1130, or 500-1130, or 600-1130, or 700-1130, or 800-1130, or 900-1130, or 1000-1130 amino acids in length. Other exemplary fragments are amino acid residues 1-1130, 1-1000, 1-900, 1-800, 1-700, 1-600, 1-500, 1-400, 1-300, 1-200, 1-150, 1-100, 1-50, 50-1130, 50-1000, 50-900, 50-800, 50-700, 50-600, 50-500, 50-400, 50-300, 50-250, 50-200, 50-150, 50-100, 100-1130, 100-1000, 100-900, 100-800, 100-700, 100-600, 100-500, 100-400, 100-300, 100-250, 100-200, 100-150, and so forth. The fragments described above or sub-fragments thereof (e.g., fragments of 8-50, 8-30, or 8-20 amino acid residues) preferably have one of the biological activities described below, such as increasing the T cell response by at least 1.5 fold or 2 fold. A fragment may be used as the polypeptide in the vaccines described herein or may be fused to another protein, protein fragment or a polypeptide.

In certain embodiments, an analog of ICP4.9 is based on SEQ ID NO: 1, where at least 50, 75, 100, 125, 130, 140, 145 or 150 residues from residues 391-544 are deleted. Separately or in combination, at least 20, 25, or 30 residues from residues 786-821 are deleted.

In certain embodiments, an analog of ICP4.10 is based on SEQ ID NO: 1, where at least 25, 50, 75, 90, 95, 100, 105, 110 or 115 residues from residues 391-508 are deleted. Separately or in combination, at least 25, 50, 60, 65, 70 or 75 residues from residues 786-821 are deleted.

In certain aspects, this application provides immunogenic polypeptides with at least 90%, 95%, 97%, 98%, 99%, or 99.5% identity to ICP4.9 or ICP4.10, or an immunogenic fragment or analog thereof.

Additional Features of HSV-2 Polypeptides

Typically, the polypeptides present in the vaccine formulations or pharmaceutical compositions described herein are immunogenic, either alone or as a variant, which includes polypeptides fused to another polypeptide or mixed with or complexed to an adjuvant. Variants also include sequences with less than 100% sequence identity, as described herein. In addition, one may use fragments, precursors and analogs that have an appropriate immunogenicity.

These polypeptides may be immunogenic in mammals, for example, mice, guinea pigs, or humans. An immunogenic polypeptide is typically one capable of raising a significant immune response in an assay or in a subject. Alternatively, an immunogenic polypeptide may (i) induce production of antibodies, e.g., neutralizing antibodies, that bind to the polypeptide (ii) induce $T_H1$ immunity, (iii) activate the $CD8^+$ T cell response, for example by increasing the number of $CD8^+$ T cells, increasing localization of $CD8^+$ T cells to the site of infection or reinfection, (iv) induce $T_H17$ immunity, and/or (v) activate innate immunity. In some embodiments, an immunogenic polypeptide causes the production of a detectable amount of antibody specific to that antigen.

In certain embodiments, polypeptides have less than 20%, 30%, 40%, 50%, 60% or 70% homology with human autoantigens.

A polypeptide may comprise one or more immunogenic portions and one or more non-immunogenic portions. The immunogenic portions may be identified by various methods, including protein microarrays, ELISPOT/ELISA techniques, and/or specific assays on different deletion mutants (e.g., fragments) of the polypeptide in question. Immunogenic portions may also be identified by computer algorithms. Some such algorithms, like EpiMatrix (produced by EpiVax), use a computational matrix approach. Other computational tools for identifying antigenic epitopes include PEPVAC (Promiscuous EPitope-based VACcine, hosted by Dana Farber Cancer Institute on the world wide web at the hypertext protocol transfer address of "immunax.dfci.harvard.edu/PEPVAC"), MHCPred (which uses a partial least squares approach and is hosted by The Jenner Institute on the world wide web at the hypertext protocol transfer address of "jenner.ac.uk/MHCPred"), and Syfpeithi, hosted on the world wide web at the hypertext protocol transfer address of "syfpeithi.de/".

In some embodiments, the vaccine or pharmaceutical composition may comprise fusion proteins and/or fusion DNA constructs. The underlying DNA sequences above may be modified in ways that do not affect the sequence of the protein product. For instance, the DNA sequence may be codon-optimized to improve expression in a host such as *E. coli* or an insect cell line (e.g., using the baculovirus expression system) or mammalian (e.g., Chinese Hamster Ovary) cell line. In certain embodiments, the DNA sequence may comprise an exogenous sequence, such as an exogenous signal sequence, for expression in non-mammalian cells. In particular embodiments, such as when smaller related polypeptides, including those having a molecular weight less than about 5000 daltons, e.g., 1500 to 5000 daltons, are used, modification may be useful in eliciting the desired immune response. For example, the smaller polypeptides can be conjugated to an appropriate immunogenic carrier such as proteins from other pathogenic organisms or viruses (e.g., tetanus toxoid), large proteins (e.g., keyhole limpet hemocyanin) or the like. Conjugation may be direct or indirect (e.g., via a linker). In other particular embodiments, a fusion protein may comprise a polypeptide disclosed above or an immunogenic fragment or variant thereof and a tag. A tag may be N-terminal or C-terminal. For instance, tags may be added to the nucleic acid or polypeptide to facilitate purification, detection, solubility, or confer other desirable characteristics on the protein or nucleic acid. For instance, a purification tag may be a peptide, oligopeptide, or polypeptide that may be used in affinity purification. Examples include H is, GST, TAP, FLAG, myc, HA, MBP, VSV-G, thioredoxin, V5, avidin, streptavidin, BCCP, Calmodulin, Nus, S tags, lipoprotein D, and 13 galactosidase. In some embodiments, the fused portion is short. Thus, in some instances, the fusion protein comprises no more than 1, 2, 3, 4, 5, 10, 20, or 50 additional amino acids on one or both termini of a polypeptide described above, such as consecutive amino acids from any of the polypeptides in Table 1.

In some embodiments, tags, secretion signals, or other signal sequences may be added to the C-terminal end and/or to the N-terminal end of the polypeptide. Tags may be used to aid in purification of expressed polypeptides. Exemplary tags include HHHHHH (SEQ ID NO: 130) and MSYYHHHHHH (SEQ ID NO: 131). Secretion signals may be optimized for use with non-mammalian cells, such as insect cells. An exemplary secretion signal is MKFLVNVALVFMVVYISYIYA (SEQ ID NO: 132).

A detection tag may be used to detect the tag and, consequently, any amino acid sequence fused to it. Detection tags include fluorescent proteins, proteins that bind a fluorescent label, and proteins that bind an electron-dense moeity. Examples of fluorescent proteins include dsRed, mRFP, YFP, GFP, CFP, BFP, and Venus. An example of a protein that binds a fluorescent or electron-dense label is FlAsH.

Another aspect disclosed herein is an antibody preparation generated against a composition of the invention (e.g., a composition comprising one or more, or two or more of the polypeptides listed in Table 1). Any of a variety of antibodies are included. Such antibodies include, e.g., polyclonal, monoclonal, recombinant, humanized or partially humanized, single chain, Fab, and fragments thereof, etc. The antibodies can be of any isotype, e.g., IgA, IgG, various IgG isotypes such as $IgG_1$, $IgG_2$, $IgG_{2a}$, $IgG_{2b}$, $IgG_3$, $IgG_4$, etc.; and they can be from any animal species that produces antibodies, including goat, rabbit, mouse, chicken or the like. In some embodiments, Fab molecules are expressed and assembled in a genetically transformed host like *E. coli*. A lambda vector system is available thus to express a population of Fab's with a potential diversity equal to or exceeding that of the subject generating the predecessor antibody. See Huse et al. (1989), Science 246, 1275-81.

Components of Vaccines and Pharmaceutical Compositions

In certain embodiments, the vaccines and pharmaceutical compositions comprise one or more of the polypeptides and nucleic acids described above and one or more of the following: an adjuvant, stabilizer, buffer, surfactant, controlled-release component, salt, preservative, and an antibody specific to said antigen.

Adjuvants

The vaccine formulations and pharmaceutical compositions described herein may each include an adjuvant. Adjuvants can be broadly separated into two classes, based on their principal mechanisms of action: vaccine delivery systems and immunostimulatory adjuvants (see, e.g., Singh et al., *Curr. HIV Res.* 1:309-20, 2003). Vaccine delivery systems are often particulate formulations, e.g., emulsions, microparticles, immune-stimulating complexes (ISCOMs), which may be, for example, particles and/or matrices, and liposomes. In contrast, immunostimulatory adjuvants are sometimes derived from pathogens and can represent pathogen associated molecular patterns (PAMP), e.g., lipopolysaccharides (LPS), monophosphoryl lipid (MPL), or CpG-containing DNA, which activate cells of the innate immune system.

Alternatively, adjuvants may be classified as organic and inorganic. Inorganic adjuvants include aluminum salts such as aluminum phosphate, amorphous aluminum hydroxyphosphate sulfate, and aluminum hydroxide, which are commonly used in human vaccines. Organic adjuvants comprise organic molecules including macromolecules. An example of an organic adjuvant is cholera toxin.

Adjuvants may also be classified by the response they induce, and adjuvants can activate more than one type of response. In some embodiments, the adjuvant induces the activation of $CD4^+$ T cells. The adjuvant may induce activation of $T_H1$ cells and/or activation of $T_H17$ cells and/or activation of $T_H2$ cells. Alternately, the adjuvant may induce activation of $T_H1$ cells and/or $T_H17$ cells but not activation of $T_H2$ cells, or vice versa. In some embodiments, the adjuvant induces activation of $CD8^+$ T cells. In further embodiments, the adjuvant may induce activation of Natural Killer T (NKT) cells. In some embodiments, the adjuvant induces the activation of $T_H1$ cells or $T_H17$ cells or $T_H2$ cells. In other embodiments, the adjuvant induces the activation of B cells. In yet other embodiments, the adjuvant induces the activation of APCs. These categories are not mutually exclusive; in some cases, an adjuvant activates more than one type of cell.

In certain embodiments, an adjuvant is a substance that increases the numbers or activity of APCs such as dendritic cells. In certain embodiments, an adjuvant promotes the maturation of APCs such as dendritic cells. In some embodiments, the adjuvant is or comprises a saponin. Typically, the saponin is a triterpene glycoside, such as those isolated from the bark of the *Quillaja saponaria* tree. A saponin extract from a biological source can be further fractionated (e.g., by chromatography) to isolate the portions of the extract with the best adjuvant activity and with acceptable toxicity. Typical fractions of extract from *Quillaja saponaria* tree used as adjuvants are known as fractions A and C. An exemplary saponin adjuvant is QS-21 (fraction C), which is available from Antigenics. QS-21 is an oligosaccharide-conjugated small molecule. Optionally, QS-21 may be admixed with a lipid such as 3D-MPL or cholesterol.

A particular form of saponins that may be used in vaccine formulations described herein is immunostimulating complexes (ISCOMs). ISCOMs are an art-recognized class of adjuvants, that generally comprise *Quillaja saponin* fractions and lipids (e.g., cholesterol and phospholipids such as phosphatidyl choline). In certain embodiments, an ISCOM is assembled together with a polypeptide or nucleic acid of interest. However, different saponin fractions may be used in different ratios. In addition, the different saponin fractions may either exist together in the same particles or have substantially only one fraction per particle (such that the indicated ratio of fractions A and C are generated by mixing together particles with the different fractions). In this context, "substantially" refers to less than 20%, 15%, 10%, 5%, 4%, 3%, 2% or even 1%. Such adjuvants may comprise fraction A and fraction C mixed into a ratio of 70-95 A:30-5 C, such as 70 A:30 C to 75 A:25 C; 75 A:25 C to 80 A:20 C; 80 A:20 C to 85 A:15 C; 85 A:15 C to 90 A:10 C; 90 A:10 C to 95 A:5 C; or 95 A:5 C to 99 A:1 C. ISCOMatrix, produced by CSL, and AbISCO 100 and 300, produced by Isconova, are ISCOM matrices comprising saponin, cholesterol and phospholipid (lipids from cell membranes), which form cage-like structures typically 40-50 nm in diameter. Posintro, produced by Nordic Vaccines, is an ISCOM matrix where the immunogen is bound to the particle by a multitude of different mechanisms, e.g., electrostatic interaction by charge modification, incorporation of chelating groups, or direct binding.

In some embodiments, the adjuvant is a TLR ligand. TLRs are proteins that may be found on leukocyte membranes, and recognize foreign antigens (including microbial antigens). An exemplary TLR ligand is IC-31, which is available from Intercell. IC-31 comprises an anti-microbial peptide, KLK, and an immunostimulatory oligodeoxynucleotide, ODN1a. IC-31 has TLR9 agonist activity. Another example is CpG-containing DNA. Different varieties of CpG-containing DNA are available from Prizer (Coley): Vaxlmmune is CpG 7909 (a (CpG)-containing oligodeoxynucleotide), and Actilon is CpG 10101 (a (CpG)-containing oligodeoxy-nucleotide).

In some embodiments, the adjuvant is a nanoemulsion. One exemplary nanoemulsion adjuvant is Nanostat Vaccine, produced by Nanobio. This nanoemulsion is a high-energy, oil-in-water emulsion. This nanoemulsion typically has a size of 150-400 nanometers, and includes surfactants to provide stability. More information about Nanostat can be found in U.S. Pat. Nos. 6,015,832, 6,506,803, 6,559,189, 6,635,676, and 7,314,624.

In some embodiments, an adjuvant includes a cytokine. In some embodiments, the cytokine is an interleukin such as IL-1, IL-6, IL-12, IL-17 and IL-23. In some embodiments, the cytokine is granulocyte-macrophage colony-stimulating factor (GM-CSF). The adjuvant may include cytokine as a purified polypeptide. Alternatively, the adjuvant may include nucleic acids encoding the cytokine.

Adjuvants may be covalently bound to antigens (e.g., the polypeptides described above). In some embodiments, the adjuvant may be a protein which induces inflammatory responses through activation of APCs. In some embodiments, one or more of these proteins can be recombinantly fused with an antigen of choice, such that the resultant fusion molecule promotes dendritic cell maturation, activates dendritic cells to produce cytokines and chemokines, and ultimately, enhances presentation of the antigen to T cells and initiation of T cell responses (see Wu et al., Cancer Res 2005; 65(11), pp 4947-4954). Other exemplary adjuvants that may be covalently bound to antigens comprise polysaccharides, synthetic peptides, lipopeptides, and nucleic acids.

The adjuvant can be used alone or in combination of two or more kinds Adjuvants may be directly conjugated to antigens. Adjuvants may also be combined to increase the magnitude of the immune response to the antigen. Typically, the same adjuvant or mixture of adjuvants is present in each dose of a vaccine. Optionally, however, an adjuvant may be administered with the first dose of vaccine and not with subsequent doses (i.e. booster shots). Alternatively, a strong adjuvant may be administered with the first dose of vaccine and a weaker adjuvant or lower dose of the strong adjuvant may be administered with subsequent doses. The adjuvant can be administered before the administration of the antigen, concurrent with the administration of the antigen or after the administration of the antigen to a subject (sometimes within 1, 2, 6, or 12 hours, and sometimes within 1, 2, or 5 days). Certain adjuvants are appropriate for human patients, non-human animals, or both.

Additional Components of Vaccines and Pharmaceutical Compositions

In addition to the antigens and the adjuvants described above, a vaccine formulation or pharmaceutical composition may include one or more additional components.

In certain embodiments, the vaccine formulation or pharmaceutical composition may include one or more stabilizers such as sugars (such as sucrose, glucose, or fructose), phosphate (such as sodium phosphate dibasic, potassium phosphate monobasic, dibasic potassium phosphate, or monosodium phosphate), glutamate (such as monosodium L-glutamate), gelatin (such as processed gelatin, hydrolyzed gelatin, or porcine gelatin), amino acids (such as arginine, asparagine, histidine, L-histidine, alanine, valine, leucine, isoleucine, serine, threonine, lysine, phenylalanine, tyrosine, and the alkyl esters thereof), inosine, or sodium borate.

In certain embodiments, the vaccine formulation or pharmaceutical composition includes one or more buffers such as a mixture of sodium bicarbonate and ascorbic acid. In some embodiments, the vaccine formulation may be administered in saline, such as phosphate buffered saline (PBS), or distilled water.

In certain embodiments, the vaccine formulation or pharmaceutical composition includes one or more surfactants such as polysorbate 80 (Tween 80), Polyethylene glycol tert-octylphenyl ether t-Octylphenoxypolyethoxyethanol 4-(1,1,3,3-Tetramethylbutyl)phenyl-polyethylene glycol (TRITON X-100); Polyoxyethylenesorbitan monolaurate Polyethylene glycol sorbitan monolaurate (TWEEN 20); and 4-(1,1,3,3-Tetramethylbutyl)phenol polymer with formaldehyde and oxirane (TYLOXAPOL). A surfactant can be ionic or nonionic.

In certain embodiments, the vaccine formulation or pharmaceutical composition includes one or more salts such as sodium chloride, ammonium chloride, calcium chloride, or potassium chloride.

In certain embodiments, a preservative is included in the vaccine. In other embodiments, no preservative is used. A preservative is most often used in multi-dose vaccine vials, and is less often needed in single-dose vaccine vials. In certain embodiments, the preservative is 2-phenoxyethanol, methyl and propyl parabens, benzyl alcohol, and/or sorbic acid.

In certain embodiments, the vaccine formulation or pharmaceutical composition is a controlled-release formulation.

DNA Vaccines

In certain aspects, the vaccine comprises one or more of the nucleic acids disclosed herein. When a nucleic acid vaccine is administered to a patient, the corresponding gene product (such as a desired antigen) is produced in the patient's body. In some embodiments, nucleic acid vaccine vectors that include optimized recombinant polynucleotides can be delivered to a mammal (including humans) to induce a therapeutic or prophylactic immune response. The nucleic acid may be, for example, DNA, RNA, or a synthetic nucleic acid. The nucleic acid may be single stranded or double-stranded.

Nucleic acid vaccine vectors (e.g., adenoviruses, liposomes, papillomaviruses, retroviruses, etc.) can be administered directly to the mammal for transduction of cells in vivo. The nucleic acid vaccines can be formulated as pharmaceutical compositions for administration in any suitable manner, including parenteral administration. Plasmid vectors are typically more efficient for gene transfer to muscle tissue. The potential to deliver DNA vectors to mucosal surfaces by oral administration has also been reported (PLGA encapsulated Rotavirus and Hepatitis B) and DNA plasmids have been utilized for direct introduction of genes into other tissues. DNA vaccines have been introduced into animals primarily by intramuscular injection, by gene gun delivery, or by electroporation. After being introduced, the plasmids are generally maintained episomally without replication. Expression of the encoded proteins has been shown to persist for extended time periods, providing stimulation of B and T cells.

In determining the effective amount of the vector to be administered in the treatment or prophylaxis of an infection or other condition, the physician evaluates vector toxicities, progression of the disease, and the production of anti-vector antibodies, if any. Often, the dose equivalent of a naked nucleic acid from a vector is from about 1 μg to 1 mg for a typical 70 kilogram patient, and doses of vectors used to deliver the nucleic acid are calculated to yield an equivalent amount of therapeutic nucleic acid. Administration can be accomplished via single or divided doses. The toxicity and therapeutic efficacy of the nucleic acid vaccine vectors can be determined using standard pharmaceutical procedures in cell cultures or experimental animals.

A nucleic acid vaccine can contain DNA, RNA, a modified nucleic acid, or a combination thereof. In some embodiments, the vaccine comprises one or more cloning or expression vectors; for instance, the vaccine may comprise a plurality of expression vectors each capable of autonomous expression of a nucleotide coding region in a mammalian cell to produce at least one immunogenic polypeptide. An expression vector often includes a eukaryotic promoter sequence, such as the nucleotide sequence of a strong eukaryotic promoter, operably linked to one or more coding regions. The compositions and methods herein may involve the use of any particular eukaryotic promoter, and a wide variety are known, such as a CMV or RSV promoter. The promoter can be, but need not be, heterologous with respect to the host cell. The promoter used may be a constitutive promoter.

A vector useful in the present compositions and methods can be circular or linear, single-stranded or double stranded and can be a plasmid, cosmid, or episome. In a suitable embodiment, each nucleotide coding region is on a separate vector; however, it is to be understood that one or more coding regions can be present on a single vector, and these coding regions can be under the control of a single or multiple promoters.

Numerous plasmids may be used for the production of nucleic acid vaccines. Suitable embodiments of the nucleic acid vaccine employ constructs using the plasmids VR1012 (Vical Inc., San Diego Calif.), pCMVI.UBF3/2 (S. Johnston, University of Texas) or pcDNA3.1 (InVitrogen Corporation, Carlsbad, Calif.) as the vector. In addition, the vector construct can contain immunostimulatory sequences (ISS), such as unmethylated dCpG motifs, that stimulate the animal's immune system. The nucleic acid vaccine can also encode a fusion product containing the immunogenic polypeptide. Plasmid DNA can also be delivered using attenuated bacteria as delivery system, a method that is suitable for DNA vaccines that are administered orally. Bacteria are transformed with an independently replicating plasmid, which becomes released into the host cell cytoplasm following the death of the attenuated bacterium in the host cell.

DNA vaccines, including the DNA encoding the desired antigen, can be introduced into a host cell in any suitable form including, the fragment alone, a linearized plasmid, a circular plasmid, a plasmid capable of replication, an episome, RNA, etc. Preferably, the gene is contained in a plasmid. In certain embodiments, the plasmid is an expression vector. Individual expression vectors capable of expressing the genetic material can be produced using standard recombinant techniques. See e.g., Maniatis et al., 1985 Molecular Cloning: A Laboratory Manual or DNA Cloning, Vol. I and II (D. N. Glover, ed., 1985) for general cloning methods.

Routes of administration include, but are not limited to, intramuscular, intranasal, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Typical routes of administration include intramuscular, intraperitoneal, intradermal and subcutaneous injection. Genetic constructs may be administered by means including, but not limited to, traditional syringes, needleless injection devices, "microprojectile bombardment gene guns", or other physical methods such as electroporation ("EP"), "hydrodynamic method", or ultrasound. DNA vaccines can be delivered by any method that can be used to deliver DNA as long as the DNA is expressed and the desired antigen is made in the cell.

In some embodiments, a DNA vaccine is delivered via known transfection reagents such as cationic liposomes, fluorocarbon emulsion, cochleate, tubules, gold particles, biodegradable microspheres, or cationic polymers. Cochleate delivery vehicles are stable phospholipid calcium precipitants consisting of phosphatidyl serine, cholesterol, and calcium; this nontoxic and noninflammatory transfection reagent can be present in a digestive system. Biodegradable microspheres comprise polymers such as poly(lactide-co-glycolide), a polyester that can be used in producing microcapsules of DNA for transfection. Lipid-based microtubes often consist of a lipid of spirally wound two layers packed with their edges joined to each other. When a tubule is used, the nucleic acid can be arranged in the central hollow part thereof for delivery and controlled release into the body of an animal.

In some embodiments, DNA vaccine is delivered to mucosal surfaces via microspheres. Bioadhesive microspheres can be prepared using different techniques and can be tailored to adhere to any mucosal tissue including those found in eye, nasal cavity, urinary tract, colon and gastrointestinal tract, offering the possibilities of localized as well as systemic controlled release of vaccines. Application of bioadhesive microspheres to specific mucosal tissues can also be used for localized vaccine action. In some embodiments, an alternative approach for mucosal vaccine delivery is the direct administration to mucosal surfaces of a plasmid DNA expression vector which encodes the gene for a specific protein antigen.

The DNA plasmid vaccines according to the present invention are formulated according to the mode of administration to be used. In some embodiments where DNA plasmid vaccines are injectable compositions, they are sterile, and/or pyrogen free and/or particulate free. In some embodiments, an isotonic formulation is preferably used. Generally, additives for isotonicity can include sodium chloride, dextrose, mannitol, sorbitol and lactose. In some embodiments, isotonic solutions such as phosphate buffered saline are preferred. In some embodiments, stabilizers include gelatin and albumin. In some embodiments, a vasoconstriction agent is added to the formulation. In some embodiments, a stabilizing agent that allows the formulation to be stable at room or ambient temperature for extended periods of time, such as LGS or other polycations or polyanions is added to the formulation.

In some embodiments, the DNA vaccine may further comprises a pharmacologically acceptable carrier or diluent. Suitable carriers for the vaccine are well known to those skilled in the art and include but are not limited to proteins, sugars, etc. Such carriers may be aqueous or non-aqueous solutions, suspensions, and emulsions. Examples of non-aqueous carriers are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's or fixed oils. Intravenous vehicles include fluid and nutrient replenishers, electrolyte replenishers such as those based on Ringer's dextrose, and the like. Preservatives and antimicrobials include antioxidants, chelating agents, inert gases and the like. Preferred preservatives include formalin, thimerosal, neomycin, polymyxin B and amphotericin B.

An alternative approach to delivering the nucleic acid to an animal involves the use of a viral or bacterial vector. Examples of suitable viral vectors include adenovirus, polio virus, pox viruses such as alphaviruses, vaccinia, canary pox, and fowl pox, herpes viruses, including catfish herpes virus, adenovirus-associated vector, and retroviruses. Virus-like vectors include virosomes and virus-like particles. Exemplary bacterial vectors include attenuated forms of *Salmonella, Shigella, Edwardsiella ictaluri, Yersinia ruckerii*, and *Listeria monocytogenes*. In some embodiments, the nucleic acid is a vector, such as a plasmid, that is capable of autologous expression of the nucleotide sequence encoding the immunogenic polypeptide.

Use of Vaccines

The vaccines described herein may be used for prophylactic and/or therapeutic treatment of herpes, including HSV-1 and particularly HSV-2. The subject receiving the vaccination may be a male or a female, and may be a child or adult. In some embodiments, the subject being treated is a human. In other embodiments, the subject is a non-human animal.

Prophylactic Use

In prophylactic embodiments, the HSV-2 vaccine is administered to a subject to induce an immune response that can help protect against the establishment of HSV-2.

In some embodiments, the vaccine compositions of the invention confer protective immunity, allowing a vaccinated individual to exhibit delayed onset of symptoms or reduced severity of symptoms (e.g., reduced number of lesions at the onset of infection), as the result of his/her exposure to the vaccine (e.g., a memory response). In certain embodiments, the reduction in severity of symptoms is at least 25%, 40%, 50%, 60%, 70%, 80% or even 90%. Some vaccinated individuals may display no symptoms upon contact with, HSV-2, or even no infection by HSV-2. Protective immunity is typically achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Humoral immunity is typically the result of IgG antibodies and IgM antibodies in serum. For example, the IgG titer can be raised by 1.5-fold, 2-fold, 3-fold, 4-fold, 5-fold, 10-fold, 20-fold, 50-fold, or even 100-fold or more following administration of a vaccine formulation described herein. Cellular immunity can be achieved through cytotoxic T lymphocytes or through delayed-type hypersensitivity that involves macrophages and T lymphocytes, as well as other mechanisms involving T cells without a requirement for antibodies. In particular, cellular immunity may be mediated by $T_H1$ cells or $T_H17$ cells. Activation of $T_H1$ cells can be measured by secretion of IFN-γ, relative to the level of IFN-γ released in response to a polypeptide that does not generate an immunologic response. In certain embodiments, the amount of IFN-γ released is 1.5-fold, 2-fold, 3-fold, 4-fold, 5-fold, 10-fold, 20-fold, 50-fold or even 100-fold greater. The primary result of protective immunity is the destruction of HSV-2 viral particles or inhibition of HSV-2's ability to replicate. In some embodiments, the protective immunity conferred by presentation of antigen before exposure to HSV-2 will reduce the likelihood of seroconversion to an HSV-2-positive status.

The duration of protective immunity is preferably as long as possible. In certain embodiments, vaccine formulations produce protective immunity lasting six months, one year, two years, five years, ten years, twenty years or even a lifetime.

In some embodiments, a combination of specific polypeptides may prove efficacious for inhibiting HSV-2 infection or the onset of symptoms described above. An exemplary vaccine formulation for prophylactic use may comprise a pharmaceutically-acceptable carrier, a first polypeptide consisting of SEQ ID NOS: 136, a second polypeptide consisting of SEQ ID NO: 1 or 4, and optionally a third polypeptide consisting of the other of SEQ ID NOS: 1 and 4, or immunogenic fragments thereof. In some embodiments, the second or third polypeptide consists of polypeptide fragments of SEQ ID NO: 1, such as the polypeptides of SEQ ID NOS: 2, 8-16, 138 and 139, or immunogenic fragments thereof. In some embodiments, the vaccine formulation for prophylactic use may comprise a first polypeptide consisting of SEQ ID NO: 136, a second polypeptide consisting of SEQ ID NO: 4 or SEQ ID NO: 5, a third polypeptide selected from the group consisting of SEQ ID NOS: 2, 8-16, 138 and 139, and optionally a fourth polypeptide selected from the group consisting of SEQ ID NOS: 2, 8-16, 138 and 139, or immunogenic fragments thereof.

In other embodiments, a vaccine formulation for prophylactic use comprises a pharmaceutically-acceptable carrier and a nucleic acid having a nucleotide sequence that encodes at least one of SEQ ID NOS: 1, 3, 5, 38, 136 or 138, or an immunogenic fragment thereof. For example, the nucleic acids can have a nucleotide sequence comprising at least one of SEQ ID NOS: 39, 46, 118, 137 or 140, or a fragment thereof that encodes an immunogenic polypeptide.

Therapeutic Use

In therapeutic applications, the vaccine comprising a polypeptide or nucleic acid of the invention may be administered to a patient suffering from HSV-2, in an amount sufficient to treat the patient. Treating the patient, in this case, may refer to delaying or reducing symptoms of HSV-2 in an infected individual. In some embodiments, treating the patient refers to reducing the duration of lesions, reducing the number of lesions, reducing the duration of symptoms per episode, and/or otherwise reducing the intensity of symptoms per episode. In certain embodiments, the vaccine reduces the duration or severity of mild symptoms; in some embodiments, the vaccine reduces the duration or severity of serious symptoms. In some embodiments, the vaccine reduces viral shedding and therefore the transmissibility of HSV-2 from the vaccinated patient. In certain embodiments, the reductions described above are at least 25%, 30%, 40%, 50%, 60%, 70%, 80% or even 90%. In certain embodiments, the reductions described above include the complete cessation of symptoms, viral shedding and/or future outbreaks (e.g., by blocking the ability of the virus to establish latency in sensory ganglia).

In therapeutic embodiments, the HSV-2 vaccine is administered to an individual post-infection. The HSV-2 vaccine may be administered shortly after infection, e.g. before symptoms manifest, or may be administered during or after manifestation of symptoms. In some embodiments, the HSV-2 vaccine may prevent endogenous reactivation of earlier infection. In some embodiments, a post-infection vaccine could be administered to patients in high-risk groups.

The duration of therapeutic effects of a vaccine formulation disclosed herein is preferably as long as possible. In certain embodiments, vaccine formulations produce therapeutic effects lasting one month, two months, three months, six months, one year, two years, five years, ten years, twenty years or even a lifetime.

In some embodiments, a combination of specific polypeptides may prove efficacious for treating a patient suffering from HSV-2 as described above. An exemplary vaccine formulation for therapeutic use may comprise a pharmaceutically-acceptable carrier, a first polypeptide consisting of SEQ ID NOS: 136, a second polypeptide consisting of SEQ ID NO: 1 or 4, and optionally a third polypeptide consisting of the other of SEQ ID NOS: 1 and 4, or immunogenic fragments thereof. In some embodiments, the second or third polypeptide consists of polypeptide fragments of SEQ ID NO: 1, such as the polypeptides of SEQ ID NOS: 2, 8-16, 138 and 139, or immunogenic fragments thereof. In some embodiments, the vaccine formulation for therapeutic use may comprise a first polypeptide consisting of SEQ ID NO: 136, a second polypeptide consisting of SEQ ID NO: 4 or SEQ ID NO: 5, a third polypeptide selected from the group consisting of SEQ ID NOS: 2, 8-16, 138 and 139, and optionally a fourth polypeptide selected from the group consisting of SEQ ID NOS: 2, 8-16, 138 and 139, or immunogenic fragments thereof.

In other embodiments, a vaccine formulation for therapeutic use comprises a pharmaceutically-acceptable carrier and a nucleic acid having a nucleotide sequence that encodes at least one of SEQ ID NOS: 1, 3, 5, 38, 136 or 138 or an immunogenic fragment thereof. For example, the nucleic acids can have a nucleotide sequence comprising at least one of SEQ ID NOS: 39, 46, 118, 137 or 140, or a fragment thereof that encodes an immunogenic polypeptide.

Assaying Vaccination Efficacy

The efficacy of vaccination with the vaccines disclosed herein may be determined in a number of ways.

Vaccine efficacy may be assayed in various model systems. Suitable model systems used to study HSV-2 include a guinea pig model and a mouse model, as described in the examples below. Briefly, the animals are vaccinated and then challenged with HSV-2 or the vaccine is administered to already-infected animals. The response of the animals to the HSV-2 challenge or the vaccine is then compared with control animals, using one of the measures described above. A similar assay could be used for clinical testing of humans. The treatment and prophylactic effects described above represent additional ways of determining efficacy of a vaccine.

In addition, efficacy may be evaluated by in vitro immunization of naïve human peripheral blood mononuclear cells (PBMC), where APCs are exposed to the vaccine and then the APCs are co-cultured with naïve T cells from the same donor to evaluate the primary response to immunization in a test tube. An activation of the T-cells by 1.5-fold, 2-fold, 5-fold, 10-fold, 20-fold, 50-fold or 100-fold or more relative to activation of T-cells using APCs not exposed to a vaccine, in certain embodiments, is considered an adequate response.

Vaccine efficacy may further be determined by viral neutralization assays. Briefly, animals are immunized and serum is collected on various days post-immunization. Serial dilutions of serum are pre-incubated with virus during which time antibodies in the serum that are specific for the virus will bind to it. The virus/serum mixture is then added to permissive cells to determine infectivity by a plaque assay. If antibodies in the serum neutralize the virus, there are fewer plaques compared to the control group.

Uses of Pharmaceutical Compositions

Defense Against HSV Infection

The pharmaceutical compositions of the present disclosure are designed to elicit an immune response against HSV-2. Compositions described herein may stimulate an innate immune response, an antibody response or a cell-mediated immune response, or a combination of these responses, in the subject to which it is administered. In some embodiments, the composition stimulates immune cells at the peripheral site of infection or sensory ganglia, such as neutrophils, macrophages, and NK cells. The composition may stimulate infiltration by macrophages; production of antiviral compounds such as nitric oxide, TNF-α, interferons (IFN), and interleukin 12 (IL-12) by neutrophils; and/or stimulation of NK cells to produce IFN-γ. IL-2, IFN-α and IFN-β production may also be triggered by the polypeptides of the present composition, and are believed to aid in controlling infection.

In some embodiments, the composition comprises antigens that stimulate production of neutralizing antibodies. Neutralizing antibodies may target the glycoproteins of the viral envelope, which mediate the interaction of virions with host cell and are responsible for attachment, binding, and entry of HSV-2 into cells. Accordingly, an exemplary composition comprises one or more glycoproteins described above or encoded by nucleic acids described above. Immunogenic antigens and/or epitopes as described herein may be administered separately, in series, or in combination with one another.

In some embodiments, the composition elicits a cell-mediated response, which may involve $CD4^+$ T cells, $CD8^+$ T cells and/or production of antiviral cytokines. The composition may trigger IL-17 secretion by $T_H17$ cells. The composition may trigger IFN-γ secretion, for example through the activation of the innate immune response, and mediate $CD8^+$ T cell clearing of the virus. IFN-γ is also secreted by $T_H1$ cells, $T_C$ cells, dendritic cells, and NK cells, and the composition may trigger IFN-γ secretion by any of these cell types. Such activity of $CD8^+$ T cells may be cytolytic, or, alternately, may be regulated by inhibitor molecules on the surface of the neurons which prevent neuronal killing. $CD4^+$ and/or $CD8^+$ T cells may play a role in maintaining latency of the virus, thus preventing reactivation. In some embodiments, the composition boosts a $CD4^+$ T cell response and/or a $CD8^+$ T cell response that prevents reactivation of the virus from its latent state.

In some embodiments, the composition blocks the ability of HSV to evade the host immune response, or, alternately, boosts immune responses normally evaded by HSV. In some embodiments, the composition inhibits HSV-2 from shifting the immunological balance towards tolerance of HSV antigens. HSV-2 may mediate tolerance through $T_H2$ cells. First, HSV-2 may induce suppressor T cells, such as $CD4^+$ $CD25^+$ T cells and Tr1 cells that secrete IL-10, a $T_H2$ cytokine $T_H2$ cytokines downregulate costimulatory molecules and inhibit the maturation and function of antigen-presenting dendritic cells. In addition, infection with HSV-2 inhibits the maturation and migration of dendritic cells, which are essential for efficient induction of $CD8^+$ killer T cells. Notably, $T_H2$ cytokines are produced during recurrence of HSV-2 infection, in contrast to $T_H1$ cytokines, which are produced during recurrence-free episodes. Thus, in certain embodiments, the compositions of the invention repress suppressor T cells and/or induce maturation or migration or both of dendritic cells.

In some embodiments, methods of inducing an immune response against HSV-2 in a mammal comprise administering the compositions described above. The composition may be used to induce an immune response at different time points, such as before exposure to HSV-2, after initial infection with HSV-2, before or after HSV-2 has established latency, before or after HSV-2 shedding occurs, and/or before or after recurrent outbreaks occur. In some embodiments, an immune response against HSV-2 may be induced at one or more of the timepoints above. The composition may induce a $T_H1$ response and/or a $T_H17$ response but not a $T_H2$ response, or may activate the responses at the same time or at different times.

In some embodiments, administration of the composition reduces symptoms associated with initial infection, latency, or recurrent infection with HSV. Such a composition may reduce incidence and/or severity of lesions, sores, pain, irritation, itching, fever, malaise, headache, viral shedding, or prodromes associated with HSV infection or outbreak.

In some embodiments, one or more antibodies to antigens of HSV-2 may be administered to individuals in order to produce passive immunity. Passive immunity results from the transfer of active humoral immunity in the form of ready-made antibodies, from one individual to another. Passive immunization may be used when there is a high risk of infection and insufficient time for the body to develop its own immune response, or to reduce the symptoms of ongoing or immunosuppressive diseases. Adoptive transfer of T cells may provide another method of eliciting an immune response to HSV-2 antigens in patients. In one embodiment, autologous T cells may be expanded on APCs presenting the antigens derived from the polypeptides described above. Subsequently, the expanded HSV-2-specific T cells are transferred back into the patient from which the T cells were derived.

Diagnostic Uses

This application provides, inter alia, a rapid, inexpensive, sensitive, and specific method for detection of HSV-2 in patients. In this respect it should be useful to hospitals and physicians examining and treating patients with or at risk for HSV-2 infection. As used herein, “patient” refers to an individual (such as a human) that either has an HSV-2 infection or has the potential to contract an HSV-2 infection.

In some embodiments, one may use an antibody against one of the polypeptides described herein, such as those of Table 1 and/or Table 2, to detect HSV-2 in an individual. The instant disclosure also provides a method of phenotyping biological samples from patients suspected of having a HSV-2 infection that involves: (a) rendering a biological sample amenable to immunoassay, if necessary; (b) contacting the sample with an appropriate HSV-2-specific antibody or antigen-binding portion thereof under conditions that allow for binding of the antibody or antigen-binding portion to an epitope of HSV-2; and (c) determining if the sample shows the presence of HSV-2 as compared to a control tissue; where if the test tissue shows the presence of HSV-2, the patient is identified as likely having a HSV-2 infection.

Alternatively, one may use the polypeptides described above to detect anti-HSV-2 antibodies in an individual. The instant disclosure also provides a method of phenotyping biological samples from patients suspected of having a HSV-2 infection: (a) rendering a biological sample amenable to an affinity assay such as ELISA, if necessary; (b) contacting the sample with a HSV-2-specific antigen or portion thereof under conditions that allow for binding of the antigen to any host antibodies present in the sample; and (c) determining if the sample shows the presence of HSV-2 as compared to a control tissue; where if the test tissue shows the presence of HSV-2, the patient is identified as likely having a HSV-2 infection. The aforementioned test may be appropriately adjusted to detect other viral infections, for instance by using a homolog (from another viral species) of the proteins described above, such as in Table 1 and/or Table 2.

A number of methods for measuring antibody-antigen binding are known in the art, including ELISA (enzyme-linked immunosorbent assay), Western blotting, competition assay, and spot-blot. The detection step may be, for instance, chemiluminescent, fluorescent, or colorimetric. One suitable method for measuring antibody-protein binding is the Luminex xMAP system, where peptides are conjugated to a dye-containing microsphere. Certain systems, including the xMAP system, are amenable to measuring several different markers in multiplex, and could be used to measure levels of antibodies at once. In some embodiments, other systems are used to assay a plurality of markers in multiplex. For example, profiling may be performed using any of the following systems: antigen microarrays, bead microarrays, nanobarcodes particle technology, arrayed proteins from cDNA expression libraries, protein in situ array, protein arrays of living transformants, universal protein array, lab-on-a-chip microfluidics, and peptides on pins. Another type of clinical assay is a chemiluminescent assay to detect antibody binding. In some such assays, including the VITROS Eci anti-HCV assay, antibodies are bound to a solid-phase support made up of microparticles in liquid suspension, and a surface fluorometer is used to quantify the enzymatic generation of a fluorescent product.

In other embodiments, one may use the polypeptides described above, such as those of Table 1 and/or Table 2, to detect T cells that are specific to HSV-2. The instant disclosure provides a method of phentoyping biological samples from patients suspected of having a HSV-2 infection, involving (a) rendering a biological sample amenable to an assay for activation of T cells, if necessary, (b) contacting the sample with a HSV-2-specific polypeptide or portion thereof under conditions that allow APCs to process the polypeptide, and (c) determining activation of the T cells in response to the HSV-2-specific polypeptide, where an elevated T cell activation relative to an uninfected patient indicates HSV-2 infection. This diagnostic assay is intended to detect the presence of HSV-2-specific T cells in any patients, including those patients who have been exposed to HSV-2 but have not seroconverted to produce detectable levels of anti-HSV-2 antibodies.

T cell activation may be measured using many assays, including cytokine-specific ELISA, cell proliferation measured by tritiated thymidine incorporation or membrane intercolating (PKH-67) or cytoplasmic (CFSE) dyes, ELISPOT, flow cytometry, and bead arrays. In addition, one may measure the T cell response in T cell lines or in T cell hybridomas from mice or humans that are specific for the antigens. Readouts for activated T cells include proliferation, cytokine production, or readout of a surrogate enzyme expressed by the hybridoma that is induced when the T cell or T cell hybridoma is activated in response to an antigen. For example, activation of a T cell response may be detected by T cell hybridoma that is engineered to produce β-galactosidase. β-galactosidase may be detected through the use of colorimetric β-galactosidase substrates such as chlorophenyl red β-D galactopyranoside (CPRG).

Infection with HSV-2 may be acute or latent. In some embodiments, if the biological sample shows the presence of HSV-2, one may administer a therapeutically effective amount of the compositions and therapies described herein to the patient. The biological sample may comprise, for example, blood, semen, urine, vaginal fluid, mucus, saliva, feces, urine, cerebrospinal fluid, or a tissue sample. In some embodiments, the biological sample is an organ intended for transplantation. In certain embodiments, before the detection step, the biological sample is subject to culture conditions that promote the growth of HSV-2.

The diagnostic tests herein may be used to detect HSV-2 in a variety of samples, including samples taken from patients and samples obtained from other sources. For example, the diagnostic tests may be used to detect HSV-2 on objects such as medical instruments. In some embodiments, the tests herein may be performed on samples taken from animals such as agricultural animals (cows, pigs, chickens, goats, horses and the like), companion animals (dogs, cats, birds, and the like), or wild animals. In certain embodiments, the tests herein may be performed on samples taken from cell cultures such as cultures of human cells that produce a therapeutic protein, cultures of bacteria intended to produce a useful biological molecule, or cultures of cells grown for research purposes.

The invention also includes a method of determining the location of a HSV-2 infection in a patient comprising: (a) administering a pharmaceutical composition comprising a labeled HSV-2 antibody or antigen-binding portion thereof to the patient, (b) detecting the label, and (c) determining if the patient has HSV-2 compared to a control. In certain embodiments, the method further comprises, if the patient has an HSV-2 infection, administering a therapeutically effective amount of a composition described herein to the patient. The method may further comprise determining the infected cell types and/or volume of the HSV-2 in the patient. This method may be used to evaluate the spread of HSV-2 in the patient and determine whether a localized therapy is appropriate.

In some embodiments, the polypeptides described herein may be used to make a prognosis of the course of infection. In some embodiments, T cell or antibody responses specific for the polypeptides herein may be detected in a sample taken from a patient. If antibodies or T cells are present at normal levels, it would indicate that the patient has raised an effective immune response against the pathogen. If antibodies or T cells are absent, or present at reduced levels, it would indicate that the patient is failing to raise a sufficient response against the pathogen, and a more aggressive treatment would be recommended. In some embodiments, antibody or T cells present at reduced levels refers to responses that are present at less than 50%, 20%, 10%, 5%, 2%, or 1% the typical level in a patient with a protective immune response. T cell responses may be detected by methods known in the art such as T cell proliferation, ELISPOT or ELISA, and antibodies may be detected by affinity for any of the antigens described herein, using methods known in the art such as ELISA.

In some embodiments, detection of T cells specific for HSV-2 antigens may be used to predict the progress and symptoms of HSV-2 infection in a patient. After infection with HSV-2, some patients remain asymptomatic, although the virus may establish latency. Other patients exhibit symptoms of HSV-2 infection, and may experience recurrent outbreaks. The HSV-2 antigens found in asymptomatic patients may differ from those antigens found in patients who present symptoms and/or recurrent outbreaks. Accordingly, the detection methods of the present invention may be used to distinguish between subgroups within the population of patients infected with HSV-2. Subgroups may be further divided into patients who experience frequent outbreaks and those who infrequently or never experience outbreaks, or patients who shed high levels of virus and those who shed low levels or do not shed. The categorization of patients, based on the presence and levels of T cell responses to certain HSV-2 antigens but not others, may help health care practitioners to determine appropriate treatment regimens. Similarly, differences in the magnitude of T cell responses and/or differences in the combination and levels of cytokines produced by T cells may also be used to predict the progress and symptoms of HSV-2 infection in a patient. Thus, an infected patient whose complement of HSV-2 antigens to which T cells respond predicts severe symptoms, frequent outbreaks, and/or high levels of viral shedding may require more intensive antiviral therapy and/or a longer course of therapeutic treatment than a patient whose complement of HSV-2 antigens predicts an asymptomatic infection.

It will be understood by one of skill in the art that the methods herein are not limited to detection of HSV-2. Other embodiments include the detection of related viruses including viruses with proteins homologous to the proteins described above, such as those in Table 1 and/or Table 2. Such related viruses include, for example, other members of the Herpesviridae family. Depending on the homology, these related viruses may also include viruses that are not members of the Herpesviridae family.

Use in Groups with Increased Risk for Infection by HSV-2

Essentially any individual has a certain risk of infection with HSV-2. However, certain sub-populations have an increased risk of infection. In some embodiments, patients receiving the composition for HSV-2 are immunocompromised.

An immunocompromising condition arising from a medical treatment is likely to expose the individual in question to a higher risk of infection. It is possible to treat an infection prophylactically in an individual having the immunocompromised condition before or during treatments known to generate such a condition. By prophylactically treating with the antigen before or during a treatment known to generate such a condition it is possible to prevent a subsequent infection or to reduce the risk of the individual contracting an infection due to the immunocompromised condition. Should the individual contract an infection, e.g., following a treatment leading to an immunocompromised condition, it is also possible to treat the infection by administering to the individual an antigen composition.

In certain embodiments, the compositions are administered to children or adult patients. In other embodiments, compositions are appropriate for pregnant women who were infected before becoming pregnant, or who became infected during pregnancy, such as to inhibit infection of a fetus or baby. The compositions may also be administered to neonates and infants who became infected in utero or during delivery.

Doses and Routes of Administration

Dosage Amounts and Timing

The amount of antigen in each vaccine dose is selected as an effective amount, which induces a prophylactic or therapeutic response, as described above, in either a single dose or over multiple doses. Preferably, the dose is without significant adverse side effects in typical vaccines. Such amount will vary depending upon which specific antigen is employed. Generally, it is expected that a dose will comprise 1-1000 μg of protein, in some instances 2-100 μg, for instance 4-40 μg. Alternatively, a dose will comprise 10-6000 μg of nucleic acid, in some instances 20-4000 μg, for instance 30-4000 μg. An optimal amount for a particular vaccine can be ascertained by standard studies involving observation of antibody titers, T cell activation levels, and other responses in subjects. In some embodiments, the appropriate amount of antigen to be delivered will depend on the age, weight, and health (e.g., immunocompromised status) of a subject. When present, typically an adjuvant will be present in amounts from 1 μg-250 μg per dose, for example 50-150 μg, 75-125 μg or 100 μg.

In some embodiments, only one dose of the vaccine is administered to achieve the results described above. In other embodiments, following an initial vaccination, subjects receive one or more boost vaccinations, for a total of two, three, four or five vaccinations. Advantageously, the number is three or fewer. A boost vaccination may be administered, for example, about 1 month, 2 months, 4 months, 6 months, or 12 months after the initial vaccination, such that one vaccination regimen involves administration at 0, 0.5-2 and 4-8 months. It may be advantageous to administer split doses of vaccines which may be administered by the same or different routes.

In some embodiments, the invention supplies a treatment regimen comprising a first dose of vaccine and a second, third or fourth dose of vaccine (a boost vaccine). In exemplary embodiments, a first dose of vaccine comprises one or more polypeptide antigens, or nucleic acids encoding one or more polypeptide antigens, or a combination of one or more polypeptide antigens and nucleic acids encoding the same or other protein antigens. In some embodiments, a boost vaccine is formulated with the same polypeptide antigens, nucleic acids, or polypeptide antigens and nucleic acids as the first dose. In some embodiments, a boost vaccine is formulated with different polypeptide antigens, nucleic acids, or polypeptide antigens and nucleic acids from the first dose. In some embodiments, the first dose may comprise only polypeptide antigens and boost vaccine may comprise only nucleic acids, or the first dose may comprise only nucleic acids and boost vaccine may comprise only polypeptide. In some embodiments, the first dose may comprise polypeptide antigens and nucleic acids, and boost vaccine may comprise only protein antigens or only nucleic acids. In some embodiments, the first dose may comprise only protein antigens or only nucleic acids, and boost vaccine may comprise protein antigens and nucleic acids. In certain embodiments where the boost vaccine is a polypeptide, the polypeptide is gL2 (SEQ ID NO: 3) or ICP4 (SEQ ID NO: 1) or an immunogenic fragment thereof (e.g., ICP4.2, and gL2s v.2, SEQ ID NOS: 2 and 136), optionally in combination with one or more of the adjuvants described above, particularly one or more of the ISCOMs. Such polypeptide boost vaccines are particularly useful in conjunction with any one of the nucleic acid vaccines described above (e.g., nucleic acids having nucleotide sequences that encode at least one of SEQ ID NOS: 1, 3, 5, 38, 136 or 138, or an immunogenic fragment thereof).

The pharmaceutical compositions described herein may take on a variety of dosage forms. In certain embodiments, the composition is provided in solid or powdered (e.g., lyophilized) form; it also may be provided in solution form. In certain embodiments, a dosage form is provided as a dose of lyophilized composition and at least one separate sterile container of diluent.

In some embodiments, the antigen is delivered to a patient at an amount of 1 μmol per dose. In some embodiments, the antigen is delivered at a dose ranging from 10 nmol to 100 nmol per dose. The appropriate amount of antigen to be delivered may be determined by one of skill in the art. In some embodiments, the appropriate amount of antigen to be delivered will depend on the age, weight, and health (e.g., immunocompromised status) of a subject.

Pharmaceutical compositions disclosed herein are (in some embodiments) administered in amounts sufficient to elicit production of antibodies as part of an immunogenic response. In some embodiments, the composition may be formulated to contain 5 μg/0.5 ml or an amount ranging from 10 μg/1 ml to 200 μg/1 ml of an antigen. In other embodiments, the composition may comprise a combination of antigens. The plurality of antigens may each be the same concentration, or may be different concentrations.

In some embodiments, the composition will be administered in a dose escalation manner, such that successive administrations of the composition contain a higher concentration of composition than previous administrations. In some embodiments, the composition will be administered in a manner such that successive administrations of the composition contain a lower concentration of composition than previous administrations.

In therapeutic applications, compositions are administered to a patient suffering from a disease in an amount sufficient to cure or at least partially arrest the disease and its complications.

Therapeutic applications of a composition described herein include reducing transmissibility, slowing disease progression, reducing viral shedding, or eliminating recurrent infections in patients that have been infected with HSV-2, such as by 90%, 80%, 70%, 60%, 50%, 40%, 30%, 20% or 10% of the levels at which they would occur in individuals who are not treated with the composition. The composition may also reduce the quantity of HSV-2 shed by infected individuals, inhibit the expression of proteins required for reactivation of HSV-2 from the latent stage in infected patients, and/or inhibit replication of HSV-2 in neurons of infected patients, such as by 90%, 80%, 70%, 60%, 50%, 40%, 30%, 20%, or 10% of the levels at which they would occur in individuals not treated with the composition.

In prophylactic embodiments, compositions are administered to a human or other mammal to induce an immune response that can inhibit the establishment of an infectious disease or other condition. In some embodiments, a composition may partially block the virus from establishing latency or reduce the efficiency with which latency is established.

In some embodiments, only one dose (administration) of the composition is given. In other embodiments, the composition is administered in multiple doses. In various embodiments, the composition is administered once, twice, three times, or more than three times. The number of doses administered to a subject is dependent upon the antigen, the extent of the disease or the expected exposure to the disease, and the response of a subject to the composition.

In some embodiments, the compositions are administered in combination with antimicrobial molecules. Antimicrobial molecules may include antiviral molecules. Many antiviral molecules are currently known in the art, and target one or more stage of the viral life cycle, including viral attachment to host cells, release of viral genes and/or enzymes into the host cell, replication of viral components using host-cell machinery, assembly of viral components into complete viral particles, and release of viral particles to infect new hosts.

Routes of Administration

The vaccine formulations and pharmaceutical compositions herein can be delivered by administration to an individual, typically by systemic administration (e.g., intravenous, intraperitoneal, intramuscular, intradermal, subcutaneous, transdermal, subdermal, intracranial, intranasal, mucosal, anal, vaginal, oral, sublingual, buccal route or they can be inhaled) or they can be administered by topical application.

In some embodiments, the composition may be administered directly to the likely sites of infection. In female patients, the composition may be applied topically to mucosal membranes, or delivered vaginally or rectally using devices and methods known in the art. The vaginal and rectal routes of delivery permit extended, continuous or pulsed delivery and administration of composition dosages, and may be administered either before or after exposure to HSV, depending on the use of a prophylactic or therapeutic composition. In male patients, the composition may be applied topically to the skin or mucosal membranes, or delivered rectally. In both patient populations, the composition may also be targeted to the sensory ganglia.

An HSV-2 vaccine or pharmaceutical composition is often administered via the intramuscular route. Typically, in this route, the vaccine is injected into an accessible area of muscle tissue. Intramuscular injections are, in some embodiments, given in the deltoid, vastus lateralis, ventrogluteal or dorsogluteal muscles. The injection is typically given at an approximately 90° angle to the surface of the skin, so the vaccine penetrates the muscle.

An HSV-2 vaccine may also be administered subcutaneously. The injection is typically given at a 45° angle to the surface of the skin, so the vaccine is administered to the subcutis and not the muscle.

In some embodiments, the HSV-2 vaccine is administered intradermally. Intradermal administration is similar to subcutaneous administration, but the injection is not as deep and the target skin layer is the dermis. The injection is typically given at a 10-15° angle to the surface of the skin, so the vaccine is delivered just beneath the epidermis.

In some embodiments, the HSV-2 vaccine is administered by electroporation. Delivery by electroporation may be intramuscular or intradermal. Suitable devices for electroporation include devices made by Inovio Pharmaceuticals, Inc. (Blue Bell, Pa.) and the TriGrid™ Delivery System made by Ichor Medical Systems, Inc. (San Diego, Calif.).

Formulations

The vaccine formulation may be suitable for administration to a human patient, and vaccine preparation may conform to USFDA guidelines. In some embodiments, the vaccine formulation is suitable for administration to a non-human animal. In some embodiments, the vaccine is substantially free of either endotoxins or exotoxins. Endotoxins include pyrogens, such as lipopolysaccharide (LPS) molecules. The vaccine may also be substantially free of inactive protein fragments. In some embodiments, the vaccine has lower levels of pyrogens than industrial water, tap water, or distilled water. Other vaccine components may be purified using methods known in the art, such as ion-exchange chromatography, ultrafiltration, or distillation. In other embodiments, the pyrogens may be inactivated or destroyed prior to administration to a patient. Raw materials for vaccines, such as water, buffers, salts and other chemicals may also be screened and depyrogenated. All materials in the vaccine may be sterile, and each lot of the vaccine may be tested for sterility. Thus, in certain embodiments the endotoxin levels in the vaccine fall below the levels set by the USFDA, for example 0.2 endotoxin (EU)/kg of product for an intrathecal injectable composition; 5 EU/kg of product for a non-intrathecal injectable composition, and 0.25-0.5 EU/ml for sterile water.

In some embodiments, the vaccine comprising a polypeptide contains less than 5%, 2%, 1%, 0.5%, 0.2%, 0.1% of other, undesired unpolypeptides, relative to the amount of desired polypeptides. In some embodiments, the vaccine contains less than 5%, less than 2%, less than 1%, less than 0.5%, less than 0.2%, or less than 0.1% DNA and/or RNA.

It is preferred that the vaccine has low or no toxicity, within a reasonable risk-benefit ratio.

The formulations suitable for introduction of the pharmaceutical composition vary according to route of administration. Formulations suitable for parenteral administration, such as, for example, by intraarticular (in the joints), intravenous, intramuscular, intradermal, intraperitoneal, intranasal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials.

Injection solutions and suspensions can be prepared from sterile powders, granules, and tablets of the kind previously described. Cells transduced by the packaged nucleic acid can also be administered intravenously or parenterally.

Formulations suitable for oral administration can consist of (a) liquid solutions, such as an effective amount of the polypeptides or packaged nucleic acids suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. The pharmaceutical compositions can be encapsulated, e.g., in liposomes, or in a formulation that provides for slow release of the active ingredient.

The antigens, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable formulations for vaginal or rectal administration include, for example, suppositories, which consist of the polypeptides or packaged nucleic acids with a suppository base. Suitable suppository bases include natural or synthetic triglycerides or paraffin hydrocarbons. In addition, it is also possible to use gelatin rectal capsules which consist of a combination of the polypeptides or packaged nucleic acids with a base, including, for example, liquid triglycerides, polyethylene glycols, and paraffin hydrocarbons. The formulation may be suitable for administration to a human patient, and the preparation may conform to US FDA guidelines. In some embodiments, the formulation is suitable for administration to a non-human animal. In some embodiments, the composition is substantially free of either endotoxins or exotoxins. Endotoxins may include pyrogens, such as lipopolysaccharide (LPS) molecules. The composition may also be substantially free of inactive protein fragments which may cause a fever or other side effects. In some embodiments, the composition contains less than 1%, less than 0.1%, less than 0.01%, less than 0.001%, or less than 0.0001% of endotoxins, exotoxins, and/or inactive protein fragments. In some embodiments, the composition has lower levels of pyrogens than industrial water, tap water, or distilled water. Other components may be purified using methods known in the art, such as ion-exchange chromatography, ultrafiltration, or distillation. In other embodiments, the pyrogens may be inactivated or destroyed prior to administration to a patient. Raw materials for compositions, such as water, buffers, salts and other chemicals may also be screened and depyrogenated. All materials in the composition may be sterile, and each lot of the composition may be tested for sterility. Thus, in certain embodiments the endotoxin levels in the composition fall below the levels set by the USFDA: 0.2 endotoxin (EU)/kg of product for an intrathecal injectable composition; 5 EU/kg of product for a non-intrathecal injectable composition, and 0.25-0.5 EU/ml for sterile water.

In certain embodiments, the preparation comprises less than 50%, 20%, 10%, or 5% (by dry weight) contaminating protein. In certain embodiments, the desired molecule is present in the substantial absence of other biological macromolecules, such as other proteins (particularly other proteins which may substantially mask, diminish, confuse or alter the characteristics of the component proteins, either as purified preparations or in their function in the subject reconstituted mixture). In certain embodiments, at least 80%, 90%, 95%, 99%, or 99.8% (by dry weight) of biological macromolecules of the same type present (but water, buffers, and other small molecules, especially molecules having a molecular weight of less than 5000, can be present).

It is preferred that the composition has low or no toxicity, within a reasonable risk-benefit ratio. In certain embodiments, the composition comprises ingredients at concentrations that are less than $LD_{50}$ measurements for the animal being treated with the composition. $LD_{50}$ measurements may be obtained in mice or other experimental model systems, and extrapolated to humans and other animals. Methods for estimating the $LD_{50}$ of compounds in humans and other animals are well-known in the art. A composition, and any component within it, might have an $LD_{50}$ value in rats of greater than 100 g/kg, greater than 50 g/kg, greater than 20 g/kg, greater than 10 g/kg, greater than 5 g/kg, greater than 2 g/kg, greater than 1 g/kg, greater than 500 mg/kg, greater than 200 mg/kg, greater than 100 mg/kg, greater than 50 mg/kg, greater than 20 mg/kg, or greater than 10 mg/kg. In some embodiments, the therapeutic index of the composition (measured as the toxic dose for 50% of the population ($TD_{50}$) divided by the minimum effective dose for 50% of the population ($ED_{50}$)), is greater than 1, greater than 10, or greater than 100.

Preparation and Storage of Vaccines Formulations and Immunogenic Compositions

The HSV-2 vaccines described herein may be produced using a variety of techniques. For example, a polypeptide may be produced using recombinant DNA technology in a suitable host cell. A suitable host cell may be bacterial, yeast, mammalian, or other type of cell. The host cell may be modified to express an exogenous copy of one of the relevant polypeptide genes. Typically, the gene is operably linked to appropriate regulatory sequences such as a strong promoter and a polyadenylation sequence. In some embodiments, the promoter is inducible or repressible. Other regulatory sequences may provide for secretion or excretion of the polypeptide of interest or retention of the polypeptide of interest in the cytoplasm or in the membrane, depending on how one wishes to purify the polypeptide. The gene may be present on an extrachromosomal plasmid, or may be integrated into the host genome. One of skill in the art will recognize that it is not necessary to use a nucleic acid 100% identical to the naturally-occurring sequence. Rather, some alterations to these sequences are tolerated and may be desirable. For instance, the nucleic acid may be altered to take advantage of the degeneracy of the genetic code such that the encoded polypeptide remains the same. In some embodiments, the gene is codon-optimized to improve expression in a particular host. The nucleic acid may be produced, for example, by PCR or by chemical synthesis.

Once a recombinant cell line has been produced, a polypeptide may be isolated from it. The isolation may be accomplished, for example, by affinity purification techniques or by physical separation techniques (e.g., a size column).

In a further aspect of the present disclosure, there is provided a method of manufacture comprising mixing one or more polypeptides or an immunogenic fragment or variant thereof with a carrier and/or an adjuvant. In some embodiments, the adjuvant is one that stimulates a $T_H1$ cell response.

In some embodiments, antigens for inclusion in compositions of the invention may be produced in cell culture. One method comprises providing one or more mammalian expression vectors and cloning nucleotides encoding two or more polypeptides selected from polypeptides having an amino acid sequence of any one of SEQ ID NOS: 1-38, 135, 136, 138 or 139, then expressing and isolating the polypeptides.

In some embodiments, nucleic acids for inclusion in compositions of the invention may be produced by replication in a bacterial host such as *E. coli* and purified by standard RNA or DNA purification methods.

The immunogenic polypeptides described herein, and nucleic acid compositions that express the polypeptides, can be packaged in packs, dispenser devices, and kits for administering nucleic acid compositions to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition, such as those disclosed herein.

EXEMPLIFICATION

Example 1: Identification of HSV-2 Antigens

A library of HSV-2 polypeptides (from HSV-2 Strain G, Lot #7C0013, from Advanced Biotechnologies Inc, Maryland) was prepared and screened with peripheral blood mononuclear cells (PBMC) from human donors. Briefly, a library of HSV polypeptides was expressed by bacteria and mixed with APCs. The APCs, in turn, presented HSV-derived peptides to lymphocytes that had been isolated from human patients infected with HSV-2. The patients belonged to several populations, as described below. Lymphocyte responses from each population were compared for reactivity to each expressed protein, and the screen detected antigens that induced reactive lymphocytes with greater frequency in one patient population as compared to the others. Infected but asymptomatic, and exposed but seronegative patients may activate protective immune responses that patients who experience frequent outbreaks do not; in particular, exposed but seronegative patients are presumed to have mounted sterilizing immunity to HSV-2 infection. It is believed that a unique set of polypeptides will activate lymphocytes from these patient populations.

The release of IFN-γ from $CD4^+$ T cells and $CD8^+$ T cells from each population was measured by ELISA following exposure to candidate antigens. Antigens were selected on the basis of the fold increase of IFN-γ released, relative to the level of IFN-γ released by frequent recurrers who experience more than four outbreaks per year, as well as the frequency of responders in the infected but asymptomatic, or exposed but seronegative populations, compared to frequent and less-frequent recurrers.

Identification of Antigens Encoded by UL10, UL19, UL40, US4, US6, RS1 (RS1.1, RS1.2, RS1.3), UL 36 (UL36.3, UL36.4, UL36.5), UL32, and RL2

Lymphocytes were isolated from patients belonging to several populations: infected but asymptomatic (n=40), exposed but seronegative (n=40), frequent recurrers who experience four or more outbreaks per year (n=43), less-frequent recurrers who experience less than four outbreaks per year (n=19), naïve (n=10), and HSV-2$^-$/HSV-1$^+$ (n=10). Table 3 shows the frequency analysis for thirteen HSV-2 antigens encoded by UL10, UL19, UL40, US4, US6, RS1 (RS1.1, RS1.2, RS1.3), UL36 (UL36.3, UL 36.4, UL36.5), UL32, and RL2 in the exposed patient cohort compared to the recurrer cohorts (frequent and less-frequent recurrers combined).

TABLE 3

Frequency analysis for antigens encoded by UL10, UL19, UL40, US4, US6, RS1 (RS1.1, RS1.2, RS1.3), UL36 (UL36.3, UL36.4, UL36.5), UL32 and RL2

| | | Frequency Analysis (HSV-1/HSV-2 seronegative) | |
|---|---|---|---|
| HSV-2 Gene | Protein Name | % response from exposed donors | fold increase over recurrer response |
| UL10 | gM2 | 23% | 1.4 |
| UL19 | VP5 | — | — |
| UL40 | ribonucleotide reductase | 36% | 3.0 |
| US4 | gG2 | 24% | 1.6 |
| US6 | gD2 | 27% | 1.9 |
| RS1 | ICP4 | | |
| RS1.1 | | 54% | 3.0 |
| RS1.2 | | 46% | 2.3 |
| RS1.3 | | 23% | 1.2 |
| UL36 | Major tegument | | |
| UL36.3 | protein | 46% | 2.3 |
| UL36.4 | | 46% | 4.2 |
| UL36.5 | | 31% | 1.9 |
| UL32 | DNA cleavage & packaging proteiin | — | — |
| RL2 | ICP0 | 45% | 1.6 |

Identification of Antigens Encoded by UL1, UL49.5, and UL54

Lymphocytes were isolated from patients belonging to several populations: infected but asymptomatic (n=40), exposed but seronegative (n=40), frequent recurrers who experience four or more outbreaks per year (n=43), less-frequent recurrers who experience less than four outbreaks per year (n=19), naïve (n=10), and HSV-2$^-$/HSV-1$^+$ (n=10).

Table 4 shows the frequency analysis for three HSV-2 antigens encoded by UL1, UL49.5 and UL54, in the exposed patient cohort compared to the recurrer cohorts (frequent and less-frequent recurrers combined).

TABLE 4

Frequency analysis for antigens encoded by UL1, UL49.5, and UL54

| | | Frequency Analysis (HSV-1/HSV-2 seronegative) | |
|---|---|---|---|
| HSV-2 Gene | Protein Name | % response from exposed donors | fold increase over recurrer response |
| UL1 | gL2s v.2 | 64% | 2.7 |
| UL49.5 | (virion p) | 37% | 2.1 |
| UL54 | ICP27 | 22% | 5.8 |

Identification of Antigens Encoded by RL1, UL2, and UM

Lymphocytes were isolated from patients belonging to several populations: infected but asymptomatic (n=40), exposed but seronegative (n=40), frequent recurrers who experience four or more outbreaks per year (n=43), less-frequent recurrers who experience less than four outbreaks per year (n=19), naïve (n=10), and HSV-2$^-$/HSV-1$^+$ (n=10).

Table 5 shows the frequency analysis for three HSV-2 antigens encoded by RL1, UL2, and UL11 in the exposed patient cohort compared to the recurrer cohorts (frequent and less-frequent recurrers combined).

TABLE 5

Frequency analysis for HSV-2 antigens encoded by RL1, UL2, and UL11

| | | Frequency Analysis (HSV-1/HSV-2 seronegative) | |
|---|---|---|---|
| HSV-2 Gene | Protein Name | % response from exposed donors | fold increase over recurrer response |
| RL1 | ICP34.5 | 45% | 1.3 |
| UL2 | DNA glycosylase | 23% | 1.4 |
| UL11 | tegument protein | 21% | <1.0 |

Example 2: In Vivo Data: Protein Antigen Immunizations

Guinea Pig Therapeutic Vaccination Protocol [Protocol A]

Female Hartley guinea pigs were challenged intravaginally with HSV-2 strain MS at $5\times10^5$ pfu to establish a genital tract infection. Animals were monitored for infection by vaginal swab on day 1 post-infection, and acute disease between days 3 and 14 post-infection. On day 14, after resolution of primary disease, the animals were randomized into groups of 12 and immunized subcutaneously with antigen (each HSV-2 polypeptide at 15 μg dose) plus adjuvant (50 μg dose of an ISCOM matrix with a 91:9 mixture of *Quillaja saponin* matrices A and C). Each group received a total of 3 vaccinations, on days 14, 21, and 35 post-infection. Genital swabs were collected during the vaccination period to monitor viral shedding, and daily observations were recorded. Symptoms were scored on a scale from 0 to 4 based upon severity, 0=no symptoms; 1=redness or swelling; 2=a few small vesicles; 3=several large vesicles; 4=several large vesicles with maceration. In addition, animals with lesions intermediate in severity between the above scores were given a score of 0.5, 1.5, 2.5, or 3.5.

Exemplary Therapeutic Vaccination Studies with ICP4.2, gD2ΔTMR, and gD2

The results of exemplary studies are presented below in Tables 6-10. The neutralizing antibody titer was determined at day 41 post-infection and 7 days after third immunization using an average of 4 out of the 12-20 animals in each group. The mean recurrent lesion scores and mean lesion days were each determined from day 15 to day 63 or day 70 post-infection. The lesion scores represent total lesions for each group from day 15 to 60 and then a mean was calculated. Mean lesion days represent the mean number of days post-infection that immunized or non-immunized animals had herpetic lesions present. Vaginal-swab samples were collected from all animals for 12 days between days 20-63 post-infection and stored at −80° C. until assayed for virus shedding titers by quantitative real-time PCR.

TABLE 6

Results of therapeutic vaccination studies with ICP4.2 (SEQ ID NO: 2): lesions

| Groups N = 12 | Dose | Neutralizing Antibody Titer | Mean Recurrent Lesion Score | % Reduction | Mean Lesion Days | % Reduction |
|---|---|---|---|---|---|---|
| Phosphate-Buffered Saline | — | 1:263 | 8.1 | — | 9.0 | — |
| adjuvant only | 50 μg × 3 | 1:331 | 7.1 | 14 | 8.5 | 6 |
| ICP4.2 + adjuvant | 15 μg × 3 | 1:1079 | 4.3 | 47 | 5.1 | 44 |

TABLE 7

Results of therapeutic vaccination studies with ICP4.2 (SEQ ID NO: 2): viral shedding

| Groups | No. of animals with no detectable viral shedding/total | Mean number of days viral shedding detected ± SEM | % Reduction | P value* |
|---|---|---|---|---|
| Phosphate-Buffered Saline | 0/11 | 4.5 ± 0.8 | — | — |
| Adjuvant only | 0/12 | 4.4 ± 0.7 | 2 | 0.971 |
| ICP4.2 + adjuvant | 5/11 | 1.5 ± 0.5 | 67 | 0.004 |

TABLE 8

Results of therapeutic vaccination studies with gD2ΔTMR (SEQ ID NO: 4): lesions

| Groups | Mean Recurrent Lesion Score | % Reduction | Mean Lesion Days | % Reduction |
|---|---|---|---|---|
| Adjuvant only | 8.7 | — | 11.7 | — |
| gD2ΔTMR + adjuvant | 5.7 | 34 | 8.6 | 26 |

TABLE 9

Results of therapeutic vaccination studies with gD2 (SEQ ID NO: 5): lesions

| Groups N = 12 | Dose | Neutralizing Antibody Titer | Mean Recurrent Lesion Score | % Reduction | Mean Lesion Days | % Reduction |
|---|---|---|---|---|---|---|
| Phosphate-Buffered Saline | — | 1:263 | 8.1 | — | 9.0 | — |
| Adjuvant only | 50 μg × 3 | 1:331 | 7.1 | 14 | 8.5 | 6 |
| gD2 + adjuvant | 15 μg × 3 | >1:6400 | 4.0 | 51 (p = 0.04) | 5.0 | 45 |

TABLE 10

| Results of therapeutic vaccination studies with gD2 (SEQ ID NO: 5): viral shedding | | | | |
|---|---|---|---|---|
| Groups | No. of animals with no detectable viral shedding/total | Mean number of days viral shedding detected ± SEM | % Reduction | P value* |
| Phosphate-Buffered Saline | 0/11 | 4.5 ± 0.8 | — | — |
| Adjuvant only | 0/12 | 4.4 ± 0.7 | 2 | 0.971 |
| gD2 + adjuvant | 4/12 | 2.4 ± 0.6 | 47 | 0.047 |

Murine Prophylactic Vaccination Protocol [Protocol B]

Female C57BL/6 mice from 6 to 8 weeks of age were immunized subcutaneously with antigen (HSV-2 polypeptide) plus adjuvant (12 μg dose of an ISCOM matrix with a 82:18 mixture of *Quillaja saponin* matrices A and C) on day 0 and day 9. On day 11, estrous cycles were synchronized with Depo Provera and then the mice were challenged on day 16 via intravaginal deposition of 10 times the $LD_{50}$ of HSV-2 strain 333 while under anaesthesia. All animals were monitored for morbidity (clinical score) and mortality, and body weights and vaginal swabs were collected between days 17 and 28 post-infection. Clinical scores were recorded using the following scale: 0=no symptoms, 1=vaginal erythema, 2=vaginal erythema and edema, 3=vaginal herpetic lesions, 4=unilateral paralysis or severe genital ulceration, and 5=bilateral paralysis or death.

Exemplary Murine Prophylactic Vaccination Studies with VP5, gD2ΔTMR, and gD2ΔTMR Plus ICP4.2

In the experimental group, mice were immunized subcutaneously with either 5 μg or 10 μg of antigen plus adjuvant (12 μg dose of an ISCOM matrix with an 82:18 mixture of *Quillaja saponin* matrices A and C) on day 0 and day 9. Control animals received phosphate buffered saline (PBS) only, or adjuvant only.

Mice receiving PBS only or adjuvant only all died by day 9 post-challenge (no survivors). In contrast, mice receiving antigen largely survived to day 9, and 20-75% survived to day 12 post-challenge. The severity of disease symptoms (genital and neurological disease) were also scored at either day 9 or 10 post-challenge. Mice immunized with ISCOM adjuvant plus VP5, gD2ΔTMR, or gD2ΔTMR plus ICP4.2 showed a significant decrease in disease symptoms compared to the PBS only or adjuvant only groups.

TABLE 11

| Results of murine prophylactic vaccination studies | | | | |
|---|---|---|---|---|
| Groups | Mean Disease Score Day 10 | % Reduction | P value* | % Survival Day 12 |
| PBS only/adjuvant only | 4.81 | — | — | 00 |
| VP5 + adjuvant | 3.13 | 35 | 00.146 | 338 |
| | | | 00.023 | 775 |
| gD2ΔTMR + adjuvant | 1.44 | 70 | | |
| gD2ΔTMR + ICP4.2 + adjuvant | 0.75 | 84 | 00.020 | 88 |

*Student's t test relative to PBS only/adjuvant only control

Results of Murine Prophylactic Vaccination Studies with gL2s v.2, ICP4, and gD2ΔTMR In the experimental group, C57BL/6 mice are immunized subcutaneously with either 5 μg or 10 μg of antigen plus adjuvant (24 μg dose of an ISCOM matrix with a 91:9 mixture of *Quillaja saponin* matrices A and C) on day 0 and day 21. Control animals receive phosphate buffered saline (PBS) only, or adjuvant only. Animals are challenged intravaginally with $10^4$ PFU HSV-2 strain 333 seven days after the last immunization. In some cases, a subset of unchallenged animals is euthanized on the day of challenge for immunogenicity experiments to monitor T cell and antibody responses to the vaccine. All challenged mice are monitored for morbidity (clinical score) and mortality, and body weights and vaginal swabs for viral shedding evaluation are collected between days 17 and 28 post-infection, as described above. Clinical scores are recorded and compared across experimental and control groups of mice.

Guinea Pig Prophylactic Vaccination Protocol [Protocol C]

Female Hartley guinea pigs from 250-350 grams (weight) were immunized subcutaneously with 15 μg of antigen plus adjuvant (50 μg dose of an ISCOM matrix with a 91:9 mixture of *Quillaja saponin* matrices A and C) on day 0 and day 14-21. Sera were collected by toenail clip 2-3 weeks after the boost and then the guinea pigs were challenged via intravaginal deposition of $5\times10^5$ PFU of HSV-2 strain MS. Vaginal-swab samples were collected from all animals on days 30 and 32 and stored at −80° C. until assayed for virus titers by quantitative real-time PCR. Guinea pigs were evaluated daily (day 1-14), and primary genital skin disease was quantified using a lesion severity score scale from 1-4. Numerical scores were assigned to specific disease signs as follows: 0, no disease; 1, redness or swelling; 2, a few small vesicles; 3, several large vesicles; 4, several large vesicles with maceration. At the end of the study, the guinea pigs were euthanized, and the dorsal root ganglia (DRG) were harvested, stored at −80° C. until they were processed for quantitative real-time PCR analysis.

TABLE 12

| Results of guinea pig prophylactic vaccination studies with gD2ΔTMR and VP5 | | | | | |
|---|---|---|---|---|---|
| Groups | Viral titer, PFU/ml Day 2 | Total mean acute lesion score | % Reduction | Copies HSV-2 DNA/ 1 μg DRG DNA | % Reduction |
| Adjuvant only | $2.3\times10^6$ | 22.6 | — | 959 | — |
| gD2ΔTMR + Adjuvant | $1.7\times10^6$ | 7.7 | 66% | 274 | 71% |
| VP5 + adjuvant | $0.6\times10^6$ | 18.2 | 17% | 283 | 70% |

Vaccination studies are also performed with gL2s v.2, ICP4, and gD2ΔTMR. Female Hartley guinea pigs from 250-350 grams (weight) are immunized subcutaneously with 15 μg of antigen(s) plus adjuvant (50 μg dose of an ISCOM matrix with a 91:9 mixture of *Quillaja saponin* matrix A and matrix C) on day 0 and day 21. Control animals receive phosphate buffered saline (PBS) only, or adjuvant only. Sera are collected by toenail clip after immunization for monitoring total IgG responses and antibody neutralization of virus in vitro, and the immunized guinea pigs are challenged via intravaginal deposition of $5\times10^5$ PFU of HSV-2 strain MS. Animals are monitored for acute infection for 15 days post challenge. Vaginal-swab samples are collected from all animals on days 2, 4, and 6 after challenge and stored at −80° C. until assayed for virus titers by quantitative real-time PCR. Guinea pigs are evaluated daily (day 1-14), and primary genital skin disease is quantified using a lesion severity score scale from 1-4. Numerical scores are assigned to specific disease signs as follows: 0, no disease; 1, redness or swelling; 2, a few small vesicles; 3, several large vesicles; 4, several large vesicles with maceration. After the acute phase, animals are monitored daily (day 15-63) for recurrences. Groups are evaluated for length of time to first recurrence, monitored for genital skin disease, and in some cases, vaginal swabs taken at regular intervals to monitor viral shedding. At the end of the study (around D63 post challenge), the guinea pigs are euthanized, and the dorsal root ganglia (DRG) are harvested, stored at −80° C. until they are processed for viral titers by quantitative real-time PCR analysis.

Immunogenicity Assay I (Standard) [Protocol D]

Mice were immunized subcutaneously in the scruff of the neck with a 100 μl injection of 5 μg antigen plus adjuvant (12 μg dose of an ISCOM matrix with a 82:18 mixture of *Quillaja saponin* matrices A and C) in saline. The mice received one or two injections, 7 days apart. Analysis of immunogenicity occurred 7 days after the final injection.

The immunogenicity assay was an ex vivo IFN-γ ELISPOT. $CD4^+$ and $CD8^+$ T cells were enriched from the spleen and separately analyzed. For the ELISPOT assay, membrane plates were prepared by coating them overnight with capture antibody and subsequently blocked by supplemented medium for a minimum of 2 hours at 37° C. The mice were euthanized and their spleens harvested. The T cells were then prepared by sorting the splenocytes for $CD4^+$ and $CD8^+$ T cells using magnetic beads. The blocking solution was washed out from ELISPOT plates and the T cells were added to the blocked plates. The plates were returned to the incubator to allow the T cells to settle. APCs were prepared by pulsing naïve T cell-depleted splenocytes with antigen for 2 hours at 37° C. For $CD4^+$ ELISPOTs, APCs were pulsed with whole protein. For $CD8^+$ ELISPOTs, APCs were pulsed with *E. coli* expressing protein plus cLLO. A medium control was APCs incubated for 2 hours at 37° C. with no additional antigen. The pulsed APCs were irradiated and added to appropriate wells of plates containing T cells. Phorbol myristate acetate (PMA) and ionomycin were added to separate T cell-containing control wells as a positive control. The plates were allowed to incubate for 18 hours at 37° C. under 5% $CO_2$. The plates were then developed using a secondary biotinylated antibody, horseradish peroxidase (HRP) and 3-amino-9-ethylcarbazole (AEC) substrate.

1. Results of Immunogenicity Assay I with ICP4.2

Immunogenicity assay I showed a robust immunogenic response for both one- and two-injection regimens with ICP4.2. For the one-]injection regimen, the number of IFN-γ spots per 200,000 T cells were 8 and 101 for $CD4^+$ and $CD8^+$ T cells, respectively. For the two-injection regimen, there were 50 and 70 spots, respectively. In contrast, less than 15 spots were observed for media or adjuvant alone in either $CD4^+$ or $CD8^+$ T cells.

2. Results of Immunogenicity Assay I with gD2ΔTMR and gD2

Figure 1B:
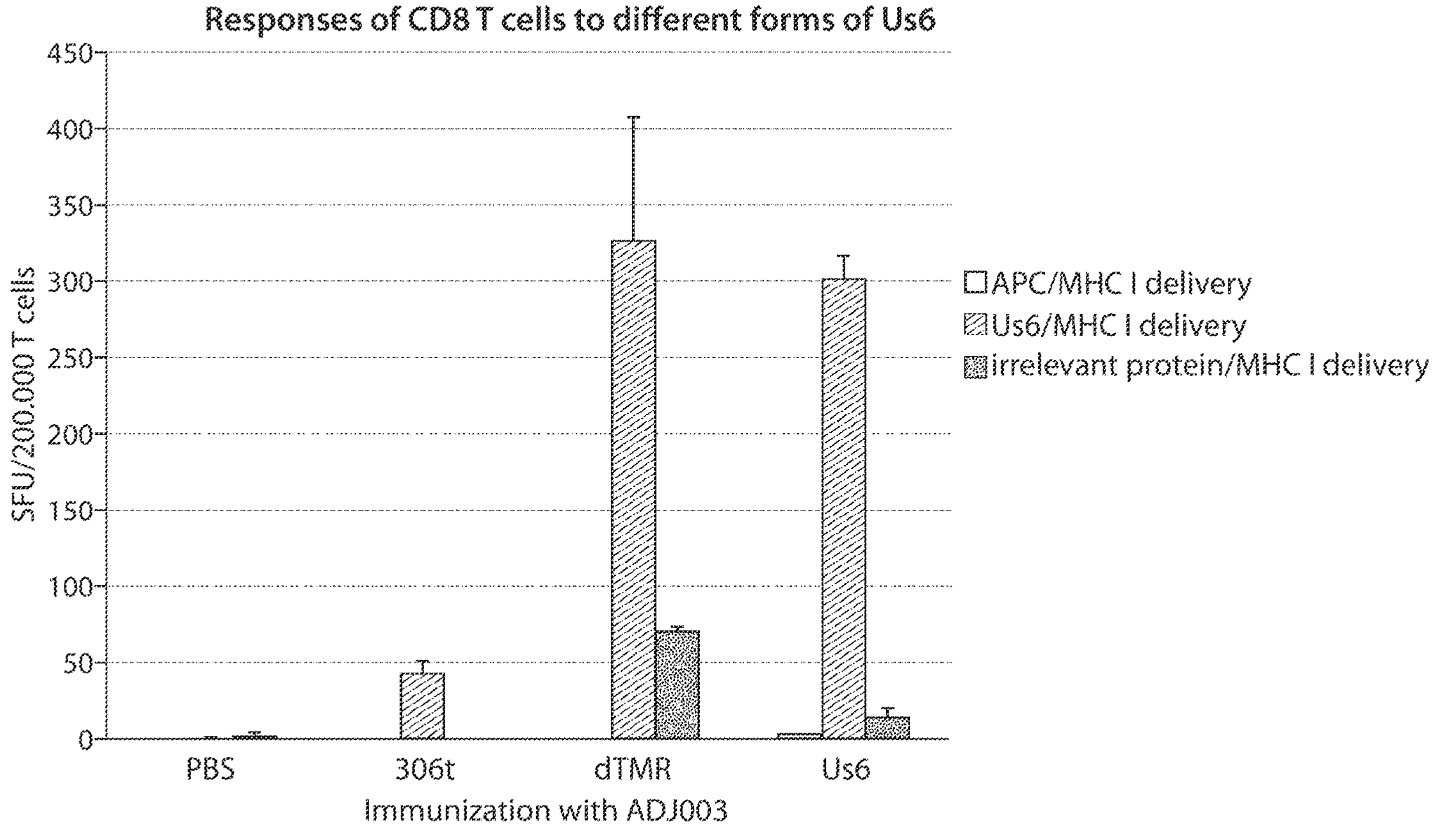

Exemplary results of immunogenicity assay I are shown in FIGS. 1A and B. Robust $CD4^+$ and $CD8^+$ T cell responses were obtained for both full-length gD2 and for gD2ΔTMR. In contrast, immunization with gD2 antigen truncated immediately upstream of the transmembrane domain (denoted 306t in FIG. 1) resulted in significantly reduced responses.

Immunogenicity Assay II (Rapid) [Protocol E]

Recombinant *E. coli* from an HSV-2 orfeome library were induced to express gL2 or fragments of ICP4 protein (ICP4.2, and polypeptides encoded by RS1.1, RS1.3.1 and RS 1.3.2). The protein was retained within bacterial cells. The bacteria were then fixed with PFA, washed extensively with PBS and stored at −80° C. until used for immunization.

Three mice per group were immunized intraperitoneally with $1\times10^8$ bacteria in PBS. Mice received 1-2 additional boosters at 1 week intervals. Seven days after the last boost, sera were collected and analyzed in an HSV-2 neutralization assay. Five-fold serial dilutions were prepared for plasma or serum samples in a 96-well round-bottom plate, followed by the addition of 50 PFUs HSV-2 (strain 333) to each well. The plates were covered and incubated at 37° C. for 1 hour. 200 μl of the virus-serum mixtures was transferred in duplicate to Vero cells grown in a 48-well tissue culture plate and incubated for 1 hour at 37° C. 300 μl of DMEM containing 2% FBS was then added to each well and the plates were incubated for 48 hours at 37° C. To visualize virus plaques, the plates were stained with crystal violet.

TABLE 13

Results of HSV-2 neutralization assay with gL2, ICP4.2, and ICP4 polypeptides encoded by RS1.1, RS1.3.1 and RS1.3.2

| Immunogen | HSV-2 Neutralizating Antibody Titer* |
|---|---|
| *E coli*//gL2 | 1:50 |
| *Ecoli*//ICP4.1 | <1:20 |
| *Ecoli*//ICP4.2 | <1:20 |
| *E. coli*/ICP4.3.1 | 1:100 |
| *E. coli*//ICP4.3.2 | <1:20 |
| Positive control (DL11 Mab) | 1:2500 |
| Negative control (naïve mouse serum) | <1:20 |

* Serum dilution that inhibits 50% of virus control

Immunogenicity Assay III (Overlapping Peptide Pools) [Protocol F]

Mice were immunized with 2 μg/mouse of pooled, overlapping peptides (OLP) spanning the entire sequence of gL2 and ICP4 fragments encoded by RS1.3.1 and RS1.3.2. OLPs were formulated in TiterMax adjuvant (Alexis Biochemical) in a total volume of 100 μl per mouse where adjuvant represented ⅓ of the subcutaneous dose. Mice were immunized on day 0, boosted on day 6 and spleens and blood were collected on day 11. Single cell suspensions were prepared from spleens and erythrocytes were lysed. The splenocyte suspensions were then divided into halves. The first half was separated into APCs, $CD4^+$ and $CD8^+$ T cells; 200,000 T cells were seeded per well of an IFN-γ ELISPOT plate and stimulated with 100,000 APCs and OLP pool corresponding to immunization, irrelevant peptide, positive and negative control. Cells were incubated in plates overnight, after which the plates were developed and spots per well were counted. The second half of each splenocyte suspension was run as unseparated splenocytes (400,000/well), pulsed with peptides, and assayed as described above.

Figure 2A:
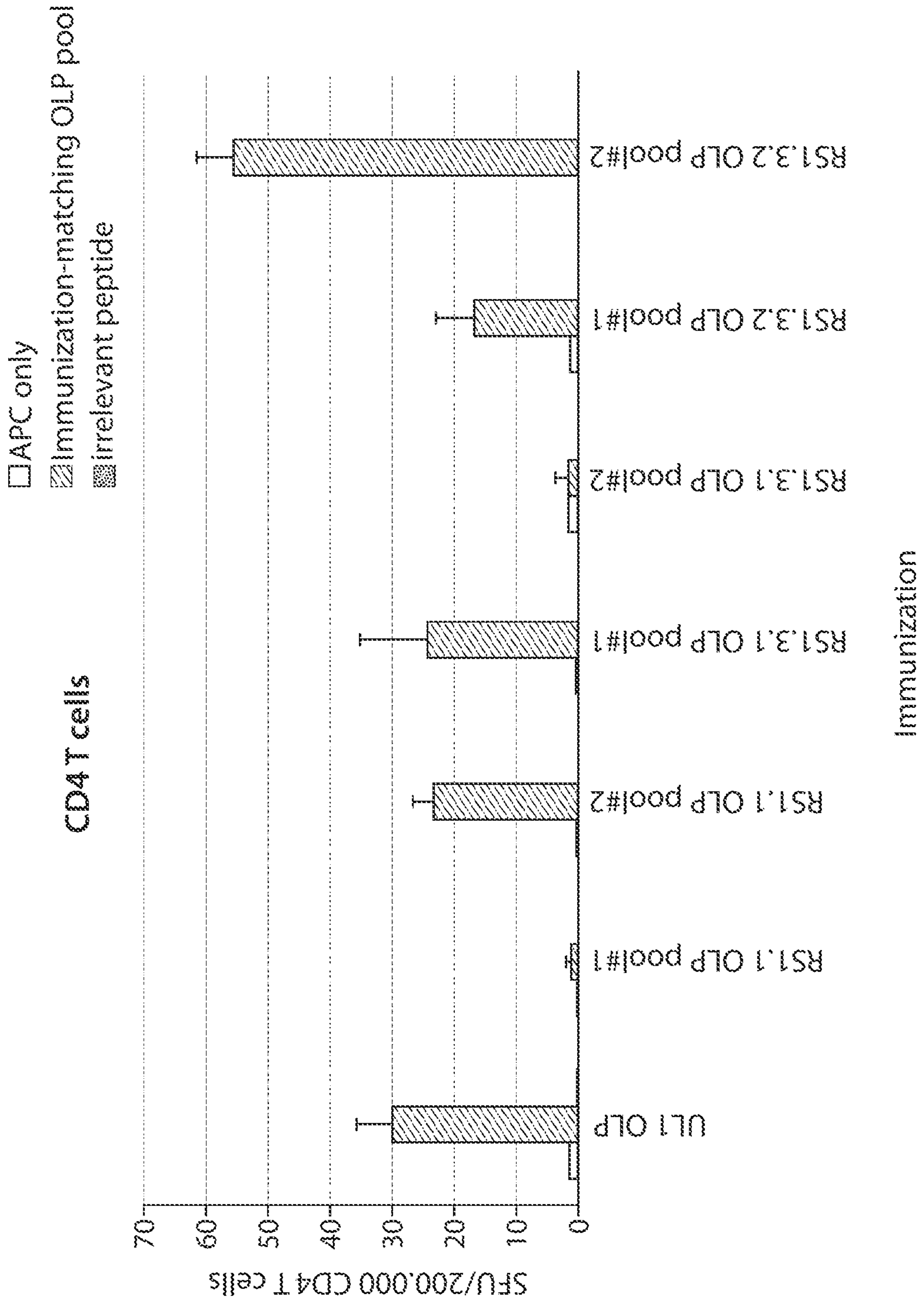
FIGS. 2A and B depict exemplary graphs illustrating, respectively, $CD4^+$ and $CD8^+$ T cell responses following immunization with pooled, overlapping peptides spanning gL2 or ICP4 fragments encoded by RS1.1, RS1.3.1 and RS1.3.2.
Figure 2B:
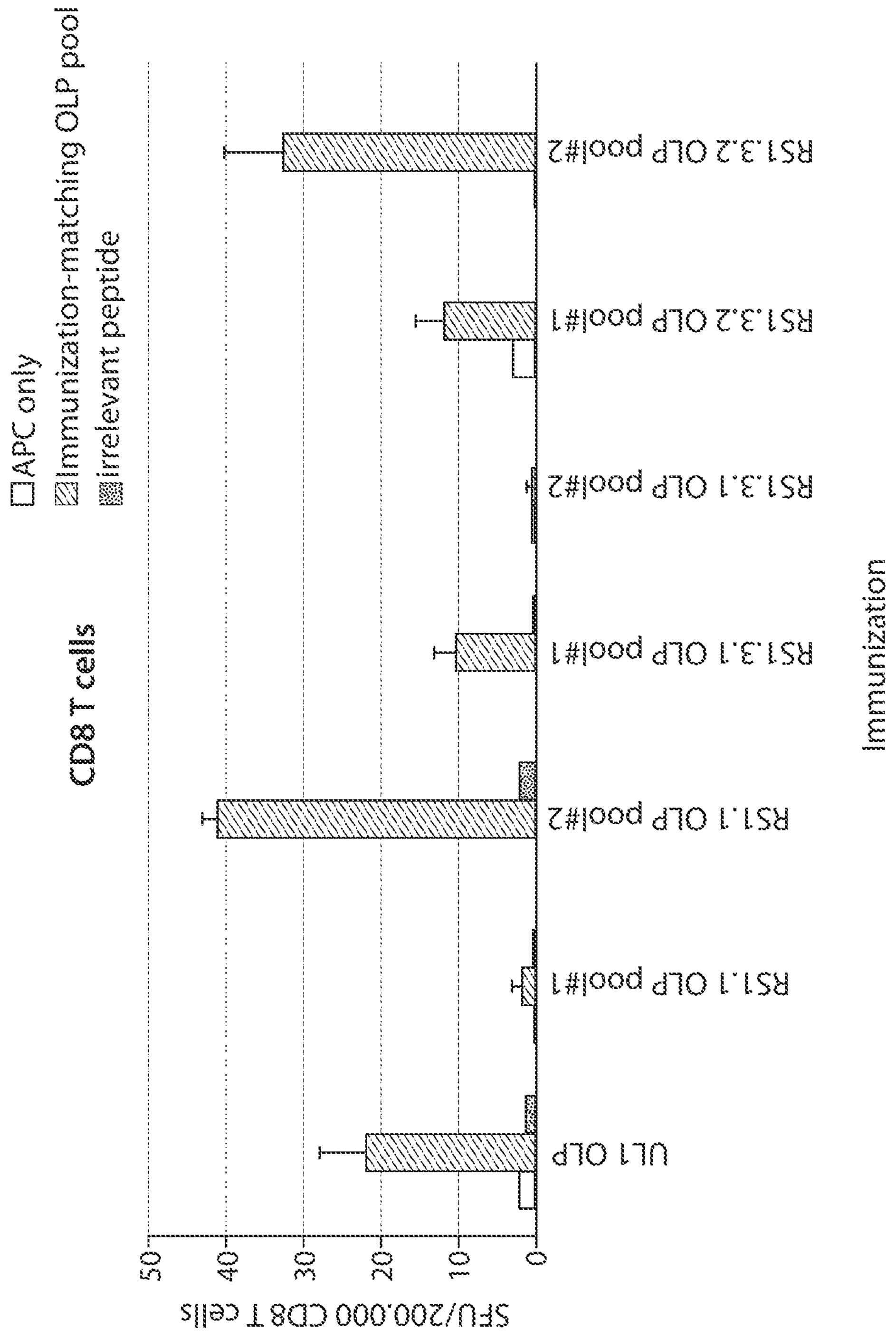

Exemplary results are shown in FIGS. 2A and B as magnitude of response per immunization group.

Vaccination with One and Two Antigens [Protocol G]

Figure 3A:
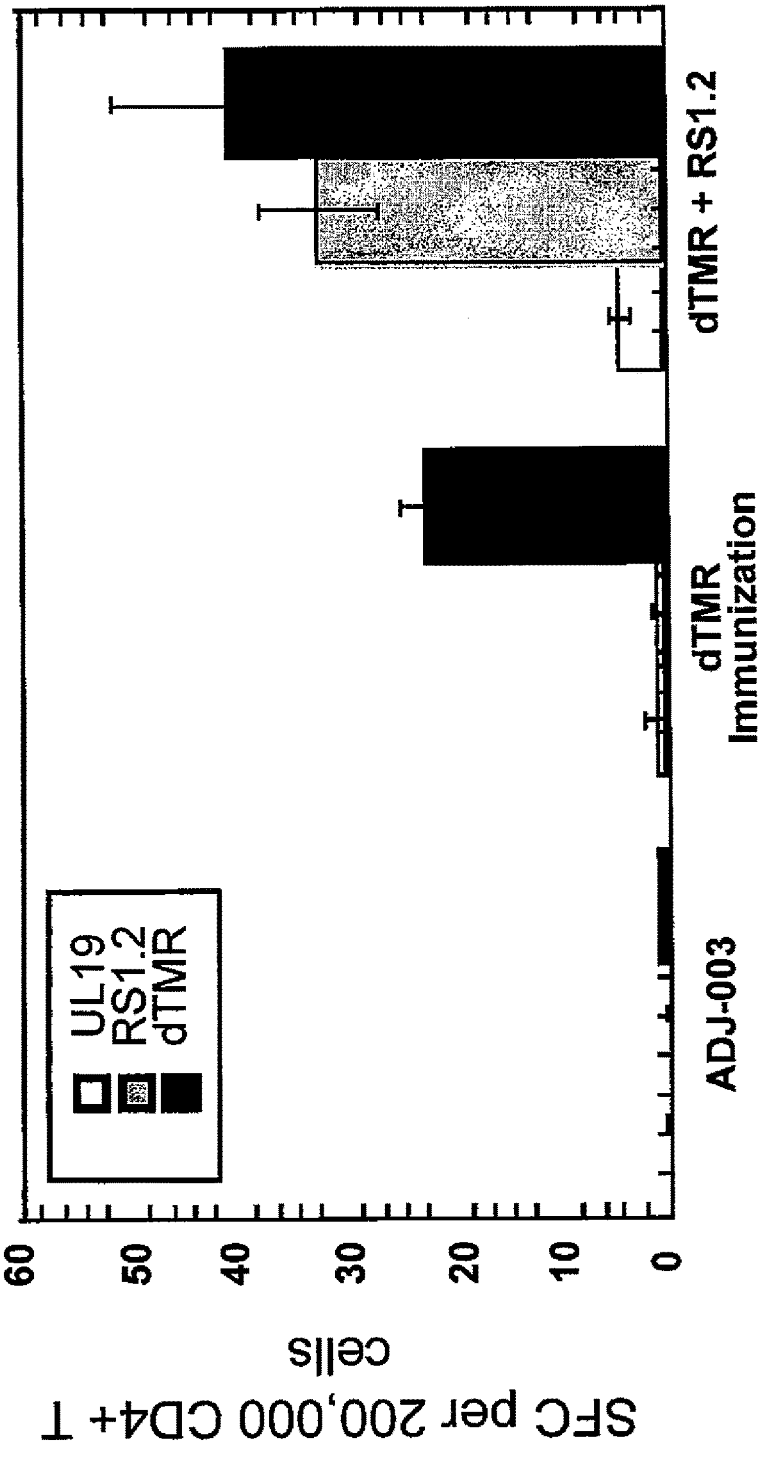
FIGS. 3A and B depict exemplary graphs illustrating, respectively, $CD4^+$ and $CD8^+$ T cell responses following immunization with gD2ΔTMR, or gD2ΔTMR and ICP4.2.
Figure 3B:
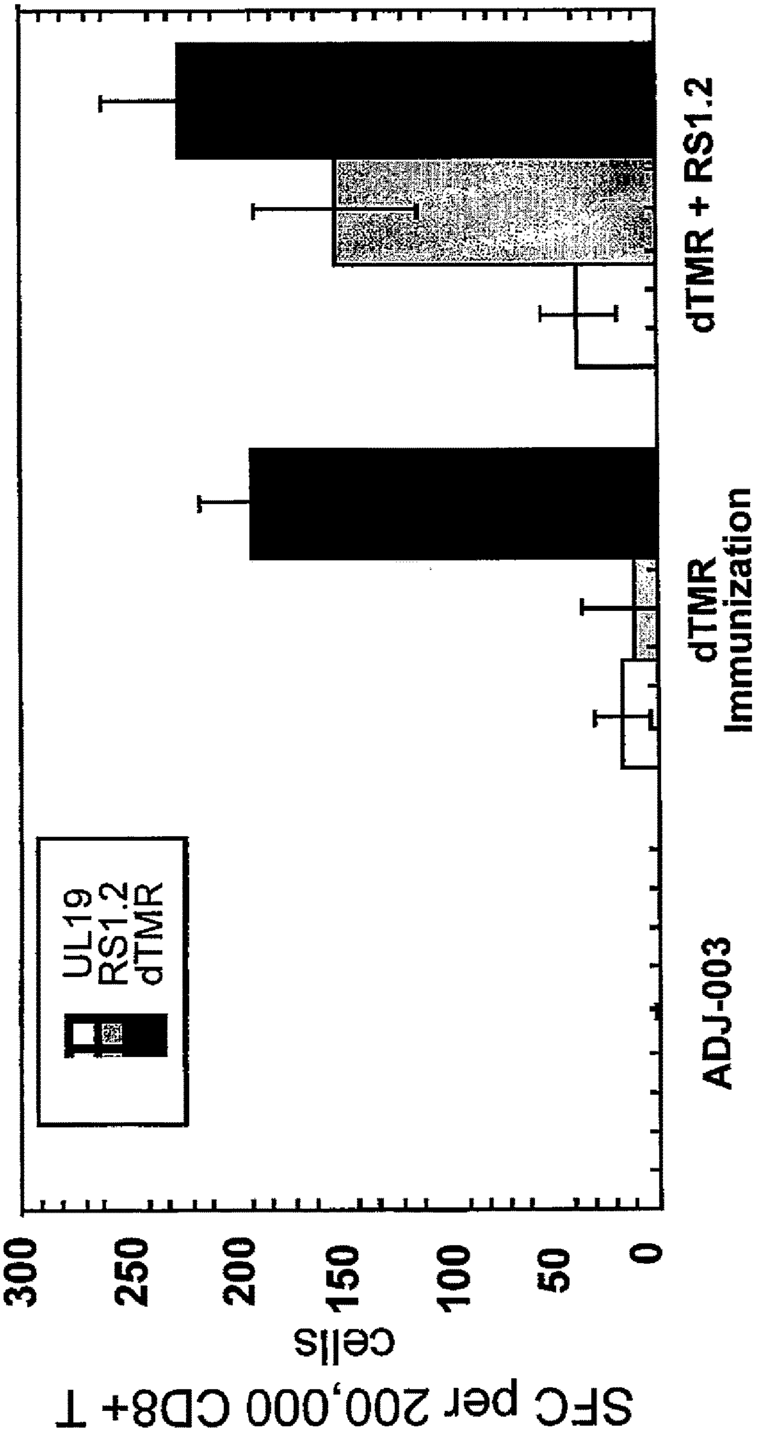

Exemplary Study 1. Immunogenicity of gD2ΔTMR and gD2ΔTMR Plus ICP4 in C57BL/6 Mice Purified protein was mixed with adjuvant and immunized into naïve mice to evaluate the ability to make $CD4^+$ and $CD8^+$ T cell responses to the protein antigens. Briefly, antigen alone (gD2ΔTMR (5 μg)) or combinations of antigens (gD2ΔTMR and ICP4.2 (10 μg)) were mixed with adjuvant (12 μg dose of an ISCOM matrix with a 82:18 mixture of *Quillaja saponin* matrices A and C) and administered subcutaneously to mice, twice, 9 days apart. Seven days after the second immunization, mice were euthanized and spleens were harvested for ex vivo IFN-γ ELISPOT assays. $CD4^+$ and $CD8^+$ T cells were enriched using antibody-coated magnetic beads and then co-cultured on IFN-γ-specific antibody-coated membranes in 96-well plates. APCs were naïve splenocytes pulsed with specific or non-specific purified proteins (as indicated) and irradiated with an x-ray irradiator. After 18 hour co-culture of T cells and APCs, captured IFN-γ was detected with a biotinylated secondary IFN-γ-specific antibody and visualized with horseradish peroxidase and 3-amino-9-ethylcarbazole substrate. Data are reported as the number of IFN-γ spot forming units per $2\times10^5$ T cells±standard deviation of three mice per group. As illustrated in FIGS. 3A and B, the number of IFN-γ spot forming units per $CD4^+$ T cells or $CD8^+$ T cells is increased in mice immunized with gD2ΔTMR antigen combined with ICP4.2 compared to gD2ΔTMR antigen alone.

Exemplary Study 2. Combination of gD2 and ICP4.2 Plus Adjuvant Immunization Reduced Disease Symptoms and Mortality in Mice The ability to trigger protective immunity after immunization with the ICP4.2 protein in combination with gD2 plus adjuvant was evaluated in a lethal HSV-2 challenge mouse model. Briefly, eight C57BL/6 mice per group were immunized with either gD2 (2 μg) or ICP4.2 (10 μg) plus adjuvant individually or with the combination of both antigens plus adjuvant. Formulations were administered subcutaneously in the scruff of the neck, twice, 9 days apart. Estrus cycles were synchronized with Depo Provera 5 days prior to virus infection, and animals were challenged intravaginally 7 days after the second immunization with 20 times the $LD_{50}$ of HSV-2 strain 333. Disease symptoms were scored post-infection, and survival monitored. Disease severity scores were as follows: 0=no symptoms, 1=redness, 2=redness and swelling, 3=herpetic lesions, 4=severe ulceration or unilateral paralysis, and 5=bilateral paralysis or death.

TABLE 14

Effect of HSV-2 proteins gD2 and ICP4.2 on disease symptoms, viral replication and mortality

| Antigen (dose) ^N = 8 | Mean disease score Day 7 | Reduction in disease score | P value** | Reduction in virus titer | % Survival Day 11 |
|---|---|---|---|---|---|
| PBS | 3.5 ± 0.3 | — | — | — | 0% |
| gD2* (2 ug) | 2.5 ± 0.2 | 29% | 0.016 | 0% | 25% |
| ICP4.2 (10 ug) | 1.7 ± 0.4 | 51% | 0.005 | 0% | 13% |
| gD2 (2 ug) + ICP4.2 (10 ug) | 1.3 ± 0.3 | 63% | 0.0004 | 20% | 50% |

^all groups received adjuvant;
*full-length protein;
**Student's t test

Exemplary Study 3. Combination of gD2ΔTMR and ICP4.2 Plus Adjuvant Immunization Reduced Disease Symptoms and Mortality in Mice Mice were immunized with a combination of gD2ΔTMR and ICP4.2 antigens and challenged as described above. Mice immunized with the combination of antigens plus adjuvant showed a lower mean disease score at ten days after virus challenge compared to animals receiving gD2ΔTMR with adjuvant.

TABLE 15

Effect of HSV-2 proteins gD2ΔTMR and gD2ΔTMR plus ICP4.2 on disease symptoms and survival rate in mice

| Groups | Mean Disease Score Day 10 | % Reduction | P value* | % Survival Day 12 |
|---|---|---|---|---|
| Adjuvant only | 4.81 | — | — | 00% |
| gD2ΔTMR + adjuvant | 1.44 | 70 | 0.023 | 75% |
| gD2ΔTMR + ICP4.2 + adjuvant | 0.75 | 84 | 0.020 | 88% |

Exemplary Study 4. Combination of gD2 and ICP4.2 Plus Adjuvant Immunization Reduces Severity of Recurrent Lesions when Administered Therapeutically to HSV-2 Infected Guinea Pigs The ability to affect HSV-2 reactivation in infected guinea pigs after therapeutic immunization with antigens plus adjuvant was evaluated. Briefly, female Hartley guinea pigs were infected intravaginally with $5\times10^5$ pfu of HSV-2 strain MS, monitored for primary disease for 14 days, and then randomized into immunization groups (N=15). Animals were immunized three times subcutaneously on day 14, 21, and 35 post-infection with antigen (15 μg) plus adjuvant (50 μg) or adjuvant alone, or vehicle control and scored daily for local disease severity. The scoring system was as follows: 0=no symptoms, 1=redness, 2=single lesions, 3=large or fused lesions, 4=severe ulceration or unilateral paralysis, and 5=bilateral paralysis or death.

Table 16 shows the data as the mean recurrent lesion score for each week after the guinea pigs recovered from their acute disease. The guinea pigs treated with a combination of gD2 and ICP4.2 antigens showed a reduction in the mean lesion score at 7 (day 42) and 14 (day 49) days after their last immunization compared to animals receiving the individual antigens with adjuvant.

TABLE 16

| Effect of HSV-2 proteins gD2 and ICP4.2 vaccine on recurrent genital skin disease Mean Recurrent Lesion Score Post HSV-2 Infection | | | | | |
|---|---|---|---|---|---|
| Antigen + Adjuvant | Day 15-21 | Day 22-28 | Day 29-35 | Day 36-42 | Day 43-49 |
| PBS | 2.00 ± 0.45 | 1.17 ± 0.35 | 1.50 ± 0.50 | 0.87 ± 0.28 | 1.33 ± 0.33 |
| gD2 | 1.00 ± 0.30 | 0.67 ± 0.24 | 0.80 ± 0.19 | 0.83 ± 0.26 | 0.77 ± 0.28 |
| ICP4.2 | 1.97 ± 0.38 | 1.07 ± 0.29 | 1.03 ± 0.33 | 0.53 ± 0.16 | 0.83 ± 0.29 |
| gD2 + ICP4.2 | 1.43 ± 0.32 | 0.80 ± 0.27 | 1.07 ± 0.33 | 0.43 ± 0.19 | 0.70 ± 0.27 |

Exemplary Study 5. Combination of gD2ΔTMR and ICP4.2 Plus Adjuvant Immunization Reduces Severity of Recurrent Lesions when Administered Therapeutically to HSV-2 Infected Guinea Pigs The ability to affect HSV-2 reactivation in infected guinea pigs after therapeutic immunization with antigens plus adjuvant was evaluated. Female Hartley guinea pigs were challenged intravaginally with HSV-2 strain MS at $5\times10^5$ pfu to establish a genital tract infection. Animals were monitored for infection by vaginal swab on day 1 post-infection, and acute disease between days 3 and 14 post-infection. On day 14, after resolution of primary disease, the animals were randomized into groups of 12 and immunized subcutaneously with antigen (each HSV-2 polypeptide at 15 μg dose) plus adjuvant (50 μg dose of an ISCOM matrix with a 91:9 mixture of *Quillaja saponin* matrices A and C). Each group received a total of 3 vaccinations, on days 14, 21, and 35 post-infection. Genital swabs were collected during the vaccination period to monitor viral shedding, and daily observations were recorded. Symptoms were scored on a scale from 0 to 4 based upon severity, 0=no symptoms; 1=redness or swelling; 2=a few small vesicles; 3=several large vesicles; 4=several large vesicles with maceration. In addition, animals with lesions intermediate in severity between the above scores were given a score of 0.5, 1.5, 2.5, or 3.5. Table 17 shows the data as the mean recurrent lesion score for each week after the guinea pigs recovered from their acute disease. The guinea pigs treated with a combination of gD2ΔTMR and ICP4.2 antigens showed a reduction in the mean lesion score after their last immunization compared to animals receiving the individual antigens with adjuvant.

TABLE 17

| Results of therapeutic vaccination studies with ICP4.2, gD2ΔTMR, and ICP4.2 plus gD2ΔTMR: lesions | | | | | | |
|---|---|---|---|---|---|---|
| Groups | Dose | Neutralizing Antibody Titer | Mean Recurrent Lesion Score | % Reduction | Mean Lesion Days | % Reduction |
| Adjuvant only | 50 μg × 3 | 1:250 | 8.9 | — | 10.3 | — |
| ICP4.2 + adjuvant | 15 μg × 3 | 1:250 | 6.6 | 26 | 7.7 | 25 |
| gD2ΔTMR + adjuvant | 15 μg × 3 | 1:750 | 7.2 | 20 | 8.3 | 20 |
| ICP4.2 + gD2ΔTMR + adjuvant | 15 μg + 15 μg × 3 | 1:620 | 6.1 (p = 0.05) | 32 | 6.9 (p = 0.04) | 33 |

Exemplary Study 6. Immunogenicity of gD2ΔTMR, ICP4.2, gD2ΔTMR Plus ICP4.2, gL2s v.2, UL40 Protein, and gL2s v.2 Plus UL40 Protein in C57BL/6 Mice Purified protein was mixed with adjuvant and immunized into naïve mice to evaluate the ability to make both antibody responses and $CD4^+$ and $CD8^+$ T cell responses to the protein antigens. Briefly, antigen alone or combinations of antigens were mixed with adjuvant (ISCOM matrix with a 91:9 mixture of *Quillaja saponin* matrices A and C) and administered subcutaneously to mice, twice, 21 days apart. Seven days after the second immunization, mice were euthanized. Blood was collected to determine antigen-specific antibody titers by direct protein ELISA assays, as described below, and spleens were harvested for ex vivo IFN-γ ELISPOT assays. $CD4^+$ and $CD8^+$ T cells were enriched using antibody-coated magnetic beads and then co-cultured on IFN-γ-specific antibody-coated membranes in 96-well plates. APCs were naïve splenocytes pulsed with specific or non-specific purified proteins (as indicated) and irradiated with an x-ray irradiator. After 18 hour co-culture of T cells and APCs, captured IFN-γ was detected with a biotinylated secondary IFN-γ-specific antibody and visualized with horseradish peroxidase and 3-amino-9-ethylcarbazole substrate. Data are reported as the number of IFN-γ spot forming units per $2\times10^5$ T cells±standard deviation of three mice per group.

Antigen-specific serum antibody titers of immunized mice were determined by direct protein ELISA. The sera were processed from blood collected above and stored at −80° C. ELISA plates were coated overnight at 4° C. with 5 μg of whole protein in 0.1 M carbonate buffer, pH 9.5. Plates were washed with TBS+0.05% Tween-20 (TBS-T) and blocked with TBS-T+1% bovine serum albumin for 1 h. Serum samples were serially diluted and incubated in the antigen-coated wells for 2 hours at room temperature. Plates were washed and probed for 1 h with goat anti-mouse alkaline-phosphatase (AP)-conjugated anti-IgG at a 1:10,000 dilution. Detection of AP activity was achieved by the addition of p-Nitrophenyl phosphate (pNPP; Sigmafast, Sigma-Aldrich), and the reaction stopped with 3N NaOH and absorbance read at 405 nm. Endpoint titers were calculated by extrapolation of the linear portion of the serial dilutions and defining the endpoint as the dilution at which the linear portion of the curve intersects with the background cut-off. The cut-off used for data calculation was 2 times the value of the negative control serum from a naïve mouse.

Figure 4A:
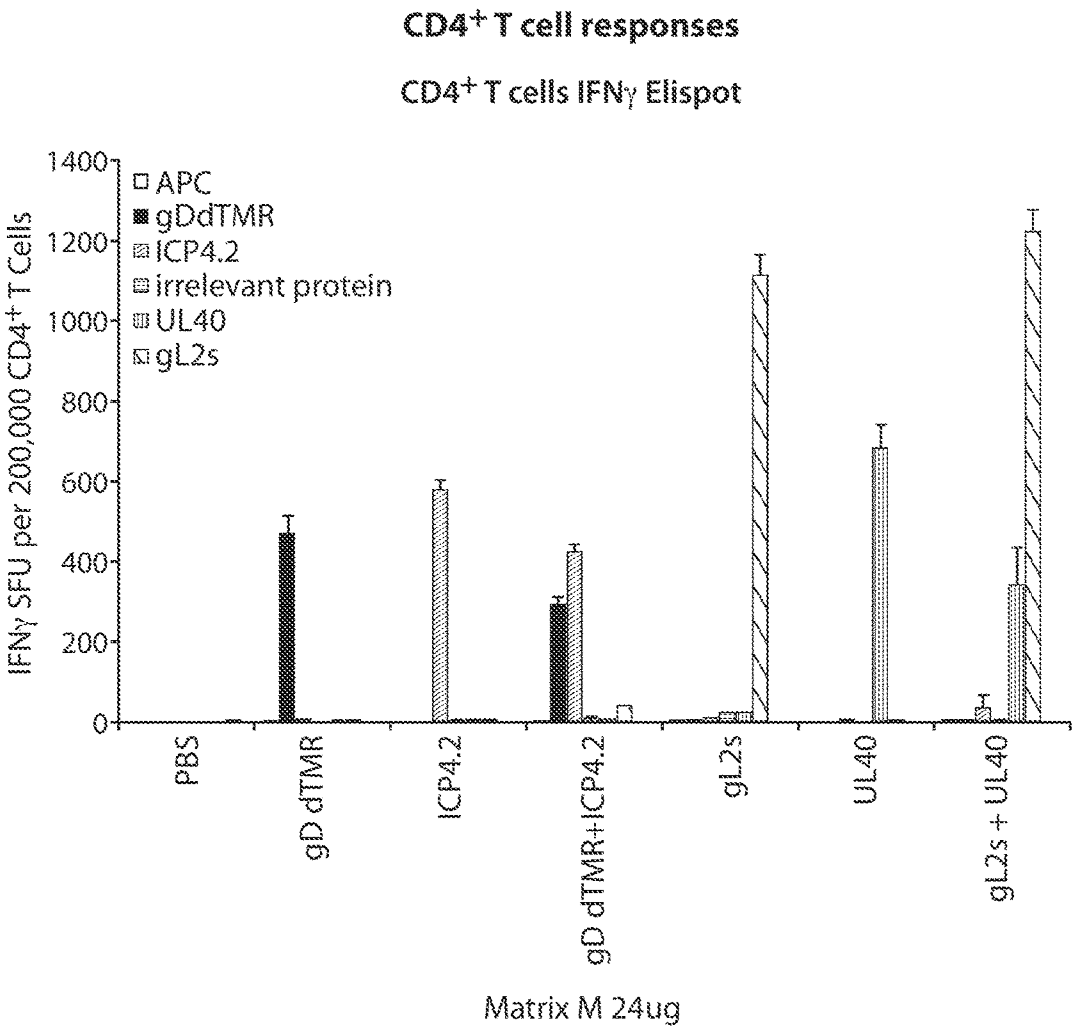
FIGS. 4A and B depict exemplary graphs illustrating the number of IFN-γ spot forming units per $2\times10^5$ $CD4^+$ (Panel A) or $CD8^+$ (Panel B) T cells, following immunization with gD2ΔTMR, ICP4.2, gD2ΔTMR plus ICP4, gL2s v.2, UL40 protein, and gL2s v.2 plus UL40 protein.
Figure 4B:
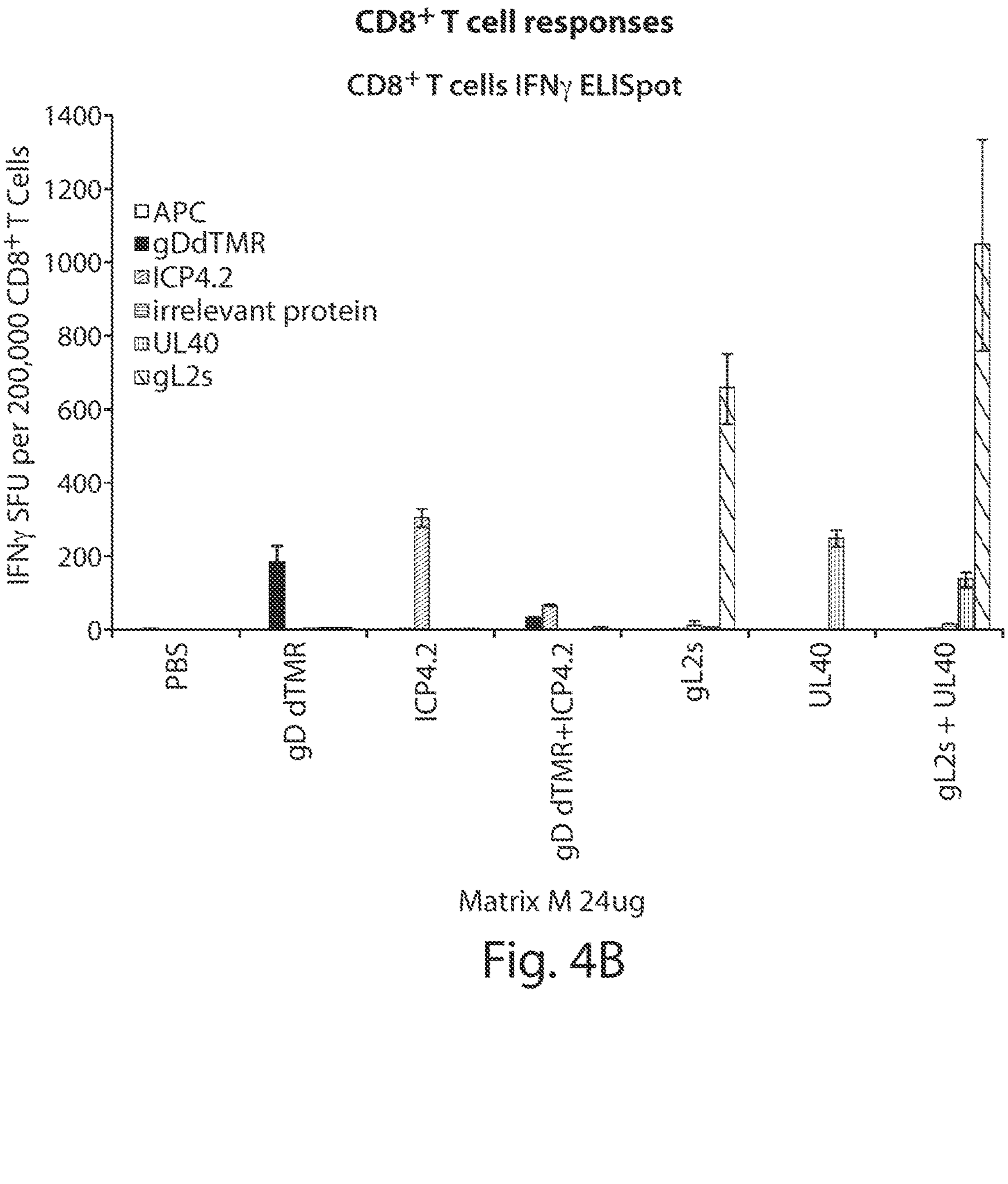

FIGS. 4A and B depict exemplary graphs illustrating the number of IFN-γ spot forming units per $2\times10^5$ $CD4^+$ (Panel A) or $CD8^+$ (Panel B) T cells, following immunization with gD2ΔTMR, ICP4.2, gD2ΔTMR plus ICP4, gL2s v.2, UL40 protein, and gL2s v.2 plus UL40 protein. Strong T cell responses specific for ICP4.2, gD2ΔTMR, UL40 and gL2 were observed when mice were immunized with individual antigens or in the following combinations: gD2ΔTMR plus ICP4.2, gL2s v.2 plus UL40 protein.

FIG. 5 illustrates IgG1 and IgG2c antibody titers against gL2s v.2, UL40 protein, and gL2s v.2 plus UL40 protein. Antibodies to gL2s v.2 and UL40 protein were observed when mice were immunized with cognate antigens, either individually or in combination. IgG1 and IgG2c subtypes of antigen-specific antibodies were detected for all antigens.

Exemplary Study 7. Immunogenicity of gL2s v.2, ICP4.2, ICP4.2 Plus gL2s v.2, ICP4.9, ICP4.9 Plus gL2s v.2, ICP4.5, and ICP4.5 Plus gL2s v.2 in C57BL/6 Mice Purified protein was mixed with adjuvant and immunized into naïve mice to evaluate the ability to make both antibody responses and $CD4^+$ and $CD8^+$ T cell responses to the protein antigens as described for Exemplary Study 6 above, except that APCs were pulsed with either the indicated purified proteins, or with pools of overlapping peptides spanning the indicated proteins. Mice received gL2s v.2, ICP4.5 at two different doses, ICP4.9 at two different doses, ICP4.2, or combinations of ICP4.5, ICP4.9, and ICP4.2 plus gL2s v.2.

Figure 6A:
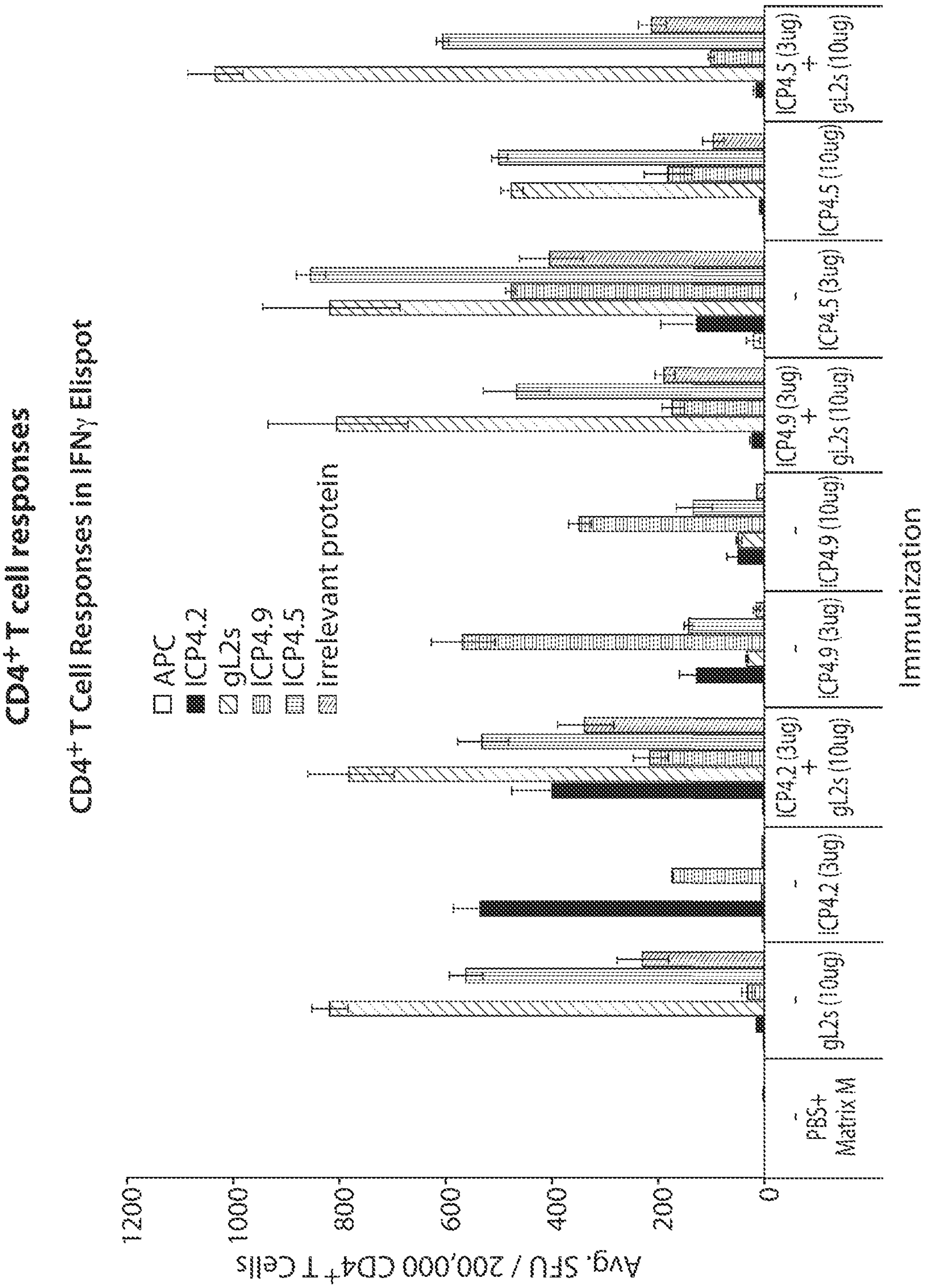
FIGS. 6A and B depict exemplary graphs illustrating the average number of IFN-γ spot forming units per $2\times10^5$ $CD4^+$ (Panel A) or $CD8^+$ (Panel B) T cells, following immunization with gL2s v.2, ICP4.2, ICP4.2 plus gL2s v.2, ICP4.9, ICP4.9 plus gL2s v.2, ICP4.5, and ICP4.5 plus gL2s v.2.
Figure 6B:
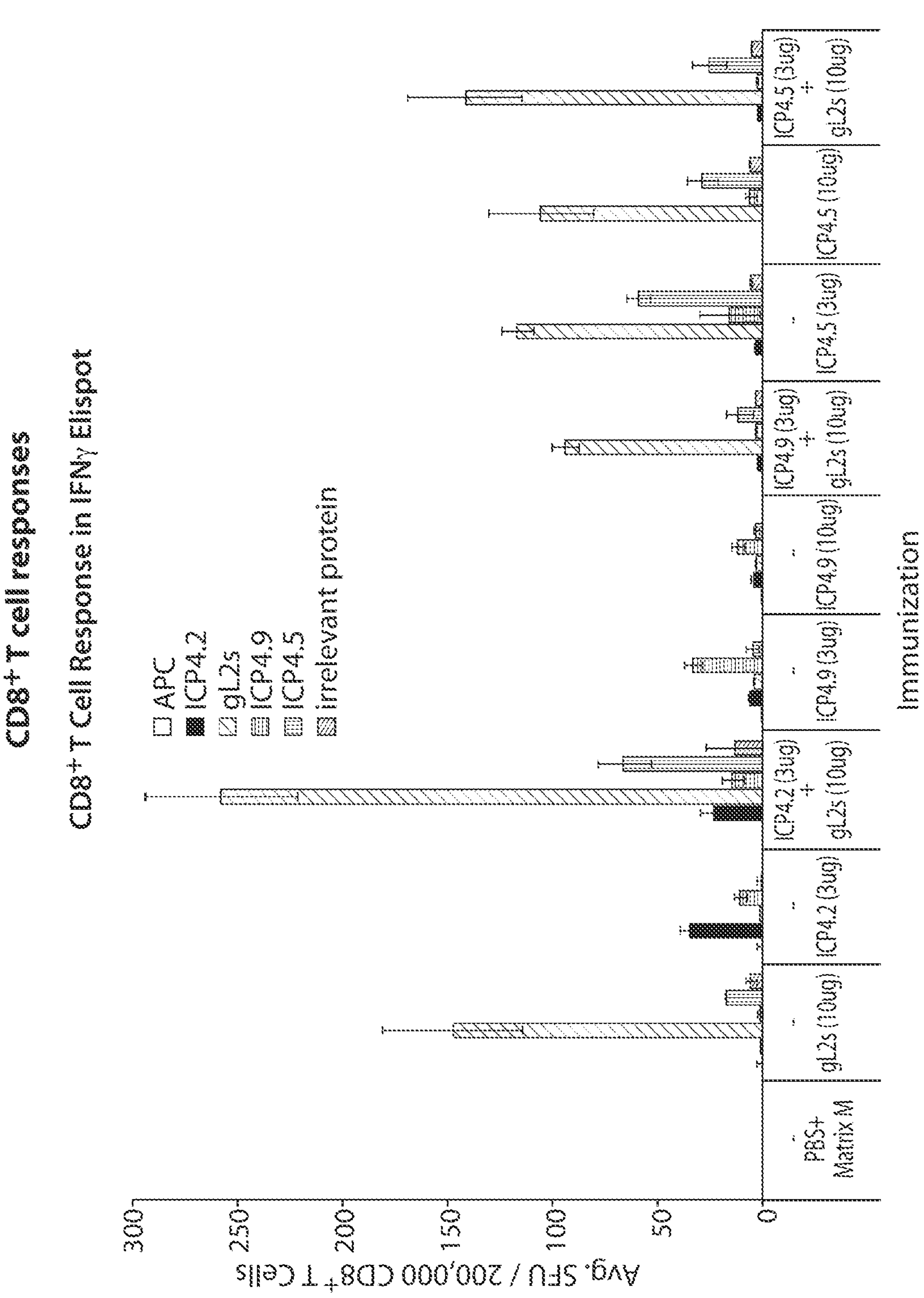
FIGS. 6C and D depict exemplary graphs illustrating the average number of IFN-γ spot forming units per $2\times10^5$ $CD4^+$ (Panel C) or $CD8^+$ (Panel D) T cells, following immunization with gL2s v.2, ICP4.2, ICP4.2 plus gL2s v.2, ICP4.9, ICP4.9 plus gL2s v.2, ICP4.5, and ICP4.5 plus gL2s v.2, as in FIGS. 6A and B, except that APCs were pulsed with pools of overlapping peptides spanning the indicated proteins rather than with purified proteins.

FIGS. 6A and B depict exemplary graphs illustrating the average number of IFN-γ spot forming units per $2\times10^5$ $CD4^+$ (Panel A) or $CD8^+$ (Panel B) T cells, following immunization with gL2s v.2, ICP4.2, ICP4.2 plus gL2s v.2, ICP4.9, ICP4.9 plus gL2s v.2, ICP4.5, and ICP4.5 plus gL2s v.2. Strong gL2s v.2, ICP4.2, ICP4.9, and ICP4.5 T cell responses were obtained. Some expected cross-reactivity due to sequence overlap among proteins was observed. Unexpected cross-reactivity was observed between gL2s v.2 and ICP4.5.

Figure 6C:
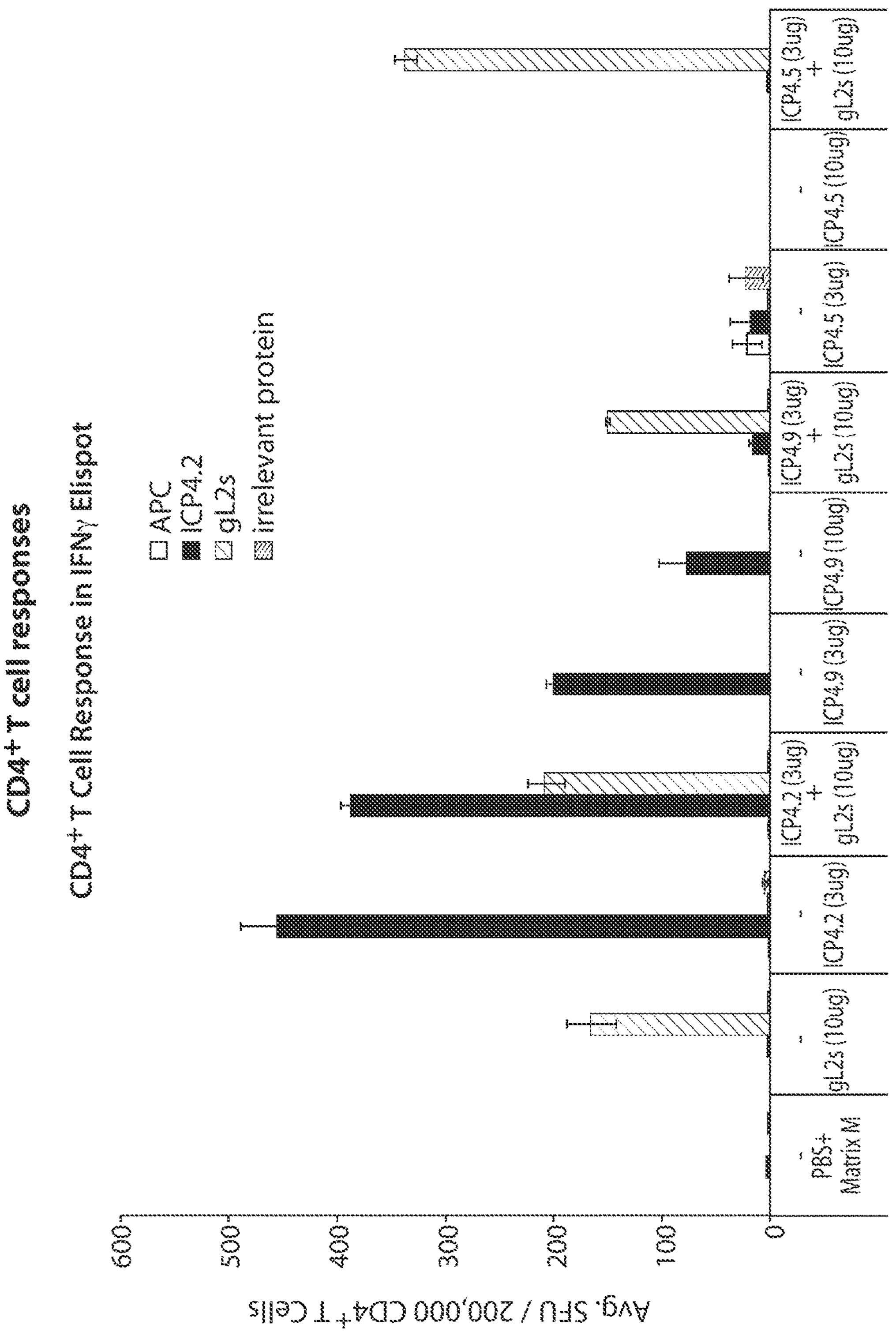
Figure 6D:
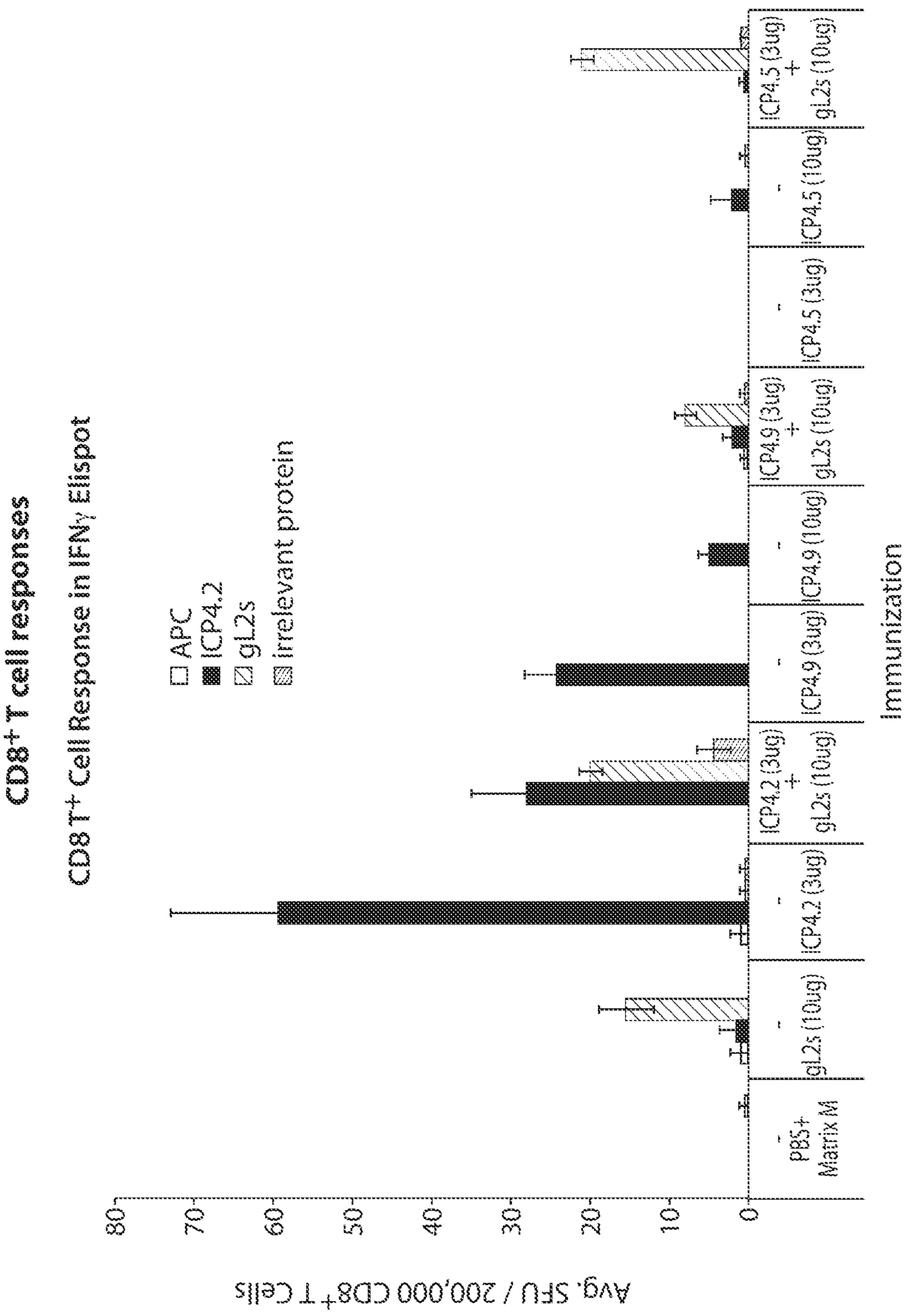

FIGS. 6C and D depict exemplary graphs illustrating the average number of IFN-γ spot forming units per $2\times10^5$ $CD4^+$ (Panel C) or $CD8^+$ (Panel D) T cells, following immunization with gL2s v.2, ICP4.2, ICP4.2 plus gL2s v.2, ICP4.9, ICP4.9 plus gL2s v.2, ICP4.5, and ICP4.5 plus gL2s v.2, as in FIGS. 6A and B, except that APCs were pulsed with pools of overlapping peptides spanning the indicated proteins rather than with purified proteins.

Figure 7:
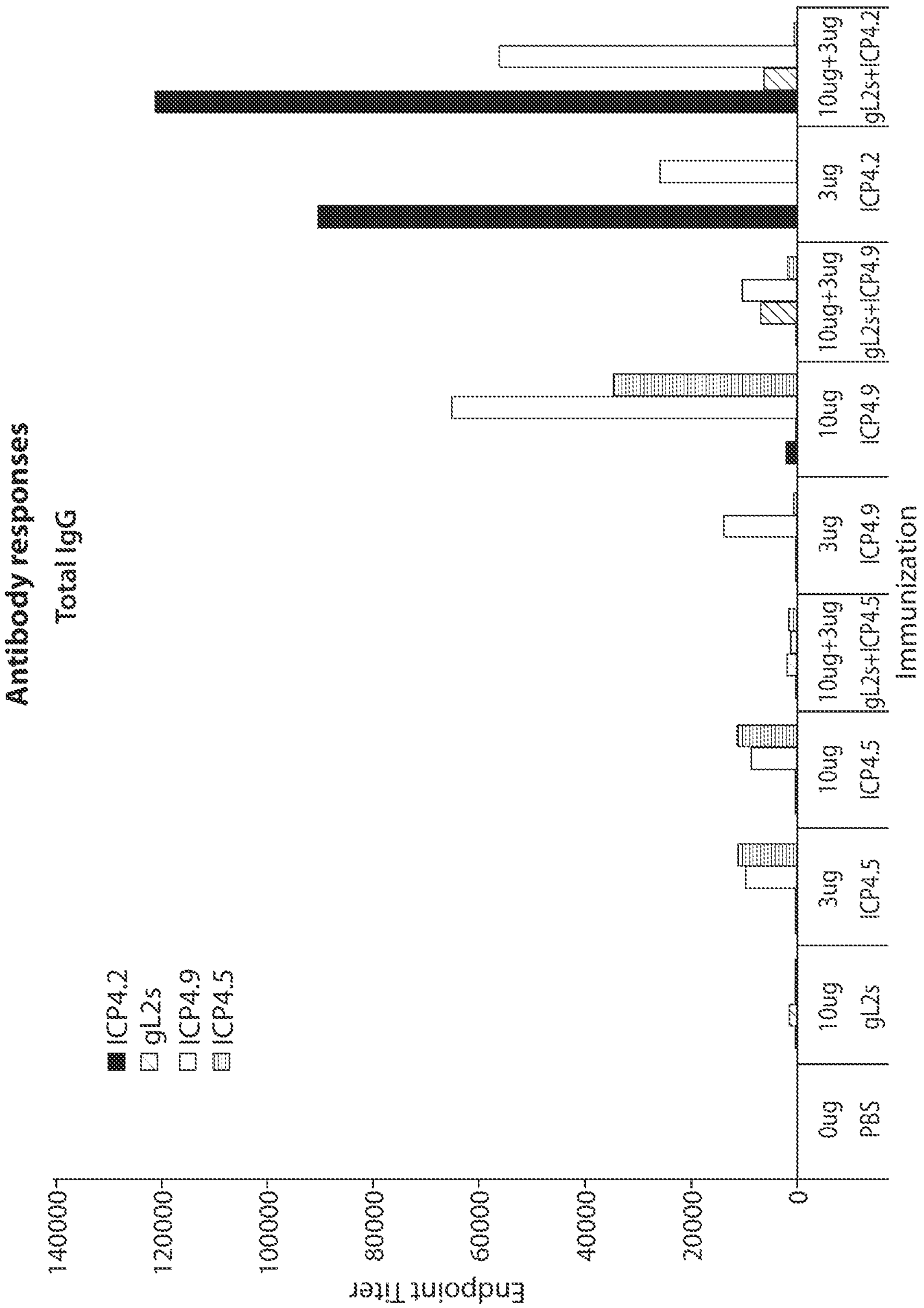
FIG. 7 depicts an exemplary graph illustrating antibody titers against gL2s v.2, ICP4.5, gL2s v.2 plus ICP4.5, ICP4.9, gL2s v.2 plus ICP4.9, ICP4.2, and gL2s v2 plus ICP4.2.

FIG. 7 depicts an exemplary graph illustrating antibody titers against gL2s v.2, ICP4.5, gL2s v.2 plus ICP4.5, ICP4.9, gL2s v.2 plus ICP4.9, ICP4.2, and gL2s v2 plus ICP4.2. Mice mounted strong antibody responses to ICP4.2, ICP4.9, and ICP4.5. Weak gL2s v.2-specific antibody responses were observed when this antigen was paired with each of the ICP4 fragments.

Example 3: In Vivo Data: Murine Prophylactic Vaccination Studies with Protein Antigen Plus DNA, and DNA Only Exemplary Studies 1 and 2. Immunization with gL2s v.2 Protein, pUs6 DNA (Encoding gD2), and pUL1 DNA (Encoding gL2) with gL2s v.2 Protein Boost Reduced Disease Symptoms and Mortality in C57BL/6 Mice In these studies, groups of C57BL/6 mice were immunized intramuscularly on day 0 and 21 with 10 μg of gL2s v.2 protein plus adjuvant (24 μg dose of an ISCOM matrix with a 91:9 mixture of *Quillaja saponin* matrix A and matrix C), or 100 μg of DNA plasmid encoding gD2 (pUs6) combined with 50 μg of DNA plasmid encoding murine IL-12 (pIL-12) as adjuvant. Another group received 100 μg of DNA plasmid encoding gL2 (pUL1) and 50 μg of pIL-12 as the prime immunization at day 0, and 10 μg of gL2s v.2 protein plus ISCOM adjuvant for the boost on day 21. Control animals received 50 μg of pIL-12 or ISCOM adjuvant only. Animals were challenged intravaginally with $10^4$ PFU HSV-2 strain 333 seven days after the last immunization. In some cases, a subset of unchallenged animals were euthanized on the day of challenge for immunogenicity experiments to monitor T cell and antibody responses to the vaccine (as described in Exemplary Studies 3 and 4 below). All challenged mice were monitored for morbidity (clinical score) and mortality, and body weights and vaginal swabs for viral shedding evaluation are collected between days 1 and 10 post-infection, as described above. Clinical scores were recorded and compared across experimental and control groups of mice.

Table 18 and Table 19 illustrate exemplary results of two separate prophylactic vaccination studies.

TABLE 18

Vaccination study 1: mouse protection results for gL2s v.2, pUs6 DNA, and pUL1 DNA with gL2s v.2 protein boost

| Groups (N = 8) | Mean Disease Score Day 14 | % Reduction | P value* | % Survival Day 14 |
|---|---|---|---|---|
| PBS + adjuvant | 4.75 | — | — | 13 |
| gL2s v.2 + adjuvant | 3.38 | 29 | 0.093 | 63 |
| pUs6 + pIL12 | 2.00 | 58 | 0.007 | 88 |
| pUL1 + pIL12/gL2s v.2 + adjuvant | 2.50 | 47 | 0.047 | 63 |

*one-sided Student's t test

Vaccination study 2: mouse protection results for gL2s v.2, pUs6 DNA, and pUL1 DNA plus gL2s v.2 boost

| Groups (N = 8) | Mean Disease Score Day 14 | % Reduction | P value* | % Survival Day 14 |
|---|---|---|---|---|
| PBS + adjuvant | 4.31 | — | — | 25 |
| gL2s v.2 + adjuvant | 3.44 | 20 | 0.238 | 50 |
| pIL12 | 4.75 | — | — | 25 |
| pUs6 + pIL12 | 2.13 | 55 | 0.010 | 88 |
| pUL1 + pIL12/gL2s v.2 + adjuvant | 2.94 | 38 | 0.075 | 63 |

*one-sided Student's t test

Exemplary Study 3. Immunogenicity of pRS1 DNA (Encoding ICP4); pUL1 DNA (Encoding gL2); pRS1 DNA (Encoding ICP4) Plus pUL1 DNA (Encoding gL2); gL2 Protein; and pUL1 DNA (Encoding gL2) with gL2s v.2 Protein Boost in C57BL/6 Mice C57BL/6 mice were immunized with plasmid DNA encoding gD2, ICP4 or gL2 along with plasmid DNA encoding IL-12 or gL2s v.2 protein with or without ISCOM adjuvant, as described in Exemplary Studies 1 and 2 above. Two groups were primed with plasmid DNA encoding gL2 and plasmid DNA encoding IL12 and boosted with gL2s v.2 protein. In addition, mice were immunized with a combination of gL2s v.2 protein and ICP4 plasmid DNA along with IL12 plasmid. Seven days post last immunizations, blood was collected to determine antigen-specific antibody titers by direct protein ELISA assays, as described below, and spleens were harvested for ex vivo IFN-γ ELISPOT assays. $CD4^+$ and $CD8^+$ T cells were enriched using antibody-coated magnetic beads and then co-cultured on IFN-γ-specific antibody-coated membranes in 96-well plates. APCs were naïve splenocytes pulsed with pools of overlapping peptides spanning indicated proteins and irradiated with an x-ray irradiator. After 18 hour co-culture of T cells and APCs, captured IFN-γ was detected with a biotinylated secondary IFN-γ-specific antibody and visualized with horseradish peroxidase and 3-amino-9-ethylcarbazole substrate. Data are reported as the number of IFN-γ spot forming units per $2\times10^5$ T cells±standard deviation of three mice per group.

Antigen-specific serum antibody titers of immunized mice were determined by direct protein ELISA. The sera were processed from blood collected above and stored at −80° C. ELISA plates were coated overnight at 4° C. with 5 μg of whole protein in 0.1 M carbonate buffer, pH 9.5. Plates were washed with TBS+0.05% Tween-20 (TBS-T) and blocked with TBS-T+1% bovine serum albumin for 1 h. Serum samples were serially diluted and incubated in the antigen-coated wells for 2 hours at room temperature. Plates were washed and probed for 1 h with goat anti-mouse alkaline-phosphatase (AP)-conjugated anti-IgG at a 1:10,000 dilution. Detection of AP activity was achieved by the addition of p-Nitrophenyl phosphate (pNPP; Sigmafast, Sigma-Aldrich), and the reaction stopped with 3N NaOH and absorbance read at 405 nm. Endpoint titers were calculated by extrapolation of the linear portion of the serial dilutions and defining the endpoint as the dilution at which the linear portion of the curve intersects with the background cut-off. The cut-off used for data calculation was 2 times the value of the negative control serum from a naïve mouse.

Figure 8A:
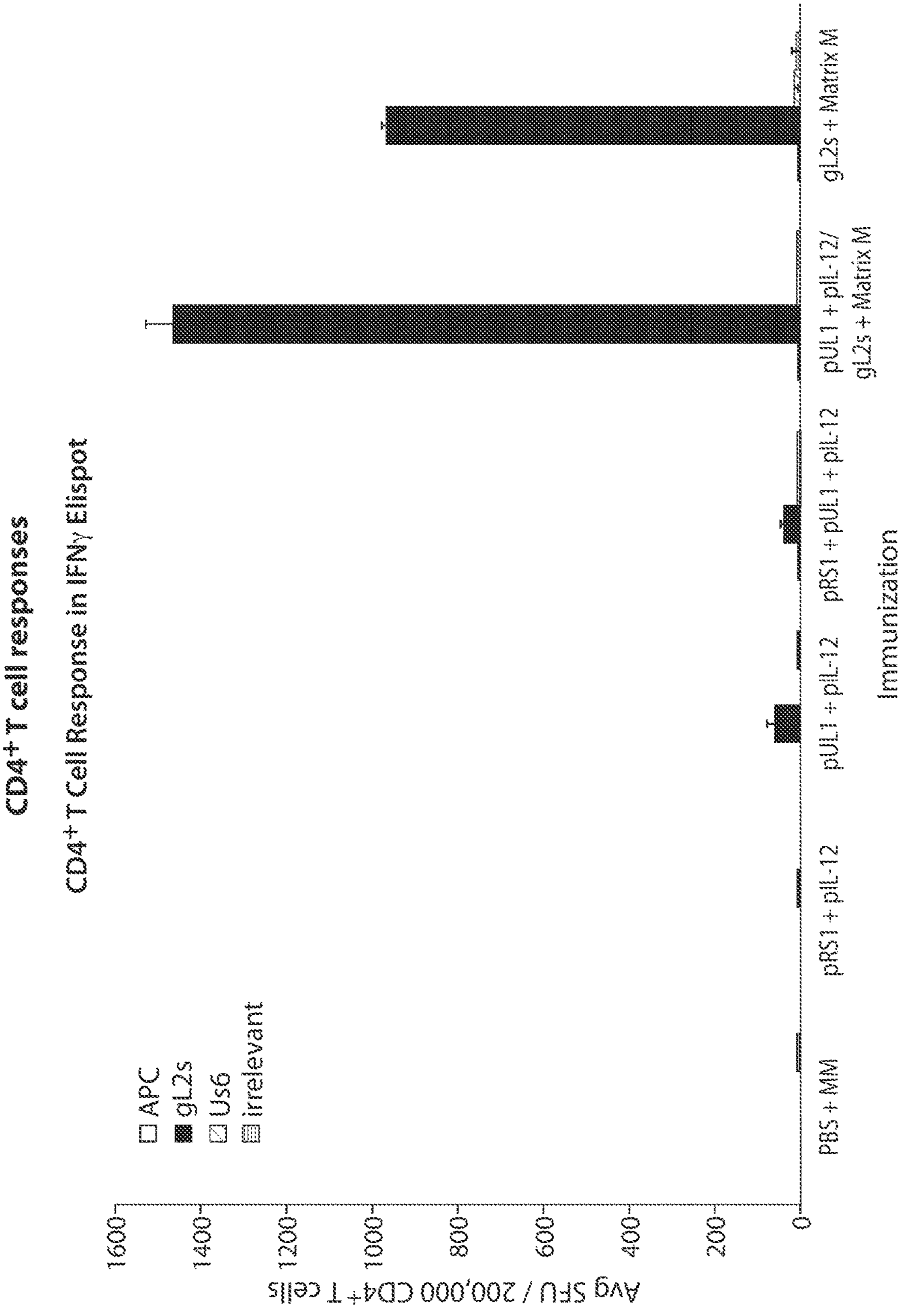
FIGS. 8A and B depict exemplary graphs illustrating the average number of IFN-γ spot forming units per $2\times10^5$ $CD4^+$ (Panel A) or $CD8^+$ (Panel B) T cells, following immunization with pRS1 DNA (encoding ICP4); pUL1 DNA (encoding gL2); pRS1 DNA (encoding ICP4) plus pUL1 DNA (encoding gL2); pUL1 DNA (encoding gL2) with gL2s v.2 protein boost; and gL2s v.2 protein.
Figure 8B:
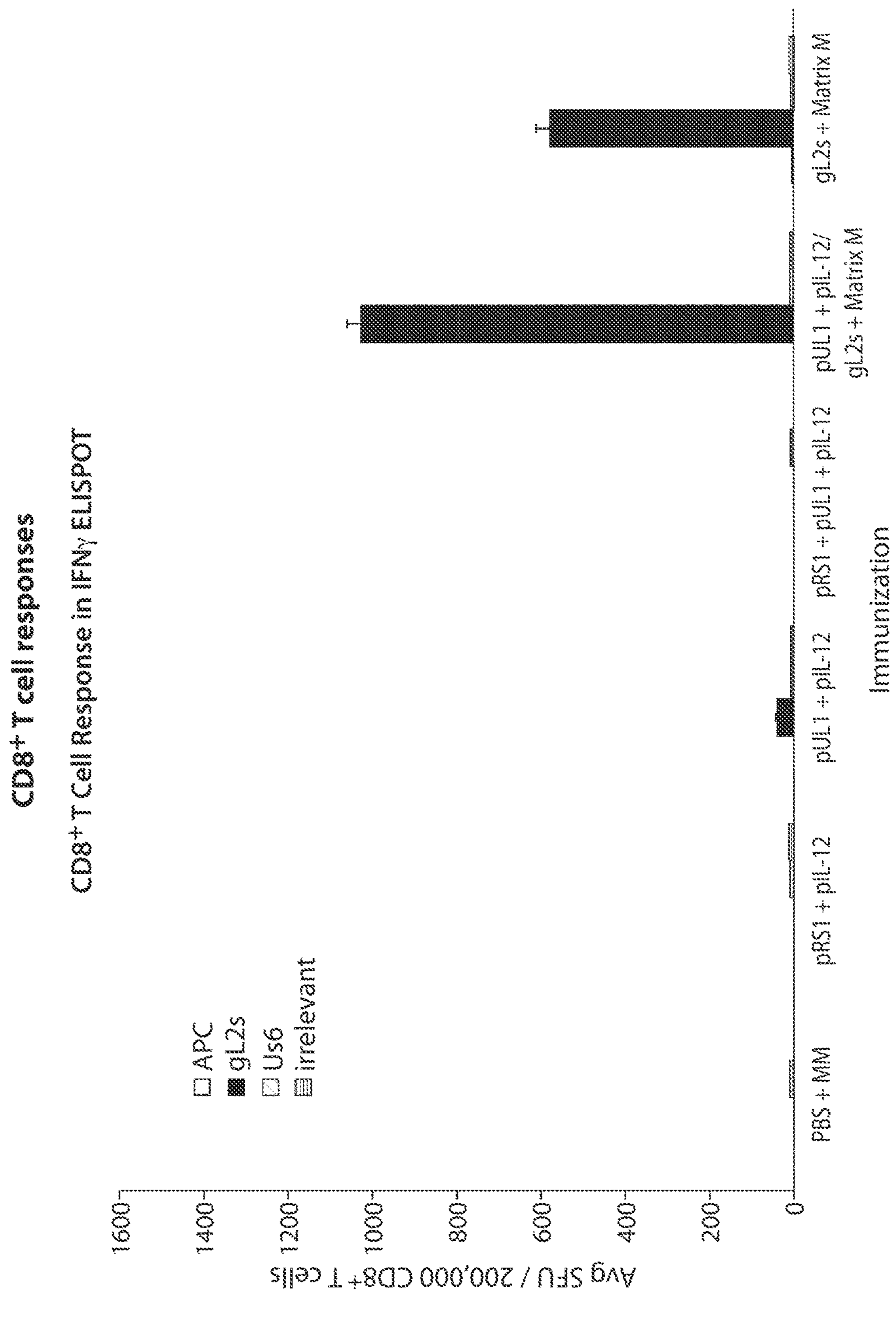

FIGS. 8A and B depict exemplary graphs illustrating the average number of IFN-γ spot forming units per $2\times10^5$ CD4 (Panel A) or CD8 (Panel B) T cells, following immunization with pRS1 DNA (encoding ICP4); pUL1 DNA (encoding gL2); pRS1 DNA (encoding ICP4) plus pUL1 DNA (encoding gL2); pUL1 DNA (encoding gL2) with gL2s v.2 protein boost; and gL2s v.2 protein. Strong gL2- or gL2s v.2-specific T cell response was observed in mice that received gL2s v.2 protein with ISCOM adjuvant for prime and boost immunizations. Even stronger response was observed in mice that were primed with pUL1 and pIL-12 DNA and boosted with gL2s v.2 protein. Weak T cell response was observed when pUL1 DNA was used for priming and boost. Very low levels of ICP4-specific T cells were detected.

Figure 9:
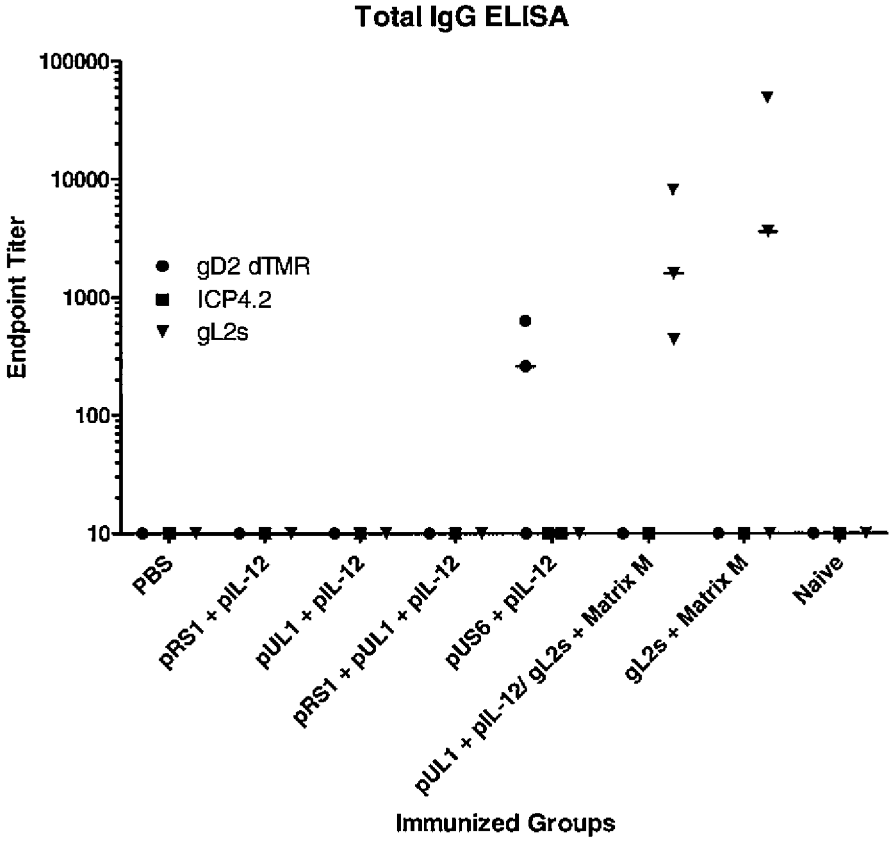
FIG. 9 depicts an exemplary graph illustrating total IgG antibody titers against ICP4.2 and gL2s v.2 (also gD2ΔTMR).

FIG. 9 depicts an exemplary graph illustrating total IgG antibody titers against ICP4.2 and gL2s v.2 (also gD2ΔTMR). Prime and/or boost with gL2s v.2 protein was required for development of gL2s v.2-specific antibodies.

Exemplary Study 4. Immunogenicity of gL2s v.2 Protein; pUL1 DNA (Encoding gL2); pUL1 DNA (Encoding gL2) with gL2s v.2 Protein Boost; pRS1 DNA (Encoding ICP4); pRS1 DNA (Encoding ICP4) Plus pUL1 DNA (Encoding gL2); and pUs6 DNA (Encoding gD2) in C57BL/6 Mice C57BL/6 mice were immunized as described in Exemplary Studies 1 and 2 above with gL2s v.2 protein plus adjuvant; pUL1 DNA (encoding gL2); pUL1 DNA (encoding gL2) with gL2s v.2 protein plus adjuvant boost; pRS1 DNA (encoding ICP4); pRS1 DNA (encoding ICP4) plus pUL1 DNA (encoding gL2); and pUs6 DNA (encoding gD2). Seven days post last immunization, spleens were harvested for ex vivo IFN-γ ELISPOT assays as described in Exemplary Study 3 above.

Figure 10A:
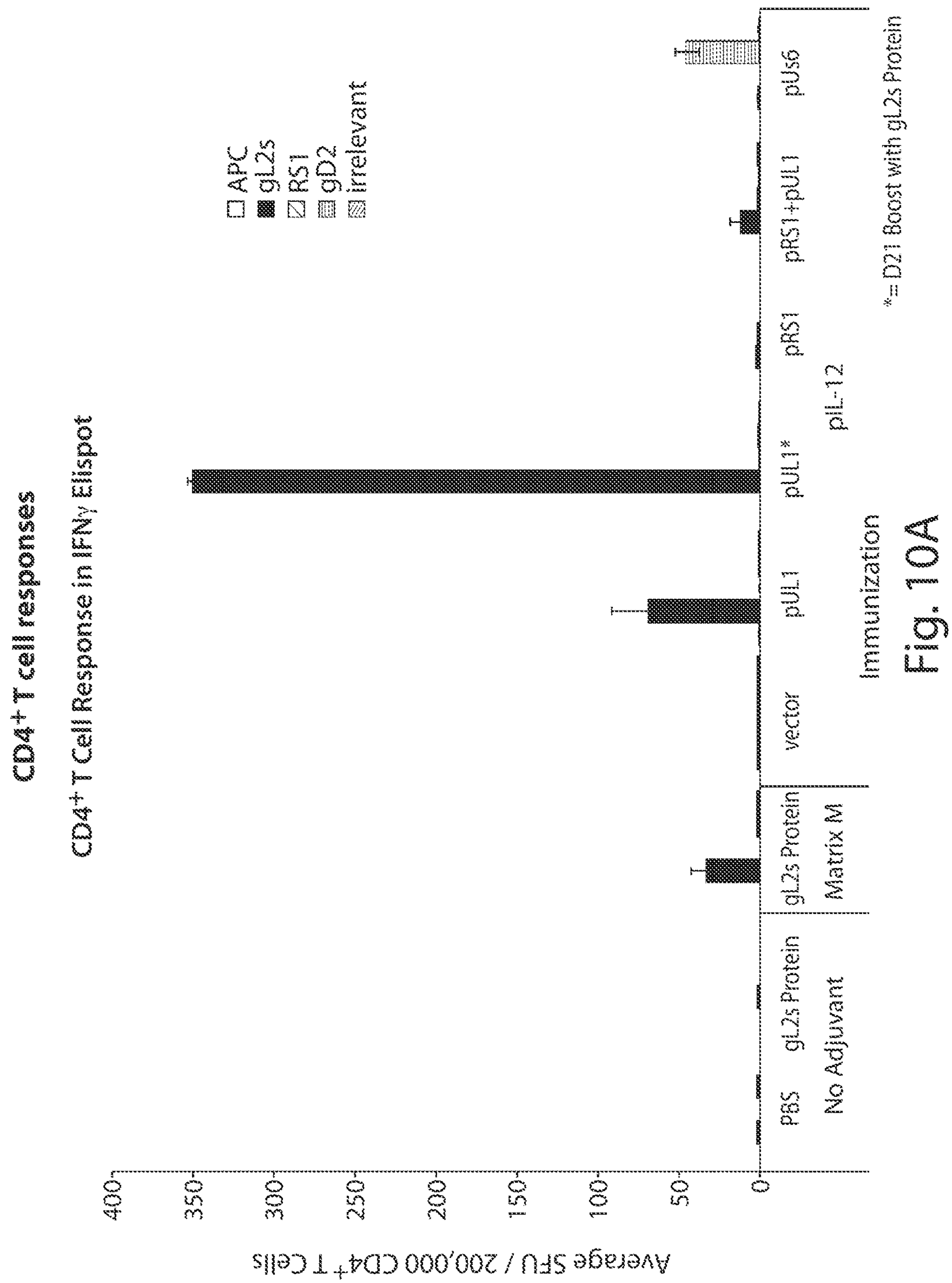
FIGS. 10A and B depict exemplary graphs illustrating the number of IFN-γ spot forming units per $2\times10^5$ $CD4^+$ (Panel A) or $CD8^+$ (Panel B) T cells, following immunization with gL2s v.2 protein; pUL1 DNA (encoding gL2); pUL1 DNA (encoding gL2) with gL2s v.2 protein boost; pRS1 DNA (encoding ICP4); pRS1 DNA (encoding ICP4) plus pUL1 DNA (encoding gL2); and pUs6 DNA (encoding gD2).
Figure 10B:
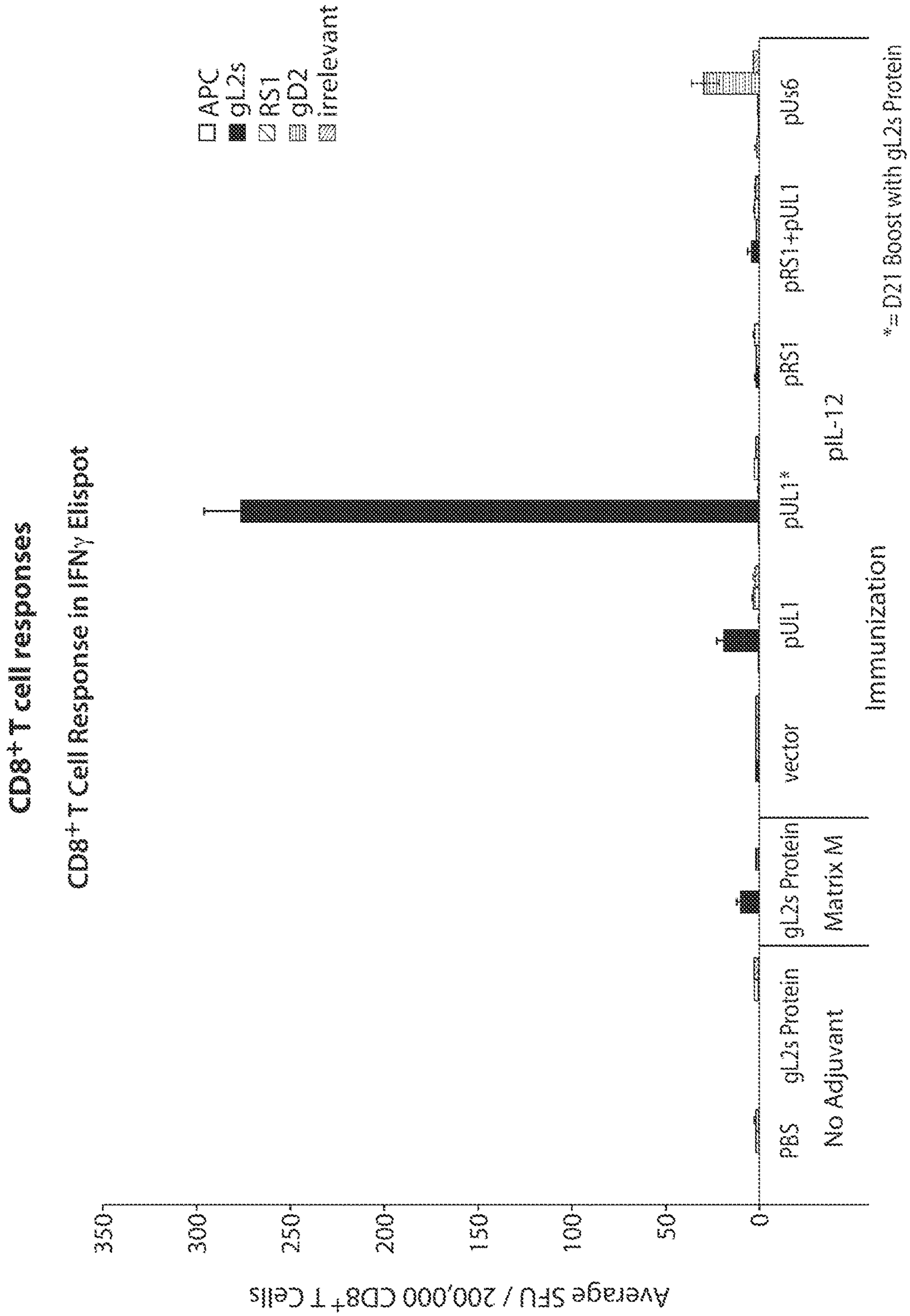

FIGS. 10A and B depict exemplary graphs illustrating the number of IFN-γ spot forming units per $2\times10^5$ CD4 (Panel A) or $CD8^+$ (Panel B) T cells, following immunization with gL2s v.2 protein; pUL1 DNA (encoding gL2); pUL1 DNA (encoding gL2) with gL2s v.2 protein boost; pRS1 DNA (encoding ICP4); pRS1 DNA (encoding ICP4) plus pUL1 DNA (encoding gL2); and pUs6 DNA (encoding gD2). Strong gL2- or gL2s v.2-specific T cell response was observed in mice that received gL2s v.2 protein with ISCOM adjuvant or mice that received pUL1 and pIL12 DNA plasmid for prime and boost immunizations. The response was augmented further in mice that were primed with pUL1 and pIL-12 DNA plasmids, then boosted with gL2s v.2 protein plus ISCOM adjuvant.

Exemplary Study 5. Immunogenicity of pRS1 DNA (Encoding ICP4), pRS1.9 DNA (Encoding ICP4.9), and pUs4 DNA (Encoding gG2) with Corresponding DNA Boost; pRS1 DNA (Encoding ICP4), pRS1.9 DNA (Encoding ICP4.9), and pUs4 DNA (Encoding gG2) with ICP4.2 Boost C57BL/6 mice were immunized as described in Exemplary Studies 1 and 2 above with plasmid DNA encoding ICP4, ICP4.9, gG2 or empty plasmid in combination with a plasmid encoding mouse IL-12. Mice were then divided into three groups. Mice of the first group were boosted on day 21 the same way they were primed. Mice of the second group were boosted on day 21 with ICP4.2 protein plus ISCOM adjuvant. Mice of the third group were boosted on days 21 and 35 the same way they were primed. Seven days post last immunization, spleens were harvested for ex vivo IFN-γ ELISPOT assays as described in Exemplary Study 3 above.

Figure 11:
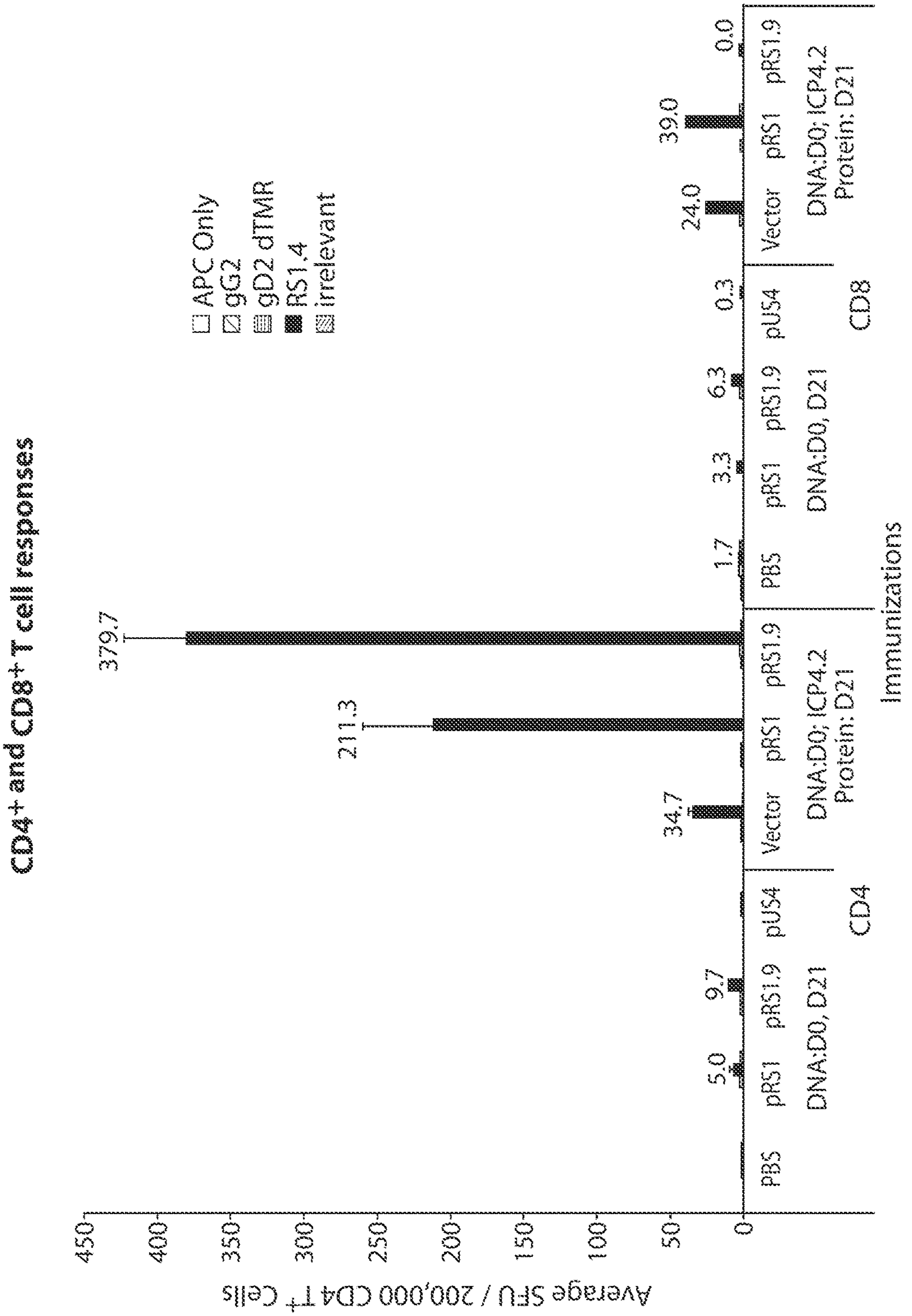
FIG. 11 depicts an exemplary graph illustrating the number of IFN-γ spot forming units per $2\times10^5$ $CD4^+$ (left panel) or $CD8^+$ (right panel) T cells, following immunization with pRS1 DNA (encoding ICP4), pRS1.9 DNA (encoding ICP4.9), and pUs4 DNA (encoding gG2) with corresponding DNA boost (first group of mice) or with ICP4.2 protein boost (second group of mice) on day 21.

FIG. 11 depicts an exemplary graph illustrating the number of IFN-γ spot forming units per $2\times10^5$ CD4 (left panel) or $CD8^+$ (right panel) T cells, following immunization with pRS1 DNA (encoding ICP4), pRS1.9 DNA (encoding ICP4.9), and pUs4 DNA (encoding gG2) with corresponding DNA boost (first group of mice) or with ICP4.2 protein boost (second group of mice) on day 21. Strong ICP4.2-specific T cell response was observed in mice primed with pRS1 or pRS1.9 DNA, then boosted with ICP4.2 protein plus ISCOM adjuvant.

Figure 12:
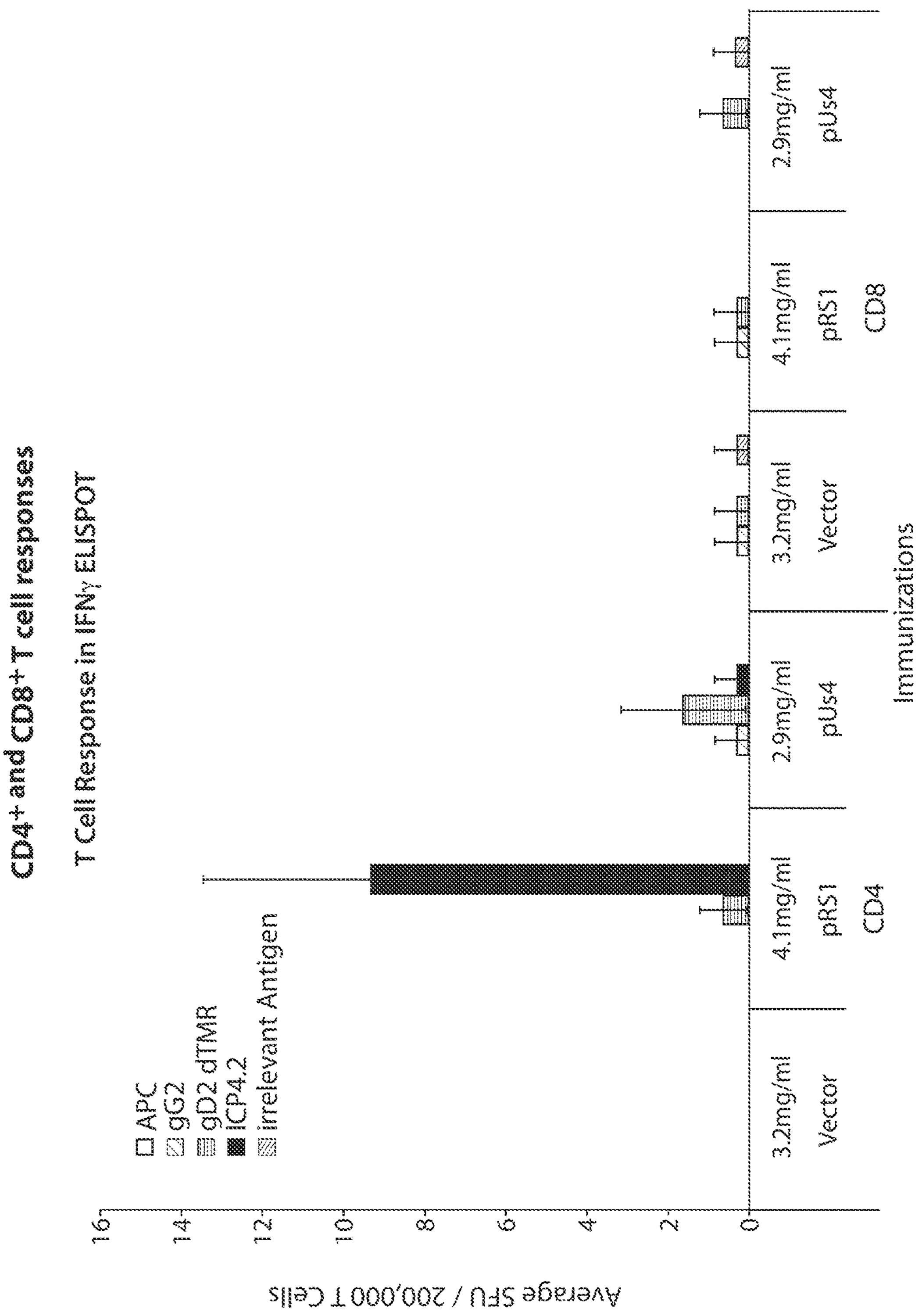
FIG. 12 depicts an exemplary graph illustrating the number of IFN-γ spot forming units per $2\times10^5$ $CD4^+$ (left panel) or $CD8^+$ (right panel) T cells, following immunization with pRS1 DNA (encoding ICP4) and pUs4 DNA (encoding gG2) with corresponding DNA boosts on days 21 and 35 (third group of mice).

FIG. 12 depicts an exemplary graph illustrating the number of IFN-γ spot forming units per $2\times10^5$ CD4 (left panel) or $CD8^+$ (right panel) T cells, following immunization with pRS1 DNA (encoding ICP4) and pUs4 DNA (encoding gG2) with corresponding DNA boosts on days 21 and 35 (third group of mice).

SEQUENCES

```
SEQ ID NO: 1 = ICP4
              SAEQRKKKKTTTTTQGRGAEVAMADEDGGRLRAAAETTGGPGSPDPADGPPPTPNPDRRPAARPGF

GWHGGPEENEDEADDAAADADADEAAPASGEAVDEPAADGVVSPRQLALLASMVDEAVRTIPSPPPERDGAQEEAAR

SPSPPRTPSMRADYGEENDDDDDDDDDDDRDAGRWVRGPETTSAVRGAYPDPMASLSPRPPAPRRHHHHHHRRRRA

PRRRSAASDSSKSGSSSSASSASSSASSSSSASASSSDDDDDDDAARAPASAADHAAGGTLGADDEEAGVPARAPGA
```

-continued

APRPSPPRAEPAPARTPAATAGRLERRRARAAVAGRDATGRFTAGRPRRVELDADAASGAFYARYRDGYVSGEPWPG

AGPPPPGRVLYGGLGDSRPGLWGAPEAEEARARFEASGAPAPVWAPELGDAAQQYALITRLLYTPDAEAMGWLQNPR

VAPGDVALDQACFRISGAARNSSSFISGSVARAVPHLGYAMAAGRFGWGLAHVAAAVAMSRRYDRAQKGFLLTSLRR

AYAPLLARENAALTGARTPDDGGDANRHDGDDARGKPAAAAAPLPSAAASPADERAVPAGYGAAGVLAALGRLSAAP

ASAPAGADDDDDDDGAGGGGGGRRAEAGRVAVECLAACRGILEALAEGFDGDLAAVPGLAGARPAAPPRPGPAGAAA

PPHADAPRLRAWLRELRFVRDALVLMRLRGDLRVAGGSEAAVAAVRAVSLVAGALGPALPRSPRLLSSAAAAAADLL

FQNQSLRPLLADTVAAADSLAAPASAPREARKRKSPAPARAPPGGAPRPPKKSRADAPRPAAAPPAGAAPPAPPTPP

PRPPRPAALTRRPAEGPDPQGGWRRQPPGPSHTPAPSAAALEAYCAPRAVAELTDHPLFPAPWRPALMFDPRALASL

AARCAAPPPGGAPAAFGPLRASGPLRRAAAWMRQVPDPEDVRVVILYSPLPGEDLAAGRAGGGPPPEWSAERGGLSC

LLAALGNRLCGPATAAWAGNWTGAPDVSALGAQGVLLLSTRDLAFAGAVEFLGLLAGACDRRLIVVNAVRAADWPAD

GPVVSRQHAYLACEVLPAVQCAVRWPAARDLRRTVLASGRVFGPGVFARVEAAHARLYPDAPPLRLCRGANVRYRVR

TRFGPDTLVPMSPREYRRAVLPALDGRAAASGAGDAMAPGAPDFCEDEAHSHRACARWGLGAPLRPVYVALGRDAVR

GGPAELRGPRREFCARALLEPDGDAPPLVLRDDADAGPPPQIRWASAAGRAGTVLAAAGGGVEVVGTAAGLATPPRR

EPVDMDAELEDDDDGLFGE

SEQ ID NO: 2 = ICP4 internal fragment (ICP4.2) encoded by construct RS1.2
MVLYGGLGDSRPGLWGAPEAEEARARFEASGAPAPVWAPELGDAAQQYALITRLLYTPDAEAMGWLQ

NPRVAPGDVALDQACFRISGAARNSSSFISGSVARAVPHLGYAMAAGRFGWGLAHVAAAVAMSRRYDRAQKGFLLTS

LRRAYAPLLARENAALTGARTPDDGGDANRRDGDDARGKPAAAAAPLPSAAASPADERAVPAGYGAAGVLAALGRLS

AAPASAPAGADDDDDDDGAGGGGGGGGGGGRRAEAGRVAVECLAACRGILEALAEGFDGDLAAVPGLAGARPAAP

PRPGPAGAAAPPHADAPRLRAWLRELRFVRDALVLMRLRGDLRVAGGSEAAVAAVRAVSLVAGALGPALPRSPRLLS

SAAAAAADLLFQNQSL

SEQ ID NO: 3 = gL2 cytoplasmic
MGFVCLFGLVVMGAWGAWGGSQATEYVLRSVIAKEVGDILRVPCMRTPADDVSWRYEAPSVIDYARI

DGIFLRYHCPGLDTFLWDRHAQRAYLVNPFLFAAGFLEDLSHSVFPADTQETTTRRALYKEIRDALGSRKQAVSHAP

VRAGCVNFDYSRTRRCVGRRDLRPANTTSTWEPPVSSDDEASSQSKPLATQPPVLALSNAPPRRVSPTRGRRRHTRL

RRN

SEQ ID NO: 4 = gD2 internal deletion dD2ΔTMR encoded by construct US6ΔTMR
NRWKYALADPSLKMADPNRFRGKNLPVLDQLTDPPGVKRVYHIQPSLEDPFQPPSI

PITVYYAVLERACRSVLLHAPSEAPQIVRGASDEARKHTYNLTIAWYRMGDNCAIPITVMEYTECPYNKSLGVCPIR

TQPRWSYYDSFSAVSEDNLGFLMHAPAFETAGTYLRLVKINDWTEITQFILEHRARASCKYALPLRIPPAACLTSKA

YQQGVTVDSIGMLPRFIPENQRTVALYSLKIAGWHGPKPPYTSTLLPPELSDTTNATQPELVPEDPEDSALLEDPAG

TVSSQIPPNWHIPSIQDVAPHHAPAAPSNPRRRAQMAPKRLRLPHIRDDDAPPSHQPLFY

SEQ ID NO: 5 = predicted sequence for gD2 encoded by US6
MGRLTSGVGTAALLVVAVGLRVVCAKYALADPSLKMADPNRFRGKNLPVLDQLTDPPGVKRVYHIQPSLEDPFQPPS

IPITVYYAVLERACRSVLLHAPSEAPQIVRGASDEARKHTYNLTIAWYRMGDNCAIPITVMEYTECPYNKSLGVCPI

RTQPRWSYYDSFSAVSEDNLGFLMHAPAFETAGTYLRLVKINDWTEITQFILEHRARASCKYALPLRIPPAACLTSK

AYQQGVTVDSIGMLPRFIPENQRTVALYSLKIAGWHGPKPPYTSTLLPPELSDTTNATQPELVPEDPEDSALLEDPA

GTVSSQIPPNWHIPSIQDVAPHHAPAAPSNPGLIIGALAGSTLAVLVIGGIAFWVRRRAQMAPKRLRLPHIRDDDAP

PSHQPLFY

SEQ ID NO: 6 = ICP34.5 encoded by RL1
MSRRRGPRRRGPRRRPRPGAPAVPRPGAPAVPRPGALPTADSQMVPAYDSGTAVESAPAASSLLRRWLLVPQADDSD

DADYAGNDDAEWANSPPSEGGGKAPEAPHAAPAAACPPPPPRKERGPQRPLPPHLALRLRTTTEYLARLSLRRRRPP

ASPPADAPRGKVCFSPRVQVRHLVAWETAARLARRGSWARERADRDRFRRRVAAAEAVIGPCLEPEARARARARARA

-continued

HEDGGPAEEEEAAAAARGSSAAAGPGRRAV

SEQ ID NO: 7 = ICP0 encoded by RL2
MEPRPGTSSRADPGPERPPRQTPGTQPAAPHAWGMLNDMQWLASSDSEEETEVGISDDDLHRDSTSE

AGSTDTEMFEAGLMDAATPPARPPAERQGSPTPADAQGSCGGGPVGEEEAEAGGGGDVCAVCTDEIAPPLRCQSFPC

LHPFCIPCMKTWIPLRNTCPLCNTPVAYLIVGVTASGSFSTIPIVNDPRTRVEAEAAVRAGTAVDFIWTGNPRTAPR

SLSLGGHTVRALSPTPPWPGTDDEDDDLADVDYVPPAPRRAPRRGGGGAGATRGTSQPAATRPAPPGAPRSSSSGGA

PLRAGVGSGSGGGPAVAAVVPRVASLPPAAGGGRAQARRVGEDAAAAEGRTPPARQPRAAQEPPIVISDSPPPSPRR

PAGPGPLSFVSSSSAQVSSGPGGGGLPQSSGRAARPRAAVAPRVRSPPRAAAAPVVSASADAAGPAPPAVPVDAHRA

PRSRMTQAQTDTQAQSLGRAGATDARGSGGPGAEGGPGVPRGTNTPGAAPHAAEGAAARPRKRRGSDSGPAASSSAS

SSAAPRSPLAPQGVGAKRAAPRRAPDSDSGDRGHGPLAPASAGAAPPSASPSSQAAVAAASSSSASSSSASSSSASS

SSASSSSASSSSASSSSASSSAGGAGGSVASASGAGERRETSLGPRAAAPRGPRKCARKTRHAEGGPEPGARDPAPG

LTRYLPIAGVSSVVALAPYVNKTVTGDCLPVLDMETGHIGAYVVLVDQTGNVADLLRAAAPAWSRRTLLPEHARNCV

RPPDYPTPPASEWNSLWMTPVGNMLFDQGTLVGALDFHGLRSRHPWSREQGAPAPAGDAPAGHGE

SEQ ID NO: 8 = ICP4 internal fragment encoded by construct RS1.1 (#1-400)
MSAEQRKKKKTTTTTQGRGAEVAMADEDGGRLRAAAETTGGPGSPDPADGPPPTPNPDRRPAARPGFGWHGGPEENE

DEADDAAADADADEAAPASGEAVDEPAADGVVSPRQLALLASMVDEAVRTIPSPPPERDGAQEEAARSPSPPRTPSM

RADYGEENDDDDDDDDDDDRDAGRWVRGPETTSAVRGAYPDPMASLSPRPPAPRRHHHHHHHRRRRAPRRRSAASDS

SKSGSSSSASSASSSASSSSSASASSSDDDDDDDAARAPASAADHAAGGTLGADDEEAGVPARAPGAAPRPSPPRAE

PAPARTPAATAGRLERRRARAAVAGRDATGRFTAGRPRRVELDADAASGAFYARYRDGYVSGEPWPGAGPPPPGRVL

YGGLGDSRPGLWGAP

SEQ ID NO: 9 = ICP4 internal fragment encoded by construct RS1.3.1 (#750-1024)
SSAAAAAADLLFQNQSLRPLLADTVAAADSLAAPASAPREARKRKSPAPARAPPGGAPRPPKKSRADAPRPAAAPPA

GAAPPAPPTPPPRPPRPAALTRRPAEGPDPQGGWRRQPPGPSHTPAPSAAALEAYCAPRAVAELTDHPLFPAPWRPA

LMFDPRALASLAARCAAPPPGGAPAAFGPLRASGPLRRAAAWMRQVPDPEDVRVVILYSPLPGEDLAAGRAGGGPPP

EWSAERGGLSCLLAALGNRLCGPATAAWAGNWTGAPDVSALGAQ

SEQ ID NO: 10 = ICP4 internal fragment encoded by construct RS1.3.2 (#1008-1319)
WAGNWTGAPDVSALGAQGVLLLSTRDLAFAGAVEFLGLLAGACDRRLIVVNAVRAADWPADGPVVSRQHAYLACEVL

PAVQCAVRWPAARDLRRTVLASGRVFGPGVFARVEAAHARLYPDAPPLRLCRGANVRYRVRTRFGPDTLVPMSPREY

RRAVLPALDGRAAASGAGDAMAPGAPDFCEDEAHSHRACARWGLGAPLRPVYVALGRDAVRGGPAELRGPRREFCAR

ALLEPDGDAPPLVLRDDADAGPPPQIRWASAAGRAGTVLAAAGGGVEVVGTAAGLATPPRREPVDMDAELEDDDDGL

FGE

SEQ ID NO: 11 = ICP4 internal fragment encoded by construct RS1.3 (#750-1319)
SSAAAAAADLLFQNQSLRPLLADTVAAADSLAAPASAPREARKRKSPAPARAPPGGAPRPPKKSRADAPRPAAAPPA

GAAPPAPPTPPPRPPRPAALTRRPAEGPDPQGGWRRQPPGPSHTPAPSAAALEAYCAPRAVAELTDHPLFPAPWRPA

LMFDPRALASLAARCAAPPPGGAPAAFGPLRASGPLRRAAAWMRQVPDPEDVRVVILYSPLPGEDLAAGRAGGGPPP

EWSAERGGLSCLLAALGNRLCGPATAAWAGNWTGAPDVSALGAQGVLLLSTRDLAFAGAVEFLGLLAGACDRRLIVV

NAVRAADWPADGPVVSRQHAYLACEVLPAVQCAVRWPAARDLRRTVLASGRVFGPGVFARVEAAHARLYPDAPPLRL

CRGANVRYRVRTRFGPDTLVPMSPREYRRAVLPALDGRAAASGAGDAMAPGAPDFCEDEAHSHRACARWGLGAPLRP

VYVALGRDAVRGGPAELRGPRREFCARALLEPDGDAPPLVLRDDADAGPPPQIRWASAAGRAGTVLAAAGGGVEVVG

TAAGLATPPRREPVDMDAELEDDDDGLFGE

SEQ ID NO: 12 = ICP4 internal fragment encoded by construct RS1.4 (#341-883)
TAGRPRRVELDADAASGAFYARYRDGYVSGEPWPGAGPPPPGRVLYGGLGDSRPGLWGAPEAEEARARFEASGAPAP

VWAPELGDAAQQYALITRLLYTPDAEAMGWLQNPRVAPGDVALDQACFRISGAARNSSSFISGSVARAVPHLGYAMA

AGRFGWGLAHVAAAVAMSRRYDRAQKGFLLTSLRRAYAPLLARENAALTGARTPDDGGDANRHDGDDARGKPAAAAA

-continued

PLPSAAASPADERAVPAGYGAAGVLAALGRLSAAPASAPAGADDDDDDGAGGGGGGRRAEAGRVAVECLAACRGIL

EALAEGFDGDLAAVPGLAGARPAAPPRPGPAGAAAPPHADAPRLRAWLRELRFVRDALVLMRLRGDLRVAGGSEAAV

AAVRAVSLVAGALGPALPRSPRLLSSAAAAAADLLFQNQSLRPLLADTVAAADSLAAPASAPREARKRKSPAPARAP

PGGAPRPPKKSRADAPRPAAAPPAGAAPPAPPTPPPRPPRPAALTRRPAEGPDPQGGWRRQPPGPSHTPAPSAAALE

AYCA

SEQ ID NO: 13 = ICP4 internal fragment encoded by construct RS1.5 (#775-1318)
AAADSLAAPASAPREARKRKSPAPARAPPGGAPRPPKKSRADAPRPAAAPPAGAAPPAPPTPPPRPPRPAALTRRPA

EGPDPQGGWRRQPPGPSHTPAPSAAALEAYCAPRAVAELTDHPLFPAPWRPALMFDPRALASLAARCAAPPPGGAPA

AFGPLRASGPLRRAAAWMRQVPDPEDVRVVILYSPLPGEDLAAGRAGGGPPPEWSAERGGLSCLLAALGNRLCGPAT

AAWAGNWTGAPDVSALGAQGVLLLSTRDLAFAGAVEFLGLLAGACDRRLIVVNAVRAADWPADGPVVSRQHAYLACE

VLPAVQCAVRWPAARDLRRTVLASGRVFGPGVFARVEAAHARLYPDAPPLRLCRGANVRYRVRTRFGPDTLVPMSPR

EYRRAVLPALDGRAAASGAGDAMAPGAPDFCEDEAHSHRACARWGLGAPLRPVYVALGRDAVRGGPAELRGPRREFC

ARALLEPDGDAPPLVLRDDADAGPPPQIRWASAAGRAGTVLAAAGGGVEVVGTAAGLATPPRREPVDMDAELEDDDD

GLFGE

SEQ ID NO: 14 = ICP4 internal fragment encoded by construct RS1.6 (#210-1318)
HHHHHHHRRRRAPRRRSAASDSSKSGSSSSASSASSSASSSSSASASSSDDDDDDDAARAPASAADHAAGGTLGADD

EEAGVPARAPGAAPRPSPPRAEPAPARTPAATAGRLERRRARAAVAGRDATGRFTAGRPRRVELDADAASGAFYARY

RDGYVSGEPWPGAGPPPPGRVLYGGLGDSRPGLWGAPEAEEARARFEASGAPAPVWAPELGDAAQQYALITRLLYTP

DAEAMGWLQNPRVAPGDVALDQACFRISGAARNSSSFISGSVARAVPHLGYAMAAGRFGWGLAHVAAAVAMSRRYDR

AQKGFLLTSLRRAYAPLLARENAALTGARTPDDGGDANRHDGDDARGKPAAAAAPLPSAAASPADERAVPAGYGAAG

VLAALGRLSAAPASAPAGADDDDDDGAGGGGGGRRAEAGRVAVECLAACRGILEALAEGFDGDLAAVPGLAGARPA

APPRPGPAGAAAPPHADAPRLRAWLRELRFVRDALVLMRLRGDLRVAGGSEAAVAAVRAVSLVAGALGPALPRSPRL

LSSAAAAAADLLFQNQSLRPLLADTVAAADSLAAPASAPREARKRKSPAPARAPPGGAPRPPKKSRADAPRPAAAPP

AGAAPPAPPTPPPRPPRPAALTRRPAEGPDPQGGWRRQPPGPSHTPAPSAAALEAYCAPRAVAELTDHPLFPAPWRP

ALMFDPRALASLAARCAAPPPGGAPAAFGPLRASGPLRRAAAWMRQVPDPEDVRVVILYSPLPGEDLAAGRAGGGPP

PEWSAERGGLSCLLAALGNRLCGPATAAWAGNWTGAPDVSALGAQGVLLLSTRDLAFAGAVEFLGLLAGACDRRLIV

VNAVRAADWPADGPVVSRQHAYLACEVLPAVQCAVRWPAARDLRRTVLASGRVFGPGVFARVEAAHARLYPDAPPLR

LCRGANVRYRVRTRFGPDTLVPMSPREYRRAVLPALDGRAAASGAGDAMAPGAPDFCEDEAHSHRACARWGLGAPLR

PVYVALGRDAVRGGPAELRGPRREFCARALLEPDGDAPPLVLRDDADAGPPPQIRWASAAGRAGTVLAAAGGGVEVV

GTAAGLATPPRREPVDMDAELEDDDDGLFGE

SEQ ID NO: 15 = ICP4 internal fragment encoded by construct RS1.7 (deletion of #391-544)
MSAEQRKKKKTTTTTQGRGAEVAMADEDGGRLRAAAETTGGPGSPDPADGPPPTPNPDRRPAARPGFGWHGGPEENE

DEADDAAADADADEAAPASGEAVDEPAADGVVSPRQLALLASMVDEAVRTIPSPPPERDGAQEEAARSPSPPRTPSM

RADYGEENDDDDDDDDDDDRDAGRWVRGPETTSAVRGAYPDPMASLSPRPPAPRRHHHHHHHRRRRAPRRRSAASDS

SKSGSSSSASSASSSASSSSSASASSSDDDDDDDAARAPASAADHAAGGTLGADDEEAGVPARAPGAAPRPSPPRAE

PAPARTPAATAGRLERRRARAAVAGRDATGRFTAGRPRRVELDADAASGAFYARYRDGYVSGEPWPGAGPPPPGRVL

YGGLGARTPDDGGDANRHDGDDARGKPAAAAAPLPSAAASPADERAVPAGYGAAGVLAALGRLSAAPASAPAGADDD

DDDGAGGGGGGRRAEAGRVAVECLAACRGILEALAEGFDGDLAAVPGLAGARPAAPPRPGPAGAAAPPHADAPRLR

AWLRELRFVRDALVLMRLRGDLRVAGGSEAAVAAVRAVSLVAGALGPALPRSPRLLSSAAAAAADLLFQNQSLRPLL

ADTVAAADSLAAPASAPREARKRKSPAPARAPPGGAPRPPKKSRADAPRPAAAPPAGAAPPAPPTPPPRPPRPAALT

RRPAEGPDPQGGWRRQPPGPSHTPAPSAAALEAYCAPRAVAELTDHPLFPAPWRPALMFDPRALASLAARCAAPPPG

-continued

GAPAAFGPLRASGPLRRAAAWMRQVPDPEDVRVVILYSPLPGEDLAAGRAGGGPPPEWSAERGGLSCLLAALGNRLC

GPATAAWAGNWTGAPDVSALGAQGVLLLSTRDLAFAGAVEFLGLLAGACDRRLIVVNAVRAADWPADGPVVSRQHAY

LACEVLPAVQCAVRWPAARDLRRTVLASGRVFGPGVFARVEAAHARLYPDAPPLRLCRGANVRYRVRTRFGPDTLVP

MSPREYRRAVLPALDGRAAASGAGDAMAPGAPDFCEDEAHSHRACARWGLGAPLRPVYVALGRDAVRGGPAELRGPR

REFCARALLEPDGDAPPLVLRDDADAGPPPQIRWASAAGRAGTVLAAAGGGVEVVGTAAGLATPPRREPVDMDAELE

DDDDGLFGE

SEQ ID NO: 16 = ICP4 internal fragment encoded by construct RS1.8 (deletion of #786-868)
MSAEQRKKKKTTTTTQGRGAEVAMADEDGGRLRAAAETTGGPGSPDPADGPPPTPNPDRRPAARPGFGWHGGPEENE

DEADDAAADADADEAAPASGEAVDEPAADGVVSPRQLALLASMVDEAVRTIPSPPPERDGAQEEAARSPSPPRTPSM

RADYGEENDDDDDDDDDDDRDAGRWVRGPETTSAVRGAYPDPMASLSPRPPAPRRHHHHHHHRRRRAPRRRSAASDS

SKSGSSSSSASSASSSASSSSSASASSSDDDDDDDAARAPASAADHAAGGTLGADDEEAGVPARAPGAAPRPSPPRAE

PAPARTPAATAGRLERRRARAAVAGRDATGRFTAGRPRRVELDADAASGAFYARYRDGYVSGEPWPGAGPPPPGRVL

YGGLGDSRPGLWGAPEAEEARARFEASGAPAPVWAPELGDAAQQYALITRLLYTPDAEAMGWLQNPRVAPGDVALDQ

ACFRISGAARNSSSFISGSVARAVPHLGYAMAAGRFGWGLAHVAAAVAMSRRYDRAQKGFLLTSLRRAYAPLLAREN

AALTGARTPDDGGDANRHDGDDARGKPAAAAAPLPSAAASPADERAVPAGYGAAGVLAALGRLSAAPASAPAGADDD

DDDDGAGGGGGGRRAEAGRVAVECLAACRGILEALAEGFDGDLAAVPGLAGARPAAPPRPGPAGAAAPPHADAPRLR

AWLRELRFVRDALVLMRLRGDLRVAGGSEAAVAAVRAVSLVAGALGPALPRSPRLLSSAAAAAADLLFQNQSLRPLL

ADTVAAADSLAAPASTPAPSAAALEAYCAPRAVAELTDHPLFPAPWRPALMFDPRALASLAARCAAPPPGGAPAAFG

PLRASGPLRRAAAWMRQVPDPEDVRVVILYSPLPGEDLAAGRAGGGPPPEWSAERGGLSCLLAALGNRLCGPATAAW

AGNWTGAPDVSALGAQGVLLLSTRDLAFAGAVEFLGLLAGACDRRLIVVNAVRAADWPADGPVVSRQHAYLACEVLP

AVQCAVRWPAARDLRRTVLASGRVFGPGVFARVEAAHARLYPDAPPLRLCRGANVRYRVRTRFGPDTLVPMSPREYR

RAVLPALDGRAAASGAGDAMAPGAPDFCEDEAHSHRACARWGLGAPLRPVYVALGRDAVRGGPAELRGPRREFCARA

LLEPDGDAPPLVLRDDADAGPPPQIRWASAAGRAGTVLAAAGGGVEVVGTAAGLATPPRREPVDMDAELEDDDDGLF

GE

SEQ ID NO: 17 = predicted sequence for uracil DNA glycosylase encoded by UL2
MFSASTTPEQPLGLSGDATPPLPTSVPLDWAAFRRAFLIDDAWRPLLEPELANPLTARLLAEYDRRCQTEEVLPPRE

DVFSWTRYCTPDDVRVVIIGQDPYHHPGQAHGLAFSVRADVPVPPSLRNVLAAVKNCYPDARMSGRGCLEKWARDGV

LLLNTTLTVKRGAAASHSKLGWDRFVGGVVQRLAARRPGLVFMLWGAHAQNAIRPDPRQHYVLKFSHPSPLSKVPFG

TCQHFLAANRYLETRDIMPIDWSV

SEQ ID NO: 18 = predicted sequence for tegument protein encoded by UL11
MGLAFSGARPCCCRHNVITTDGGEVVSLTAHEFDVVDIESEEEGNFYVPPDVRVVTRAPGPQYRRASDPPSRHTRRR

DPDVARPPATLTPPLSDSE

SEQ ID NO: 19 = gL2 secreted v.1 encoded by construct UL1s v.1
NRWGFVCLFGLVVMGAWGAWGGSQATEYVLRSVIAKEVGDILRVPCMRTPADDVSW

RYEAPSVIDYARIDGIFLRYHCPGLDTFLWDRHAQRAYLVNPFLFAAGFLEDLSHSVFPADTQETTTRRALYKEIRD

ALGSRKQAVSHAPVRAGCVNFDYSRTRRCVGRRDLRPANTTSTWEPPVSSDDEASSQSKPLATQPPVLALSNAPPRR

VSPTRGRRRHTRLRRN

SEQ ID NO: 20 = predicted sequence for VP5 encoded by construct UL19a
DYDIPTTENLYFQGMAAPARDPPGYRYAAAMVPTGSILSTIEVASHRRLFDFFARVRSDENSLYDVE

FDALLGSYCNTLSLVRFLELGLSVACVCTKFPELAYMNEGRVQFEVHQPLIARDGPHPVEQPVHNYMTKVIDRRALN

AAFSLATEAIALLTGEALDGTGISLHRQLRAIQQLARNVQAVLGAFERGTADQMLHVLLEKAPPLALLLPMQRYLDN

GRLATRVARATLVAELKRSFCDTSFFLGKAGHRREAIEAWLVDLTTATQPSVAVPRLTHADTRGRPVDGVLVTTAAI

KQRLLQSFLKVEDTEADVPVTYGEMVLNGANLVTALVMGKAVRSLDDVGRHLLEMQEEQLEANRETLDELESAPQTT

-continued

RVRADLVAIGDRLVFLEALEKRIYAATNVPYPLVGAMDLTFVLPLGLFNPAMERFAAHAGDLVPAPGHPEPRAFPPR
QLFFWGKDHQVLRLSMENAVGTVCHPSLMNIDAAVGGVNHDPVEAANPYGAYVAAPAGPGADMQQRFLNAWRQRLAH
GRVRWVAECQMTAEQFMQPDNANLALELHPAFDFFAGVADVELPGGEVPPAGPGAIQATWRVVNGNLPLALCPVAFR
DARGLELGVGRHAMAPATIAAVRGAFEDRSYPAVFYLLQAAIHGSEHVFCALARLVTQCITSYWNNTRCAAFVNDYS
LVSYIVTYLGGDLPEECMAVYRDLVAHVEALAQLVDDFTLPGPELGGQAQAELNHLMRDPALLPPLVWDCDGLMRHA
ALDRHRDCRIDAGEHEPVYAAACNVATADFNRNDGRLLHNTQARAADAADDRPHRPADWTVHHKIYYYVLVPAFSRG
RCCTAGVRFDRVYATLQNMVVPEIAPGEECPSDPVTDPAHPLHPANLVANTVNAMFHNGRVVVDGPAMLTLQVLAHN
MAERTTALLCSAAPDAGANTASTANMRIFDGALHAGVLLMAPQHLDHTIQNGEYFYVLPVHALFAGADHVANAPNFP
PALRDLARHVPLVPPALGANYFSSIRQPVVQHARESAAGENALTYALMAGYFKMSPVALYHQLKTGLHPGFGFTVVR
QDRFVTENVLFSERASEAYFLGQLQVARHETGGGVSFTLTQPRGNVDLGVGYTAVAATATVRNPVTDMGNLPQNFYL
GRGAPPLLDNAAAVYLRNAVVAGNRLGPAQPLPVFGCAQVPRRAGMDHGQDAVCEFIATPVATDINYFRRPCNPRGR
AAGGVYAGDKEGDVIALMYDHGQSDPARPFAATANPWASQRFSYGDLLYNGAYHLNGASPVLSPCFKFFTAADITAK
HRCLERLIVETGSAVSTATAASDVQFKRPPGCRELVEDPCGLFQEAYPITCASDPALLRSARDGEAHARETHFTQYL
IYDASPLKGLSL

SEQ ID NO: 21 = VP5 encoded by construct UL19ΔTEV
MAAPARDPPGYRYAAAMVPTGSILSTIEVASHRRLFDFFARVRSDENSLYDVEFDALLGSYCNTLSL
VRFLELGLSVACVCTKFPELAYMNEGRVQFEVHQPLIARDGPHPVEQPVHNYMTKVIDRRALNAAFSLATEAIALLT
GEALDGTGISLHRQLRAIQQLARNVQAVLGAFERGTADQMLHVLLEKAPPLALLLPMQRYLDNGRLATRVARATLVA
ELKRSFCDTSFFLGKAGHRREAIEAWLVDLTTATQPSVAVPRLTHADTRGRPVDGVLVTTAAIKQRLLQSFLKVEDT
EADVPVTYGEMVLNGANLVTALVMGKAVRSLDDVGRHLLEMQEEQLEANRETLDELESAPQTTRVRADLVAIGDRLV
FLEALEKRIYAATNVPYPLVGAMDLTFVLPLGLFNPAMERFAAHAGDLVPAPGHPEPRAFPPRQLFFWGKDHQVLRL
SMENAVGTVCHPSLMNIDAAVGGVNHDPVEAANPYGAYVAAPAGPGADMQQRFLNAWRQRLAHGRVRWVAECQMTAE
QFMQPDNANLALELHPAFDFFAGVADVELPGGEVPPAGPGAIQATWRVVNGNLPLALCPVAFRDARGLELGVGRHAM
APATIAAVRGAFEDRSYPAVFYLLQAAIHGSEHVFCALARLVTQCITSYWNNTRCAAFVNDYSLVSYIVTYLGGDLP
EECMAVYRDLVAHVEALAQLVDDFTLPGPELGGQAQAELNHLMRDPALLPPLVWDCDGLMRHAALDRHRDCRIDAGE
HEPVYAAACNVATADFNRNDGRLLHNTQARAADAADDRPHRPADWTVHHKIYYYVLVPAFSRGRCCTAGVRFDRVYA
TLQNMVVPEIAPGEECPSDPVTDPAHPLHPANLVANTVNAMFHNGRVVVDGPAMLTLQVLAHNMAERTTALLCSAAP
DAGANTASTANMRIFDGALHAGVLLMAPQHLDHTIQNGEYFYVLPVHALFAGADHVANAPNFPPALRDLARHVPLVP
PALGANYFSSIRQPVVQHARESAAGENALTYALMAGYFKMSPVALYHQLKTGLHPGFGFTVVRQDRFVTENVLFSER
ASEAYFLGQLQVARHETGGGVSFTLTQPRGNVDLGVGYTAVAATATVRNPVTDMGNLPQNFYLGRGAPPLLDNAAAV
YLRNAVVAGNRLGPAQPLPVFGCAQVPRRAGMDHGQDAVCEFIATPVATDINYFRRPCNPRGRAAGGVYAGDKEGDV
IALMYDHGQSDPARPFAATANPWASQRFSYGDLLYNGAYHLNGASPVLSPCFKFFTAADITAKHRCLERLIVETGSA
VSTATAASDVQFKRPPGCRELVEDPCGLFQEAYPITCASDPALLRSARDGEAHARETHFTQYLIYDASPLKGLSL SEQ ID NO: 22 = predicted sequence for ICP1/2 encoded by UL36
MIPAALPHPTMKRQGDRDIVVTGVRNQFATDLEPGGSVSCMRSSLSFLSLLFDVGPRDVLSAEAIEGCLVEGGEWTR
AAAGSGPPRMCSIIELPNFLEYPAARGGLRCVFSRVYGEVGFFGEPTAGLLETQCPAHTFFAGPWAMRPLSYTLLTI
GPLGMGLYRDGDTAYLFDPHGLPAGTPAFIAKVRAGDVYPYLTYYAHDRPKVRWAGAMVFFVPSGPGAVAPADLTAA
ALHLYGASETYLQDEPFVERRVAITHPLRGEIGGLGALFVGVVPRGDGEGSGPVVPALPAPTHVQTPGADRPPEAPR
GASGPPDTPQAGHPNRPPDDVWAAALEGTPPAKPSAPDAAASGPPHAAPPPQTPAGDAAEEAEDLRVLEVGAVPVGR
HRARYSTGLPKRRRPTWTPPSSVEDLTSGERPAPKAPPAKAKKKSAPKKKAPVAAEVPASSPTPIAATVPPAPDTPP
QSGQGGGDDGPASPSSPSVLETLGARRPPEPPGADLAQLFEVHPNVAATAVRLAARDAALAREVAACSQLTINALRS -continued

PYPAHPGLLELCVIFFFERVLAFLIENGARTHTQAGVAGPAAALLDFTLRMLPRKTAVGDFLASTRMSLADVAAHRP

LIQHVLDENSQIGRLALAKLVLVARDVIRETDAFYGDLADLDLQLRAAPPANLYARLGEWLLERSRAHPNTLFAPAT

PTHPEPLLHRIQALAQFARGEEMRVEAEAREMREALDALARGVDSVSQRAGPLTVMPVPAAPGAGGRAPCPPALGPE

AIQARLEDVRIQARRAIESAVKEYFHRGAVYSAKALQASDSHDCRFHVASAAVVPMVQLLESLPAFDQHTRDVAQRA

ALPPPPPLATSPQAILLRDLLQRGQPLDAPEDLAAWLSVLTDAATQGLIERKPLEELARSIHGINDQQARRSSGLAE

LQRFDALDAALAQQLDSDAAFVPATGPAPYVDGGGLSPEATRMAEDALRQARAMEAAKMTAELAPEARSRLRERAHA

LEAMLNDARERAKVAHDAREKFLHKLQGVLRPLPDFVGLKACPAVLATLRASLPAGWTDLADAVRGPPPEVTAALRA

DLWGLLGQYREALEHPTPDTATALAGLHPAFVVVLKTLFADAPETPVLVQFFSDHAPTIAKAVSNAINAGSAAVATA

SPAATVDAAVRAHGALADAVSALGAAARDPASPLSFLAVLADSAAGYVKATRLALEARGAIDELTTLGSAAADLVVQ

ARRACAQPEGDHAALIDAAARATTAARESLAGHEAGFGGLLHAEGTAGDHSPSGRALQELGKVIGATRRRADELEAA

VADLTAKMAAQRARGSSERWAAGVEAALDRVENRAEFDVVELRRLQALAGTHGYNPRDFRKRAEQALAANAEAVTLA

LDTAFAFNPYTPENQRHPMLPPLAAIHRLGWSAAFHAAAETYADMFRVDAEPLARLLRIAEGLLEMAQAGDGFIDYH

EAVGRLADDMTSVPGLRRYVPFFQHGYADYVELRDRLDAIRADVHRALGGVPLDLAAAAEQISAARNDPEATAELVR

TGVTLPCPSEDALVACAAALERVDQSPVKNTAYAEYVAFVTRQDTAETKDAVVRAKQQRAEATERVMAGLREALAAR

ERRAQIEAEGLANLKTMLKVVAVPATVAKTLDQARSVAEIADQVEVLLDQTEKTRELDVPAVIWLEHAQRTFETHPL

SAARGDGPGPLARHAGRLGALFDTRRRVDALRRSLEEAEAEWDEVWGRFGRVRGGAWKSPEGFRAMHEQLRALQDTT

NTVSGLRAQPAYERLSARYQGVLGAKGAERAEAVEELGARVTKHTALCARLRDEVVRRVPWEMNFDALGGLLAEFDA

AAADLAPWAVEEFRGARELIQYRMGLYSAYARAGGQTGAGAESAPAPLLVDLRALDARARASSSPEGHEVDPQLLRR

RGEAYLRAGGDPGPLVLREAVSALDLPFATSFLAPDGTPLQYALCFPAVTDKLGALLMRPEAACVRPPLPTDVLESA

PTVTAMYVLTVVNRLQLALSDAQAANFQLFGRFVRHRQATWGASMDAAAELYVALVATTLTREFGCRWAQLGWASGA

AAPRPPPGPRGSQRHCVAFNENDVLVALVAGVPEHIYNFWRLDLVRQHEYMHLTLERAFEDAAESMLFVQRLTPHPD

ARIRVLPTFLDGGPPTRGLLFGTRLADWRRGKLSETDPLAPWRSALELGTQRRDVPALGKLSPAQALAAVSVLGRMC

LPSAALAALWTCMFPDDYTEYDSFDALLAARLESGQTLGPAGGREASLPEAPHALYRPTGQHVAVLAAATHRTPAAR

VTAMDLVLAAVLLGAPVVVALRNTTAFSRESELELCLTLFDSRPGGPDAALRDVVSSDIETWAVGLLHTDLNPIENA

CLAAQLPRLSALIAERPLADGPPCLVLVDISMTPVAVLWEAPEPPGPPDVRFVGSEATEELPFVATAGDVLAASAAD

ADPFFARAILGRPFDASLLTGELFPGHPVYQRPLADEAGPSAPTAARDPRDLAGGDGGSGPEDPAAPPARQADPGVL

APTLLTDATTGEPVPPRMWAWIHGLEELASDDAGGPTPNPAPALLPPPATDQSVPTSQYAPRPIGPAATARETRPSV

PPQQNTGRVPVAPRDDPRPSPPTPSPPADAALPPPAFSGSAAAFSAAVPRVRRSRRTRAKSRAPRASAPPEGWRPPA

LPAPVAPVAASARPPDQPPTPESAPPAWVSALPLPPGPASARGAFPAPTLAPIPPPPAEGAVVPGGDRRRGRRQTTA

GPSPTPPRGPAAGPPRRLTRPAVASLSASLNSLPSPRDPADHAAAVSAAAAAVPPSPGLAPPTSAVQTSPPPLAPGP

VAPSEPLCGWVVPGGPVARRPPPQSPATKPAARTRIRARSVPQPPLPQPPLPQPPLPQPPLPQPPLPQPPLPQPPLP

QPPLPQPPLPQPPLPQPPLPPVTRTLTPQSRDSVPTPESPTHTNTHLPVSAVTSWASSLALHVDSAPPPASLLQTLH

ISSDDEHSDADSLRFSDSDDTEALDPLPPEPHLPPADEPPGPLAADHLQSPHSQFGPLPVQANAVLSRRYVRSTGRS

ALAVLIRACRRIQQQLQRTRRALFQRSNAVLTSLHHVRMLLG

SEQ ID NO: 23 = ICP1/2 internal fragment encoded by construct UL36.3.4.1

AAQRARGSSERWAAGVEAALDRVENRAEFDVVELRRLQALAGTHGYNPRDFRKRAEQALAANAEAVT

LALDTAFAFNPYTPENQRHPMLPPLAAIHRLGWSAAFHAAAETYADMFRVDAEPLARLLRIAEGLLEMAQAGDGFID

YHEAVGRLADDMTSVPGLRRYVPFFQHGYADYVELRDRLDAIRADVHRALGGVPLDLAAAAEQISAARNDPEATAEL

VRTGVTLPCPSEDALVACAAALERVDQSPVKNTAYAEYVAFVTRQDTAETKDAVVRAKQQRAEATERVMAGLREALA

ARERRAQIEAEGLANLKTMLKVVAVPATVAKTLDQARSVAEIADQVEVLLDQTEKTRELDVPAVIWLEHAQRTFETH

PLSAARGDGPGPLARHAGRLGALFDTRRRVDALRRSLEEAEAEWDEVWGRFGRVRGGAWKSPEGFRAMHEQLRALQD

-continued

TTNTVSGLRAQPAYERLSARYQGVLGAKGAERAEAVEELGARVTKHTALCARLRDEVVRRVPWEMNFDALGGLLAEF

DAAAADLAPWAVEEFRGARELIQYRMGLYSAYARAGGQTGAGAESAPAPLLVDLRALDARARASSSPEGHEVDPQLL

RRRGEAYLRAGGDPGPLVLREAVSALDLPFATSFLAPDGTPLQYALCFPAVTDKLGALLMRPEAACVRPPLPTDVLE

SAPTVTAMYVLTVVNRLQLALSDAQAANFQLFGRFVRHRQATWGASMDAAAELYVALVATTLTREFGCRWAQLGWAS

GAAAPRPPPGPRGSQRHCVAFNENDVLVALVAGVPEHIYNFWRLDLVRQHEYMHLTLERAFEDAAESMLFVQRLTPH

PDARIRVLPTFLDGGPPTRGLLFGTRLADWRRGKLSETDPLAPWRSALELGTQRRDVPALGKLSPAQALAAVSVLGR

MCLPSAALAALWTCMFPDDYTEYDSFDALLAARLESGQTLGPAGGREASL

SEQ ID NO: 24 = ICP1/2 internal fragment encoded by construct UL36.4.2.5
EYDSFDALLAARLESGQTLGPAGGREASLPEAPHALYRPTGQHVAVLAAATHRTPAARVTAMDLVLA

AVLLGAPVVVALRNTTAFSRESELELCLTLFDSRPGGPDAALRDVVSSDIETWAVGLLHTDLNPIENACLAAQLPRL

SALIAERPLADGPPCLVLVDISMTPVAVLWEAPEPPGPPDVRFVGSEATEELPFVATAGDVLAASAADADPFFARAI

LGRPFDASLLTGELFPGHPVYQRPLADEAGPSAPTAARDPRDLAGGDGGSGPEDPAAPPARQADPGVLAPTLLTDAT

TGEPVPPRMWAWIHGLEELASDDAGGPTPNPAPALLPPPATDQSVPTSQYAPRPIGPAATARETRPSVPPQQNTGRV

PVAPRDDPRPSPPTPSPPADAALPPPAFSGSAAAFSAAVPRVRRSRRTRAKSRAPRASAPPEGWRPPALPAPVAPVA

ASARPPDQPPTPESAPPAWVSALPLPPGPASARGAFPAPTLAPIPPPPAEGAVVPGGDRRRGRRQTTAGPSPTPPRG

PAAGPPRRLTRPAVASLSASLNSLPSPRDPADHAAAVSAAAAAVPPSPGLAPPTSAVQTSPPPLAPGPVAPSEPLCG

WVVPGGPVARRPPPQSPATKPAARTRIRARSVPQPPLPQPPLPQPPLPQPPLPQPPLPQPPLPQPPLPQPPLPQPPL

PQPPLPQPPLPPVTRTLTPQSRDSVPTPESPTHTNTHLPVSAVTSWASSLALHVDSAPPPASLLQTLHISSDDEHSD

ADSLRFSDSDDTEALDPLPPEPHLPPADEPPGPLAADHLQSPHSQFGPLPVQANAVLSRRYVRSTGRSALAVLIRAC

RRIQQQLQRTRRALFQRSNAVLTSLHHVRMLLG

SEQ ID NO: 25 = predicted sequence for reductase encoded by UL40
MDPAVSPASTDPLDTHASGAGAAPIPVCPTPERYFYTSQCPDINHLRSLSILNRWLETELVFVGDEE

DVSKLSEGELGFYRFLFAFLSAADDLVTENLGGLSGLFEQKDILHYYVEQECIEVVHSRVYNIIQLVLFHNNDQARR

AYVARTINHPAIRVKVDWLEARVRECDSIPEKFILMILIEGVFFAASFAAIAYLRTNNLLRVTCQSNDLISRDEAVH

TTASCYIYNNYLGGHAKPEAARVYRLFREAVDIEIGFIRSQAPTDSSILSPGALAAIENYVRFSADRLLGLIHMQPL

YSAPAPDASFPLSLMSTDKHTNFFECRSTSYAGAVVNDL

SEQ ID NO: 26 = ICP47 encoded by US12
MSWALKTTDMFLDSSRCTHRTYGDVCAEIHKREREDREAARTAVTDPELPLLCPPDVRSDPASRNPTQQTRGCARSN

ERQDRVLAP

SEQ ID NO: 27 = gM2 encoded by UL10
MGRRAPRGSPEAAPGADVAPGARAAWWVWCVQVATFIVSAICVVGLLVLASVFRDRFPCLYAPATSYAKANATVEVR

GGVAVPLRLDTQSLLATYAITSTLLLAAAVYAAVGAVTSRYERALDAARRLAAARMAMPHATLIAGNVCAWLLQITV

LLLAHRISQLAHLIYVLHFACLVYLAAHFCTRGVLSGTYLRQVHGLIDPAPTHHRIVGPVRAVMTNALLLGTLLCTA

AAAVSLNTIAALNFNFSAPSMLICLTTLFALLVVSLLLVVEGVLCHYVRVLVGPHLGAIAATGIVGLACEHYHTGGY

YVVEQQWPGAQTGVRVALALVAAFALAMAVLRCTRAYLYHRRHHTKFFVRMRDTRHRAHSALRRVRSSMRGSRRGGP

PGDPGYAETPYASVSHHAEIDRYGDSDGDPIYDEVAPDHEAELYARVQRPGPVPDAEPIYDTVEGYAPRSAGEPVYS

TVRRW

SEQ ID NO: 28 = predicted sequence for cleavage/packaging protein encoded by UL15
MFGQQLASDVQQYLERLEKQRQQKVGVDEASAGLTLGGDALRVPFLDFATATPKRHQTVVPGVGTLHDCCEHSPLFS

AVARRLLFNSLVPAQLRGRDFGGDHTAKLEFLAPELVRAVARLRFRECAPEDAVPQRNAYYSVLNTFQALHRSEAFR

QLVHFVRDFAQLLKTSFRASSLAETTGPPKKRAKVDVATHGQTYGTLELFQKMILMHATYFLAAVLLGDHAEQVNTF

LRLVFEIPLFSDTAVRHFRQRATVFLVPRRHGKTWFLVPLIALSLASFRGIKIGYTAHIRKATEPVFDEIDACLRGW

FGSSRVDHVKGETISFSFPDGSRSTIVFASSHNTNGIRGQDFNLLFVDEANFIRPDAVQTIMGFLNQANCKIIFVSS

-continued

TNTGKASTSFLYNLRGAADELLNVVTYICDDHMPRVVTHTNATACSCYILNKPVFITMDGAVRRTADLFLPDSFMQE

IIGGQARETGDDRPVLTKSAGERFLLYRPSTTTNSGLMAPELYVYVDPAFTANTRASGTGIAVVGRYRDDFIIFALE

HFFLRALTGSAPADIARCVVHSLAQVLALHPGAFRSVRVAVEGNSSQDSAVAIATHVHTEMHRILASAGANGPGPEL

LFYHCEPPGGAVLYPFFLLNKQKTPAFEYFIKKFNSGGVMASQELVSVTVRLQTDPVEYLSEQLNNLIETVSPNTDV

RMYSGKRNGAADDLMVAVIMAIYLAAPTGIPPAFFPITRTS

SEQ ID NO: 29 = predicted sequence for ICP35 encoded by UL26.5
MNPVSASGAPAPPPPGDGSYLWIPASHYNQLVTGQSAPRHPPLTACGLPAAGTVAYGHPGAGPSPHYPPPPAHPYPG

MLFAGPSPLEAQIAALVGAIAADRQAGGLPAAAGDHGIRGSAKRRRHEVEQPEYDCGRDEPDRDFPYYPGEARPEPR

PVDSRRAARQASGPHETITALVGAVTSLQQELAHMRARTHAPYGPYPPVGPYHHPHADTETPAQPPRYPAKAVYLPP

PHIAPPGPPLSGAVPPPSYPPVAVTPGPAPPLHQPSPAHAHPPPPPPGPTPPPAASLPQPEAPGAEAGALVNASSAA

HVNVDTARAADLFVSQMMGSR

SEQ ID NO: 30 = predicted sequence for polymerase encoded by UL30
MFCAAGGPASPGGKPAARAASGFFAPHNPRGATQTAPPPCRRQNFYNPHLAQTGTQPKALGPAQRHTYYSECDEFRF

IAPRSLDEDAPAEQRTGVHDGRLRRAPKVYCGGDERDVLRVGPEGFWPRRLRLWGGADHAPEGFDPTVTVFHVYDIL

EHVEHAYSMRAAQLHERFMDAITPAGTVITLLGLTPEGHRVAVHVYGTRQYFYMNKAEVDRHLQCRAPRDLCERLAA

ALRESPGASFRGISADHFEAEVVERADVYYYETRPTLYYRVFVRSGRALAYLCDNFCPAIRKYEGGVDATTRFILDN

PGFVTFGWYRLKPGRGNAPAQPRPPTAFGTSSDVEFNCTADNLAVEGAMCDLPAYKLMCFDIECKAGGEDELAFPVA

ERPEDLVIQISCLLYDLSTTALEHILLFSLGSCDLPESHLSDLASRGLPAPVVLEFDSEFEMLLAFMTFVKQYGPEF

VTGYNIINFDWPFVLTKLTEIYKVPLDGYGRMNGRGVFRVWDIGQSHFQKRSKIKVNGMVNIDMYGIITDKVKLSSY

KLNAVAEAVLKDKKKDLSYRDIPAYYASGPAQRGVIGEYCVQDSLLVGQLFFKFLPHLELSAVARLAGINITRTIYD

GQQIRVFTCLLRLAGQKGFILPDTQGRFRGLDKEAPKRPAVPRGEGERPGDGNGDEDKDDDEDGDEDGDEREEVARE

TGGRHVGYQGARVLDPTSGFHVDPVVVFDFASLYPSIIQAHNLCFSTLSLRPEAVAHLEADRDYLEIEVGGRRLFFV

KAHVRESLLSILLRDWLAMRKQIRSRIPQSTPEEAVLLDKQQAAIKVVCNSVYGFTGVQHGLLPCLHVAATVTTIGR

EMLLATRAYVHARWAEFDQLLADFPEAAGMRAPGPYSMRIIYGDTDSIFVLCRGLTAAGLVAMGDKMASHISRALFL

PPIKLECEKTFTKLLLIAKKKYIGVICGGKMLIKGVDLVRKNNCAFINRTSRALVDLLFYDDTVSGAAAALAERPAE

EWLARPLPEGLQAFGAVLVDAHRRITDPERDIQDFVLTAELSRHPRAYTNKRLAHLTVYYKLMARRAQVPSIKDRIP

YVIVAQTREVEETVARLAALRELDAAAPGDEPAPPAALPSPAKRPRETPSHADPPGGASKPRKLLVSELAEDPGYAI

ARGVPLNTDYYFSHLLGAACVTFKALFGNNAKITESLLKRFIPETWHPPDDVAARLRAAGFGPAGAGATAEETRRML

HRAFDTLA

SEQ ID NO: 31 = predicted sequence for helicase/primase complex encoded by UL5
MAASGGEGSRDVRAPGPPPQQPGARPAVRFRDEAFLNFTSMHGVQPIIARIRELSQQQLDVTQVPRLQWFRDVAALE

VPTGLPLREFPFAAYLITGNAGSGKSTCVQTLNEVLDCVVTGATRIAAQNMYVKLSGAFLSRPINTIFHEFGFRGNH

VQAQLGQHPYTLASSPASLEDLQRRDLTYYWEVILDITKRALAAHGGEDARNEFHALTALEQTLGLGQGALTRLASV

THGALPAFTRSNIIVIDEAGLLGRHLLTTVVYCWWMINALYHTPQYAGRLRPVLVCVGSPTQTASLESTFEHQKLRC

SVRQSENVLTYLICNRTLREYTRLSHSWAIFINNKRCVEHEFGNLMKVLEYGLPITEEHMQFVDRFVVPESYITNPA

NLPGWTRLFSSHKEVSAYMAKLHAYLKVTREGEFVVFTLPVLTFVSVKEFDEYRRLTQQPTLTMEKWITANASRITN

YSQSQDQDAGHVRCEVHSKQQLVVARNDITYVLNSQVAVTARLRKMVFGFDGTFRTFEAVLRDDSFVKTQGETSVEF

AYRFLSRLMFGGLIHFYNFLQRPGLDATQRTLAYGRLGELTAELLSLRRDAAGASATRAADTSDRSPGERAFNFKHL

GPRDGGPDDFPDDDLDVIFAGLDEQQLDVFYCHYALEEPETTAAVHAQFGLLKRAFLGRYLILRELFGEVFESAPFS

TYVDNVIFRGCELLTGSPRGGLMSVALQTDNYTLMGYTYTRVFAFAEELRRRHATAGVAEFLEESPLPYIVLRDQHG

FMSVVNTNISEFVESIDSTELAMAINADYGISSKLAMTITRSQGLSLDKVAICFTPGNLRLNSAYVAMSRTTSSEFL

HMNLNPLRERHERDDVISEHILSALRDPNVVIVY

-continued

SEQ ID NO: 32 = predicted sequence for helicase/primase complex encoded by UL8
MEAPGIVWVEESVSAITLYAVWLPPRTRDCLHALLYLVCRDAAGEARARFAEVSVGSSDLQDFYGSPDVSAPGAVAA

ARAATAPAASPLEPLGDPTLWRALYACVLAALERQTGRWALFVPLRLGWDPQTGLVVRVERASWGPPAAPRAALLDV

EAKVDVDPLALSARVAEHPGARLAWARLAAIRDSPQCASSASLAVTITTRTARFAREYTTLAFPPTRKEGAFADLVE

VCEVGLRPRGHPQRVTARVLLPRGYDYFVSAGDGFSAPALVALFRQWHTTVHAAPGALAPVFAFLGPGFEVRGGPVQ

YFAVLGFPGWPTFTVPAAAAAESARDLVRGAAATHAACLGAWPAVGARVVLPPRAWPAVASEAAGRLLPAFREAVAR

WHPTATTIQLLDPPAAVGPVWTARFCFSGLQAQLLAALAGLGEAGLPEARGRAGLERLDALVAAAPSEPWARAVLER

LVPDACDACPALRQLLGGVMAAVCLQIEQTASSVKFAVCGGTGAAFWGLFNVDPGDADAAHGAIQDARRALEASVRA

VLSANGIRPRLAPSLAPEGVYTHVVTWSQTGAWFWNSRDDTDFLQGFPLRGAAYAAAAEVMRDALRRILRRPAAGPP

EEAVCAARGVMEDACDRFVLDAFGRRLDAEYWSVLTPPGEADDPLPQTAFRGGALLDAEQYWRRVVRVCPGGGESVG

VPVDLYPRPLVLPPVDCAHHLREILREIQLVFTGVLEGVWGEGGSFVYPFDEKIRFLFP

SEQ ID NO: 33 = predicted sequence for unknown protein encoded by UL15.5
MDGAVRRTADLFLPDSFMQEIIGGQARETGDDRPVLTKSAGERFLLYRPSTTTNSGLMAPELYVYVDPAFTANTRAS

GTGIAVVGRYRDDFIIFALEHFFLRALTGSAPADIARCVVHSLAQVLALHPGAFRSVRVAVEGNSSQDSAVAIATHV

HTEMHRILASAGANGPGPELLFYHCEPPGGAVLYPFFLLNKQKTPAFEYFIKKFNSGGVMASQELVSVTVRLQTDPV

EYLSEQLNNLIETVSPNTDVRMYSGKRNGAADDLMVAVIMAIYLAAPTGIPPAFFPITRTS

SEQ ID NO: 34 = predicted sequence for packaging protein encoded by UL32
MATSAPGVPSSAAVREESPGSSWKEGAFERPYVAFDPDLLALNEALCAELLAACHVVGVPPASALDEDVESDVAPAP

PRPRGAAREASGGRGPGSARGPPADPTAEGLLDTGPFAAASVDTFALDRPCLVCRTIELYKQAYRLSPQWVADYAFL

CAKCLGAPHCAASIFVAAFEFVYVMDHHFLRTKKATLVGSFARFALTINDIHRHFFLHCCFRTDGGVPGRHAQKQPR

PTPSPGAAKVQYSNYSFLAQSATRALIGTLASGGDDGAGAGAGGGSGTQPSLTTALMNWKDCARLLDCTEGKRGGGD

SCCTRAAARNGEFEAAAGALAQGGEPETWAYADLILLLLAGTPAVWESGPRLRAAADARRAAVSESWEAHRGARMRD

AAPRFAQFAEPQPQPDLDLGPLMATVLKHGRGRGRTGGECLLCNLLLVRAYWLAMRRLRASVVRYSENNTSLFDCIV

PVVDQLEADPEAQPGDGGRFVSLLRAAGPEAIFKHMFCDPMCAITEMEVDPWVLFGHPRADHRDELQLHKAKLACGN

EFEGRVCIALRALIYTFKTYQVFVPKPTALATFVREAGALLRRHSISLLSLEHTLCTYV

SEQ ID NO: 35 = predicted sequence for ICP1/2 fragment encoded by construct
UL36.4.2
MEYDSFDALLAARLESGQTLGPAGGREASLPEAPHALYRPTGQHVAVLAAATHRTPAARVTAMDLVLAAVLLGAPVV

VALRNTTAFSRESELELCLTLFDSRPGGPDAALRDVVSSDIETWAVGLLHTDLNPIENACLAAQLPRLSALIAERPL

ADGPPCLVLVDISMTPVAVLWEAPEPPGPPDVRFVGSEATEELPFVATAGDVLAASAADADPFFARAILGRPFDASL

LTGELFPGHPVYQRPLADEAGPSAPTAARDPRDLAGGDGGSGPEDPAAPPARQADPGVLAPTLLTDATTGEPVPPRM

WANIHGLEELASDDAGGPT

SEQ ID NO: 36 = predicted sequence for ICP27 encoded by UL54
MATDIDMLIDLGLDLSDSELEEDALERDEEGRRDDPESDSSGECSSSDEDMEDPCGDGGAEAIDAAIPKGPPARPED

AGTPEASTPRPAARRGADDPPPATTGVWSRLGTRRSASPREPHGGKVARIQPPSTKAPHPRGGRRGRRRGRGRYGPG

GADSTPKPRRRVSRNAHNQGGRHPASARTDGPGATHGEARRGGEQLDVSGGPRPRGTRQAPPPLMALSLTPPHADGR

APVPERKAPSADTIDPAVRAVLRSISERAAVERISESFGRSALVMQDPFGGMPFPAANSPWAPVLATQAGGFDAETR

RVSWETLVAHGPSLYRTFAANPRAASTAKAMRDCVLRQENLIEALASADETLAWCKMCIHHNLPLRPQDPIIGTAAA

VLENLATRLRPFLQCYLKARGLCGLDDLCSRRRLSDIKDIASFVLVILARLANRVERGVSEIDYTTVGVGAGETMHF

YIPGACMAGLIEILDTHRQECSSRVCELTASHTIAPLYVHGKYFYCNSLF

-continued

SEQ ID NO: 37 = virion protein encoded by UL49.5
MTGKPARLGRWVVLLFVALVAGVPGEPPNAAGARGVIGDAQCRGDSAGVVSVPGVLVPFYLGMTSMG

VCMIAHVYQICQRALAAGSA

SEQ ID NO: 38 = gG2 encoded by US4
NRWGSGVPGPINPPNSDVVFPGGSPVAQYCYAYPRLDDPGPLGSADAGRQDLPRRV

VRHEPLGRSFLTGGLVLLAPPVRGFGAPNATYAARVTYYRLTRACRQPILLRQYGGCRGGEPPSPKTCGSYTYTYQG

GGPPTRYALVNASLLVPIWDRAAETFEYQIELGGELHVGLLWVEVGGEGPGPTAPPQAARAEGGPCVPPVPAGRPWR

SVPPVWYSAPNPGFRGLRFRERCLPPQTPAAPSDLPRVAFAPQSLLVGITGRTFIRMARPTEDVGVLPPHWAPGALD

DGPYAPFPPRPRFRR

SEQ ID NO: 39 = RS1
ATGTCGTACTACCATCACCATCACCATCACAGTGCCGAACAGCGTAAAAAGAAAAAAACCACCACCACGACCCAAGG

ACGTGGAGCTGAAGTTGCTATGGCGGATGAGGATGGAGGCCGCTTGAGAGCTGCTGCTGAGACTACTGGAGGACCTG

GATCACCGGACCCTGCCGATGGACCCCCCCCTACACCAAACCCCGATCGTAGACCGGCTGCTAGACCTGGATTCGGA

TGGCATGGAGGACCCGAGGAAAACGAGGACGAGGCGGACGACGCCGCTGCCGACGCCGACGCCGATGAGGCTGCCCC

TGCTTCTGGAGAGGCGGTAGACGAACCTGCTGCCGATGGAGTTGTTAGCCCTAGGCAATTGGCTTTGTTGGCGAGCA

TGGTAGACGAGGCTGTGAGAACAATCCCTTCCCCTCCCCCTGAACGTGATGGAGCACAAGAGGAGGCGGCTAGGAGT

CCCTCACCACCCCGTACACCTTCTATGAGAGCGGATTACGGCGAGGAAAACGACGACGACGACGATGATGATGACGA

CGATGATCGTGATGCCGGACGCTGGGTTAGGGGACCTGAAACCACTTCTGCTGTCCGTGGAGCATACCCCGATCCTA

TGGCGAGTTTGAGCCCTAGACCACCTGCCCCGAGGAGACACCACCACCACCACCATCATAGGCGTAGACGTGCTCCT

AGACGTCGTTCTGCCGCTAGTGACTCTTCCAAATCTGGCTCTTCTTCATCTGCCTCTTCCGCTTCATCTTCGGCCTC

ATCGTCCTCTTCGGCATCCGCTTCGAGTAGTGATGATGATGATGACGACGACGCTGCTAGAGCCCCCGCTTCTGCTG

CCGACCACGCTGCTGGCGGAACTTTGGGAGCCGACGACGAGGAGGCGGGAGTTCCTGCTCGTGCCCCGGGAGCTGCT

CCGAGGCCTTCTCCACCCCGTGCTGAACCTGCTCCGGCTAGAACACCGGCCGCTACTGCTGGTAGACTGGAGCGTAG

ACGTGCCCGTGCTGCTGTGGCTGGTAGAGATGCTACTGGCCGCTTCACTGCTGGCCGTCCTAGACGTGTTGAACTGG

ACGCCGATGCTGCTTCTGGTGCTTTCTACGCCCGTTACCGTGATGGTTACGTGTCTGGTGAACCTTGGCCTGGCGCT

GGTCCACCTCCGCCCGGACGTGTACTCTACGGTGGATTGGGCGATTCTCGCCCTGGTCTGTGGGGCGCTCCGGAGGC

TGAGGAGGCTAGAGCCCGTTTCGAGGCTTCTGGTGCCCCTGCTCCTGTTTGGGCTCCTGAATTGGGCGACGCTGCTC

AACAATACGCCCTCATCACACGCTTGCTGTACACTCCCGACGCCGAGGCTATGGGATGGCTCCAAAACCCTAGAGTT

GCCCCTGGTGATGTTGCTCTGGATCAGGCTTGTTTCCGTATCTCCGGCGCTGCTCGTAACTCTTCTTCGTTCATCTC

CGGTTCTGTGGCTAGAGCTGTGCCTCACTTGGGATACGCCATGGCCGCTGGACGTTTCGGCTGGGGACTGGCTCATG

TTGCTGCCGCTGTAGCAATGTCTAGACGCTACGACCGTGCTCAAAAAGGATTCTTGCTCACGTCACTGAGGCGTGCT

TACGCCCCTTTGTTGGCCCGTGAAAACGCTGCCCTCACTGGCGCCCGTACCCCCGATGACGGTGGCGACGCCAACCG

CCACGATGGTGATGATGCTAGAGGCAAACCCGCTGCCGCTGCTGCTCCTTTGCCCTCTGCCGCCGCTTCCCCTGCCG

ATGAACGTGCTGTTCCTGCCGGTTACGGTGCCGCTGGTGTGTTGGCTGCTTTGGGACGCTTGAGTGCTGCCCCGGCT

AGTGCCCCCGCTGGTGCCGATGACGATGACGATGACGATGGTGCTGGCGGAGGCGGTGGCGGTAGACGTGCTGAGGC

TGGACGTGTTGCTGTTGAATGCCTGGCTGCCTGTAGAGGAATCTTGGAGGCTCTGGCCGAGGGATTCGACGGAGACT

TGGCGGCTGTACCGGGACTGGCGGGAGCGAGGCCTGCCGCTCCACCTCGCCCCGGTCCTGCTGGTGCTGCCGCTCCT

CCTCATGCCGACGCTCCTAGACTCCGTGCTTGGCTCCGTGAACTCCGTTTCGTTCGTGACGCTTTGGTTCTGATGAG

ACTGAGAGGCGACTTGAGAGTGGCTGGAGGATCCGAGGCTGCTGTTGCTGCTGTCCGTGCTGTTTCTTTGGTTGCTG

GTGCTTTGGGCCCTGCTTTGCCGAGATCTCCCCGTTTGTTGTCGAGTGCCGCCGCTGCTGCCGCCGATTTGTTGTTC

CAAAACCAATCCCTCCGCCCTCTGCTCGCCGACACTGTTGCCGCTGCCGATTCTCTGGCTGCTCCGGCTTCTGCCCC

ACGTGAAGCTCGTAAACGTAAATCACCCGCTCCGGCTCGTGCTCCCCCTGGTGGCGCCCCTAGACCCCCTAAAAAAT

-continued

CCCGTGCCGATGCCCCTAGACCTGCTGCTGCTCCCCCCGCTGGTGCTGCTCCCCCCGCTCCCCCTACTCCCCCCCCA

CGCCCACCTCGTCCCGCTGCCCTCACACGCCGTCCTGCTGAGGGACCCGATCCACAAGGCGGCTGGCGTAGACAACC

TCCTGGCCCATCCCATACACCGGCACCATCTGCCGCTGCTTTGGAGGCTTACTGTGCTCCTCGTGCTGTGGCTGAAC

TCACCGATCATCCGCTGTTCCCTGCTCCCTGGCGTCCCGCCCTCATGTTCGATCCTAGAGCTTTGGCTTCCTTGGCC

GCTCGTTGTGCTGCCCCTCCCCCTGGCGGTGCTCCGGCTGCTTTCGGTCCTCTCCGTGCCTCTGGTCCACTCCGCCG

TGCCGCTGCCTGGATGAGACAAGTTCCCGACCCTGAGGATGTTAGAGTTGTGATCTTGTACTCGCCCTTGCCTGGCG

AGGATTTGGCCGCTGGTAGAGCTGGCGGTGGCCCCCCTCCTGAATGGTCTGCTGAACGTGGTGGTTTGTCTTGCTTG

TTGGCCGCCCTGGGAAACCGTCTGTGTGGTCCTGCTACTGCTGCTTGGGCTGGAAACTGGACTGGCGCTCCCGATGT

TTCTGCTCTCGGTGCTCAAGGAGTTTTGCTGCTCTCTACTCGTGACTTGGCATTCGCTGGAGCTGTTGAATTCCTGG

GACTCTTGGCTGGCGCTTGTGATAGGAGACTCATCGTCGTAAACGCTGTGAGAGCTGCCGATTGGCCTGCCGATGGT

CCTGTTGTGTCTCGTCAACACGCTTACTTGGCTTGTGAAGTGTTGCCCGCTGTCCAATGTGCTGTTCGCTGGCCTGC

TGCTCGTGATCTGAGGCGTACTGTTCTGGCTAGTGGTCGTGTTTTCGGACCTGGTGTTTTCGCTCGTGTCGAAGCTG

CTCACGCTAGACTGTACCCCGATGCCCCACCCCTCCGTTTGTGTCGTGGAGCAAACGTTCGCTACCGTGTCCGTACT

CGTTTCGGACCCGATACTCTGGTTCCAATGTCCCCTCGTGAATACCGTCGTGCTGTTCTGCCTGCCCTCGATGGACG

TGCTGCCGCTTCTGGCGCTGGTGACGCTATGGCTCCTGGCGCTCCGGACTTCTGTGAGGATGAGGCTCACTCACATC

GTGCCTGTGCCCGCTGGGGACTGGGCGCTCCATTGAGGCCTGTATACGTGGCACTGGGCCGTGATGCTGTTAGAGGC

GGACCCGCTGAATTGAGAGGCCCTCGTCGTGAATTCTGTGCTAGGGCTCTGCTCGAACCCGATGGAGATGCTCCTCC

TTTGGTACTCCGTGACGACGCCGATGCTGGTCCTCCCCCACAAATTCGCTGGGCTAGTGCTGCTGGACGTGCTGGTA

CTGTATTGGCTGCTGCTGGCGGTGGCGTTGAAGTTGTTGGTACTGCCGCTGGACTCGCTACACCTCCCCGCCGTGAA

CCTGTAGACATGGATGCTGAACTCGAGGATGATGACGACGGATTGTTCGGAGAGTAATAG

SEQ ID NO: 40 = construct US6ΔTMR
ATGAAGTTCCTCGTGAACGTGGCCCTGGTGTTCATGGTGGTGTACATCAGCTACATCTACGCCAACCGTTGGAAGTA

CGCTCTGGCTGACCCATCCCTGAAGATGGCTGACCCCAACCGTTTCCGTGGCAAGAACCTGCCCGTGCTGGACCAGC

TGACCGACCCCCCTGGCGTGAAGCGTGTGTACCACATCCAGCCATCCCTCGAAGACCCCTTCCAGCCCCCCTCCATC

CCCATCACCGTGTACTACGCTGTGCTGGAACGCGCTTGCCGTTCCGTGCTGCTGCACGCTCCTTCCGAGGCTCCCCA

GATCGTGCGTGGTGCTTCCGACGAGGCTCGCAAGCACACCTACAACCTGACTATCGCTTGGTACAGGATGGGTGACA

ACTGCGCTATCCCTATCACCGTCATGGAATACACCGAGTGCCCCTACAACAAGTCCCTGGGCGTGTGCCCTATCCGT

ACCCAGCCCCGTTGGTCCTACTACGACTCCTTCAGCGCTGTGTCCGAGGACAACCTGGGTTTCCTGATGCACGCTCC

CGCTTTCGAGACTGCTGGCACCTACCTGCGTCTGGTCAAGATCAACGACTGGACCGAGATCACCCAGTTCATCCTGG

AACACCGTGCTCGTGCTTCGTGCAAGTACGCCCTGCCCCTGCGTATCCCTCCTGCTGCTTGCCTGACCTCCAAGGCT

TACCAGCAGGGCGTGACCGTGGACTCCATCGGCATGCTGCCCCGTTTCATCCCCGAGAACCAGCGTACCGTGGCTCT

GTACTCTCTGAAGATCGCTGGCTGGCACGGTCCTAAGCCCCCCTACACCTCCACTCTGCTGCCCCCTGAGCTGTCCG

ACACCACCAACGCTACTCAGCCCGAGTTGGTGCCTGAGGACCCCGAGGACTCCGCTCTGTTGGAGGACCCCGCTGGA

ACCGTGTCCTCCCAGATCCCCCCCAACTGGCACATCCCTTCCATCCAGGACGTGGCCCCTCACCACGCTCCAGCTGC

TCCCTCCAACCCCCGTCGTCGTGCTCAGATGGCTCCCAAGCGTCTGCGTCTGCCCCACATCCGTGACGACGACGCTC

CTCCATCCCACCAGCCCCTGTTCTACCACCACCACCATCACCACTAATAA

SEQ ID NO: 41 = RL1
ATGTCTCGTCGTCGTGGTCCTCGTCGTCGTGGTCCTCGTCGTCGTCCGCGTCCGGGTGCGCCGGCGGTACCACGCCC

GGGTGCGCCGGCAGTGCCGCGTCCAGGCGCACTGCCTACCGCGGACTCTCAAATGGTGCCGGCGTATGATTCTGGTA

CTGCCGTCGAATCTGCTCCGGCAGCGAGCTCCCTGCTGCGTCGTTGGCTGCTGGTCCCTCAGGCGGACGATTCCGAT

GACGCAGACTACGCGGGCAACGACGACGCGGAGTGGGCTAACAGCCCGCCAAGCGAGGGTGGTGGCAAAGCGCCGGA

-continued

GGCTCCGCACGCAGCGCCTGCCGCAGCGTGCCCGCCTCCGCCTCCTCGTAAAGAACGTGGCCCTCAACGTCCTCTGC

CGCCGCACCTGGCTCTGCGTCTGCGTACTACCACTGAGTACCTGGCGCGTCTGTCTCTGCGTCGTCGCCGTCCGCCG

GCTAGCCCGCCGGCCGATGCACCGCGTGGCAAAGTGTGCTTCTCTCCACGTGTTCAAGTTCGTCACCTGGTGGCTTG

GGAAACGGCTGCCCGTCTGGCTCGCCGTGGCAGCTGGGCACGTGAGCGCGCAGACCGTGACCGCTTCCGTCGCCGTG

TGGCGGCTGCTGAAGCCGTTATCGGCCCGTGCCTGGAACCTGAGGCTCGCGCTCGCGCGCGTGCGCGCGCTCGTGCC

CACGAAGATGGCGGTCCAGCAGAGGAAGAAGAGGCAGCTGCAGCAGCGCGCGGTAGCTCCGCGGCTGCGGGTCCAGG

TCGTCGTGCCGTA

SEQ ID NO: 42 = RL2
ATGTCGTACTACCATCACCATCACCATCACATGGAGCCACGTCCTGGTACTTCTTCTCGCGCTGATCCTGGTCCTGA

ACGTCCGCCACGCCAGACTCCGGGCACCCAGCCGGCCGCCCCTCACGCTTGGGGCATGCTGAACGATATGCAGTGGC

TGGCGTCCTCTGATTCCGAAGAGGAGACTGAGGTTGGTATCAGCGATGATGATCTGCACCGCGACTCTACCAGCGAA

GCAGGTTCCACTGACACCGAAATGTTTGAAGCGGGCCTGATGGATGCCGCGACCCCGCCGGCTCGTCCGCCGGCTGA

ACGTCAGGGTAGCCCTACGCCTGCGGATGCGCAAGGCTCTTGTGGTGGTGGTCCAGTAGGCGAAGAGGAGGCTGAGG

CCGGTGGCGGCGGTGATGTGTGTGCGGTTTGTACCGATGAAATCGCACCGCCGCTGCGTTGTCAGTCTTTCCCGTGC

CTGCACCCGTTTTGCATTCCGTGCATGAAAACCTGGATCCCGCTGCGCAACACTTGCCCGCTGTGCAACACTCCGGT

TGCTTATCTGATCGTTGGTGTAACCGCATCTGGTTCCTTTTCTACCATCCCGATTGTCAACGACCCACGTACGCGTG

TTGAGGCGGAGGCGGCTGTACGTGCGGGCACCGCGGTGGACTTTATCTGGACCGGTAACCCGCGCACCGCGCCACGC

TCCCTGTCTCTGGGTGGCCATACCGTTCGTGCTCTGAGCCCGACCCCACCTTGGCCAGGCACCGATGACGAAGACGA

CGATCTGGCTGACGTTGACTATGTTCCGCCGGCACCGCGTCGCGCACCACGCCGTGGTGGCGGTGGCGCCGGTGCGA

CGCGCGGTACCTCCCAGCCGGCAGCAACTCGCCCAGCACCGCCGGGTGCCCCGCGTTCTAGCAGCTCCGGTGGCGCA

CCGCTGCGTGCTGGCGTGGGTTCTGGTTCCGGTGGTGGTCCGGCCGTGGCGGCTGTCGTCCCGCGTGTGGCTTCTCT

GCCACCGGCAGCTGGTGGCGGTCGTGCTCAAGCTCGTCGTGTCGGCGAGGACGCAGCGGCTGCTGAGGGCCGTACTC

CACCGGCCCGTCAACCGCGCGCAGCACAGGAACCGCCGATCGTGATCTCCGATTCCCCGCCACCGAGCCCGCGTCGC

CCGGCGGGTCCGGGTCCGCTGTCTTTTGTATCCTCCAGCTCTGCTCAGGTAAGCAGCGGTCCTGGCGGTGGCGGCCT

GCCACAGTCCTCTGGTCGTGCTGCTCGTCCTCGTGCGGCGGTTGCTCCTCGTGTACGTTCTCCGCCACGCGCTGCTG

CCGCGCCGGTCGTTTCTGCCTCTGCTGACGCGGCAGGTCCGGCTCCGCCTGCAGTTCCGGTTGATGCACACCGTGCA

CCGCGCTCTCGTATGACCCAGGCGCAGACTGATACCCAGGCACAATCCCTGGGTCGCGCGGGTGCGACTGACGCTCG

TGGTAGCGGTGGTCCGGGCGCTGAAGGTGGCCCGGGTGTTCCACGCGGTACTAACACTCCGGGCGCTGCGCCACACG

CGGCTGAAGGTGCGGCTGCACGTCCGCGTAAACGTCGTGGTTCCGACAGCGGTCCGGCTGCAAGCAGCAGCGCGAGC

TCTTCCGCTGCGCCTCGCAGCCCGCTGGCGCCGCAGGGTGTTGGCGCCAAGCGTGCTGCTCCGCGTCGTGCACCGGA

CTCCGATTCTGGCGACCGCGGTCACGGCCCGCTGGCCCCTGCTAGCGCAGGCGCTGCGCCGCCATCCGCCAGCCCGT

CTTCTCAGGCAGCTGTGGCTGCGGCGTCCTCTTCTTCCGCTAGCAGCTCTTCCGCCTCTTCTAGCAGCGCGTCCTCT

AGCAGCGCATCTTCCTCTTCTGCTTCTTCTTCTAGCGCTTCTAGCTCTTCCGCGTCCTCTTCCGCTGGCGGTGCAGG

CGGCTCTGTTGCTTCCGCCAGCGGCGCAGGTGAGCGTCGTGAAACGAGCCTGGGCCCACGTGCTGCTGCACCGCGTG

GCCCGCGTAAGTGTGCGCGCAAGACCCGCCACGCTGAAGGCGGTCCGGAGCCGGGTGCGCGTGATCCGGCTCCGGGT

CTGACCCGTTACCTGCCGATTGCGGGTGTGTCCTCCGTTGTGGCACTGGCGCCGTATGTGAACAAAACTGTCACGGG

CGATTGCCTGCCTGTTCTGGACATGGAAACCGGTCATATCGGCGCTTACGTCGTTCTGGTTGACCAAACCGGCAACG

TGGCGGATCTGCTGCGTGCGGCCGCTCCGGCTTGGTCCCGTCGTACCCTGCTGCCGGAACATGCTCGCAACTGTGTA

CGCCCACCGGATTACCCAACCCCGCCGGCCTCCGAGTGGAACTCCCTGTGGATGACCCCGGTTGGTAACATGCTGTT

CGACCAGGGCACGCTGGTTGGTGCTCTGGACTTTCACGGCCTGCGCTCCCGTCACCCGTGGTCCCGTGAGCAAGGCG

CTCCGGCCCCTGCGGGCGATGCCCCGGCTGGCCACGGCGAGAGTACTAGAGGATCATAA

-continued

SEQ ID NO: 43 = construct UL36.3.4.1

ATGTCGTACTACCATCACCATCACCATCACGCCGCTCAACGTGCTAGGGGATCCTCTGAACGCTGGGCTGCTGGTGT

CGAGGCTGCTTTGGATAGAGTGGAGAACCGTGCCGAATTCGATGTTGTCGAGCTGAGGAGACTCCAAGCTTTGGCTG

GTACTCACGGCTACAACCCTCGTGATTTCCGTAAACGTGCCGAACAGGCTTTGGCGGCAAACGCTGAGGCCGTAACA

TTGGCTCTGGACACTGCCTTCGCTTTCAACCCATACACGCCCGAAAACCAACGTCATCCTATGCTCCCACCTCTCGC

TGCTATTCACCGCCTGGGATGGAGCGCTGCTTTCCATGCTGCTGCTGAAACTTACGCCGACATGTTCCGTGTCGATG

CCGAACCACTGGCTAGACTGCTCCGTATCGCTGAGGGACTGCTGGAGATGGCTCAAGCTGGCGACGGATTCATCGAT

TACCATGAGGCTGTCGGTAGACTGGCCGATGATATGACTTCTGTGCCCGGATTGAGGCGCTACGTTCCTTTCTTCCA

ACATGGCTACGCCGATTACGTGGAACTGAGAGATCGCCTGGATGCTATTAGGGCCGACGTCCATAGAGCACTCGGTG

GTGTTCCGCTGGATTTGGCGGCTGCTGCCGAACAAATTTCCGCTGCTCGTAACGATCCTGAGGCTACTGCTGAATTG

GTCCGTACTGGTGTAACATTGCCTTGCCCTAGTGAGGACGCTCTCGTGGCTTGTGCTGCTGCCCTGGAGAGAGTCGA

TCAATCTCCCGTGAAAAACACGGCTTACGCCGAATACGTTGCCTTCGTGACCCGTCAAGACACTGCTGAGACTAAAG

ACGCTGTGGTCCGTGCTAAACAACAACGTGCTGAGGCCACTGAACGTGTTATGGCTGGCCTGAGAGAGGCTCTGGCT

GCTAGAGAACGTCGTGCTCAAATTGAGGCTGAGGGATTGGCAAACCTGAAAACCATGCTCAAAGTCGTGGCTGTACC

CGCTACTGTTGCTAAAACTCTCGACCAGGCTCGTAGTGTTGCCGAAATTGCCGATCAAGTCGAAGTGTTGCTGGATC

AAACCGAAAAAACTCGTGAACTGGATGTGCCTGCTGTGATCTGGCTCGAACACGCCCAAAGAACATTCGAGACACAC

CCTTTGTCTGCCGCTCGTGGTGATGGTCCTGGACCCTTGGCTCGTCATGCTGGCCGCCTCGGTGCCCTCTTCGATAC

TCGTCGTAGAGTAGACGCCTTGAGGAGATCCCTGGAGGAGGCTGAGGCTGAATGGGACGAAGTTTGGGGACGCTTCG

GTAGAGTGAGGGGCGGAGCGTGGAAATCTCCGGAGGGATTCCGTGCAATGCATGAGCAACTGAGGGCCCTCCAAGAC

ACAACAAACACCGTGTCTGGCCTGAGGGCTCAACCTGCTTACGAACGCTTGTCTGCTCGCTACCAAGGAGTACTCGG

AGCGAAAGGCGCTGAGAGAGCTGAGGCTGTTGAGGAACTCGGTGCTCGTGTCACTAAACACACCGCTCTGTGTGCTA

GGCTGAGAGATGAGGTCGTCCGTAGAGTGCCTTGGGAAATGAACTTCGATGCTCTGGGAGGATTGTTGGCTGAGTTC

GATGCCGCTGCTGCCGATTTGGCACCTTGGGCTGTAGAGGAATTCCGTGGTGCTAGAGAACTCATTCAATACCGTAT

GGGCCTGTACTCTGCCTACGCTAGAGCTGGAGGACAAACTGGTGCTGGAGCTGAATCTGCTCCTGCTCCTTTGCTCG

TGGATCTGAGGGCTTTGGATGCTCGTGCTCGTGCTTCTTCTTCCCCTGAGGGACATGAAGTGGACCCACAACTGCTG

AGGAGGCGTGGAGAGGCTTACTTGAGAGCTGGCGGCGACCCTGGACCTCTCGTGCTCCGTGAAGCTGTTTCTGCTTT

GGACCTGCCATTCGCCACATCTTTCTTGGCCCCCGATGGAACTCCCCTCCAATACGCTTTGTGCTTCCCTGCCGTAA

CGGACAAACTCGGAGCTTTGCTCATGAGGCCCGAGGCCGCTTGTGTTAGACCTCCTTTGCCTACCGATGTGCTGGAA

TCTGCCCCAACTGTGACTGCCATGTACGTACTCACTGTGGTCAACCGCCTCCAACTGGCATTGAGTGATGCTCAAGC

GGCAAACTTCCAACTGTTCGGTCGTTTCGTTCGTCATAGGCAGGCAACCTGGGGAGCGTCAATGGATGCCGCCGCTG

AATTGTACGTTGCCCTGGTGGCTACAACTCTCACACGTGAATTCGGTTGTCGCTGGGCACAATTGGGATGGGCTAGT

GGAGCTGCTGCTCCTAGACCCCCACCTGGACCCCGTGGCTCACAACGTCACTGTGTGGCATTCAACGAGAACGATGT

CCTCGTCGCTTTGGTTGCCGGTGTTCCCGAACACATCTACAACTTCTGGCGCCTGGACTTGGTCCGTCAACACGAGT

ACATGCACCTCACACTGGAGCGTGCCTTCGAGGATGCTGCCGAGTCTATGCTCTTCGTTCAACGCCTCACTCCACAT

CCCGACGCTCGTATTAGAGTTCTGCCGACCTTCTTGGATGGTGGTCCTCCTACACGTGGTCTGTTGTTCGGAACCCG

CTTGGCGGACTGGCGTCGTGGTAAACTGTCTGAAACCGACCCATTGGCCCCATGGAGATCTGCTTTGGAACTCGGAA

CCCAACGTCGTGACGTGCCTGCTTTGGGAAAACTGTCCCCTGCTCAAGCTTTGGCCGCTGTGTCGGTACTGGGCCGT

ATGTGCTTGCCCTCGGCTGCCTTGGCTGCTTTGTGGACCTGTATGTTCCCCGACGACTACACTGAATACGACTCATT

CGACGCCCTCTTGGCGGCTCGCCTGGAATCGGGACAAACATTGGGACCTGCTGGCGGTAGAGAGGCTTCATTGTAAT

AG

-continued

SEQ ID NO: 44 = construct UL36.4.2.5
ATGTCGTACTACCATCACCATCACCATCACGAATACGACTCCTTCGACGCTTTGTTGGCTGCTAGACTGGAATCTGG

TCAAACCTTGGGACCCGCTGGCGGTAGAGAGGCTTCTTTGCCCGAGGCTCCTCATGCTTTGTACCGTCCAACCGGAC

AACATGTTGCTGTGTTGGCGGCTGCTACTCATAGAACCCCTGCTGCTCGTGTTACTGCTATGGACCTGGTCTTGGCG

GCCGTTTTGCTGGGCGCTCCTGTGGTGGTCGCTCTGAGAAACACTACTGCCTTCTCCCGTGAATCCGAATTGGAACT

GTGCCTCACCCTGTTCGATTCTCGTCCCGGCGGACCGGATGCTGCCCTGAGAGATGTGGTATCCTCCGACATTGAAA

CCTGGGCTGTGGGCTTGCTCCACACCGATTTGAACCCTATTGAGAACGCTTGCTTGGCGGCTCAACTGCCACGCTTG

TCTGCCCTCATTGCTGAACGTCCTTTGGCCGATGGACCCCCTTGTTTGGTGTTGGTGGACATTTCGATGACACCTGT

CGCTGTTTTGTGGGAGGCCCCTGAACCACCTGGCCCTCCCGATGTTCGTTTCGTCGGTAGCGAGGCCACTGAGGAAT

TGCCTTTCGTGGCTACTGCTGGTGATGTTTTGGCGGCGAGTGCTGCCGATGCCGATCCTTTCTTCGCTCGTGCTATC

CTGGGCCGTCCTTTCGATGCTTCTCTGCTCACTGGTGAACTGTTCCCTGGTCACCCCGTTTACCAACGTCCCCTGGC

GGATGAGGCTGGTCCTTCTGCTCCTACTGCCGCTCGTGATCCTAGAGATCTGGCTGGAGGCGACGGTGGATCCGGAC

CTGAGGATCCCGCTGCTCCACCTGCTAGACAGGCCGATCCTGGTGTTTTGGCTCCTACTCTGCTCACCGATGCTACT

ACTGGCGAACCTGTGCCACCCCGTATGTGGGCTTGGATTCATGGACTGGAGGAACTGGCTTCCGATGATGCCGGCGG

TCCTACCCCAAACCCTGCCCCGGCTTTGCTGCCCCCTCCTGCTACGGATCAATCTGTCCCCACTTCCCAATACGCCC

CTAGACCAATTGGCCCGGCTGCCACTGCTAGAGAAACTCGTCCTTCCGTTCCCCCTCAACAAAACACTGGTCGTGTC

CCTGTGGCTCCACGTGATGACCCTAGACCTTCCCCCCCTACTCCTTCCCCCCCTGCCGATGCTGCTTTGCCACCTCC

TGCCTTCTCTGGTTCTGCTGCTGCTTTCTCCGCTGCTGTTCCACGTGTTCGTCGTTCTAGGCGTACTCGTGCCAAAT

CCCGTGCCCCTCGTGCTTCTGCCCCACCCGAGGGATGGCGTCCCCCCGCTTTGCCTGCCCCTGTTGCTCCTGTGGCG

GCTTCTGCTCGTCCCCCCGATCAACCTCCTACTCCCGAATCTGCTCCCCCGGCTTGGGTTTCCGCTCTGCCATTGCC

ACCCGGACCTGCTAGTGCTCGTGGTGCTTTCCCTGCTCCAACCTTGGCCCCTATTCCCCCACCCCCCGCTGAGGGAG

CTGTTGTTCCCGGTGGTGATCGTAGACGTGGTCGCCGTCAAACAACTGCTGGACCATCCCCTACACCGCCACGTGGC

CCGGCTGCTGGTCCTCCTCGTCGCCTCACTAGGCCTGCTGTTGCTAGTCTGTCCGCTTCTTTGAACTCTCTGCCTTC

CCCCCGTGATCCTGCCGATCATGCTGCTGCCGTTTCTGCTGCCGCCGCTGCCGTACCACCTTCACCTGGACTGGCTC

CCCCAACTTCTGCTGTCCAAACCTCTCCTCCTCCCTTGGCGCCTGGTCCTGTTGCCCCATCTGAACCTTTGTGTGGC

TGGGTTGTGCCTGGAGGCCCTGTTGCTAGACGTCCCCCACCCCAATCTCCGGCTACTAAACCGGCTGCTCGTACCCG

TATTAGGGCTCGTTCTGTGCCCCAACCACCCTTGCCCCAACCTCCACTGCCTCAACCCCCCTTGCCTCAACCCCCTC

TCCCCCAACCACCTCTGCCTCAACCTCCGCTGCCCCAACCTCCTTTGCCCCAACCTCCTTTGCCCCAACCTCCTTTG

CCCCAACCTCCGCTGCCCCAACCTCCGCTGCCACCTGTTACTCGTACACTCACTCCCCAATCTCGTGACTCTGTGCC

TACACCTGAGTCTCCAACTCACACAAACACCCACTTGCCCGTTAGTGCTGTGACTTCTTGGGCTTCGTCCCTGGCTC

TCCATGTGGATTCTGCCCCTCCCCCTGCTTCATTGCTCCAAACTCTCCACATTTCCTCCGATGATGAACACTCCGAC

GCCGACTCACTCCGCTTCTCCGATTCCGATGACACTGAGGCTCTCGATCCTTTGCCTCCTGAACCTCACTTGCCACC

TGCCGATGAACCCCCCGGACCTCTGGCTGCCGACCATCTCCAATCACCTCACTCACAATTCGGTCCTTTGCCCGTTC

AAGCGAACGCTGTTCTGTCTCGTCGTTACGTGAGATCAACTGGCCGTTCTGCCTTGGCTGTGCTCATTAGAGCTTGT

CGCCGTATCCAACAACAACTCCAGCGTACTAGGAGAGCACTCTTCCAACGCTCAAACGCCGTGCTCACATCACTCCA

CCATGTCCGTATGCTCTTGGGATAATAG

SEQ ID NO: 45 = US12
ATGTCTTGGGCTCTGAAAACCACCGACATGTTCCTGGACTCTTCTCGTTGCACCCACCGTACCTACGGTGACGTTTG

CGCTGAAATCCACAAACGTGAACGTGAAGACCGTGAAGCTGCTCGTACCGCTGTTACCGACCCGGAACTGCCGCTGC

TGTGCCCGCCGGACGTTCGTTCTGACCCGGCTTCTCGTAACCCGACCCAGCAGACCCGTGGTTGCGCTCGTTCTAAC

GAACGTCAGGACCGTGTTCTGGCTCCGTGA

-continued

SEQ ID NO: 46 = US4
ATGAAGTTCCTCGTGAACGTGGCCCTGGTGTTCATGGTGGTGTACATCAGCTACATCTACGCTAACCGTTGGGGTTC

CGGCGTGCCCGGTCCCATCAACCCCCCCAACTCCGACGTGGTGTTCCCCGGTGGTTCCCCCGTGGCTCAGTACTGCT

ACGCTTACCCCCGTCTGGACGACCCTGGTCCCCTGGGTTCTGCTGACGCTGGTCGTCAGGACCTGCCCCGTCGTGTC

GTGCGTCACGAGCCCCTGGGTCGTAGCTTCCTGACCGGTGGCCTGGTGCTGTTGGCTCCCCCTGTGCGCGGTTTCGG

TGCTCCCAACGCTACCTACGCTGCTCGTGTGACCTACTACCGTCTGACCCGTGCTTGCCGTCAGCCCATCCTGCTGC

GTCAGTACGGTGGTTGCCGTGGTGGAGAGCCCCCATCCCCCAAGACCTGCGGTTCTTACACCTACACCTACCAGGGT

GGTGGTCCCCCTACCCGTTACGCTCTGGTCAACGCTTCCCTGCTGGTGCCCATCTGGGACCGTGCTGCTGAGACTTT

CGAGTACCAGATCGAGCTGGGTGGCGAGCTGCACGTGGGTCTGCTGTGGGTGGAAGTGGGTGGAGAGGGTCCCGGTC

CTACCGCTCCTCCTCAGGCTGCTCGTGCTGAGGGTGGTCCTTGCGTGCCACCCGTGCCTGCTGGTCGTCCTTGGCGT

TCCGTGCCCCCCGTGTGGTACTCCGCTCCCAACCCCGGTTTCCGCGGTCTGCGTTTCCGTGAGCGTTGCCTGCCTCC

CCAGACCCCTGCTGCTCCTTCCGACCTGCCTCGTGTGGCTTTCGCTCCCCAGTCCCTGCTCGTGGGTATCACCGGTC

GTACCTTCATCCGTATGGCTCGTCCCACCGAGGACGTGGGTGTCCTGCCTCCTCACTGGGCTCCAGGTGCTCTGGAC

GACGGTCCCTACGCTCCCTTCCCCCCTCGTCCCCGTTTCCGTCGTCACCACCACCATCACCACTAATAA

SEQ ID NO: 117 = construct RS1.2
ATGTCGTACTACCATCACCATCACCATCACATGGTGCTGTACGGCGGGCTGGGCGACAGCCGCCCCGGCCTCTGGGG

GGCGCCCGAGGCGGAGGAGGCGCGGGCCCGGTTCGAGGCCTCGGGCGCCCCGGCGCCCGTGTGGGCGCCCGAGCTGG

GCGACGCGGCGCAGCAGTACGCCCTGATCACGCGGCTGCTGTACACGCCGGACGCGGAGGCGATGGGGTGGCTCCAG

AACCCGCGCGTGGCGCCCGGGGACGTGGCGCTGGACCAGGCCTGCTTCCGGATCTCGGGCGCGGCGCGCAACAGCAG

CTCCTTCATCTCCGGCAGCGTGGCGCGGGCCGTGCCCCACCTGGGGTACGCCATGGCGGCGGGCCGCTTCGGCTGGG

GCCTGGCGCACGTGGCGGCCGCCGTGGCCATGAGCCGCCGCTACGACCGCGCGCAGAAGGGCTTCCTGCTGACCAGC

CTGCGCCGCGCCTACGCGCCCCTGCTGGCGCGCGAGAACGCGGCGCTGACCGGGGCGCGGACCCCCGACGACGGCGG

CGACGCCAACCGCCGCGACGGCGACGACGCCCGCGGGAAGCCCGCCGCCGCCGCCGCCCCGTTGCCGTCGGCGGCGG

CGTCGCCGGCCGACGAGCGCGCGGTGCCCGCCGGCTACGGCGCCGCGGGGGTGCTCGCCGCCCTGGGGCGCCTGAGC

GCCGCGCCCGCCTCCGCGCCGGCCGGGGCCGACGACGACGACGACGACGACGGCGCCGGCGGTGGTGGCGGTGG

TGGCGGTGGTGGCGGCGGCCGGCGCGCGGAGGCGGGCCGCGTGGCCGTGGAGTGCCTGGCCGCCTGCCGCGGGATCC

TGGAGGCGCTGGCGGAGGGCTTCGACGGCGACCTGGCGGCCGTGCCGGGGCTGGCCGGAGCCCGGCCCGCCGCGCCC

CCGCGCCCGGGGCCCGCGGGCGCGGCCGCCCCGCCGCACGCCGACGCGCCCCGCCTGCGCGCCTGGCTGCGCGAGCT

GCGGTTCGTGCGCGACGCGCTGGTGCTGATGCGCCTGCGCGGGGACCTGCGCGTGGCCGGCGGCAGCGAGGCCGCCG

TGGCCGCCGTGCGCGCCGTGAGCCTGGTCGCCGGGGCCCTGGGCCCGGCGCTGCCGCGGAGCCCGCGCCTGCTGAGC

TCCGCCGCCGCCGCCGCCGCGGACCTGCTCTTCCAGAACCAGAGCCTGAGTACTAGAGGATCATAA

SEQ ID NO: 118 = UL1
ATGTCGTACTACCATCACCATCACCATCACATGGGGTTCGTCTGTCTGTTTGGGCTTGTCGTTATGGGAGCCTGGGG

GGCGTGGGGTGGGTCACAGGCAACCGAATATGTTCTTCGTAGTGTTATTGCCAAAGAGGTGGGGGACATACTAAGAG

TGCCTTGCATGCGGACCCCCGCGGACGATGTTTCTTGGCGCTACGAGGCCCCGTCCGTTATTGACTATGCCCGCATA

GACGGAATATTTCTTCGCTATCACTGCCCGGGGTTGGACACGTTTTTGTGGGATAGGCACGCCCAGAGGGCGTATCT

TGTTAACCCCTTTCTCTTTGCGGCGGGATTTTTGGAGGACTTGAGTCACTCTGTGTTTCCGGCCGACACCCAGGAAA

CAACGACGCGCCGGGCCCTTTATAAAGAGATACGCGATGCGTTGGGCAGTCGAAAACAGGCCGTCAGCCACGCACCC

GTCAGGGCCGGGTGTGTAAACTTTGACTACTCACGCACTCGCCGCTGCGTCGGGCGACGCGATTTACGGCCTGCCAA

CACCACGTCAACGTGGGAACCGCCTGTGTCGTCGGACGATGAAGCGAGCTCGCAGTCGAAGCCCCTCGCCACCCAGC

CGCCCGTCCTCGCCCTTTCGAACGCCCCCCCACGGCGGGTCTCCCCGACGCGAGGTCGGCGCCGGCATACTCGCCTC

CGACGCAACTGA

-continued

SEQ ID NO: 119 = construct UL1s

ATGAAGTTCCTCGTGAACGTGGCCCTGGTGTTCATGGTGGTGTACATCAGCTACATCTACGCCAACCGTTGGGGGTT

CGTCTGTCTGTTTGGGCTTGTCGTTATGGGAGCCTGGGGGGCGTGGGGTGGGTCACAGGCAACCGAATATGTTCTTC

GTAGTGTTATTGCCAAAGAGGTGGGGGACATACTAAGAGTGCCTTGCATGCGGACCCCCGCGGACGATGTTTCTTGG

CGCTACGAGGCCCCGTCCGTTATTGACTATGCCCGCATAGACGGAATATTTCTTCGCTATCACTGCCCGGGGTTGGA

CACGTTTTTGTGGGATAGGCACGCCCAGAGGGCGTATCTTGTTAACCCCTTTCTCTTTGCGGCGGGATTTTTGGAGG

ACTTGAGTCACTCTGTGTTTCCGGCCGACACCCAGGAAACAACGACGCGCCGGGCCCTTTATAAAGAGATACGCGAT

GCGTTGGGCAGTCGAAAACAGGCCGTCAGCCACGCACCCGTCAGGGCCGGGTGTGTAAACTTTGACTACTCACGCAC

TCGCCGCTGCGTCGGGCGACGCGATTTACGGCCTGCCAACACCACGTCAACGTGGGAACCGCCTGTGTCGTCGGACG

ATGAAGCGAGCTCGCAGTCGAAGCCCCTCGCCACCCAGCCGCCCGTCCTCGCCCTTTCGAACGCCCCCCCACGGCGG

GTCTCCCCGACGCGAGGTCGGCGCCGGCATACTCGCCTCCGACGCAACCATCACCATCACCATCACTGA

SEQ ID NO: 120 = construct UL19ΔTEV

ATGTCGTACTACCATCACCATCACCATCACATGGCCGCTCCTGCCCGCGACCCCCCGGGTTACCGGTACGCCGCGGC

CATGGTGCCCACCGGCTCCATCCTGAGTACGATCGAGGTGGCGTCCCACCGCAGACTCTTTGATTTTTTCGCCCGCG

TGCGCTCCGACGAAAACAGCCTGTATGACGTAGAGTTTGACGCCCTGCTGGGGTCCTACTGCAACACCCTGTCGCTC

GTGCGCTTTCTGGAGCTCGGCCTGTCCGTGGCGTGCGTGTGCACCAAGTTCCCGGAGCTGGCTTACATGAACGAAGG

GCGTGTGCAGTTCGAGGTCCACCAGCCCCTCATCGCCCGCGACGGCCCGCACCCCGTCGAGCAGCCCGTGCATAATT

ACATGACGAAGGTCATCGACCGCCGGGCCCTGAACGCCGCCTTCAGCCTGGCCACCGAGGCCATTGCCCTGCTCACG

GGGGAGGCCCTGGACGGGACGGGCATTAGCCTGCATCGCCAGCTGCGCGCCATCCAGCAGCTCGCGCGCAACGTCCA

GGCCGTCCTGGGGGCGTTTGAGCGCGGCACGGCCGACCAGATGCTGCACGTGCTGTTGGAGAAGGCGCCTCCCCTGG

CCCTGCTGTTGCCCATGCAACGATATCTCGACAACGGGCGCCTGGCGACCAGGGTTGCCCGGGCGACCCTGGTCGCC

GAGCTGAAGCGGAGCTTTTGCGACACGAGCTTCTTCCTGGGCAAGGCGGGCCATCGCCGCGAGGCCATCGAGGCCTG

GCTCGTGGACCTGACCACGGCGACGCAGCCGTCCGTGGCCGTGCCCCGCCTGACGCACGCCGACACGCGCGGGCGGC

CGGTCGACGGGGTGCTGGTCACCACCGCCGCCATCAAACAGCGCCTCCTGCAGTCCTTCCTGAAGGTGGAGGACACC

GAGGCCGACGTGCCGGTGACCTACGGCGAGATGGTCTTGAACGGGGCCAACCTCGTCACGGCGCTGGTGATGGGCAA

GGCCGTGCGGAGCCTGGACGACGTGGGCCGCCACCTGCTGGAGATGCAGGAGGAGCAACTCGAGGCGAACCGGGAGA

CGCTGGATGAACTCGAAAGCGCCCCCCAGACAACGCGCGTGCGCGCGGATCTGGTGGCCATAGGCGACAGGCTGGTC

TTCCTGGAGGCCCTGGAGAAGCGCATCTACGCCGCCACCAACGTGCCCTACCCCCTGGTGGGCGCCATGGACCTGAC

GTTCGTCCTGCCCCTGGGGCTGTTCAACCCGGCCATGGAGCGCTTCGCCGCGCACGCCGGGGACCTGGTGCCCGCCC

CCGGCCACCCGGAGCCCCGCGCGTTCCCTCCCCGGCAGCTGTTTTTTTGGGGAAAGGACCACCAGGTTCTGCGGCTG

TCCATGGAGAACGCGGTCGGGACCGTGTGTCATCCTTCGCTCATGAACATCGACGCGGCCGTCGGGGGCGTGAACCA

CGACCCCGTCGAGGCCGCGAATCCGTACGGGGCGTACGTCGCGGCCCCGGCCGGCCCCGGCGCGGACATGCAGCAGC

GTTTTCTGAACGCCTGGCGGCAGCGCCTCGCCCACGGCCGGGTCCGGTGGGTCGCCGAGTGCCAGATGACCGCGGAG

CAGTTCATGCAGCCCGACAACGCCAACCTGGCTCTGGAGCTGCACCCCGCGTTCGACTTCTTCGCGGGCGTGGCCGA

CGTCGAGCTTCCCGGCGGCGAAGTCCCCCCGGCCGGTCCGGGGGCGATCCAGGCCACCTGGCGCGTGGTCAACGGCA

ACCTGCCCCTGGCGCTGTGTCCGGTGGCGTTTCGTGACGCCCGGGGCCTGGAGCTCGGCGTTGGCCGCCACGCCATG

GCGCCGGCTACCATAGCCGCCGTCCGCGGGGCGTTCGAGGACCGCAGCTACCCGGCGGTGTTCTACCTGCTGCAAGC

CGCGATTCACGGCAGCGAGCACGTGTTCTGCGCCCTGGCGCGGCTCGTGACTCAGTGCATCACCAGCTACTGGAACA

ACACGCGATGCGCGGCGTTCGTGAACGACTACTCGCTGGTCTCGTACATCGTGACCTACCTCGGGGGCGACCTCCCC

GAGGAGTGCATGGCCGTGTATCGGGACCTGGTGGCCCACGTCGAGGCCCTGGCCCAGCTGGTGGACGACTTTACCCT

GCCGGGCCCGGAGCTGGGCGGGCAGGCTCAGGCCGAGCTGAATCACCTGATGCGCGACCCGGCGCTGCTGCCGCCCC

TCGTGTGGGACTGCGACGGCCTTATGCGACACGCGGCCCTGGACCGCCACCGAGACTGCCGGATTGACGCGGGGGAG

-continued

CACGAGCCCGTCTACGCGGCGGCGTGCAACGTGGCGACGGCCGACTTTAACCGCAACGACGGCCGGCTGCTGCACAA

CACCCAGGCCCGCGCGGCCGACGCCGCCGACGACCGGCCGCACCGGCCGGCCGACTGGACCGTCCACCACAAAATCT

ACTATTACGTGCTGGTGCCGGCCTTCTCGCGGGGGCGCTGCTGCACCGCGGGGGTCCGCTTCGACCGCGTGTACGCC

ACGCTGCAGAACATGGTGGTCCCGGAGATCGCCCCCGGCGAGGAGTGCCCGAGCGATCCCGTGACCGACCCCGCCCA

CCCGCTGCATCCCGCCAATCTGGTGGCCAACACGGTCAACGCCATGTTCCACAACGGGCGCGTCGTCGTCGACGGGC

CCGCCATGCTCACGCTGCAGGTGCTGGCGCACAACATGGCCGAGCGCACGACGGCGCTGCTGTGCTCCGCGGCGCCC

GACGCGGGCGCCAACACCGCGTCGACGGCCAACATGCGCATCTTCGACGGGGCGCTGCACGCCGGCGTGCTGCTCAT

GGCCCCCCAGCACCTGGACCACACCATCCAAAATGGCGAATACTTCTACGTCCTGCCCGTCCACGCGCTGTTTGCGG

GCGCCGACCACGTGGCCAACGCGCCCAACTTCCCCCCGGCCCTGCGCGACCTGGCGCGCCACGTCCCCCTGGTCCCC

CCGGCCCTGGGGGCCAACTACTTCTCCTCCATCCGCCAGCCCGTGGTGCAGCACGCCCGCGAGAGCGCGGCGGGGGA

GAACGCGCTGACCTACGCGCTCATGGCGGGGTACTTCAAGATGAGCCCCGTGGCCCTGTATCACCAGCTCAAGACGG

GCCTCCACCCCGGGTTCGGGTTCACCGTCGTGCGGCAGGACCGCTTCGTGACCGAGAACGTGCTGTTTTCCGAGCGC

GCGTCGGAGGCGTACTTTCTGGGCCAGCTCCAGGTGGCCCGCCACGAAACGGGCGGGGGGGTCAGCTTCACGCTCAC

CCAGCCGCGCGGAAACGTGGACCTGGGTGTGGGCTACACCGCCGTCGCGGCCACGGCCACCGTCCGCAACCCCGTTA

CGGACATGGGCAACCTCCCCCAAAACTTTTACCTCGGCCGCGGGGCCCCCCCGCTGCTAGACAACGCGGCCGCCGTG

TACCTGCGCAACGCGGTCGTGGCGGGAAACCGGCTGGGGCCGGCCCAGCCCCTCCCGGTCTTTGGCTGCGCCCAGGT

GCCGCGGCGCGCCGGCATGGACCACGGGCAGGATGCCGTGTGTGAGTTCATCGCCACCCCCGTGGCCACGGACATCA

ACTACTTTCGCCGGCCCTGCAACCCGCGGGGACGCGCGGCCGGCGGCGTGTACGCGGGGGACAAGGAGGGGGACGTC

ATAGCCCTCATGTACGACCACGGCCAGAGCGACCCGGCGCGGCCCTTCGCGGCCACGGCCAACCCGTGGGCGTCGCA

GCGGTTCTCGTACGGGGACCTGCTGTACAACGGGGCCTATCACCTCAACGGGGCCTCGCCCGTCCTCAGCCCCTGCT

TCAAGTTCTTCACCGCGGCCGACATCACGGCCAAACATCGCTGCCTGGAGCGTCTTATCGTGGAAACGGGATCGGCG

GTATCCACGGCCACCGCTGCCAGCGACGTGCAGTTTAAGCGCCCGCCGGGGTGCCGCGAGCTCGTGGAAGACCCGTG

CGGCCTGTTTCAGGAAGCCTACCCGATCACCTGCGCCAGCGACCCCGCCCTGCTACGCAGCGCCCGCGATGGGGAGG

CCCACGCGCGAGAGACCCACTTTACGCAGTATCTCATCTACGACGCCTCCCCGCTAAAGGGCCTGTCTCTGTAA

SEQ ID NO: 121 = construct RS1.1

ATGAGTGCCGAACAGCGTAAAAAGAAAAAAACCACCACCACGACCCAAGGACGTGGAGCTGAAGTTGCTATGGCGGA

TGAGGATGGAGGCCGCTTGAGAGCTGCTGCTGAGACTACTGGAGGACCTGGATCACCGGACCCTGCCGATGGACCCC

CCCCTACACCAAACCCCGATCGTAGACCGGCTGCTAGACCTGGATTCGGATGGCATGGAGGACCCGAGGAAAACGAG

GACGAGGCGGACGACGCCGCTGCCGACGCCGACGCCGATGAGGCTGCCCCTGCTTCTGGAGAGGCGGTAGACGAACC

TGCTGCCGATGGAGTTGTTAGCCCTAGGCAATTGGCTTTGTTGGCGAGCATGGTAGACGAGGCTGTGAGAACAATCC

CTTCCCCTCCCCCTGAACGTGATGGAGCACAAGAGGAGGCGGCTAGGAGTCCCTCACCACCCCGTACACCTTCTATG

AGAGCGGATTACGGCGAGGAAAACGACGACGACGACGATGATGATGACGACGATGATCGTGATGCCGGACGCTGGGT

TAGGGGACCTGAAACCACTTCTGCTGTCCGTGGAGCATACCCCGATCCTATGGCGAGTTTGAGCCCTAGACCACCTG

CCCCGAGGAGACACCACCACCACCACCATCATAGGCGTAGACGTGCTCCTAGACGTCGTTCTGCCGCTAGTGACTCT

TCCAAATCTGGCTCTTCTTCATCTGCCTCTTCCGCTTCATCTTCGGCCTCATCGTCCTCTTCGGCATCCGCTTCGAG

TAGTGATGATGATGATGACGACGACGCTGCTAGAGCCCCCGCTTCTGCTGCCGACCACGCTGCTGGCGGAACTTTGG

GAGCCGACGACGAGGAGGCGGGAGTTCCTGCTCGTGCCCCGGGAGCTGCTCCGAGGCCTTCTCCACCCCGTGCTGAA

CCTGCTCCGGCTAGAACACCGGCCGCTACTGCTGGTAGACTGGAGCGTAGACGTGCCCGTGCTGCTGTGGCTGGTAG

AGATGCTACTGGCCGCTTCACTGCTGGCCGTCCTAGACGTGTTGAACTGGACGCCGATGCTGCTTCTGGTGCTTTCT

ACGCCCGTTACCGTGATGGTTACGTGTCTGGTGAACCTTGGCCTGGCGCTGGTCCACCTCCGCCCGGACGTGTACTC

TACGGTGGATTGGGCGATTCTCGCCCTGGTCTGTGGGGCGCTCCG

SEQ ID NO: 122 = construct RS1.3.1
TCGAGTGCCGCCGCTGCTGCCGCCGATTTGTTGTTCCAAAACCAATCCCTCCGCCCTCTGCTCGCCGACACTGTTGC
CGCTGCCGATTCTCTGGCTGCTCCGGCTTCTGCCCCACGTGAAGCTCGTAAACGTAAATCACCCGCTCCGGCTCGTG
CTCCCCCTGGTGGCGCCCCTAGACCCCCTAAAAAATCCCGTGCCGATGCCCCTAGACCTGCTGCTGCTCCCCCCGCT
GGTGCTGCTCCCCCCGCTCCCCCTACTCCCCCCCCACGCCCACCTCGTCCCGCTGCCCTCACACGCCGTCCTGCTGA
GGGACCCGATCCACAAGGCGGCTGGCGTAGACAACCTCCTGGCCCATCCCATACACCGGCACCATCTGCCGCTGCTT
TGGAGGCTTACTGTGCTCCTCGTGCTGTGGCTGAACTCACCGATCATCCGCTGTTCCCTGCTCCCTGGCGTCCCGCC
CTCATGTTCGATCCTAGAGCTTTGGCTTCCTTGGCCGCTCGTTGTGCTGCCCCTCCCCCTGGCGGTGCTCCGGCTGC
TTTCGGTCCTCTCCGTGCCTCTGGTCCACTCCGCCGTGCCGCTGCCTGGATGAGACAAGTTCCCGACCCTGAGGATG
TTAGAGTTGTGATCTTGTACTCGCCCTTGCCTGGCGAGGATTTGGCCGCTGGTAGAGCTGGCGGTGGCCCCCCTCCT
GAATGGTCTGCTGAACGTGGTGGTTTGTCTTGCTTGTTGGCCGCCCTGGGAAACCGTCTGTGTGGTCCTGCTACTGC
TGCTTGGGCTGGAAACTGGACTGGCGCTCCCGATGTTTCTGCTCTCGGTGCTCAA SEQ ID NO: 123 = construct RS1.3.2
TGGGCTGGAAACTGGACTGGCGCTCCCGATGTTTCTGCTCTCGGTGCTCAAGGAGTTTTGCTGCTCTCTACTCGTGA
CTTGGCATTCGCTGGAGCTGTTGAATTCCTGGGACTCTTGGCTGGCGCTTGTGATAGGAGACTCATCGTCGTAAACG
CTGTGAGAGCTGCCGATTGGCCTGCCGATGGTCCTGTTGTGTCTCGTCAACACGCTTACTTGGCTTGTGAAGTGTTG
CCCGCTGTCCAATGTGCTGTTCGCTGGCCTGCTGCTCGTGATCTGAGGCGTACTGTTCTGGCTAGTGGTCGTGTTTT
CGGACCTGGTGTTTTCGCTCGTGTCGAAGCTGCTCACGCTAGACTGTACCCCGATGCCCCACCCCTCCGTTTGTGTC
GTGGAGCAAACGTTCGCTACCGTGTCCGTACTCGTTTCGGACCCGATACTCTGGTTCCAATGTCCCCTCGTGAATAC
CGTCGTGCTGTTCTGCCTGCCCTCGATGGACGTGCTGCCGCTTCTGGCGCTGGTGACGCTATGGCTCCTGGCGCTCC
GGACTTCTGTGAGGATGAGGCTCACTCACATCGTGCCTGTGCCCGCTGGGGACTGGGCGCTCCATTGAGGCCTGTAT
ACGTGGCACTGGGCCGTGATGCTGTTAGAGGCGGACCCGCTGAATTGAGAGGCCCTCGTCGTGAATTCTGTGCTAGG
GCTCTGCTCGAACCCGATGGAGATGCTCCTCCTTTGGTACTCCGTGACGACGCCGATGCTGGTCCTCCCCCACAAAT
TCGCTGGGCTAGTGCTGCTGGACGTGCTGGTACTGTATTGGCTGCTGCTGGCGGTGGCGTTGAAGTTGTTGGTACTG
CCGCTGGACTCGCTACACCTCCCCGCCGTGAACCTGTAGACATGGATGCTGAACTCGAGGATGATGACGACGGATTG
TTCGGAGAG SEQ ID NO: 124 = construct RS1.3
TCGAGTGCCGCCGCTGCTGCCGCCGATTTGTTGTTCCAAAACCAATCCCTCCGCCCTCTGCTCGCCGACACTGTTGC
CGCTGCCGATTCTCTGGCTGCTCCGGCTTCTGCCCCACGTGAAGCTCGTAAACGTAAATCACCCGCTCCGGCTCGTG
CTCCCCCTGGTGGCGCCCCTAGACCCCCTAAAAAATCCCGTGCCGATGCCCCTAGACCTGCTGCTGCTCCCCCCGCT
GGTGCTGCTCCCCCCGCTCCCCCTACTCCCCCCCCACGCCCACCTCGTCCCGCTGCCCTCACACGCCGTCCTGCTGA
GGGACCCGATCCACAAGGCGGCTGGCGTAGACAACCTCCTGGCCCATCCCATACACCGGCACCATCTGCCGCTGCTT
TGGAGGCTTACTGTGCTCCTCGTGCTGTGGCTGAACTCACCGATCATCCGCTGTTCCCTGCTCCCTGGCGTCCCGCC
CTCATGTTCGATCCTAGAGCTTTGGCTTCCTTGGCCGCTCGTTGTGCTGCCCCTCCCCCTGGCGGTGCTCCGGCTGC
TTTCGGTCCTCTCCGTGCCTCTGGTCCACTCCGCCGTGCCGCTGCCTGGATGAGACAAGTTCCCGACCCTGAGGATG
TTAGAGTTGTGATCTTGTACTCGCCCTTGCCTGGCGAGGATTTGGCCGCTGGTAGAGCTGGCGGTGGCCCCCCTCCT
GAATGGTCTGCTGAACGTGGTGGTTTGTCTTGCTTGTTGGCCGCCCTGGGAAACCGTCTGTGTGGTCCTGCTACTGC
TGCTTGGGCTGGAAACTGGACTGGCGCTCCCGATGTTTCTGCTCTCGGTGCTCAAGGAGTTTTGCTGCTCTCTACTC
GTGACTTGGCATTCGCTGGAGCTGTTGAATTCCTGGGACTCTTGGCTGGCGCTTGTGATAGGAGACTCATCGTCGTA
AACGCTGTGAGAGCTGCCGATTGGCCTGCCGATGGTCCTGTTGTGTCTCGTCAACACGCTTACTTGGCTTGTGAAGT
GTTGCCCGCTGTCCAATGTGCTGTTCGCTGGCCTGCTGCTCGTGATCTGAGGCGTACTGTTCTGGCTAGTGGTCGTG
TTTTCGGACCTGGTGTTTTCGCTCGTGTCGAAGCTGCTCACGCTAGACTGTACCCCGATGCCCCACCCCTCCGTTTG -continued

TGTCGTGGAGCAAACGTTCGCTACCGTGTCCGTACTCGTTTCGGACCCGATACTCTGGTTCCAATGTCCCCTCGTGA

ATACCGTCGTGCTGTTCTGCCTGCCCTCGATGGACGTGCTGCCGCTTCTGGCGCTGGTGACGCTATGGCTCCTGGCG

CTCCGGACTTCTGTGAGGATGAGGCTCACTCACATCGTGCCTGTGCCCGCTGGGGACTGGGCGCTCCATTGAGGCCT

GTATACGTGGCACTGGGCCGTGATGCTGTTAGAGGCGGACCCGCTGAATTGAGAGGCCCCTCGTCGTGAATTCTGTGC

TAGGGCTCTGCTCGAACCCGATGGAGATGCTCCTCCTTTGGTACTCCGTGACGACGCCGATGCTGGTCCTCCCCCAC

AAATTCGCTGGGCTAGTGCTGCTGGACGTGCTGGTACTGTATTGGCTGCTGCTGGCGGTGGCGTTGAAGTTGTTGGT

ACTGCCGCTGGACTCGCTACACCTCCCCGCCGTGAACCTGTAGACATGGATGCTGAACTCGAGGATGATGACGACGG

ATTGTTCGGAGAG

SEQ ID NO: 125 = construct RS1.4
ACTGCTGGCCGTCCTAGACGTGTTGAACTGGACGCCGATGCTGCTTCTGGTGCTTTCTACGCCCGTTACCGTGATGG

TTACGTGTCTGGTGAACCTTGGCCTGGCGCTGGTCCACCTCCGCCCGGACGTGTACTCTACGGTGGATTGGGCGATT

CTCGCCCTGGTCTGTGGGGCGCTCCGGAGGCTGAGGAGGCTAGAGCCCGTTTCGAGGCTTCTGGTGCCCCTGCTCCT

GTTTGGGCTCCTGAATTGGGCGACGCTGCTCAACAATACGCCCTCATCACACGCTTGCTGTACACTCCCGACGCCGA

GGCTATGGGATGGCTCCAAAACCCTAGAGTTGCCCCTGGTGATGTTGCTCTGGATCAGGCTTGTTTCCGTATCTCCG

GCGCTGCTCGTAACTCTTCTTCGTTCATCTCCGGTTCTGTGGCTAGAGCTGTGCCTCACTTGGGATACGCCATGGCC

GCTGGACGTTTCGGCTGGGGACTGGCTCATGTTGCTGCCGCTGTAGCAATGTCTAGACGCTACGACCGTGCTCAAAA

AGGATTCTTGCTCACGTCACTGAGGCGTGCTTACGCCCCTTTGTTGGCCCGTGAAAACGCTGCCCTCACTGGCGCCC

GTACCCCCGATGACGGTGGCGACGCCAACCGCCACGATGGTGATGATGCTAGAGGCAAACCCGCTGCCGCTGCTGCT

CCTTTGCCCTCTGCCGCCGCTTCCCCTGCCGATGAACGTGCTGTTCCTGCCGGTTACGGTGCCGCTGGTGTGTTGGC

TGCTTTGGGACGCTTGAGTGCTGCCCCGGCTAGTGCCCCCGCTGGTGCCGATGACGATGACGATGACGATGGTGCTG

GCGGAGGCGGTGGCGGTAGACGTGCTGAGGCTGGACGTGTTGCTGTTGAATGCCTGGCTGCCTGTAGAGGAATCTTG

GAGGCTCTGGCCGAGGGATTCGACGGAGACTTGGCGGCTGTACCGGGACTGGCGGGAGCGAGGCCTGCCGCTCCACC

TCGCCCCGGTCCTGCTGGTGCTGCCGCTCCTCCTCATGCCGACGCTCCTAGACTCCGTGCTTGGCTCCGTGAACTCC

GTTTCGTTCGTGACGCTTTGGTTCTGATGAGACTGAGAGGCGACTTGAGAGTGGCTGGAGGATCCGAGGCTGCTGTT

GCTGCTGTCCGTGCTGTTTCTTTGGTTGCTGGTGCTTTGGGCCCTGCTTTGCCGAGATCTCCCCGTTTGTTGTCGAG

TGCCGCCGCTGCTGCCGCCGATTTGTTGTTCCAAAACCAATCCCTCCGCCCTCTGCTCGCCGACACTGTTGCCGCTG

CCGATTCTCTGGCTGCTCCGGCTTCTGCCCCACGTGAAGCTCGTAAACGTAAATCACCCGCTCCGGCTCGTGCTCCC

CCTGGTGGCGCCCCTAGACCCCCTAAAAAATCCCGTGCCGATGCCCCTAGACCTGCTGCTGCTCCCCCCGCTGGTGC

TGCTCCCCCCGCTCCCCCTACTCCCCCCCCACGCCCACCTCGTCCCGCTGCCCTCACACGCCGTCCTGCTGAGGGAC

CCGATCCACAAGGCGGCTGGCGTAGACAACCTCCTGGCCCATCCCATACACCGGCACCATCTGCCGCTGCTTTGGAG

GCTTACTGTGCT

SEQ ID NO: 126 = construct RS1.5
GCCGCTGCCGATTCTCTGGCTGCTCCGGCTTCTGCCCCACGTGAAGCTCGTAAACGTAAATCACCCGCTCCGGCTCG

TGCTCCCCCTGGTGGCGCCCCTAGACCCCCTAAAAAATCCCGTGCCGATGCCCCTAGACCTGCTGCTGCTCCCCCCG

CTGGTGCTGCTCCCCCCGCTCCCCCTACTCCCCCCCCACGCCCACCTCGTCCCGCTGCCCTCACACGCCGTCCTGCT

GAGGGACCCGATCCACAAGGCGGCTGGCGTAGACAACCTCCTGGCCCATCCCATACACCGGCACCATCTGCCGCTGC

TTTGGAGGCTTACTGTGCTCCTCGTGCTGTGGCTGAACTCACCGATCATCCGCTGTTCCCTGCTCCCTGGCGTCCCG

CCCTCATGTTCGATCCTAGAGCTTTGGCTTCCTTGGCCGCTCGTTGTGCTGCCCCTCCCCCTGGCGGTGCTCCGGCT

GCTTTCGGTCCTCTCCGTGCCTCTGGTCCACTCCGCCGTGCCGCTGCCTGGATGAGACAAGTTCCCGACCCTGAGGA

TGTTAGAGTTGTGATCTTGTACTCGCCCTTGCCTGGCGAGGATTTGGCCGCTGGTAGAGCTGGCGGTGGCCCCCCTC

CTGAATGGTCTGCTGAACGTGGTGGTTTGTCTTGCTTGTTGGCCGCCCTGGGAAACCGTCTGTGTGGTCCTGCTACT

-continued

GCTGCTTGGGCTGGAAACTGGACTGGCGCTCCCGATGTTTCTGCTCTCGGTGCTCAAGGAGTTTTGCTGCTCTCTAC

TCGTGACTTGGCATTCGCTGGAGCTGTTGAATTCCTGGGACTCTTGGCTGGCGCTTGTGATAGGAGACTCATCGTCG

TAAACGCTGTGAGAGCTGCCGATTGGCCTGCCGATGGTCCTGTTGTGTCTCGTCAACACGCTTACTTGGCTTGTGAA

GTGTTGCCCGCTGTCCAATGTGCTGTTCGCTGGCCTGCTGCTCGTGATCTGAGGCGTACTGTTCTGGCTAGTGGTCG

TGTTTTCGGACCTGGTGTTTTCGCTCGTGTCGAAGCTGCTCACGCTAGACTGTACCCCGATGCCCCACCCCTCCGTT

TGTGTCGTGGAGCAAACGTTCGCTACCGTGTCCGTACTCGTTTCGGACCCGATACTCTGGTTCCAATGTCCCCTCGT

GAATACCGTCGTGCTGTTCTGCCTGCCCTCGATGGACGTGCTGCCGCTTCTGGCGCTGGTGACGCTATGGCTCCTGG

CGCTCCGGACTTCTGTGAGGATGAGGCTCACTCACATCGTGCCTGTGCCCGCTGGGGACTGGGCGCTCCATTGAGGC

CTGTATACGTGGCACTGGGCCGTGATGCTGTTAGAGGCGGACCCGCTGAATTGAGAGGCCCTCGTCGTGAATTCTGT

GCTAGGGCTCTGCTCGAACCCGATGGAGATGCTCCTCCTTTGGTACTCCGTGACGACGCCGATGCTGGTCCTCCCCC

ACAAATTCGCTGGGCTAGTGCTGCTGGACGTGCTGGTACTGTATTGGCTGCTGCTGGCGGTGGCGTTGAAGTTGTTG

GTACTGCCGCTGGACTCGCTACACCTCCCCGCCGTGAACCTGTAGACATGGATGCTGAACTCGAGGATGATGACGAC

GGATTGTTCGGAGAG

SEQ ID NO: 127 = construct RS1.6

CACCACCACCACCACCATCATAGGCGTAGACGTGCTCCTAGACGTCGTTCTGCCGCTAGTGACTCTTCCAAATCTGG

CTCTTCTTCATCTGCCTCTTCCGCTTCATCTTCGGCCTCATCGTCCTCTTCGGCATCCGCTTCGAGTAGTGATGATG

ATGATGACGACGACGCTGCTAGAGCCCCCGCTTCTGCTGCCGACCACGCTGCTGGCGGAACTTTGGGAGCCGACGAC

GAGGAGGCGGGAGTTCCTGCTCGTGCCCCGGGAGCTGCTCCGAGGCCTTCTCCACCCCGTGCTGAACCTGCTCCGGC

TAGAACACCGGCCGCTACTGCTGGTAGACTGGAGCGTAGACGTGCCCGTGCTGCTGTGGCTGGTAGAGATGCTACTG

GCCGCTTCACTGCTGGCCGTCCTAGACGTGTTGAACTGGACGCCGATGCTGCTTCTGGTGCTTTCTACGCCCGTTAC

CGTGATGGTTACGTGTCTGGTGAACCTTGGCCTGGCGCTGGTCCACCTCCGCCCGGACGTGTACTCTACGGTGGATT

GGGCGATTCTCGCCCTGGTCTGTGGGGCGCTCCGGAGGCTGAGGAGGCTAGAGCCCGTTTCGAGGCTTCTGGTGCCC

CTGCTCCTGTTTGGGCTCCTGAATTGGGCGACGCTGCTCAACAATACGCCCTCATCACACGCTTGCTGTACACTCCC

GACGCCGAGGCTATGGGATGGCTCCAAAACCCTAGAGTTGCCCCTGGTGATGTTGCTCTGGATCAGGCTTGTTTCCG

TATCTCCGGCGCTGCTCGTAACTCTTCTTCGTTCATCTCCGGTTCTGTGGCTAGAGCTGTGCCTCACTTGGGATACG

CCATGGCCGCTGGACGTTTCGGCTGGGGACTGGCTCATGTTGCTGCCGCTGTAGCAATGTCTAGACGCTACGACCGT

GCTCAAAAAGGATTCTTGCTCACGTCACTGAGGCGTGCTTACGCCCCTTTGTTGGCCCGTGAAAACGCTGCCCTCAC

TGGCGCCCGTACCCCCGATGACGGTGGCGACGCCAACCGCCACGATGGTGATGATGCTAGAGGCAAACCCGCTGCCG

CTGCTGCTCCTTTGCCCTCTGCCGCCGCTTCCCCTGCCGATGAACGTGCTGTTCCTGCCGGTTACGGTGCCGCTGGT

GTGTTGGCTGCTTTGGGACGCTTGAGTGCTGCCCCGGCTAGTGCCCCCGCTGGTGCCGATGACGATGACGATGACGA

TGGTGCTGGCGGAGGCGGTGGCGGTAGACGTGCTGAGGCTGGACGTGTTGCTGTTGAATGCCTGGCTGCCTGTAGAG

GAATCTTGGAGGCTCTGGCCGAGGGATTCGACGGAGACTTGGCGGCTGTACCGGGACTGGCGGGAGCGAGGCCTGCC

GCTCCACCTCGCCCCGGTCCTGCTGGTGCTGCCGCTCCTCCTCATGCCGACGCTCCTAGACTCCGTGCTTGGCTCCG

TGAACTCCGTTTCGTTCGTGACGCTTTGGTTCTGATGAGACTGAGAGGCGACTTGAGAGTGGCTGGAGGATCCGAGG

CTGCTGTTGCTGCTGTCCGTGCTGTTTCTTTGGTTGCTGGTGCTTTGGGCCCTGCTTTGCCGAGATCTCCCCGTTTG

TTGTCGAGTGCCGCCGCTGCTGCCGCCGATTTGTTGTTCCAAAACCAATCCCTCCGCCCTCTGCTCGCCGACACTGT

TGCCGCTGCCGATTCTCTGGCTGCTCCGGCTTCTGCCCCACGTGAAGCTCGTAAACGTAAATCACCCGCTCCGGCTC

GTGCTCCCCCTGGTGGCGCCCCTAGACCCCCTAAAAAATCCCGTGCCGATGCCCCTAGACCTGCTGCTGCTCCCCCC

GCTGGTGCTGCTCCCCCCGCTCCCCCTACTCCCCCCCCACGCCCACCTCGTCCCGCTGCCCTCACACGCCGTCCTGC

TGAGGGACCCGATCCACAAGGCGGCTGGCGTAGACAACCTCCTGGCCCATCCCATACACCGGCACCATCTGCCGCTG

CTTTGGAGGCTTACTGTGCTCCTCGTGCTGTGGCTGAACTCACCGATCATCCGCTGTTCCCTGCTCCCTGGCGTCCC

-continued

GCCCTCATGTTCGATCCTAGAGCTTTGGCTTCCTTGGCCGCTCGTTGTGCTGCCCCTCCCCCTGGCGGTGCTCCGGC

TGCTTTCGGTCCTCTCCGTGCCTCTGGTCCACTCCGCCGTGCCGCTGCCTGGATGAGACAAGTTCCCGACCCTGAGG

ATGTTAGAGTTGTGATCTTGTACTCGCCCTTGCCTGGCGAGGATTTGGCCGCTGGTAGAGCTGGCGGTGGCCCCCCT

CCTGAATGGTCTGCTGAACGTGGTGGTTTGTCTTGCTTGTTGGCCGCCCTGGGAAACCGTCTGTGTGGTCCTGCTAC

TGCTGCTTGGGCTGGAAACTGGACTGGCGCTCCCGATGTTTCTGCTCTCGGTGCTCAAGGAGTTTTGCTGCTCTCTA

CTCGTGACTTGGCATTCGCTGGAGCTGTTGAATTCCTGGGACTCTTGGCTGGCGCTTGTGATAGGAGACTCATCGTC

GTAAACGCTGTGAGAGCTGCCGATTGGCCTGCCGATGGTCCTGTTGTGTCTCGTCAACACGCTTACTTGGCTTGTGA

AGTGTTGCCCGCTGTCCAATGTGCTGTTCGCTGGCCTGCTGCTCGTGATCTGAGGCGTACTGTTCTGGCTAGTGGTC

GTGTTTTCGGACCTGGTGTTTTCGCTCGTGTCGAAGCTGCTCACGCTAGACTGTACCCCGATGCCCCACCCCTCCGT

TTGTGTCGTGGAGCAAACGTTCGCTACCGTGTCCGTACTCGTTTCGGACCCGATACTCTGGTTCCAATGTCCCCTCG

TGAATACCGTCGTGCTGTTCTGCCTGCCCTCGATGGACGTGCTGCCGCTTCTGGCGCTGGTGACGCTATGGCTCCTG

GCGCTCCGGACTTCTGTGAGGATGAGGCTCACTCACATCGTGCCTGTGCCCGCTGGGGACTGGGCGCTCCATTGAGG

CCTGTATACGTGGCACTGGGCCGTGATGCTGTTAGAGGCGGACCCGCTGAATTGAGAGGCCCTCGTCGTGAATTCTG

TGCTAGGGCTCTGCTCGAACCCGATGGAGATGCTCCTCCTTTGGTACTCCGTGACGACGCCGATGCTGGTCCTCCCC

CACAAATTCGCTGGGCTAGTGCTGCTGGACGTGCTGGTACTGTATTGGCTGCTGCTGGCGGTGGCGTTGAAGTTGTT

GGTACTGCCGCTGGACTCGCTACACCTCCCCGCCGTGAACCTGTAGACATGGATGCTGAACTCGAGGATGATGACGA

CGGATTGTTCGGAGAGTAA

SEQ ID NO: 128 = construct RS1.7

ATGAGTGCCGAACAGCGTAAAAAGAAAAAAACCACCACCACGACCCAAGGACGTGGAGCTGAAGTTGCTATGGCGGA

TGAGGATGGAGGCCGCTTGAGAGCTGCTGCTGAGACTACTGGAGGACCTGGATCACCGGACCCTGCCGATGGACCCC

CCCCTACACCAAACCCCGATCGTAGACCGGCTGCTAGACCTGGATTCGGATGGCATGGAGGACCCGAGGAAAACGAG

GACGAGGCGGACGACGCCGCTGCCGACGCCGACGCCGATGAGGCTGCCCCTGCTTCTGGAGAGGCGGTAGACGAACC

TGCTGCCGATGGAGTTGTTAGCCCTAGGCAATTGGCTTTGTTGGCGAGCATGGTAGACGAGGCTGTGAGAACAATCC

CTTCCCCTCCCCCTGAACGTGATGGAGCACAAGAGGAGGCGGCTAGGAGTCCCTCACCACCCCGTACACCTTCTATG

AGAGCGGATTACGGCGAGGAAAACGACGACGACGACGATGATGATGACGACGATGATCGTGATGCCGGACGCTGGGT

TAGGGGACCTGAAACCACTTCTGCTGTCCGTGGAGCATACCCCGATCCTATGGCGAGTTTGAGCCCTAGACCACCTG

CCCCGAGGAGACACCACCACCACCACCATCATAGGCGTAGACGTGCTCCTAGACGTCGTTCTGCCGCTAGTGACTCT

TCCAAATCTGGCTCTTCTTCATCTGCCTCTTCCGCTTCATCTTCGGCCTCATCGTCCTCTTCGGCATCCGCTTCGAG

TAGTGATGATGATGATGACGACGACGCTGCTAGAGCCCCCGCTTCTGCTGCCGACCACGCTGCTGGCGGAACTTTGG

GAGCCGACGACGAGGAGGCGGGAGTTCCTGCTCGTGCCCCGGGAGCTGCTCCGAGGCCTTCTCCACCCCGTGCTGAA

CCTGCTCCGGCTAGAACACCGGCCGCTACTGCTGGTAGACTGGAGCGTAGACGTGCCCGTGCTGCTGTGGCTGGTAG

AGATGCTACTGGCCGCTTCACTGCTGGCCGTCCTAGACGTGTTGAACTGGACGCCGATGCTGCTTCTGGTGCTTTCT

ACGCCCGTTACCGTGATGGTTACGTGTCTGGTGAACCTTGGCCTGGCGCTGGTCCACCTCCGCCCGGACGTGTACTC

TACGGTGGATTGGGCGCCCGTACCCCCGATGACGGTGGCGACGCCAACCGCCACGATGGTGATGATGCTAGAGGCAA

ACCCGCTGCCGCTGCTGCTCCTTTGCCCTCTGCCGCCGCTTCCCCTGCCGATGAACGTGCTGTTCCTGCCGGTTACG

GTGCCGCTGGTGTGTTGGCTGCTTTGGGACGCTTGAGTGCTGCCCCGGCTAGTGCCCCCGCTGGTGCCGATGACGAT

GACGATGACGATGGTGCTGGCGGAGGCGGTGGCGGTAGACGTGCTGAGGCTGGACGTGTTGCTGTTGAATGCCTGGC

TGCCTGTAGAGGAATCTTGGAGGCTCTGGCCGAGGGATTCGACGGAGACTTGGCGGCTGTACCGGGACTGGCGGGAG

CGAGGCCTGCCGCTCCACCTCGCCCCGGTCCTGCTGGTGCTGCCGCTCCTCCTCATGCCGACGCTCCTAGACTCCGT

GCTTGGCTCCGTGAACTCCGTTTCGTTCGTGACGCTTTGGTTCTGATGAGACTGAGAGGCGACTTGAGAGTGGCTGG

AGGATCCGAGGCTGCTGTTGCTGCTGTCCGTGCTGTTTCTTTGGTTGCTGGTGCTTTGGGCCCTGCTTTGCCGAGAT

-continued

CTCCCCGTTTGTTGTCGAGTGCCGCCGCTGCTGCCGCCGATTTGTTGTTCCAAAACCAATCCCTCCGCCCTCTGCTC

GCCGACACTGTTGCCGCTGCCGATTCTCTGGCTGCTCCGGCTTCTGCCCCACGTGAAGCTCGTAAACGTAAATCACC

CGCTCCGGCTCGTGCTCCCCCTGGTGGCGCCCCTAGACCCCCTAAAAAATCCCGTGCCGATGCCCCTAGACCTGCTG

CTGCTCCCCCCGCTGGTGCTGCTCCCCCCGCTCCCCCTACTCCCCCCCCACGCCCACCTCGTCCCGCTGCCCTCACA

CGCCGTCCTGCTGAGGGACCCGATCCACAAGGCGGCTGGCGTAGACAACCTCCTGGCCCATCCCATACACCGGCACC

ATCTGCCGCTGCTTTGGAGGCTTACTGTGCTCCTCGTGCTGTGGCTGAACTCACCGATCATCCGCTGTTCCCTGCTC

CCTGGCGTCCCGCCCTCATGTTCGATCCTAGAGCTTTGGCTTCCTTGGCCGCTCGTTGTGCTGCCCCTCCCCCTGGC

GGTGCTCCGGCTGCTTTCGGTCCTCTCCGTGCCTCTGGTCCACTCCGCCGTGCCGCTGCCTGGATGAGACAAGTTCC

CGACCCTGAGGATGTTAGAGTTGTGATCTTGTACTCGCCCTTGCCTGGCGAGGATTTGGCCGCTGGTAGAGCTGGCG

GTGGCCCCCCTCCTGAATGGTCTGCTGAACGTGGTGGTTTGTCTTGCTTGTTGGCCGCCCTGGGAAACCGTCTGTGT

GGTCCTGCTACTGCTGCTTGGGCTGGAAACTGGACTGGCGCTCCCGATGTTTCTGCTCTCGGTGCTCAAGGAGTTTT

GCTGCTCTCTACTCGTGACTTGGCATTCGCTGGAGCTGTTGAATTCCTGGGACTCTTGGCTGGCGCTTGTGATAGGA

GACTCATCGTCGTAAACGCTGTGAGAGCTGCCGATTGGCCTGCCGATGGTCCTGTTGTGTCTCGTCAACACGCTTAC

TTGGCTTGTGAAGTGTTGCCCGCTGTCCAATGTGCTGTTCGCTGGCCTGCTGCTCGTGATCTGAGGCGTACTGTTCT

GGCTAGTGGTCGTGTTTTCGGACCTGGTGTTTTCGCTCGTGTCGAAGCTGCTCACGCTAGACTGTACCCCGATGCCC

CACCCCTCCGTTTGTGTCGTGGAGCAAACGTTCGCTACCGTGTCCGTACTCGTTTCGGACCCGATACTCTGGTTCCA

ATGTCCCCTCGTGAATACCGTCGTGCTGTTCTGCCTGCCCTCGATGGACGTGCTGCCGCTTCTGGCGCTGGTGACGC

TATGGCTCCTGGCGCTCCGGACTTCTGTGAGGATGAGGCTCACTCACATCGTGCCTGTGCCCGCTGGGGACTGGGCG

CTCCATTGAGGCCTGTATACGTGGCACTGGGCCGTGATGCTGTTAGAGGCGGACCCGCTGAATTGAGAGGCCCTCGT

CGTGAATTCTGTGCTAGGGCTCTGCTCGAACCCGATGGAGATGCTCCTCCTTTGGTACTCCGTGACGACGCCGATGC

TGGTCCTCCCCCACAAATTCGCTGGGCTAGTGCTGCTGGACGTGCTGGTACTGTATTGGCTGCTGCTGGCGGTGGCG

TTGAAGTTGTTGGTACTGCCGCTGGACTCGCTACACCTCCCCGCCGTGAACCTGTAGACATGGATGCTGAACTCGAG

GATGATGACGACGGATTGTTCGGAGAG

SEQ ID NO: 129 = construct RS1.8

ATGAGTGCCGAACAGCGTAAAAAGAAAAAAACCACCACCACGACCCAAGGACGTGGAGCTGAAGTTGCTATGGCGGA

TGAGGATGGAGGCCGCTTGAGAGCTGCTGCTGAGACTACTGGAGGACCTGGATCACCGGACCCTGCCGATGGACCCC

CCCCTACACCAAACCCCGATCGTAGACCGGCTGCTAGACCTGGATTCGGATGGCATGGAGGACCCGAGGAAAACGAG

GACGAGGCGGACGACGCCGCTGCCGACGCCGACGCCGATGAGGCTGCCCCTGCTTCTGGAGAGGCGGTAGACGAACC

TGCTGCCGATGGAGTTGTTAGCCCTAGGCAATTGGCTTTGTTGGCGAGCATGGTAGACGAGGCTGTGAGAACAATCC

CTTCCCCTCCCCCTGAACGTGATGGAGCACAAGAGGAGGCGGCTAGGAGTCCCTCACCACCCCGTACACCTTCTATG

AGAGCGGATTACGGCGAGGAAAACGACGACGACGACGATGATGATGACGACGATGATCGTGATGCCGGACGCTGGGT

TAGGGGACCTGAAACCACTTCTGCTGTCCGTGGAGCATACCCCGATCCTATGGCGAGTTTGAGCCCTAGACCACCTG

CCCCGAGGAGACACCACCACCACCACCATCATAGGCGTAGACGTGCTCCTAGACGTCGTTCTGCCGCTAGTGACTCT

TCCAAATCTGGCTCTTCTTCATCTGCCTCTTCCGCTTCATCTTCGGCCTCATCGTCCTCTTCGGCATCCGCTTCGAG

TAGTGATGATGATGATGACGACGACGCTGCTAGAGCCCCCGCTTCTGCTGCCGACCACGCTGCTGGCGGAACTTTGG

GAGCCGACGACGAGGAGGCGGGAGTTCCTGCTCGTGCCCCGGGAGCTGCTCCGAGGCCTTCTCCACCCCGTGCTGAA

CCTGCTCCGGCTAGAACACCGGCCGCTACTGCTGGTAGACTGGAGCGTAGACGTGCCCGTGCTGCTGTGGCTGGTAG

AGATGCTACTGGCCGCTTCACTGCTGGCCGTCCTAGACGTGTTGAACTGGACGCCGATGCTGCTTCTGGTGCTTTCT

ACGCCCGTTACCGTGATGGTTACGTGTCTGGTGAACCTTGGCCTGGCGCTGGTCCACCTCCGCCCGGACGTGTACTC

TACGGTGGATTGGGCGATTCTCGCCCTGGTCTGTGGGGCGCTCCGGAGGCTGAGGAGGCTAGAGCCCGTTTCGAGGC

TTCTGGTGCCCCTGCTCCTGTTTGGGCTCCTGAATTGGGCGACGCTGCTCAACAATACGCCCTCATCACACGCTTGC

-continued

TGTACACTCCCGACGCCGAGGCTATGGGATGGCTCCAAAACCCTAGAGTTGCCCCTGGTGATGTTGCTCTGGATCAG

GCTTGTTTCCGTATCTCCGGCGCTGCTCGTAACTCTTCTTCGTTCATCTCCGGTTCTGTGGCTAGAGCTGTGCCTCA

CTTGGGATACGCCATGGCCGCTGGACGTTTCGGCTGGGGACTGGCTCATGTTGCTGCCGCTGTAGCAATGTCTAGAC

GCTACGACCGTGCTCAAAAAGGATTCTTGCTCACGTCACTGAGGCGTGCTTACGCCCCTTTGTTGGCCCGTGAAAAC

GCTGCCCTCACTGGCGCCCGTACCCCCGATGACGGTGGCGACGCCAACCGCCACGATGGTGATGATGCTAGAGGCAA

ACCCGCTGCCGCTGCTGCTCCTTTGCCCTCTGCCGCCGCTTCCCCTGCCGATGAACGTGCTGTTCCTGCCGGTTACG

GTGCCGCTGGTGTGTTGGCTGCTTTGGGACGCTTGAGTGCTGCCCCGGCTAGTGCCCCCGCTGGTGCCGATGACGAT

GACGATGACGATGGTGCTGGCGGAGGCGGTGGCGGTAGACGTGCTGAGGCTGGACGTGTTGCTGTTGAATGCCTGGC

TGCCTGTAGAGGAATCTTGGAGGCTCTGGCCGAGGGATTCGACGGAGACTTGGCGGCTGTACCGGGACTGGCGGGAG

CGAGGCCTGCCGCTCCACCTCGCCCCGGTCCTGCTGGTGCTGCCGCTCCTCCTCATGCCGACGCTCCTAGACTCCGT

GCTTGGCTCCGTGAACTCCGTTTCGTTCGTGACGCTTTGGTTCTGATGAGACTGAGAGGCGACTTGAGAGTGGCTGG

AGGATCCGAGGCTGCTGTTGCTGCTGTCCGTGCTGTTTCTTTGGTTGCTGGTGCTTTGGGCCCTGCTTTGCCGAGAT

CTCCCCGTTTGTTGTCGAGTGCCGCCGCTGCTGCCGCCGATTTGTTGTTCCAAAACCAATCCCTCCGCCCTCTGCTC

GCCGACACTGTTGCCGCTGCCGATTCTCTGGCTGCTCCGGCTTCTACACCGGCACCATCTGCCGCTGCTTTGGAGGC

TTACTGTGCTCCTCGTGCTGTGGCTGAACTCACCGATCATCCGCTGTTCCCTGCTCCCTGGCGTCCCGCCCTCATGT

TCGATCCTAGAGCTTTGGCTTCCTTGGCCGCTCGTTGTGCTGCCCCTCCCCCTGGCGGTGCTCCGGCTGCTTTCGGT

CCTCTCCGTGCCTCTGGTCCACTCCGCCGTGCCGCTGCCTGGATGAGACAAGTTCCCGACCCTGAGGATGTTAGAGT

TGTGATCTTGTACTCGCCCTTGCCTGGCGAGGATTTGGCCGCTGGTAGAGCTGGCGGTGGCCCCCCTCCTGAATGGT

CTGCTGAACGTGGTGGTTTGTCTTGCTTGTTGGCCGCCCTGGGAAACCGTCTGTGTGGTCCTGCTACTGCTGCTTGG

GCTGGAAACTGGACTGGCGCTCCCGATGTTTCTGCTCTCGGTGCTCAAGGAGTTTTGCTGCTCTCTACTCGTGACTT

GGCATTCGCTGGAGCTGTTGAATTCCTGGGACTCTTGGCTGGCGCTTGTGATAGGAGACTCATCGTCGTAAACGCTG

TGAGAGCTGCCGATTGGCCTGCCGATGGTCCTGTTGTGTCTCGTCAACACGCTTACTTGGCTTGTGAAGTGTTGCCC

GCTGTCCAATGTGCTGTTCGCTGGCCTGCTGCTCGTGATCTGAGGCGTACTGTTCTGGCTAGTGGTCGTGTTTTCGG

ACCTGGTGTTTTCGCTCGTGTCGAAGCTGCTCACGCTAGACTGTACCCCGATGCCCCACCCCTCCGTTTGTGTCGTG

GAGCAAACGTTCGCTACCGTGTCCGTACTCGTTTCGGACCCGATACTCTGGTTCCAATGTCCCCTCGTGAATACCGT

CGTGCTGTTCTGCCTGCCCTCGATGGACGTGCTGCCGCTTCTGGCGCTGGTGACGCTATGGCTCCTGGCGCTCCGGA

CTTCTGTGAGGATGAGGCTCACTCACATCGTGCCTGTGCCCGCTGGGGACTGGGCGCTCCATTGAGGCCTGTATACG

TGGCACTGGGCCGTGATGCTGTTAGAGGCGGACCCGCTGAATTGAGAGGCCCTCGTCGTGAATTCTGTGCTAGGGCT

CTGCTCGAACCCGATGGAGATGCTCCTCCTTTGGTACTCCGTGACGACGCCGATGCTGGTCCTCCCCCACAAATTCG

CTGGGCTAGTGCTGCTGGACGTGCTGGTACTGTATTGGCTGCTGCTGGCGGTGGCGTTGAAGTTGTTGGTACTGCCG

CTGGACTCGCTACACCTCCCCGCCGTGAACCTGTAGACATGGATGCTGAACTCGAGGATGATGACGACGGATTGTTC

GGAGAG

SEQ ID NO: 130 = His tag
HHHHHH

SEQ ID NO: 131 = Tag
MSYYHHHHHH

SEQ ID NO: 132 = Secretion Signal
MKFLVNVALVFMVVYISYIYA

SEQ ID NO: 133 = UL49.5
ATGTCGTACTACCATCACCATCACCATCACATGACGGGGAAACCCGCAAGACTGGGCCGCTGGGTGGTGCTGTTGTT

CGTCGCGCTCGTCGCGGGCGTGCCCGGGGAGCCGCCGAACGCGGCAGGCGCACGCGGCGTTATCGGGGACGCGCAAT

GCCGGGGCGACAGCGCCGGTGTGGTGTCCGTCCCGGGGGTCCTGGTGCCCTTTTATCTAGGCATGACCTCGATGGGC

GTATGTATGATCGCGCACGTGTATCAGATATGCCAGCGGGCACTGGCCGCCGGGTCAGCCTGA

-continued

SEQ ID NO: 134 = UL10
ATGGGACGCCGGGCCCCCAGGGGATCCCCCGAGGCCGCGCCGGGCGCCGACGTCGCGCCCGGGGCGCGGGCGGCGTG

GTGGGTCTGGTGTGTGCAGGTGGCGACGTTCATCGTCTCGGCCATCTGCGTCGTGGGGCTCCTGGTGCTGGCCTCTG

TGTTCCGGGACAGGTTTCCCTGCCTTTACGCCCCCGCGACCTCTTATGCGAAGGCGAACGCCACGGTCGAGGTGCGC

GGGGGTGTAGCCGTCCCCCTCCGGTTGGACACGCAGAGCCTGCTGGCCACGTACGCAATTACGTCTACGCTGTTGCT

GGCGGCGGCCGTGTACGCCGCGGTGGGCGCGGTGACCTCGCGCTACGAGCGCGCGCTGGATGCGGCCCGTCGCCTGG

CGGCGGCCCGTATGGCGATGCCACACGCCACGCTAATCGCCGGAAACGTCTGCGCGTGGCTGTTGCAGATCACAGTC

CTGCTGCTGGCCCACCGCATCAGCCAGCTGGCCCACCTTATCTACGTCCTGCACTTTGCGTGCCTCGTGTATCTCGC

GGCCCATTTTTGCACCAGGGGGGTCCTGAGCGGGACGTACCTGCGTCAGGTTCACGGCCTGATTGACCCGGCGCCGA

CGCACCATCGTATCGTCGGTCCGGTGCGGGCAGTAATGACAAACGCCTTATTACTGGGCACCCTCCTGTGCACGGCC

GCCGCCGCGGTCTCGTTGAACACGATCGCCGCCCTGAACTTCAACTTTTCCGCCCCGAGCATGCTCATCTGCCTGAC

GACGCTGTTCGCCCTGCTTGTCGTGTCGCTGTTGTTGGTGGTCGAGGGGGTGCTGTGTCACTACGTGCGCGTGTTGG

TGGGCCCCCACCTCGGGGCCATCGCCGCCACCGGCATCGTCGGCCTGGCCTGCGAGCACTACCACACCGGTGGTTAC

TACGTGGTGGAGCAGCAGTGGCCGGGGGCCCAGACGGGAGTCCGCGTCGCCCTGGCGCTCGTCGCCGCCTTTGCCCT

CGCCATGGCCGTGCTTCGGTGCACGCGCGCCTACCTGTATCACCGGCGACACCACACTAAATTTTTCGTGCGCATGC

GCGACACCCGGCACCGCGCCCATTCGGCGCTTCGACGCGTACGCAGCTCCATGCGCGGTTCTAGGCGTGGCGGGCCG

CCCGGAGACCCGGGCTACGCGGAAACCCCCTACGCGAGCGTGTCCCACCACGCCGAGATCGACCGGTATGGGGATTC

CGACGGGGACCCGATCTACGACGAAGTGGCCCCCGACCACGAGGCCGAGCTCTACGCCCGAGTGCAACGCCCCGGGC

CTGTGCCCGACGCCGAGCCCATTTACGACACCGTGGAGGGGTATGCGCCAAGGTCCGCGGGGGAGCCGGTGTACAGC

ACCGTTCGGCGATGGTAG

SEQ ID NO: 135 = uracil DNA glycosylase encoded by UL2
MKRARSRSPSPPSRPSSPFRTPPHGGSPRREVGAGILASDATSHVCIASHPGSGAGQPTRLAAGSAVQRRRPRGCPP

GVMFSASTTPEQPLGLSGDATPPLPTSVPLDWAAFRRAFLIDDAWRPLLEPELANPLTARLLAEYDRRCQTEEVLPP

REDVFSWTRYCTPDDVRVVIIGQDPYHHPGQAHGLAFSVRADVPVPPSLRNVLAAVKNCYPDARMSGRGCLEKWARD

GVLLLNTTLTVKRGAAASHSKLGWDRFVGGVVQRLAARRPGLVFMLWGAHAQNAIRPDPRQHYVLKFSHPSPLSKVP

FGTCQHFLAANRYLETRDIMPIDWSV

SEQ ID NO: 136 = gL2 secreted v.2 encoded by construct UL1s v.2
AGSQATEYVLRSVIAKEVGDILRVPCMRTPADDVSWRYEAPSVIDYARIDGIFLRYHCPGLDTFLWDRHAQRAYLVN

PFLFAAGFLEDLSHSVFPADTQETTTRRALYKEIRDALGSRKQAVSHAPVRAGCVNFDYSRTRRCVGRRDLRPANTT

STWEPPVSSDDEASSQSKPLATQPPVLALSNAPPRRVSPTRGRRRHTRLRRN

SEQ ID NO: 137 = UL1s v.2
ATGAAGTTCCTCGTGAACGTGGCCCTGGTGTTCATGGTGGTGTACATCAGCTACATCTACGCCGCCGGGTCACAGGC

AACCGAATATGTTCTTCGTAGTGTTATTGCCAAAGAGGTGGGGGACATACTAAGAGTGCCTTGCATGCGGACCCCCG

CGGACGATGTTTCTTGGCGCTACGAGGCCCCGTCCGTTATTGACTATGCCCGCATAGACGGAATATTTCTTCGCTAT

CACTGCCCGGGGTTGGACACGTTTTTGTGGGATAGGCACGCCCAGAGGGCGTATCTTGTTAACCCCTTTCTCTTTGC

GGCGGGATTTTTGGAGGACTTGAGTCACTCTGTGTTTCCGGCCGACACCCAGGAAACAACGACGCGCCGGGCCCTTT

ATAAAGAGATACGCGATGCGTTGGGCAGTCGAAAACAGGCCGTCAGCCACGCACCCGTCAGGGCCGGGTGTGTAAAC

TTTGACTACTCACGCACTCGCCGCTGCGTCGGGCGACGCGATTTACGGCCTGCCAACACCACGTCAACGTGGGAACC

GCCTGTGTCGTCGGACGATGAAGCGAGCTCGCAGTCGAAGCCCCTCGCCACCCAGCCGCCCGTCCTCGCCCTTTCGA

ACGCCCCCCCACGGCGGGTCTCCCCGACGCGAGGTCGGCGCCGGCATACTCGCCTCCGACGCAACCATCACCATCAC

CATCACTGA

-continued

SEQ ID NO: 138 = ICP4 internal fragment encoded by construct RS1.9 (deletion of #391-544 and #786-821)
MSAEQRKKKKTTTTTQGRGAEVAMADEDGGRLRAAAETTGGPGSPDPADGPPPTPNPDRRPAARPGFGWHGGPEENE

DEADDAAADADADEAAPASGEAVDEPAADGVVSPRQLALLASMVDEAVRTIPSPPPERDGAQEEAARSPSPPRTPSM

RADYGEENDDDDDDDDDDDRDAGRWVRGPETTSAVRGAYPDPMASLSPRPPAPRRHHHHHHHRRRRAPRRRSAASDS

SKSGSSSSASSASSSASSSSSASASSSDDDDDDDAARAPASAADHAAGGTLGADDEEAGVPARAPGAAPRPSPPRAE

PAPARTPAATAGRLERRRARAAVAGRDATGRFTAGRPRRVELDADAASGAFYARYRDGYVSGEPWPGAGPPPPGRVL

YGGLGRTPDDGGDANRHDGDDARGKPAAAAAPLPSAAASPADERAVPAGYGAAGVLAALGRLSAAPASAPAGADDD

DDDGAGGGGGGRRAEAGRVAVECLAACRGILEALAEGFDGDLAAVPGLAGARPAAPPRPGPAGAAAPPHADAPRLRA

WLRELRFVRDALVLMRLRGDLRVAGGSEAAVAAVRAVSLVAGALGPALPRSPRLLSSAAAAAADLLFQNQSLRPLLA

DTVAAADSLAAPASAAAPPAGAAPPAPPTPPPRPPRPAALTRRPAEGPDPQGGWRRQPPGPSHTPAPSAAALEAYCA

PRAVAELTDHPLFPAPWRPALMFDPRALASLAARCAAPPPGGAPAAFGPLRASGPLRRAAAWMRQVPDPEDVRVVIL

YSPLPGEDLAAGRAGGGPPPEWSAERGGLSCLLAALGNRLCGPATAAWAGNWTGAPDVSALGAQGVLLLSTRDLAFA

GAVEFLGLLAGACDRRLIVVNAVRAADWPADGPVVSRQHAYLACEVLPAVQCAVRWPAARDLRRTVLASGRVFGPGV

FARVEAAHARLYPDAPPLRLCRGANVRYRVRTRFGPDTLVPMSPREYRRAVLPALDGRAAASGAGDAMAPGAPDFCE

DEAHSHRACARWGLGAPLRPVYVALGRDAVRGGPAELRGPRREFCARALLEPDGDAPPLVLRDDADAGPPPQIRWAS

AAGRAGTVLAAAGGGVEVVGTAAGLATPPRREPVDMDAELEDDDDGLFGE

SEQ ID NO: 139 = ICP4 internal fragment encoded by construct RS1.10 (deletion of # 391-508 and #786-821)
MSAEQRKKKKTTTTTQGRGAEVAMADEDGGRLRAAAETTGGPGSPDPADGPPPTPNPDRRPAARPGFGWHGGPEENE

DEADDAAADADADEAAPASGEAVDEPAADGVVSPRQLALLASMVDEAVRTIPSPPPERDGAQEEAARSPSPPRTPSM

RADYGEENDDDDDDDDDDDRDAGRWVRGPETTSAVRGAYPDPMASLSPRPPAPRRHHHHHHHRRRRAPRRRSAASDS

SKSGSSSSASSASSSASSSSSASASSSDDDDDDDAARAPASAADHAAGGTLGADDEEAGVPARAPGAAPRPSPPRAE

PAPARTPAATAGRLERRRARAAVAGRDATGRFTAGRPRRVELDADAASGAFYARYRDGYVSGEPWPGAGPPPPGRVL

YGGLGAMSRRYDRAQKGFLLTSLRRAYAPLLARENAALTGARTPDDGGDANRHDGDDARGKPAAAAAPLPSAAASPA

DERAVPAGYGAAGVLAALGRLSAAPASAPAGADDDDDDDGAGGGGGGRRAEAGRVAVECLAACRGILEALAEGFDGD

LAAVPGLAGARPAAPPRPGPAGAAAPPHADAPRLRAWLRELRFVRDALVLMRLRGDLRVAGGSEAAVAAVRAVSLVA

GALGPALPRSPRLLSSAAAAAADLLFQNQSLRPLLADTVAAADSLAAPASAAAPPAGAAPPAPPTPPPRPPRPAALT

RRPAEGPDPQGGWRRQPPGPSHTPAPSAAALEAYCAPRAVAELTDHPLFPAPWRPALMFDPRALASLAARCAAPPPG

GAPAAFGPLRASGPLRRAAAWMRQVPDPEDVRVVILYSPLPGEDLAAGRAGGGPPPEWSAERGGLSCLLAALGNRLC

GPATAAWAGNWTGAPDVSALGAQGVLLLSTRDLAFAGAVEFLGLLAGACDRRLIVVNAVRAADWPADGPVVSRQHAY

LACEVLPAVQCAVRWPAARDLRRTVLASGRVFGPGVFARVEAAHARLYPDAPPLRLCRGANVRYRVRTRFGPDTLVP

MSPREYRRAVLPALDGRAAASGAGDAMAPGAPDFCEDEAHSHRACARWGLGAPLRPVYVALGRDAVRGGPAELRGPR

REFCARALLEPDGDAPPLVLRDDADAGPPPQIRWASAAGRAGTVLAAAGGGVEVVGTAAGLATPPRREPVDMDAELE

DDDDGLFGE

SEQ ID NO: 140 = construct RS1.9
ATGAGTGCCGAACAGCGTAAAAAGAAAAAAACCACCACCACGACCCAAGGACGTGGAGCTGAAGTTGCTATGGCGGA

TGAGGATGGAGGCCGCTTGAGAGCTGCTGCTGAGACTACTGGAGGACCTGGATCACCGGACCCTGCCGATGGACCCC

CCCCTACACCAAACCCCGATCGTAGACCGGCTGCTAGACCTGGATTCGGATGGCATGGAGGACCCGAGGAAAACGAG

GACGAGGCGGACGACGCCGCTGCCGACGCCGACGCCGATGAGGCTGCCCCTGCTTCTGGAGAGGCGGTAGACGAACC

TGCTGCCGATGGAGTTGTTAGCCCTAGGCAATTGGCTTTGTTGGCGAGCATGGTAGACGAGGCTGTGAGAACAATCC

CTTCCCCTCCCCCTGAACGTGATGGAGCACAAGAGGAGGCGGCTAGGAGTCCCTCACCACCCCGTACACCTTCTATG

AGAGCGGATTACGGCGAGGAAAACGACGACGACGACGATGATGATGACGACGATGATCGTGATGCCGGACGCTGGGT

-continued

TAGGGGACCTGAAACCACTTCTGCTGTCCGTGGAGCATACCCCGATCCTATGGCGAGTTTGAGCCCTAGACCACCTG

CCCCGAGGAGACACCACCACCACCACCATCATAGGCGTAGACGTGCTCCTAGACGTCGTTCTGCCGCTAGTGACTCT

TCCAAATCTGGCTCTTCTTCATCTGCCTCTTCCGCTTCATCTTCGGCCTCATCGTCCTCTTCGGCATCCGCTTCGAG

TAGTGATGATGATGATGACGACGACGCTGCTAGAGCCCCCGCTTCTGCTGCCGACCACGCTGCTGGCGGAACTTTGG

GAGCCGACGACGAGGAGGCGGGAGTTCCTGCTCGTGCCCCGGGAGCTGCTCCGAGGCCTTCTCCACCCCGTGCTGAA

CCTGCTCCGGCTAGAACACCGGCCGCTACTGCTGGTAGACTGGAGCGTAGACGTGCCCGTGCTGCTGTGGCTGGTAG

AGATGCTACTGGCCGCTTCACTGCTGGCCGTCCTAGACGTGTTGAACTGGACGCCGATGCTGCTTCTGGTGCTTTCT

ACGCCCGTTACCGTGATGGTTACGTGTCTGGTGAACCTTGGCCTGGCGCTGGTCCACCTCCGCCCGGACGTGTACTC

TACGGTGGATTGGGCCGTACCCCCGATGACGGTGGCGACGCCAACCGCCACGATGGTGATGATGCTAGAGGCAAACC

CGCTGCCGCTGCTGCTCCTTTGCCCTCTGCCGCCGCTTCCCCTGCCGATGAACGTGCTGTTCCTGCCGGTTACGGTG

CCGCTGGTGTGTTGGCTGCTTTGGGACGCTTGAGTGCTGCCCCGGCTAGTGCCCCCGCTGGTGCCGATGACGATGAC

GATGACGATGGTGCTGGCGGAGGCGGTGGCGGTAGACGTGCTGAGGCTGGACGTGTTGCTGTTGAATGCCTGGCTGC

CTGTAGAGGAATCTTGGAGGCTCTGGCCGAGGGATTCGACGGAGACTTGGCGGCTGTACCGGGACTGGCGGGAGCGA

GGCCTGCCGCTCCACCTCGCCCCGGTCCTGCTGGTGCTGCCGCTCCTCCTCATGCCGACGCTCCTAGACTCCGTGCT

TGGCTCCGTGAACTCCGTTTCGTTCGTGACGCTTTGGTTCTGATGAGACTGAGAGGCGACTTGAGAGTGGCTGGAGG

ATCCGAGGCTGCTGTTGCTGCTGTCCGTGCTGTTTCTTTGGTTGCTGGTGCTTTGGGCCCTGCTTTGCCGAGATCTC

CCCGTTTGTTGTCGAGTGCCGCCGCTGCTGCCGCCGATTTGTTGTTCCAAAACCAATCCCTCCGCCCTCTGCTCGCC

GACACTGTTGCCGCTGCCGATTCTCTGGCTGCTCCGGCTTCTGCTGCTGCTCCCCCCGCTGGTGCTGCTCCCCCCGC

TCCCCCTACTCCCCCCCCACGCCCACCTCGTCCCGCTGCCCTCACACGCCGTCCTGCTGAGGGACCCGATCCACAAG

GCGGCTGGCGTAGACAACCTCCTGGCCCATCCCATACACCGGCACCATCTGCCGCTGCTTTGGAGGCTTACTGTGCT

CCTCGTGCTGTGGCTGAACTCACCGATCATCCGCTGTTCCCTGCTCCCTGGCGTCCCGCCCTCATGTTCGATCCTAG

AGCTTTGGCTTCCTTGGCCGCTCGTTGTGCTGCCCCTCCCCCTGGCGGTGCTCCGGCTGCTTTCGGTCCTCTCCGTG

CCTCTGGTCCACTCCGCCGTGCCGCTGCCTGGATGAGACAAGTTCCCGACCCTGAGGATGTTAGAGTTGTGATCTTG

TACTCGCCCTTGCCTGGCGAGGATTTGGCCGCTGGTAGAGCTGGCGGTGGCCCCCCTCCTGAATGGTCTGCTGAACG

TGGTGGTTTGTCTTGCTTGTTGGCCGCCCTGGGAAACCGTCTGTGTGGTCCTGCTACTGCTGCTTGGGCTGGAAACT

GGACTGGCGCTCCCGATGTTTCTGCTCTCGGTGCTCAAGGAGTTTTGCTGCTCTCTACTCGTGACTTGGCATTCGCT

GGAGCTGTTGAATTCCTGGGACTCTTGGCTGGCGCTTGTGATAGGAGACTCATCGTCGTAAACGCTGTGAGAGCTGC

CGATTGGCCTGCCGATGGTCCTGTTGTGTCTCGTCAACACGCTTACTTGGCTTGTGAAGTGTTGCCCGCTGTCCAAT

GTGCTGTTCGCTGGCCTGCTGCTCGTGATCTGAGGCGTACTGTTCTGGCTAGTGGTCGTGTTTTCGGACCTGGTGTT

TTCGCTCGTGTCGAAGCTGCTCACGCTAGACTGTACCCCGATGCCCCACCCCTCCGTTTGTGTCGTGGAGCAAACGT

TCGCTACCGTGTCCGTACTCGTTTCGGACCCGATACTCTGGTTCCAATGTCCCCTCGTGAATACCGTCGTGCTGTTC

TGCCTGCCCTCGATGGACGTGCTGCCGCTTCTGGCGCTGGTGACGCTATGGCTCCTGGCGCTCCGGACTTCTGTGAG

GATGAGGCTCACTCACATCGTGCCTGTGCCCGCTGGGGACTGGGCGCTCCATTGAGGCCTGTATACGTGGCACTGGG

CCGTGATGCTGTTAGAGGCGGACCCGCTGAATTGAGAGGCCCTCGTCGTGAATTCTGTGCTAGGGCTCTGCTCGAAC

CCGATGGAGATGCTCCTCCTTTGGTACTCCGTGACGACGCCGATGCTGGTCCTCCCCCACAAATTCGCTGGGCTAGT

GCTGCTGGACGTGCTGGTACTGTATTGGCTGCTGCTGGCGGTGGCGTTGAAGTTGTTGGTACTGCCGCTGGACTCGC

TACACCTCCCCGCCGTGAACCTGTAGACATGGATGCTGAACTCGAGGATGATGACGACGGATTGTTCGGAGAG

SEQ ID NO: 141 = construct RS1.10
ATGAGTGCCGAACAGCGTAAAAAGAAAAAAACCACCACCACGACCCAAGGACGTGGAGCTGAAGTTGCTATGGCGGA

TGAGGATGGAGGCCGCTTGAGAGCTGCTGCTGAGACTACTGGAGGACCTGGATCACCGGACCCTGCCGATGGACCCC

CCCCTACACCAAACCCCGATCGTAGACCGGCTGCTAGACCTGGATTCGGATGGCATGGAGGACCCGAGGAAAACGAG

-continued

GACGAGGCGGACGACGCCGCTGCCGACGCCGACGCCGATGAGGCTGCCCCTGCTTCTGGAGAGGCGGTAGACGAACC

TGCTGCCGATGGAGTTGTTAGCCCTAGGCAATTGGCTTTGTTGGCGAGCATGGTAGACGAGGCTGTGAGAACAATCC

CTTCCCCTCCCCCTGAACGTGATGGAGCACAAGAGGAGGCGGCTAGGAGTCCCTCACCACCCCGTACACCTTCTATG

AGAGCGGATTACGGCGAGGAAAACGACGACGACGACGATGATGATGACGACGATGATCGTGATGCCGGACGCTGGGT

TAGGGGACCTGAAACCACTTCTGCTGTCCGTGGAGCATACCCCGATCCTATGGCGAGTTTGAGCCCTAGACCACCTG

CCCCGAGGAGACACCACCACCACCACCATCATAGGCGTAGACGTGCTCCTAGACGTCGTTCTGCCGCTAGTGACTCT

TCCAAATCTGGCTCTTCTTCATCTGCCTCTTCCGCTTCATCTTCGGCCTCATCGTCCTCTTCGGCATCCGCTTCGAG

TAGTGATGATGATGATGACGACGACGCTGCTAGAGCCCCCGCTTCTGCTGCCGACCACGCTGCTGGCGGAACTTTGG

GAGCCGACGACGAGGAGGCGGGAGTTCCTGCTCGTGCCCCGGGAGCTGCTCCGAGGCCTTCTCCACCCCGTGCTGAA

CCTGCTCCGGCTAGAACACCGGCCGCTACTGCTGGTAGACTGGAGCGTAGACGTGCCCGTGCTGCTGTGGCTGGTAG

AGATGCTACTGGCCGCTTCACTGCTGGCCGTCCTAGACGTGTTGAACTGGACGCCGATGCTGCTTCTGGTGCTTTCT

ACGCCCGTTACCGTGATGGTTACGTGTCTGGTGAACCTTGGCCTGGCGCTGGTCCACCTCCGCCCGGACGTGTACTC

TACGGTGGATTGGGCGCAATGTCTAGACGCTACGACCGTGCTCAAAAAGGATTCTTGCTCACGTCACTGAGGCGTGC

TTACGCCCCTTTGTTGGCCCGTGAAAACGCTGCCCTCACTGGCGCCCGTACCCCCGATGACGGTGGCGACGCCAACC

GCCACGATGGTGATGATGCTAGAGGCAAACCCGCTGCCGCTGCTGCTCCTTTGCCCTCTGCCGCCGCTTCCCCTGCC

GATGAACGTGCTGTTCCTGCCGGTTACGGTGCCGCTGGTGTGTTGGCTGCTTTGGGACGCTTGAGTGCTGCCCCGGC

TAGTGCCCCCGCTGGTGCCGATGACGATGACGATGACGATGGTGCTGGCGGAGGCGGTGGCGGTAGACGTGCTGAGG

CTGGACGTGTTGCTGTTGAATGCCTGGCTGCCTGTAGAGGAATCTTGGAGGCTCTGGCCGAGGGATTCGACGGAGAC

TTGGCGGCTGTACCGGGACTGGCGGGAGCGAGGCCTGCCGCTCCACCTCGCCCCGGTCCTGCTGGTGCTGCCGCTCC

TCCTCATGCCGACGCTCCTAGACTCCGTGCTTGGCTCCGTGAACTCCGTTTCGTTCGTGACGCTTTGGTTCTGATGA

GACTGAGAGGCGACTTGAGAGTGGCTGGAGGATCCGAGGCTGCTGTTGCTGCTGTCCGTGCTGTTTCTTTGGTTGCT

GGTGCTTTGGGCCCTGCTTTGCCGAGATCTCCCCGTTTGTTGTCGAGTGCCGCCGCTGCTGCCGCCGATTTGTTGTT

CCAAAACCAATCCCTCCGCCCTCTGCTCGCCGACACTGTTGCCGCTGCCGATTCTCTGGCTGCTCCGGCTTCTGCTG

CTGCTCCCCCCGCTGGTGCTGCTCCCCCCGCTCCCCCTACTCCCCCCCCACGCCCACCTCGTCCCGCTGCCCTCACA

CGCCGTCCTGCTGAGGGACCCGATCCACAAGGCGGCTGGCGTAGACAACCTCCTGGCCCATCCCATACACCGGCACC

ATCTGCCGCTGCTTTGGAGGCTTACTGTGCTCCTCGTGCTGTGGCTGAACTCACCGATCATCCGCTGTTCCCTGCTC

CCTGGCGTCCCGCCCTCATGTTCGATCCTAGAGCTTTGGCTTCCTTGGCCGCTCGTTGTGCTGCCCCTCCCCCTGGC

GGTGCTCCGGCTGCTTTCGGTCCTCTCCGTGCCTCTGGTCCACTCCGCCGTGCCGCTGCCTGGATGAGACAAGTTCC

CGACCCTGAGGATGTTAGAGTTGTGATCTTGTACTCGCCCTTGCCTGGCGAGGATTTGGCCGCTGGTAGAGCTGGCG

GTGGCCCCCCTCCTGAATGGTCTGCTGAACGTGGTGGTTTGTCTTGCTTGTTGGCCGCCCTGGGAAACCGTCTGTGT

GGTCCTGCTACTGCTGCTTGGGCTGGAAACTGGACTGGCGCTCCCGATGTTTCTGCTCTCGGTGCTCAAGGAGTTTT

GCTGCTCTCTACTCGTGACTTGGCATTCGCTGGAGCTGTTGAATTCCTGGGACTCTTGGCTGGCGCTTGTGATAGGA

GACTCATCGTCGTAAACGCTGTGAGAGCTGCCGATTGGCCTGCCGATGGTCCTGTTGTGTCTCGTCAACACGCTTAC

TTGGCTTGTGAAGTGTTGCCCGCTGTCCAATGTGCTGTTCGCTGGCCTGCTGCTCGTGATCTGAGGCGTACTGTTCT

GGCTAGTGGTCGTGTTTTCGGACCTGGTGTTTTCGCTCGTGTCGAAGCTGCTCACGCTAGACTGTACCCCGATGCCC

CACCCCTCCGTTTGTGTCGTGGAGCAAACGTTCGCTACCGTGTCCGTACTCGTTTCGGACCCGATACTCTGGTTCCA

ATGTCCCCTCGTGAATACCGTCGTGCTGTTCTGCCTGCCCTCGATGGACGTGCTGCCGCTTCTGGCGCTGGTGACGC

TATGGCTCCTGGCGCTCCGGACTTCTGTGAGGATGAGGCTCACTCACATCGTGCCTGTGCCCGCTGGGGACTGGGCG

CTCCATTGAGGCCTGTATACGTGGCACTGGGCCGTGATGCTGTTAGAGGCGGACCCGCTGAATTGAGAGGCCCTCGT

CGTGAATTCTGTGCTAGGGCTCTGCTCGAACCCGATGGAGATGCTCCTCCTTTGGTACTCCGTGACGACGCCGATGC

-continued

TGGTCCTCCCCCACAAATTCGCTGGGCTAGTGCTGCTGGACGTGCTGGTACTGTATTGGCTGCTGCTGGCGGTGGCG

TTGAAGTTGTTGGTACTGCCGCTGGACTCGCTACACCTCCCCGCCGTGAACCTGTAGACATGGATGCTGAACTCGAG

GATGATGACGACGGATTGTTCGGAGAG

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Thus, for example, reference to "a cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antigen, any method of administration, any prophylactic and/or therapeutic application, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

OTHER EMBODIMENTS

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

What is claimed is:

1. A vaccine formulation comprising a pharmaceutically-acceptable carrier, a first polypeptide consisting of an amino acid sequence having at least 95% identity to SEQ ID NO: 136, and a second polypeptide comprising an amino acid sequence having at least 95% identity to any one of SEQ ID NOS: 1, 2, 4, 5, 13, 138, 139 and SEQ ID NO:4 lacking a cytoplasmic region, or an immunogenic fragment thereof.

2. The vaccine formulation of claim 1, wherein the second polypeptide comprises an amino acid sequence having at least 95% identity to one of SEQ ID NO:4, SEQ ID NO:4 lacking a cytoplasmic region, SEQ ID NO:5, or immunogenic fragments thereof.

3. The vaccine formulation of claim 2, further comprising a third polypeptide comprising an amino acid sequence having at least 95% identity to SEQ ID NO: 2 or immunogenic fragments thereof.

4. The vaccine formulation of claim 2, further comprising a third polypeptide consisting of SEQ ID NO: 138 or immunogenic fragments thereof.

5. The vaccine formulation of claim 1, wherein the second polypeptide consists of one of SEQ ID NOS: 1, 2, 13, 138 and 139, or immunogenic fragments thereof.

6. The vaccine formulation of claim 5, further comprising a third polypeptide consisting of SEQ ID NO:4, SEQ ID NO:4 lacking a cytoplasmic region, SEQ ID NO:5, or immunogenic fragments thereof.

7. The vaccine formulation of claim 1, wherein the second polypeptide consists of SEQ ID NO:1, SEQ ID NO: 2, SEQ ID NO: 138, or immunogenic fragments thereof.

8. A vaccine formulation comprising a pharmaceutically-acceptable carrier and a polypeptide consisting of an amino acid sequence having at least 95% identity to SEQ ID NO: 136.

9. The vaccine formulation of claim 1, further comprising an adjuvant.

10. The vaccine formulation of claim 9, wherein the adjuvant is one or more purified fractions of *Quillaja saponins.*

11. The vaccine formulation of claim 10, wherein the adjuvant comprises saponin fraction A and saponin fraction C.

12. The vaccine formulation of claim 11, wherein the adjuvant comprises cholesterol, phosphatidyl choline, saponin fraction A and saponin fraction C.

13. The vaccine formulation of claim 12, wherein the adjuvant is in the form of particles.

14. The vaccine formulation of claim 13, wherein particles comprising saponin fraction A are substantially free of saponin fraction C and particles comprising saponin fraction C are substantially free of saponin fraction A.

15. The vaccine formulation of claim 9, wherein the vaccine formulation comprises 5-200 μg of each polypeptide and 5-200 μg of the adjuvant.

16. The vaccine formulation of claim 1, wherein the second polypeptide further comprises a tag.

17. A method for inhibiting HSV-2 infection in a subject, comprising administering to the subject an effective amount of a vaccine formulation according to claim 1.

18. The method of claim 17, wherein the method inhibits HSV-2 infection in a subject after a three dose regimen.

19. The method of claim 17, wherein the subject is a human.

20. The method of claim 17, wherein the subject has not been previously infected with HSV-2.

21. A method for treating HSV-2 infection in a subject, comprising administering an effective amount of a vaccine formulation according to claim 1.

22. The method of claim 21, wherein the method inhibits onset or reduces severity of HSV-2 symptoms.

23. The method of claim 22, wherein the method reduces the number of herpetic lesions.

24. The method of claim 23, wherein the method reduces the number of days a subject experiences herpetic lesions.

25. The method of claim 21, wherein the method increases the IgG titer to one or more HSV-2 antigens.

26. The method of claim 21, wherein the method increases the T cell response to one or more HSV-2 antigens.

27. The method of claim 21, wherein the method reduces the number of herpetic lesions at the onset of HSV-2 infection.

28. The method of claim 21, wherein the method inhibits onset or reduces severity of HSV-2 symptoms in a subject after a three dose regimen.

29. The method of claim 21, wherein the subject is a human.

30. The method of claim 21, wherein the subject has not been previously infected with HSV-2.

31. The vaccine formulation of claim 1, wherein upon administration to an asymptomatic subject infected with HSV-2, the vaccine formulation induces an immune response in the subject.

32. The method of claim 17, wherein the subject is infected with HSV-2 and asymptomatic.

33. The method of claim 17, wherein the subject has been exposed to HSV-2 but is seronegative.

34. The vaccine formulation of claim 1, wherein the first polypeptide consists of the amino acid sequence of SEQ ID NO:136.

35. The vaccine formulation of claim 1, wherein the formulation comprises a heterodimer comprising the first polypeptide.

36. The vaccine formulation of claim 8, wherein the formulation comprises a heterodimer comprising the polypeptide.

* * * * *